United States Patent
Grinstaff et al.

(10) Patent No.: US 12,239,718 B2
(45) Date of Patent: Mar. 4, 2025

(54) SYNTHETIC CELLULAR SIGNALING PATHWAYS AND USES THEREOF

(71) Applicant: Trustees of Boston University, Boston, MA (US)

(72) Inventors: Mark W. Grinstaff, Brookline, MA (US); Jack R. Kirsch, Cambridge, MA (US); Amanda K. Williamson, Boston, MA (US); Brett Tingley, Brighton, MA (US)

(73) Assignee: Trustees of Boston University

( * ) Notice: Subject to any disclaimer, the term of this patent is extended or adjusted under 35 U.S.C. 154(b) by 0 days.

(21) Appl. No.: 18/221,206

(22) Filed: Jul. 12, 2023

(65) Prior Publication Data
US 2024/0024505 A1    Jan. 25, 2024

Related U.S. Application Data

(60) Provisional application No. 63/388,343, filed on Jul. 12, 2022.

(51) Int. Cl.
| | | |
|---|---|---|
| *A61K 48/00* | (2006.01) | |
| *A61K 9/16* | (2006.01) | |
| *A61K 38/22* | (2006.01) | |
| *A61K 38/28* | (2006.01) | |

(52) U.S. Cl.
CPC ........ *A61K 48/0033* (2013.01); *A61K 9/1617* (2013.01); *A61K 38/2221* (2013.01); *A61K 38/28* (2013.01)

(58) Field of Classification Search
CPC .. A61K 48/00; A61K 48/0008; A61K 9/1617; A61K 38/2221
See application file for complete search history.

(56) References Cited

U.S. PATENT DOCUMENTS

| | | |
|---|---|---|
| 5,561,064 A | 10/1996 | Marquet |
| 2021/0059953 A1 | 3/2021 | Kotin |

FOREIGN PATENT DOCUMENTS

| | | | |
|---|---|---|---|
| WO | WO-0068269 A1 * | 11/2000 | ....... C07K 14/57509 |
| WO | 2021207290 A1 | 10/2021 | |

OTHER PUBLICATIONS

Merrick, Gene, 332, 1-11, (2004).*
Damase et al., Frontiers in Bioengineering and Biotech. 202: 1-24, (2021).*

* cited by examiner

*Primary Examiner* — Gyan Chandra
(74) *Attorney, Agent, or Firm* — NIXON PEABODY LLP; Ronald I. Eisenstein; Ravinderjit S. Braich

(57) ABSTRACT

The disclosure relates generally to methods and compositions for generation or enhancement of partial or complete cellular signaling pathways.

16 Claims, 30 Drawing Sheets
(10 of 30 Drawing Sheet(s) Filed in Color)
Specification includes a Sequence Listing.

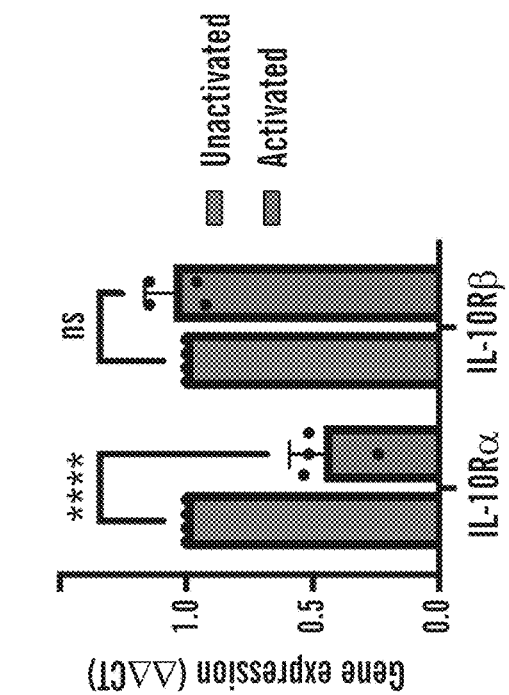
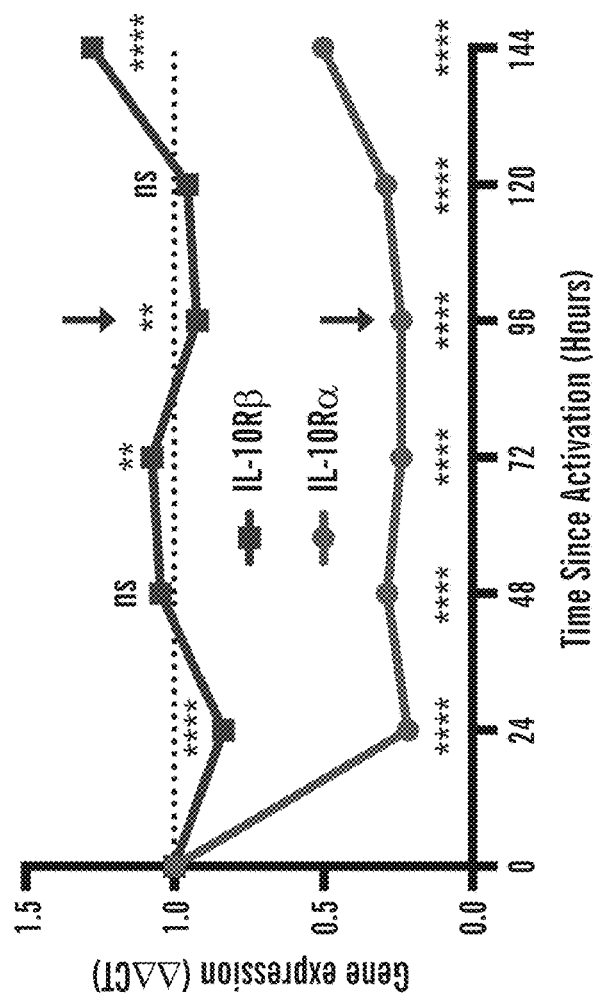
FIG. 1C
FIG. 1B

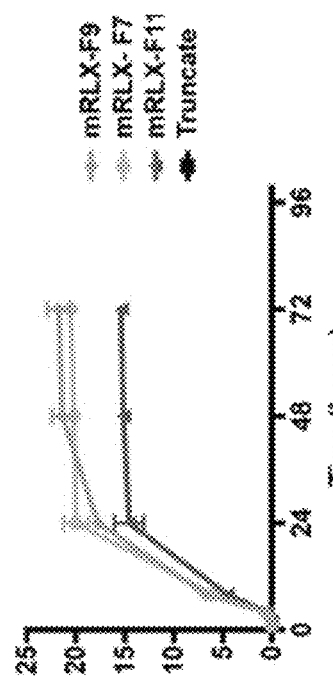
Fig. 3B
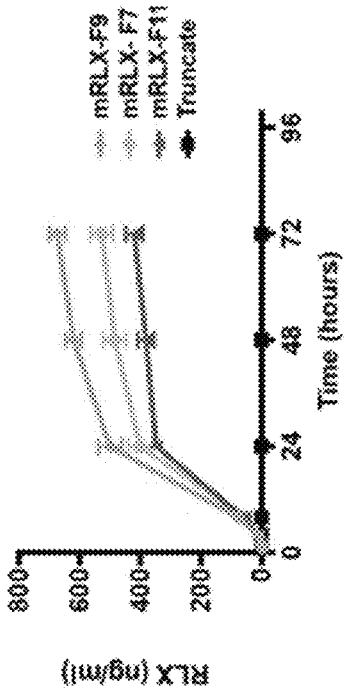
Fig. 3D
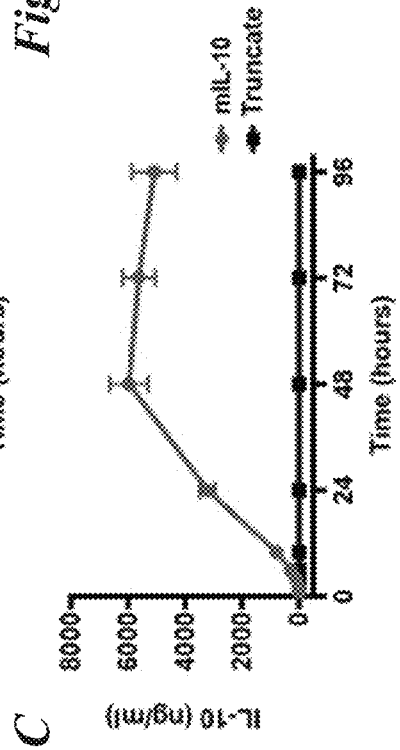
Fig. 3A
Fig. 3C
Fig. 3E
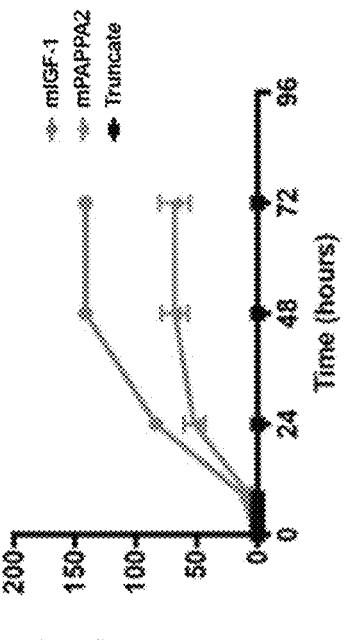

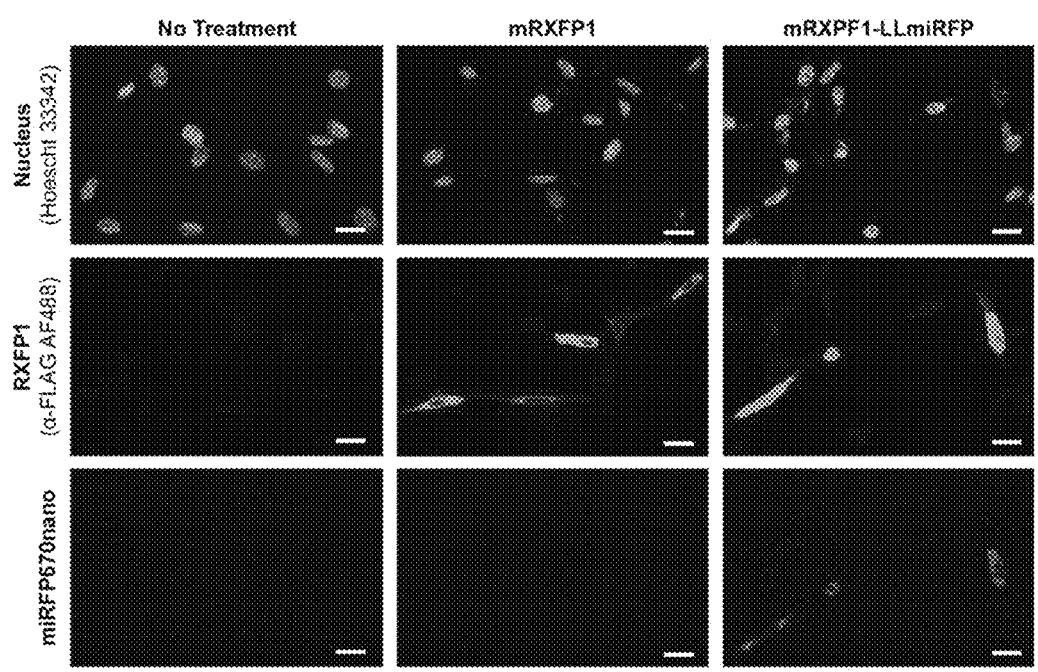

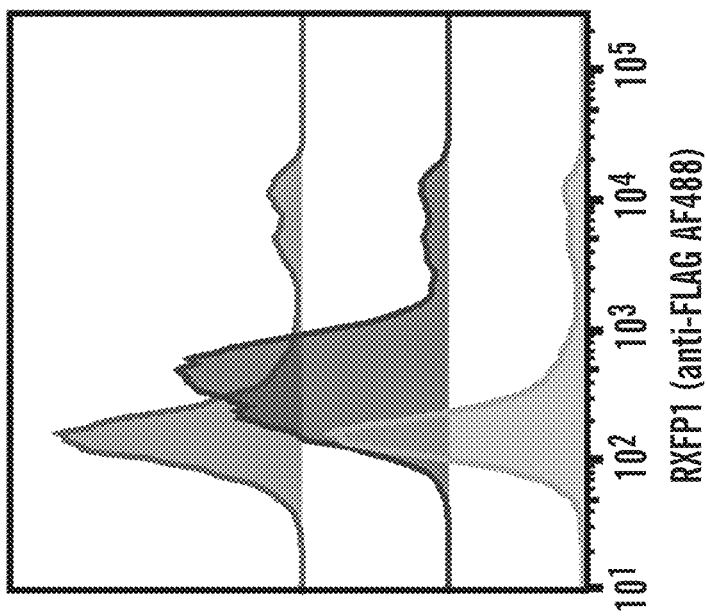
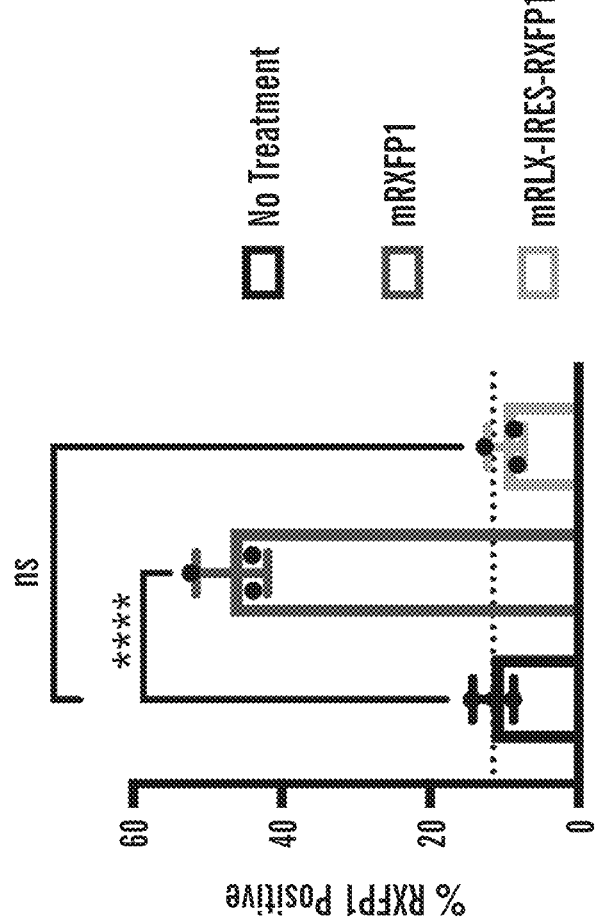
FIG. 5B

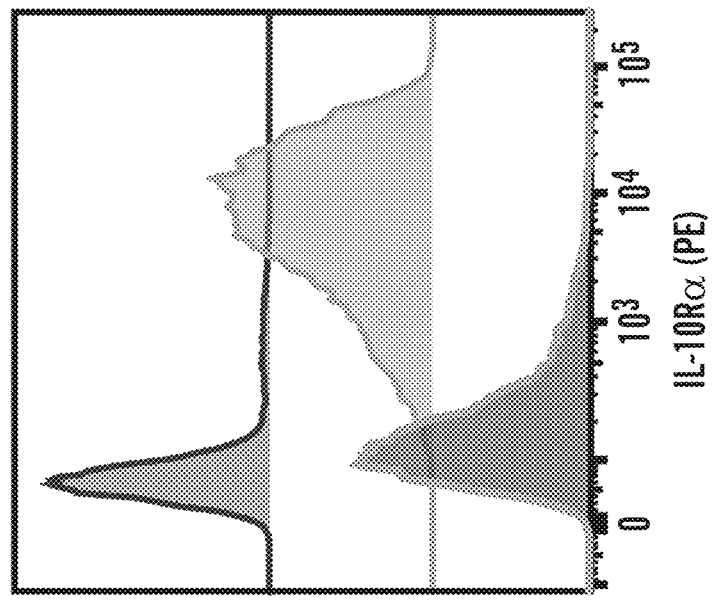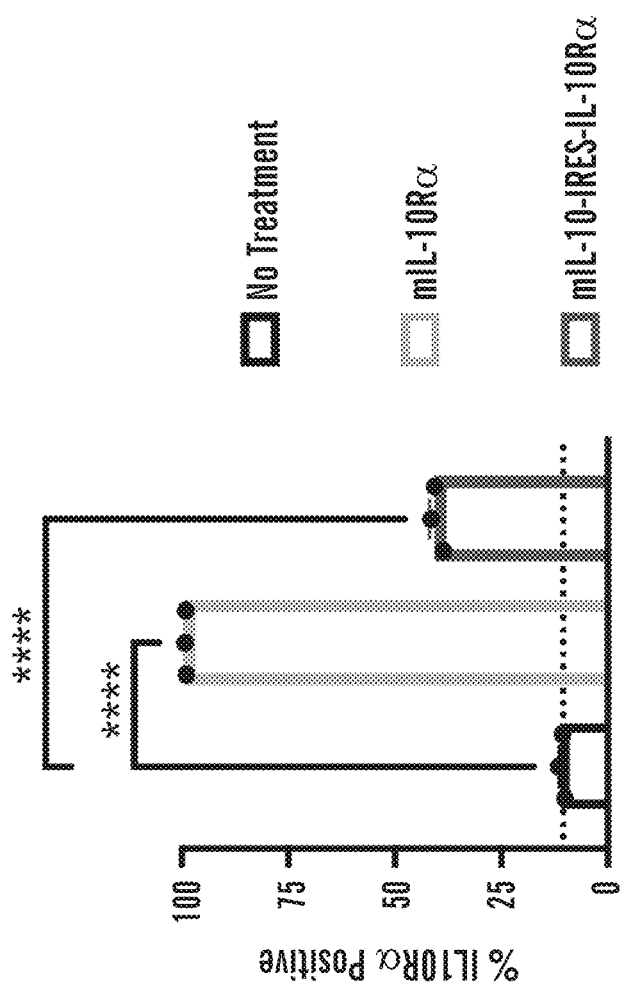
FIG. 5C

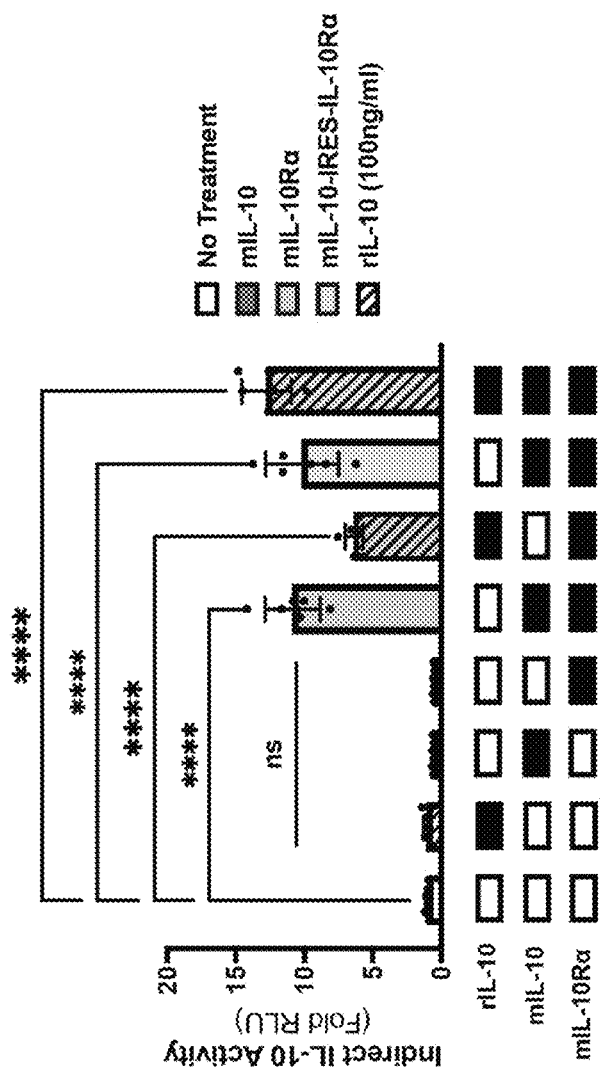
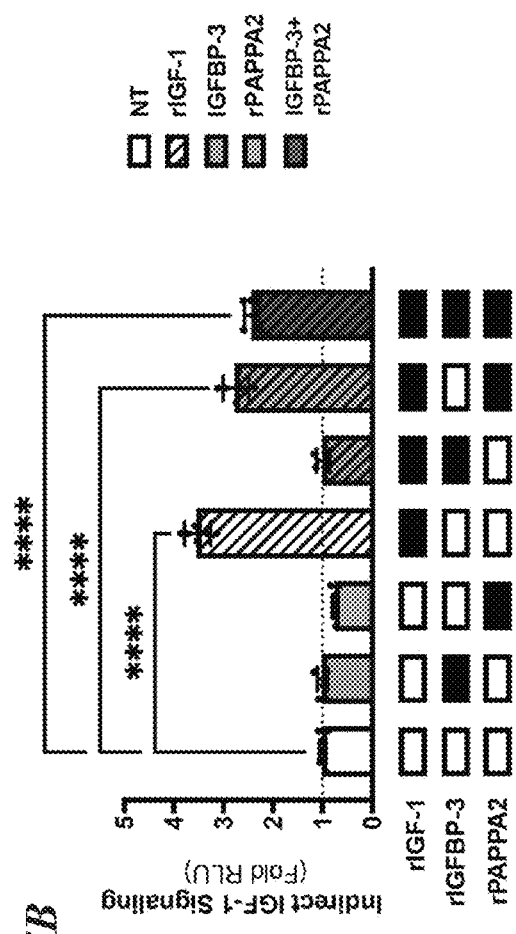
Fig. 7A
Fig. 7B

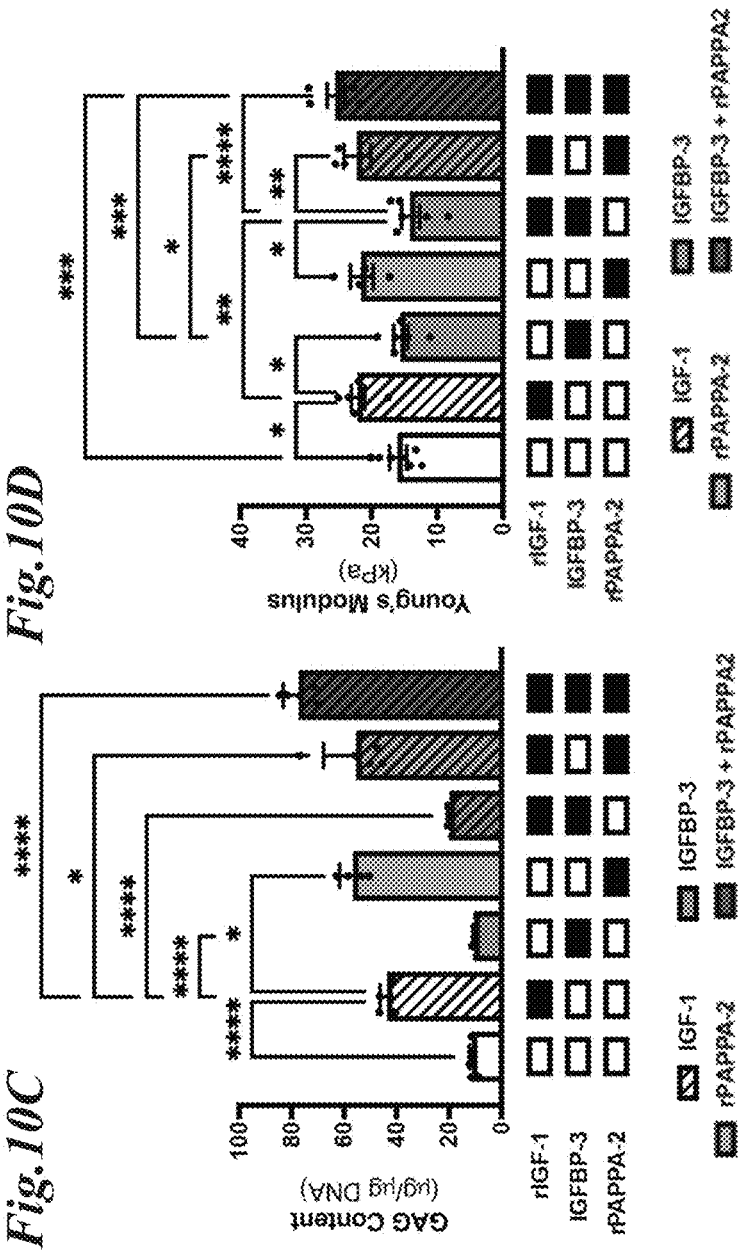

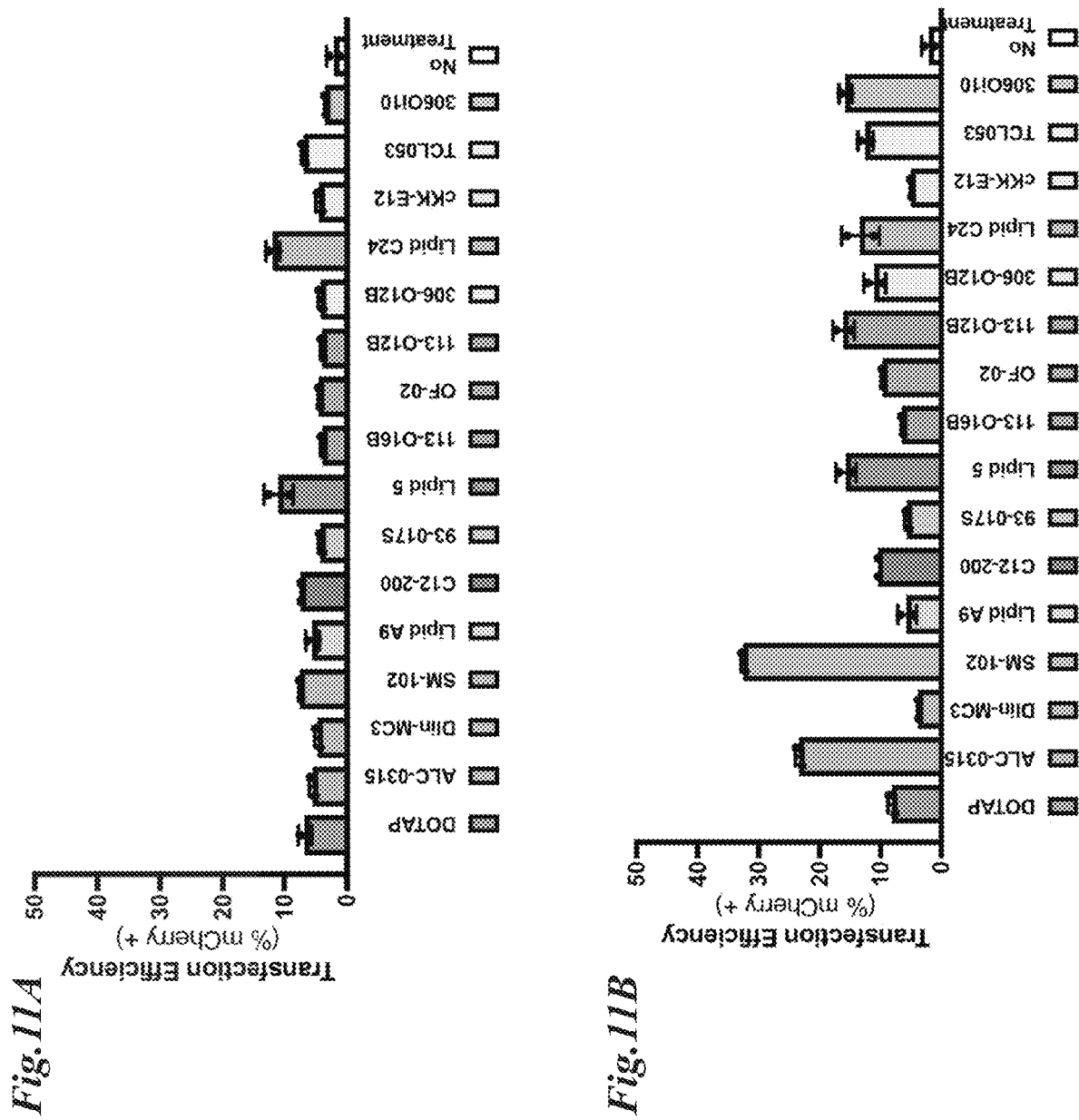

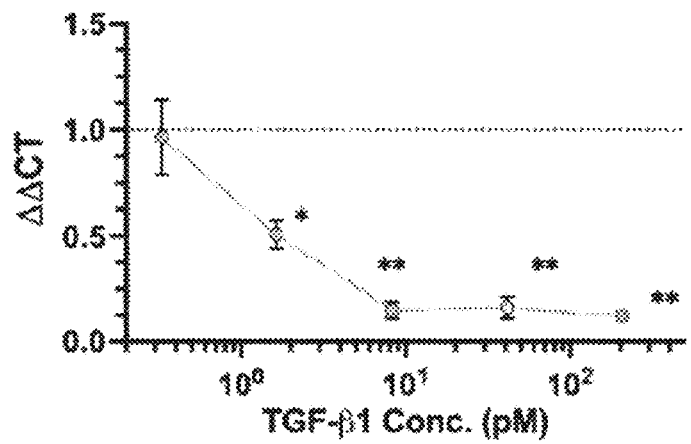
*Fig. 12*
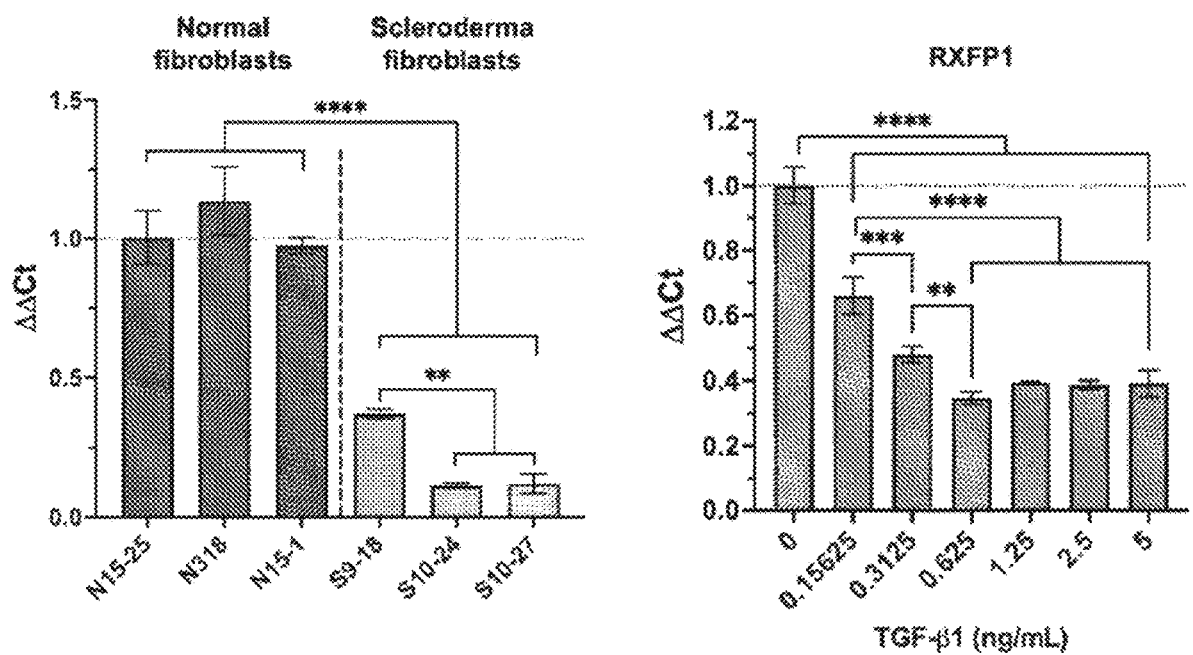
*Fig. 13A*  *Fig. 13B*

SYNTHETIC CELLULAR SIGNALING PATHWAYS AND USES THEREOF

CROSS-REFERENCE TO RELATED APPLICATIONS

This application claims benefit under 35 U.S.C. § 119(e) of U.S. Provisional Application No. 63/388,343 filed Jul. 12, 2022, the contents of which are incorporated herein by reference in its entirety.

GOVERNMENT SUPPORT

This invention was made with government support under Contract No. AR075788 awarded by the National Institutes of Health. The government has certain rights in the invention.

SEQUENCE LISTING

The instant application contains a Sequence Listing which has been submitted electronically in XML format, and is hereby incorporated by reference in its entirety. Said XML copy, created on Sep. 26, 2023 is named "701586-192350USPT_SL.xml" and is 17,108 bytes in size.

TECHNICAL FIELD

The technology described herein relates to methods and compositions for generation or enhancement of partial or complete cellular signaling pathways from exogenous polynucleotides. Wherein one or more signaling pathways, which involve at least one receptor and one ligand, are simultaneously initiated from a single exogenous polynucleotide.

BACKGROUND

Traditional therapeutic modalities rely upon delivery of small molecule agonists or antagonists to druggable, disease-relevant targets. These targets may include an element of a signaling pathway implicated in a disease state, injury or physiological condition, an enzymatic catalyst for the generation of an essential protein, or a critical ion channel which facilitates cellular communication and function. Protein therapeutics have utilized this concept by enabling delivery of enzymes, replacement of essential proteins with a recombinantly generated variant, and targeting cell-specific surface receptors and ion channels through systems like antibody-based therapies.

Nucleic acid delivery has opened the door to the next generation of therapeutic potential. From correcting disease-causing mutations, to allowing for therapeutic treatments with internal logic gates, previously untreatable diseases have become solvable challenges. Many modern biotherapeutics rely upon specific ligand-target recognition for efficacy, which helps to minimize off-target effects and increase the therapeutic window. This benefit of specificity comes at the cost of efficacy predicated on the target of the ligand being present at a high enough density to achieve a therapeutic result. When a patient does not respond to a given therapeutic ligand, the main option available is to increase the dose or switch to a different treatment. What is continually overlooked in drug development is the expression, density or concentration of the ligand target. Few mechanisms exist to address disease-state, cell-type, or patient-specific expression profiles of ligand targets.

This disclosure outlines a mechanism for simultaneous in situ translation and production of a ligand and its cognate target(s) from synthetic, exogenous messenger RNA. By supplementation of a partial or complete signaling pathway alongside the relevant ligand, the therapeutic effect can be amplified and become cell-type or disease-state independent. This disclosure demonstrates the viability of synthetic messenger RNA signaling systems in treating fibrotic, cardiovascular, immunological, oncological, and degenerative diseases.

SUMMARY

One aspect described herein provides a nucleic acid combination comprising (i) a first nucleic acid molecule encoding a ligand; and (ii) a second nucleic acid molecule encoding a target molecule, wherein the target is a cognate receptor of the ligand or an inhibitor of a suppressor of the ligand, and wherein one of the ligand and the target molecule is translated via a cap-dependent manner.

Also provided herein is a composition, vector, plasmid, or cell comprising any of the nucleic acid combinations described herein.

Also provided herein is a lipid particle comprising (i) a first nucleic acid molecule encoding a ligand; (ii) a second nucleic acid molecule encoding a target molecule; and (iii) an ionizable lipid, and wherein the target molecule is a cognate receptor of the ligand or an inhibitor of a suppressor of the ligand.

Also provided herein is a composition or cell comprising any of the lipid particles described herein.

Also provided herein is a composition comprising a first nucleic acid molecule encoding a ligand and a second nucleic acid molecule encoding a target molecule, wherein the target molecule is a cognate receptor of the ligand or an inhibitor of a suppressor of the ligand.

Provided herein is a method for activating a signaling pathway comprising administering to the subject in need thereof any of the nucleic acid combinations, lipid particles, or compositions described herein.

Also provided herein is a method for treating a disease or disorder comprising administering to a subject in need thereof any of the nucleic acid combinations, lipid particles, or compositions described herein.

BRIEF DESCRIPTION OF THE DRAWINGS

This application file contains at least one drawing executed in color. Copies of this patent application publication with color drawings will be provided by the Office upon request and payment of the necessary fee.

FIGS. 1A-1F show disease-state dependent regulation of endogenous ligand signaling pathways. FIG. 1A) IL-10Rα and IFNγ gene expression and secreted TNFα concentrations after 7 days of mixed lymphocyte reaction (MLR) between distinct pairs of human donor PBMCs. Lymphocyte (left) and monocyte (right) displayed for each gene. $4 \times 10^6$ total cells per reaction; ratio denotes cell:cell fraction of a given donor (n=3 donors) FIG. 1B) Longitudinal analysis of IL-10Rα and IL-10Rβ gene expression beginning at the time of immune activation in purified human CD3+ T cells. Activation stimulus removed at 96 hr (Arrows). FIG. 1C). IL-10Rα and IL-10Rβ gene expression after 4 days of activation in unique human donor T cells (n=4) FIG. 1D) Representative histograms and FIG. 1E) quantification of flow cytometry gating of IL-10Rα positive CD3+ T cells after 4 days of immune activation with and without TNFα

Figure 1A:
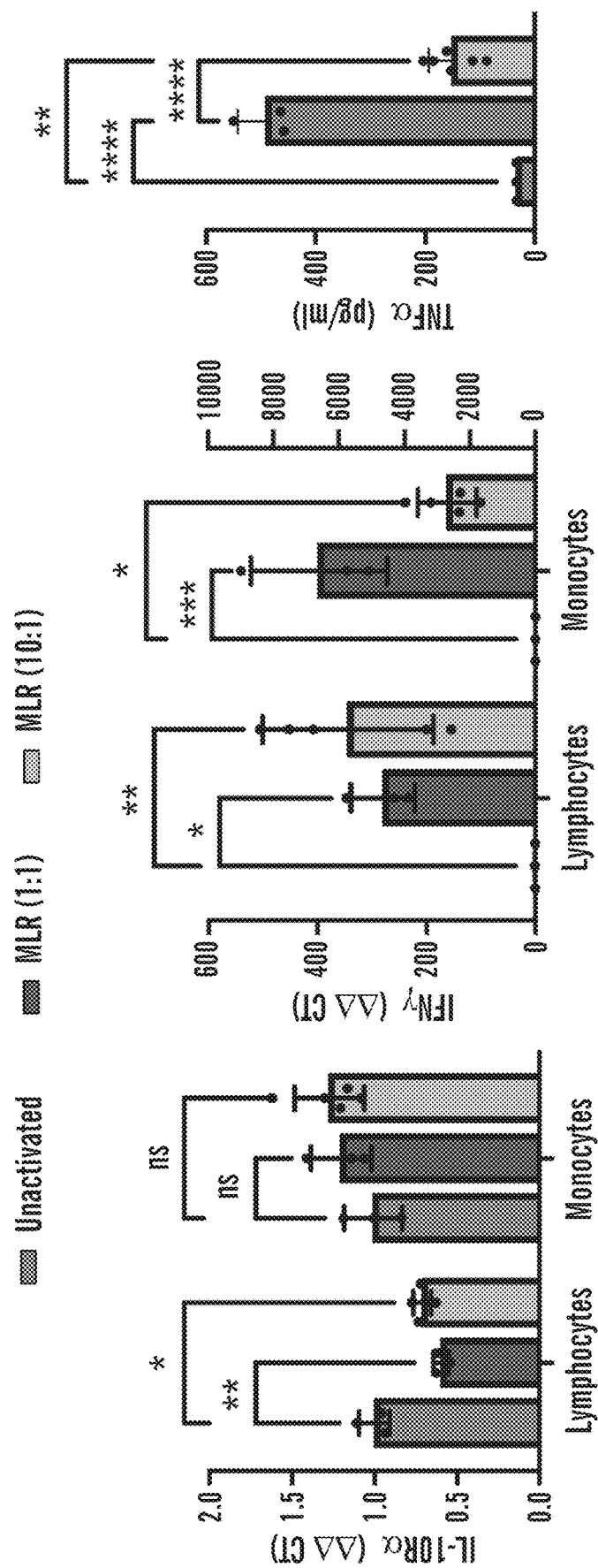
Figure 1D:
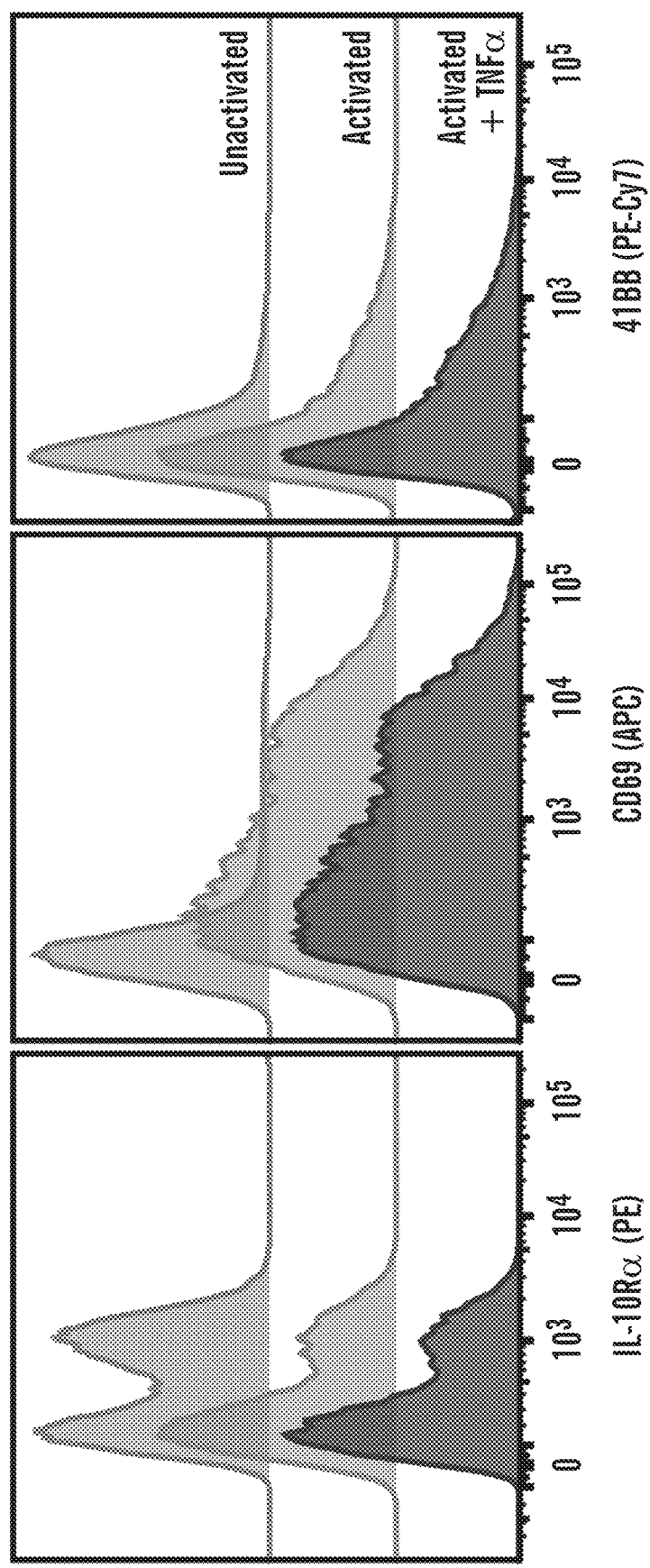
Figure 1F:
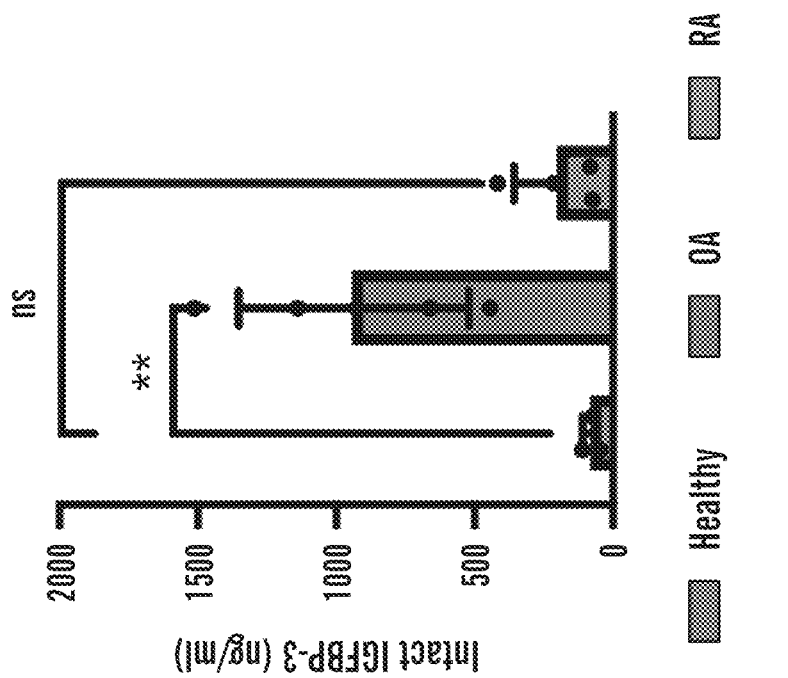
Figure 1E:
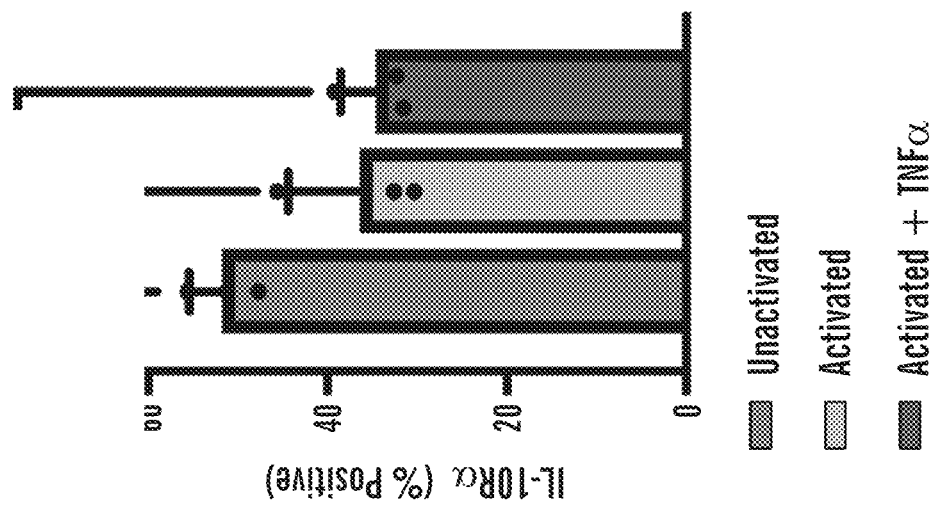

(100 ng/ml) FIG. 1F) Intact IGFBP-3 concentration of healthy (n=3), osteoarthritic (n=5), and rheumatic (n=4) human synovial fluid from live or cadaveric donors. All gene expression respective to activated control of the stated cell type. Statistical significance determined by ANOVA, using the Dunnett method to control for multiple comparisons. * $p<0.05$,  $p<0.005$, * $p<0.001$, **** $p<0.0001$.

Figure 2A:
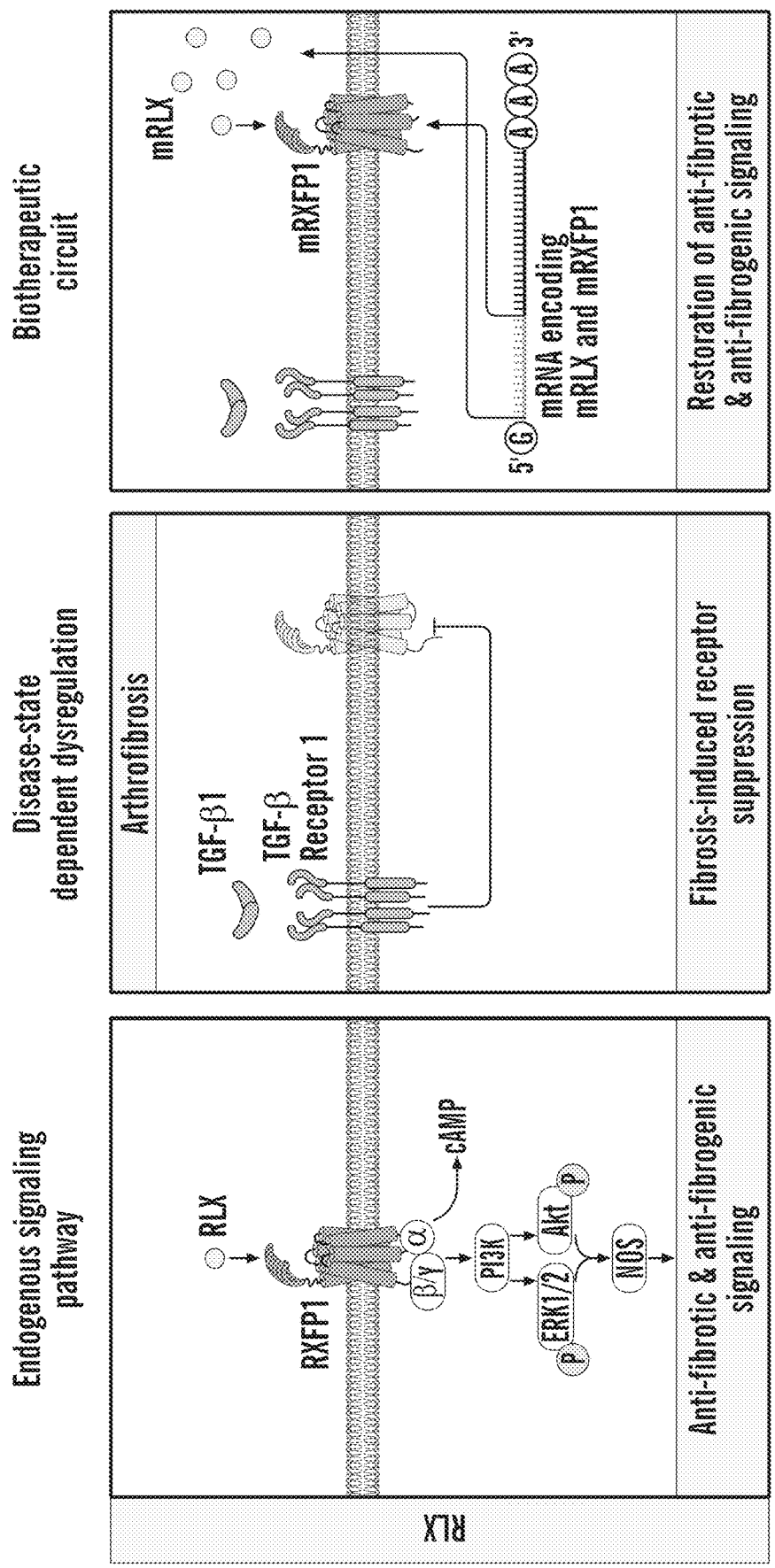
Figure 2B:
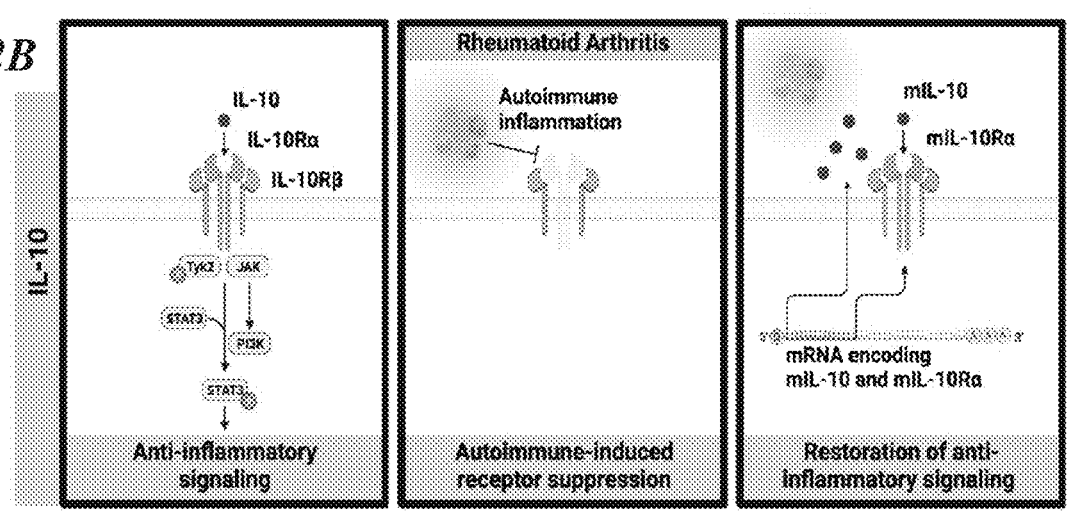
Figure 2C:
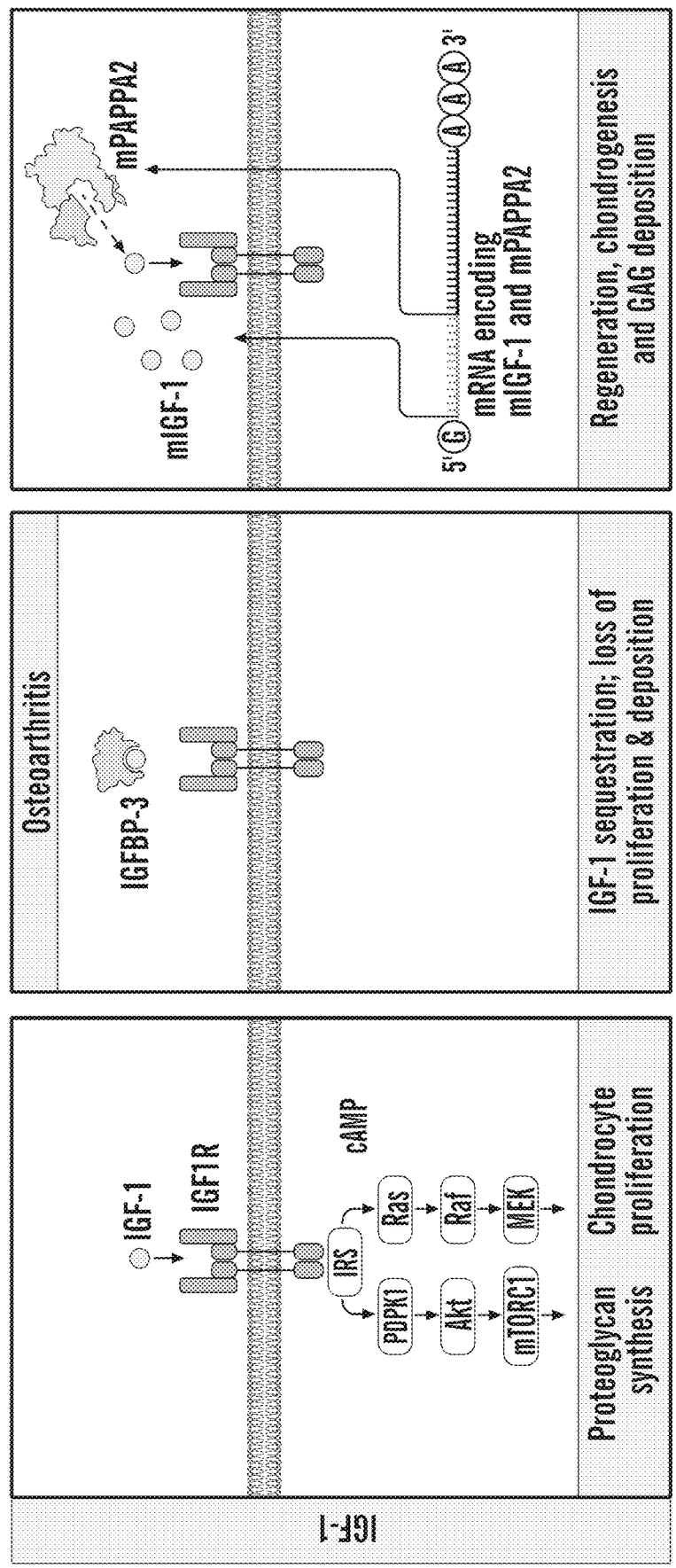

FIGS. 2A-2C show a disease-state independent biotherapeutic circuit applied to exemplary musculoskeletal diseases. FIG. 2A) The signaling pathway of RLX binding to its cognate receptor RXFP1 (left). TGF-β1 induces down regulation of RXFP1, driven by the fibrotic synovial disease, arthrofibrosis (middle). A biotherapeutic circuit capable of simultaneously expressing mRLX and mRXFP1 to induce anti-fibrotic and anti-fibrogenic signaling (right). FIG. 2B) The signaling pathway of IL-10 binding to the tetrameric complex of IL-10Rα and IL-10Rβ (left). Immune activation induces down regulation of IL-10Ra, where the auto-antigen RA stimuli is abstracted and simplified as general inflammation (middle). A biotherapeutic circuit capable of simultaneously expressing mIL-10 and mIL-10Rα to induce immunosuppression and anti-inflammatory signaling (right). FIG. 2C) The signaling pathway of IGF-1 through IGF-1R (left). The upregulation of IGFBP-3 in osteoarthritis leads to sequestration of IGF-1, preventing IGF-1R activation (middle). A biotherapeutic circuit capable of simultaneously expressing mIGF-1 and mPAPPA2 to cleave IGFBP-3, increase synovial IGF-1 bioavailability, and restore cartilage health (right).

FIGS. 3A-3E show ligand expression from mRNA circuits. Expression of mRLX variants over time in FIG. 3A) HEK293T and FIG. 3B) human fibroblast-like synoviocytes. Expression of mIL-10 in FIG. 3C) HEK293T and FIG. 3D) Jurkat T cells. FIG. 3E) Expression of mIGF-1 and mPAPPA2 in HEK293T cells. All ligands compared to cell culture supernatant of cells transfected with control truncate mRNA. Ligand concentrations displayed as average of biological replicates (n=3). Concentration determined by sandwich ELISA.

Figure 4B:
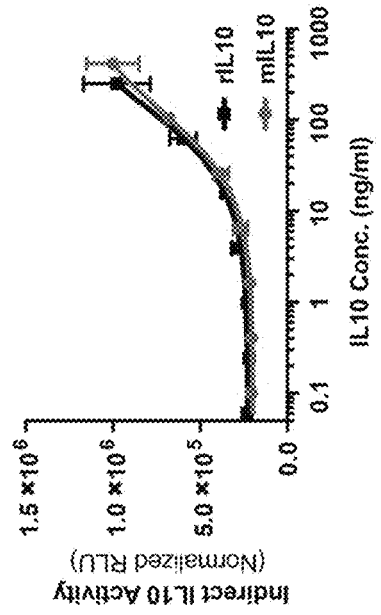
Figure 4A:
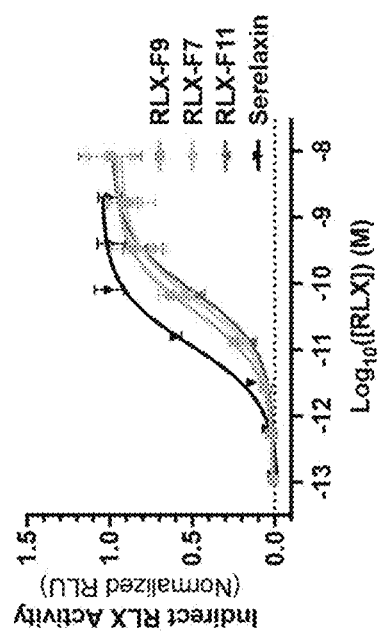
Figure 4C:
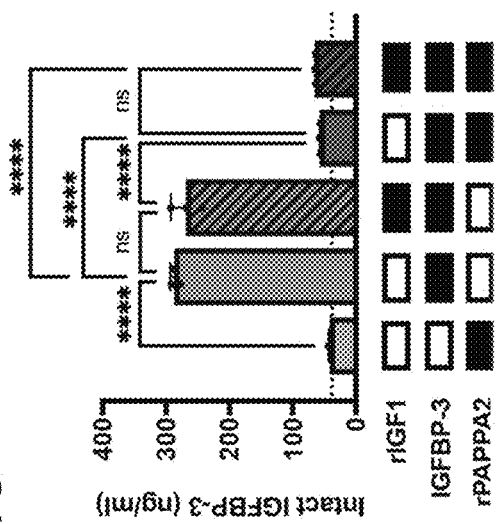
Figure 4D:
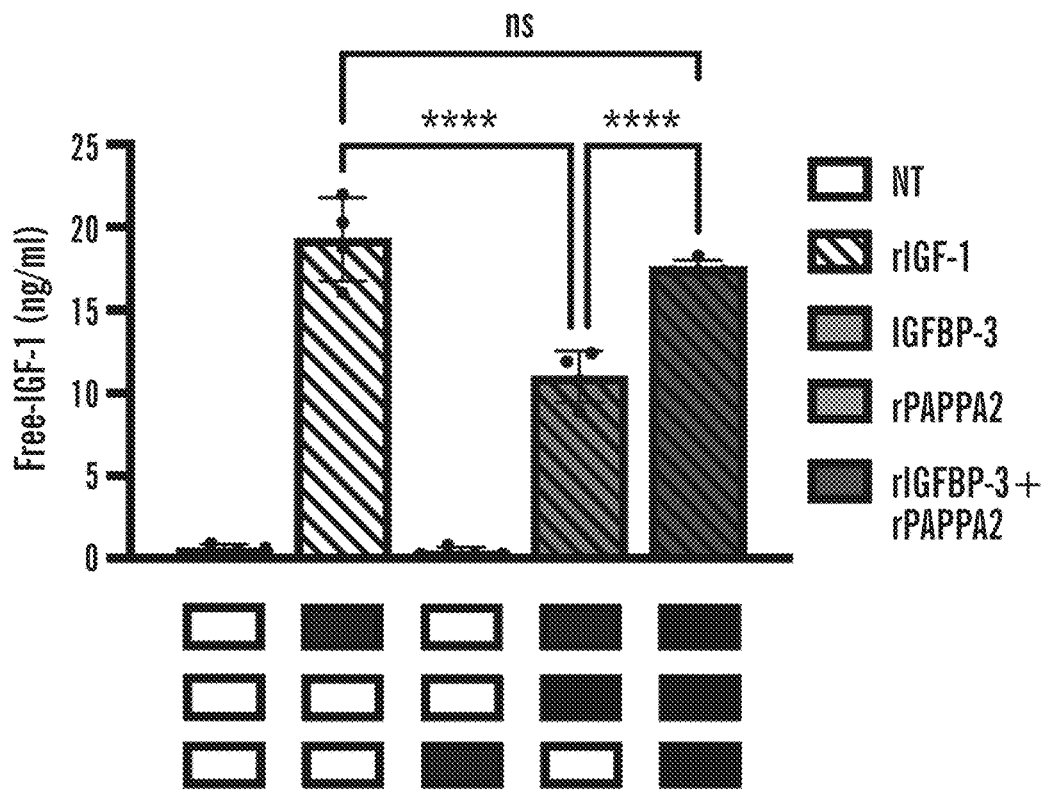
Figure 4E:
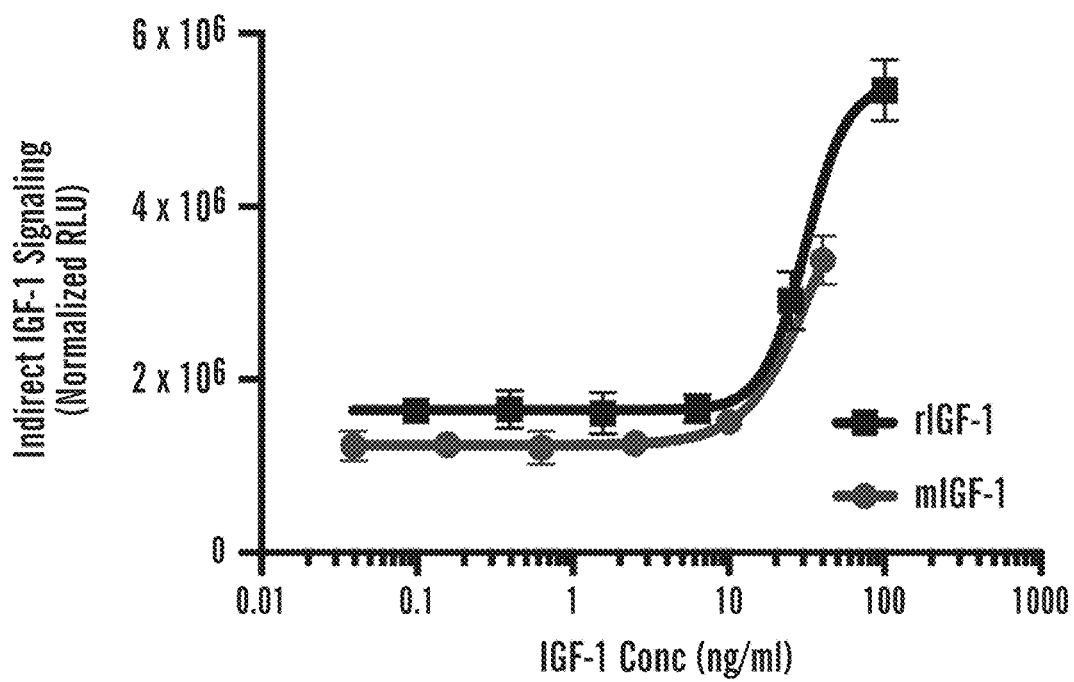

FIGS. 4A-4E show bioactivity of ligands and Pappalysin-2. FIG. 4A) Bioactivity of mRLX variants compared to rRLX (serelaxin). RLX activity displayed as normalized luciferase expression from a cAMP responsive promoter in HEK293T cells, constitutively over-expressing RXFP1. FIG. 4B) Bioactivity of mIL-10 compared to rIL-10. IL-10 activity presented as normalized luciferase expression from a STAT3 responsive promoter in HEK293T cells, transiently over-expressing IL-10Rα; HEK293T cells naturally express IL-10Rβ FIG. 4C) Concentration of intact IGFBP-3 before and after PAPPA2 treatment. FIG. 4D) Free IGF-1 concentrations with and without PAPPA2 after sequestration by IGFBP-3. PAPPA2 activity assays measured via sandwich ELISA. FIG. 4E) Bioactivity of mIGF-1 compared to rIGF-1. IGF-1 activity presented as normalized luciferase expression from an AP-1 responsive promoter in HEK293T cells, transiently over-expressing IGF-1R, and cultured in insulin-free, minimal media. Filled, black boxes denote addition of indicated compound. Statistical significance determined by ANOVA, using the Dunnett method to control for multiple comparisons. Error bars denote standard deviation of biological replicates. **** $p<0.0001$.

FIGS. 5A-5C show characterization of receptor membrane trafficking and expression. FIG. 5A) Confocal microscopy of mRXFP1 fused to a far-red fluorescent tag, miRFP670nano. NIH3T3 cells transfected with control mRNA, mRXFP1, or mRXFP1-LLmiRFP and allowed to express for 24 hours prior to fixation and staining. Scale bar=20 μm. Flow cytometry analysis of HEK293T cells treated with monocistronic or polycistronic circuits expression FIG. 5B) mRXFP1 or FIG. 5C) mIL-10Ra. Quantification of expression positive cells (left) and representative histogram (right). Statistical significance determined by ANOVA, using the Dunnett method to control for multiple comparisons. Error bars denote standard deviation of biological replicates. **** $p<0.0001$.

Figure 6A:
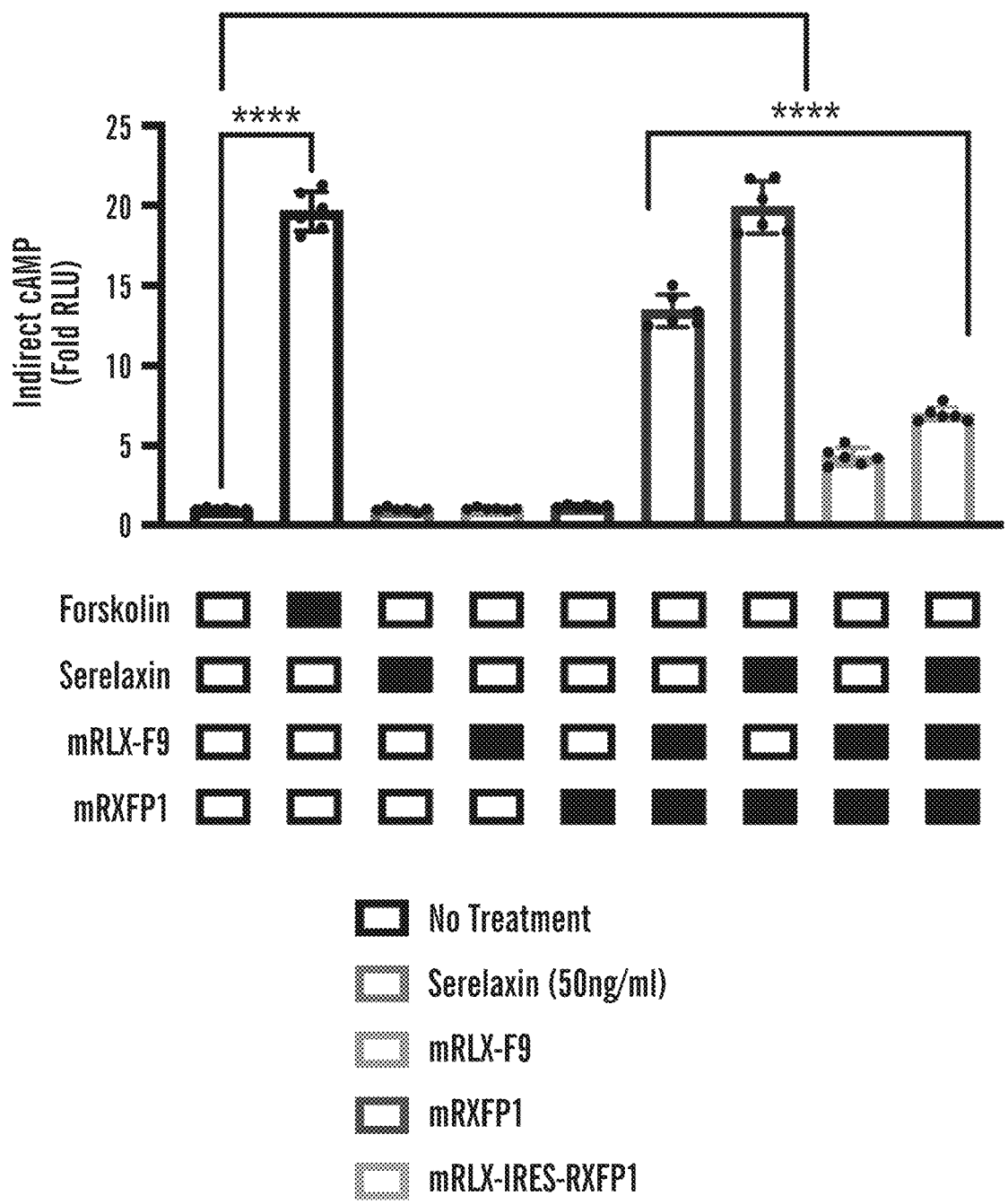
Figure 6B:
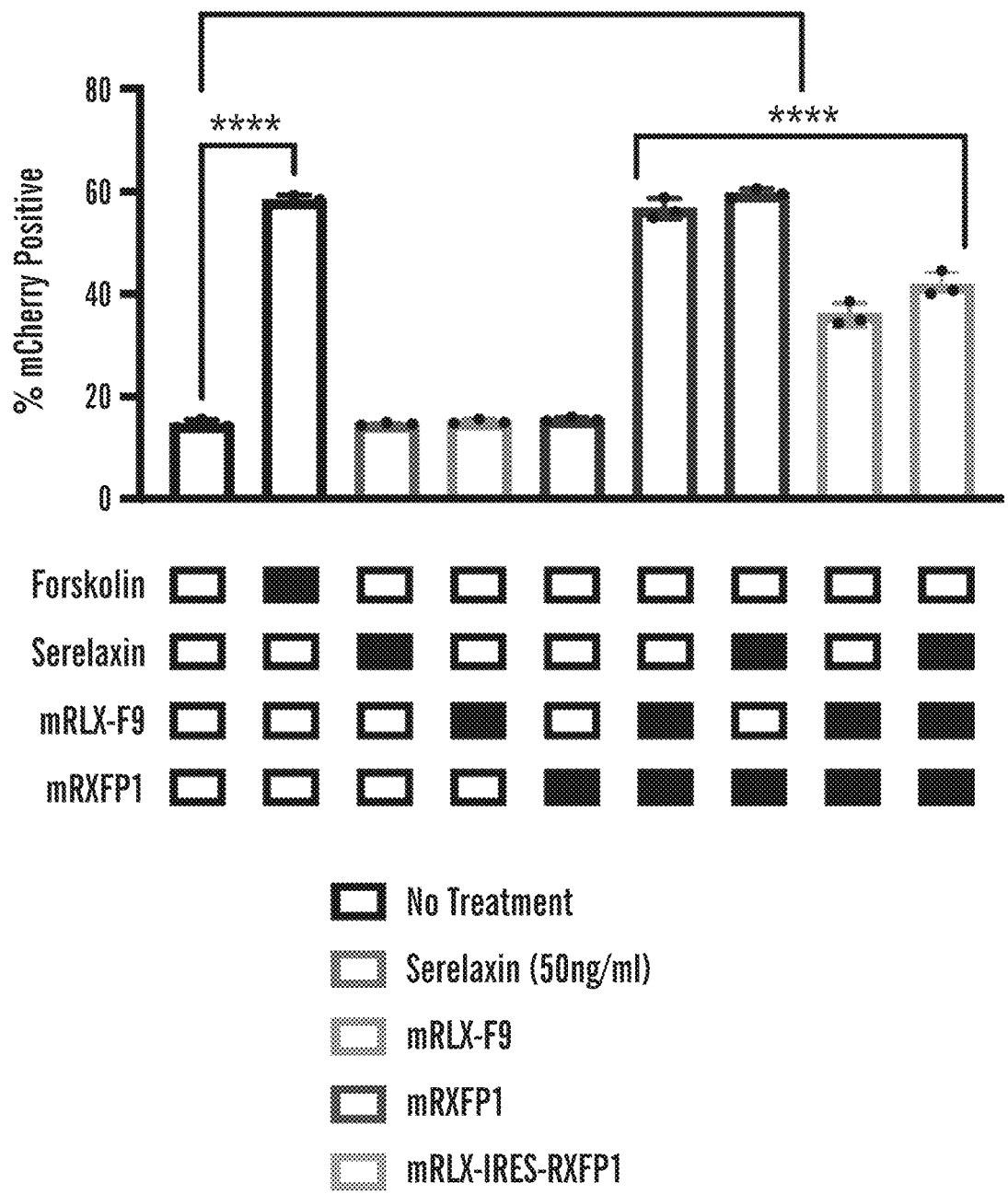
Figure 6C:
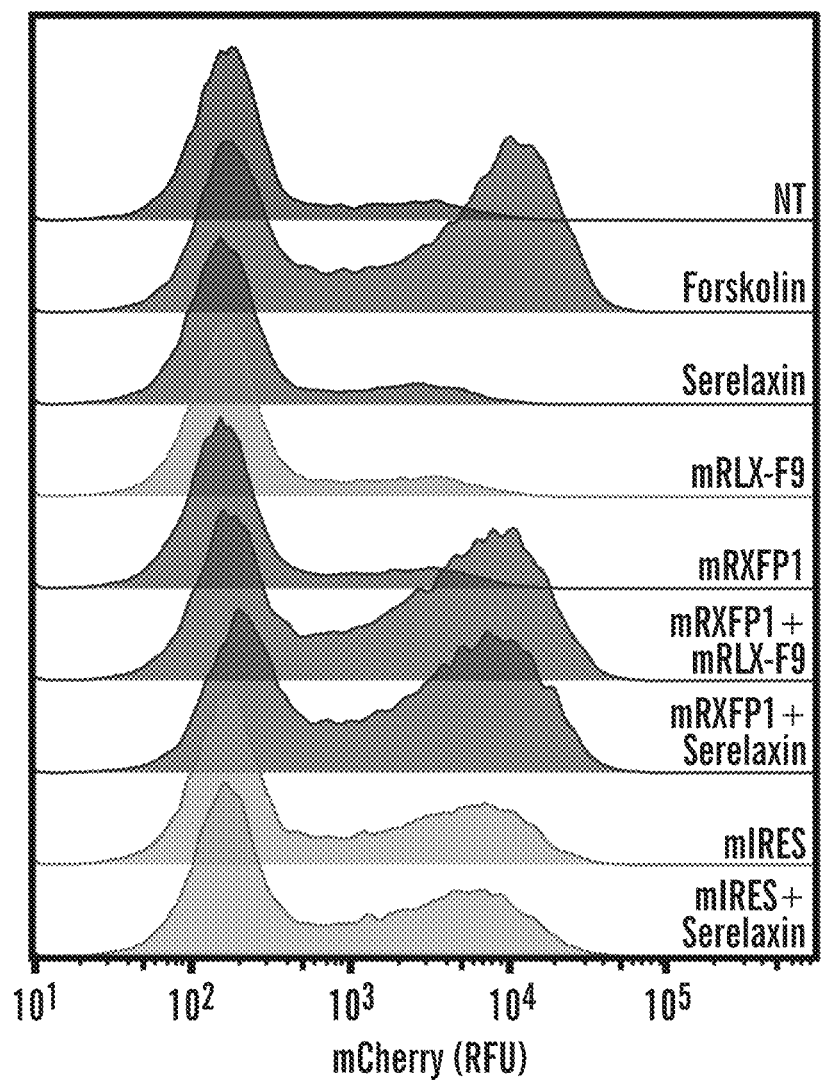
Figure 6D:
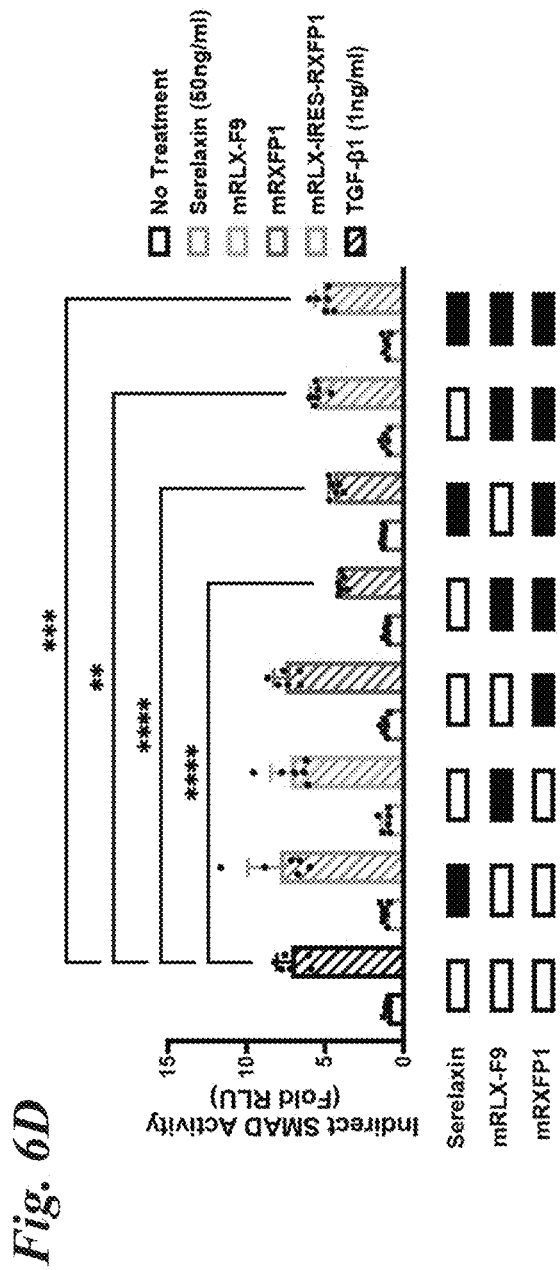

FIGS. 6A-6D show auto-activation of anti-fibrotic biotherapeutic circuit. FIG. 6A) Fold-increase in mRLX signaling as measured by cAMP activity and bioluminescence output from HEK-CRE-GLuc cells. FIG. 6B) Flow cytometry quantification and FIG. 6C) representative histograms of mRLX-treated HEK-CRE-mCherry cells. All forskolin conditions treated at 10M. FIG. 6D) Fold-decrease in SMAD activity, measured by bioluminescence output from HEK-SMAD-GLuc with and without fibrotic stimulus. All fold-change or positive expression gating relative to untreated control. Filled black boxes denote addition of indicated compound. Statistical significance determined by ANOVA, using the Dunnett method to control for multiple comparisons. Error bars denote standard deviation of biological replicates.  $p<0.005$, * $p<0.001$, **** $p<0.0001$.

FIGS. 7A and 7B show anti-inflammatory and anti-osteoarthritic circuit characterization. FIG. 7A) Fold-increase in IL-10 signaling, determined by STAT3-driven bioluminescent output from HEK-STAT3-GLuc cells. FIG. 7B) Fold-increase in IGF-1 signaling after treatment with anti-osteoarthritic circuit. Fold change relative to untreated control. Filled black boxes denote addition of indicated compound. Statistical significance determined by ANOVA, using the Dunnett method to control for multiple comparisons. Error bars denote standard deviation of biological replicates. **** $p<0.0001$.

Figure 8A:
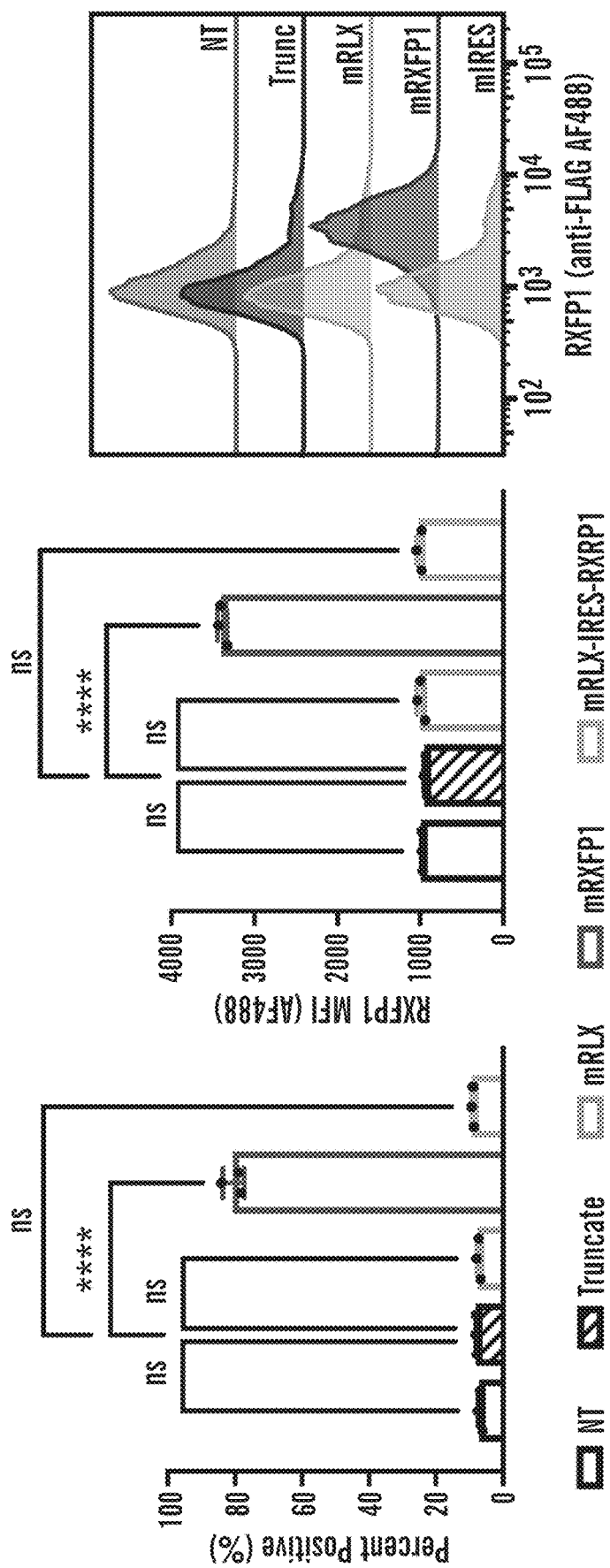
Figure 8B:
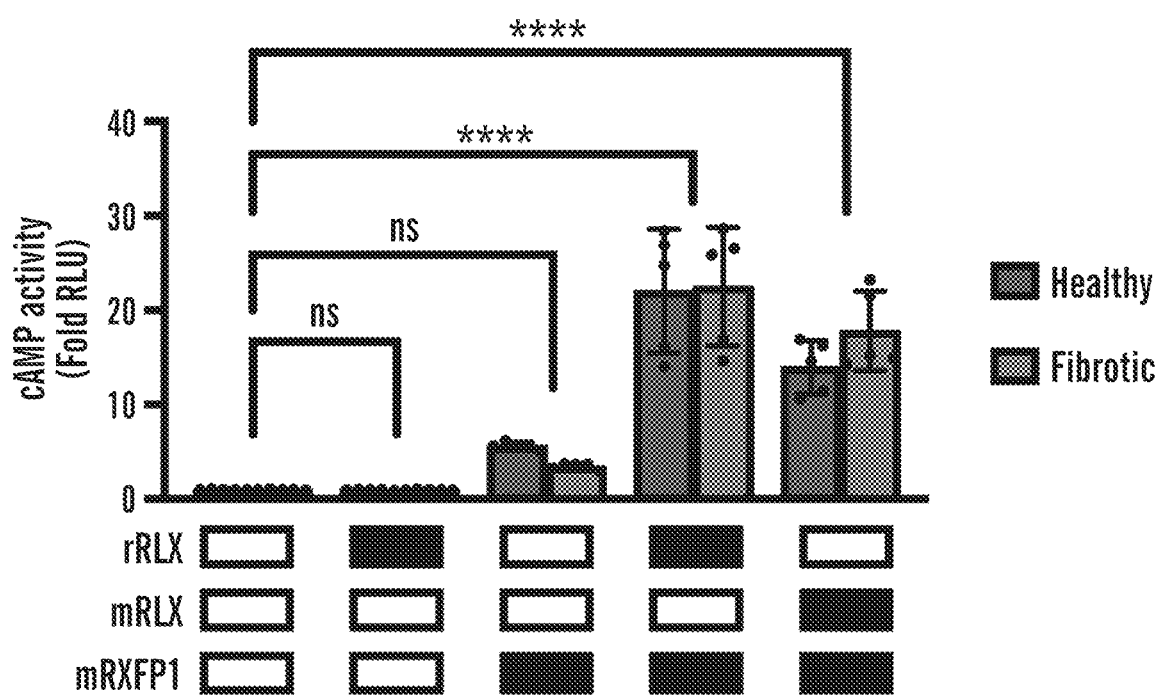

FIGS. 8A and 8B show expression and efficacy of anti-fibrotic circuit in clinically relevant tissue. FIG. 8A) mRXFP1 expression in hFLS. Quantification of percent positive expression (left), media fluorescent intensity (middle) and representative histogram (right) after mRLX-mRXFP1 electroporation. FIG. 8B) Relative intracellular cAMP content of hFLS after biotherapeutic circuit treatment in both a fibrosis-induced and healthy state. Relative expression and gating compared to untreated control. Filled black boxes denote addition of indicated compound. Statistical significance determined by ANOVA, using the Dunnett method to control for multiple comparisons. Error bars denotes standard deviation of biological replicates. **** $p<0.0001$.

Figure 9A:
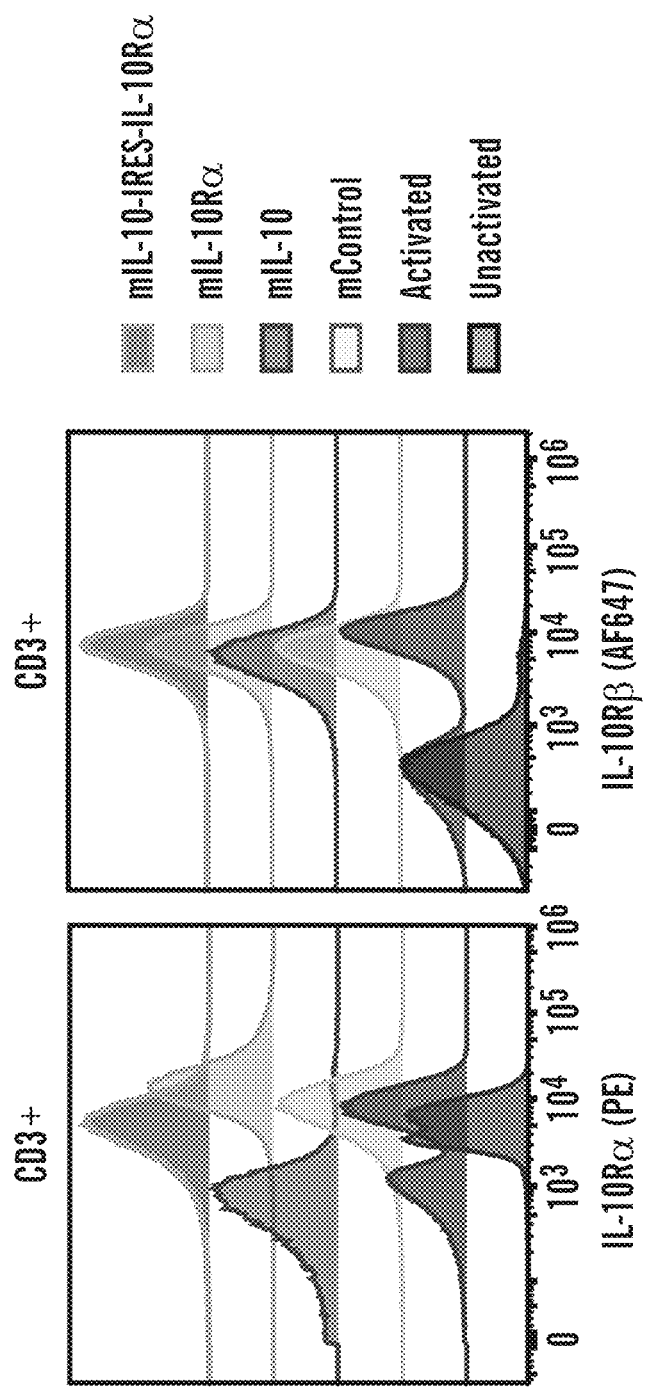
Figure 9B:
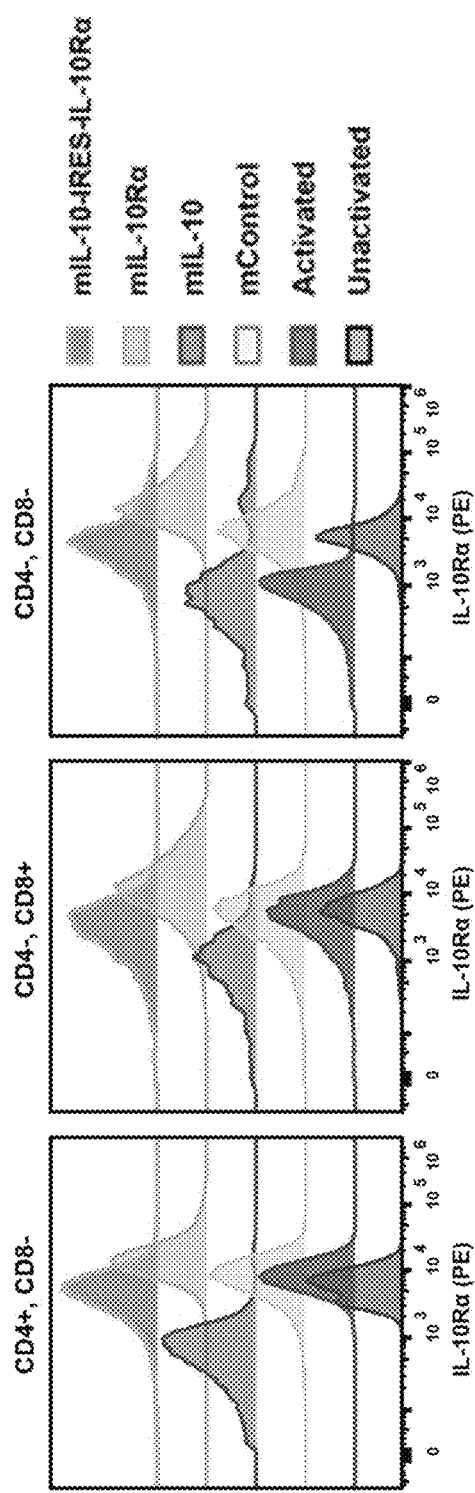
Figure 9C:
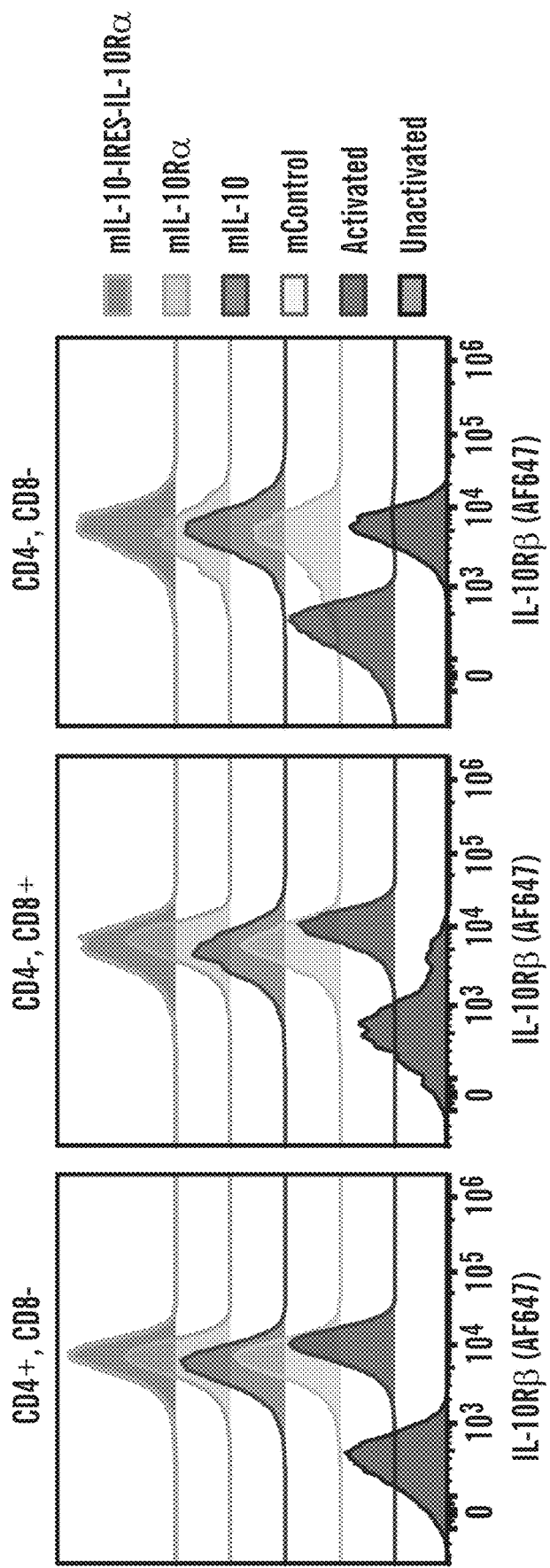

FIGS. 9A-9C show characterization of the mIL-10-mIL-10Rα circuit in immune-stimulated primary lymphocytes. FIG. 9A) IL-10Rα and IL-10Rβ expression profile of CD3+ T cells measured via flow cytometry FIG. 9B) IL-10Rα and FIG. 9C) IL-10Rβ after immunophenotyping of CD4+ and CD8+ populations with and without mIL-10-mIL-10Rα biotherapeutic circuit. All activated cells stimulated for 4 days. Unactivated control rested throughout study. mRNA introduced via electroporation.

Figure 10A:
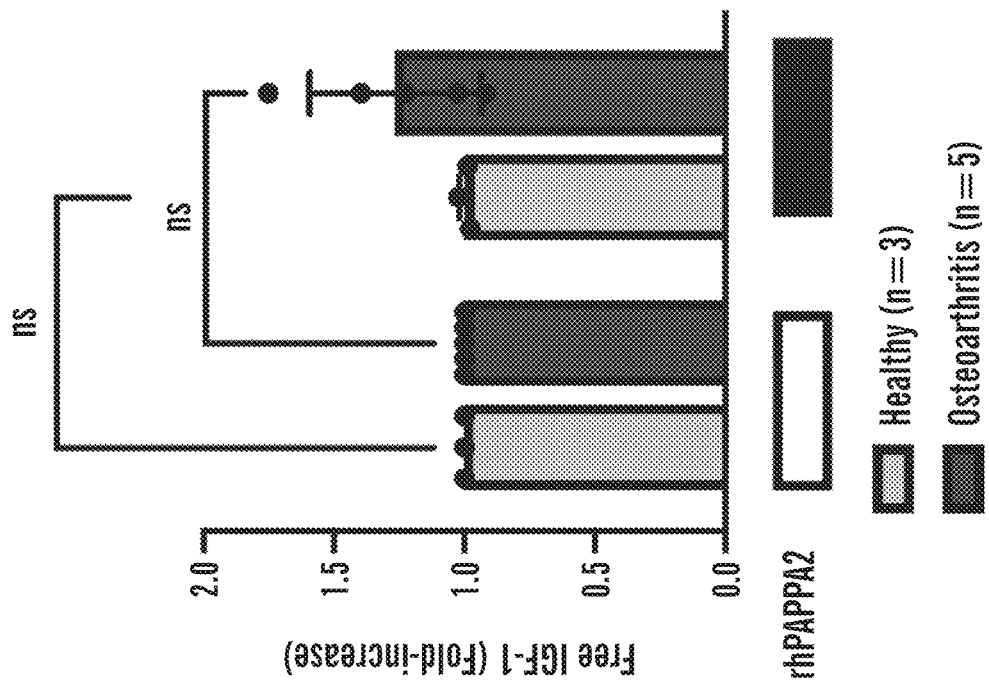

FIGS. 10A-10D show efficacy of IGF-1 biotherapeutic circuit in clinical samples and 3D cartilage models. FIG. 10A) Intact IGFBP-3 and FIG. 10B) Free IGF-1 concentrations in synovial fluid from osteoarthritis patients (n=5), compared to synovial fluid from healthy cadaveric donors (n=3), before and after treatment with PAPPA2 from conditioned media. Concentration determined by sandwich ELISA. FIG. 10C) Glycosaminoglycan content of primary bovine chondrocytes embedded in agarose constructs. 3D constructs were cultured for 45 days in insulin-free conditions treated with conditioned media containing respective treatments. GAG content normalized to total construct DNA content to account for altered cell density or proliferation during long-term culture. FIG. 10D) Equilibrium modulus of 3D construct. Filled black boxes denote addition of indicated compound. Error bars indicate standard deviation of biological replicates. Statistical significance determined by ANOVA, using the Dunnett method to control for multiple comparisons. * p<0.05,  p<0.005, * p<0.001, **** p<0.0001.

FIGS. 11A-11D show screening a library of ionizable lipids in synovial tissue. mRNA encoding a fluorescent reporter was encapsulated into lipid nanoparticles formulated from a library of ionizable lipids. LNP composition (i.e., lipid molar ratio and RNA N:P ratio) was maintained for all formulations. Transfection efficiency of FIG. 11A) DSPC and FIG. 11B) DOPE containing LNPs compared to no treatment control. Relative cell viability of FIG. 11C) DSPC and FIG. 11D) DOPE LNPs determined by FSC/SSC gating.

FIG. 12 shows disease-state specific regulation of an exemplary ligand target in human fibroblast like synoviocytes. Effect of TGF-I31 (orange) treatment on RXFP1 mRNA gene expression level as assessed by qPCR. * p<0.05, ** p<0.005.

FIGS. 13A ans 13B show disease state specific regulation of an exemplary ligand target in healthy and scleroderma human dermal fibroblasts. (FIG. 13A) RXFP1 gene expression in isolated dermal fibroblasts from healthy patients and patients with scleroderma, as assessed by qPCR. ΔΔCT calculation performed relative to cells from healthy patient N15-25. (FIG. 13B) RXFP1 gene expression as a function of TGF-I31 treatment in healthy human dermal fibroblasts. ΔΔCT calculation performed relative to no treatment condition. * p<0.05,  p<0.005, * p<0.0005, **** p<0.0001

Figure 14:
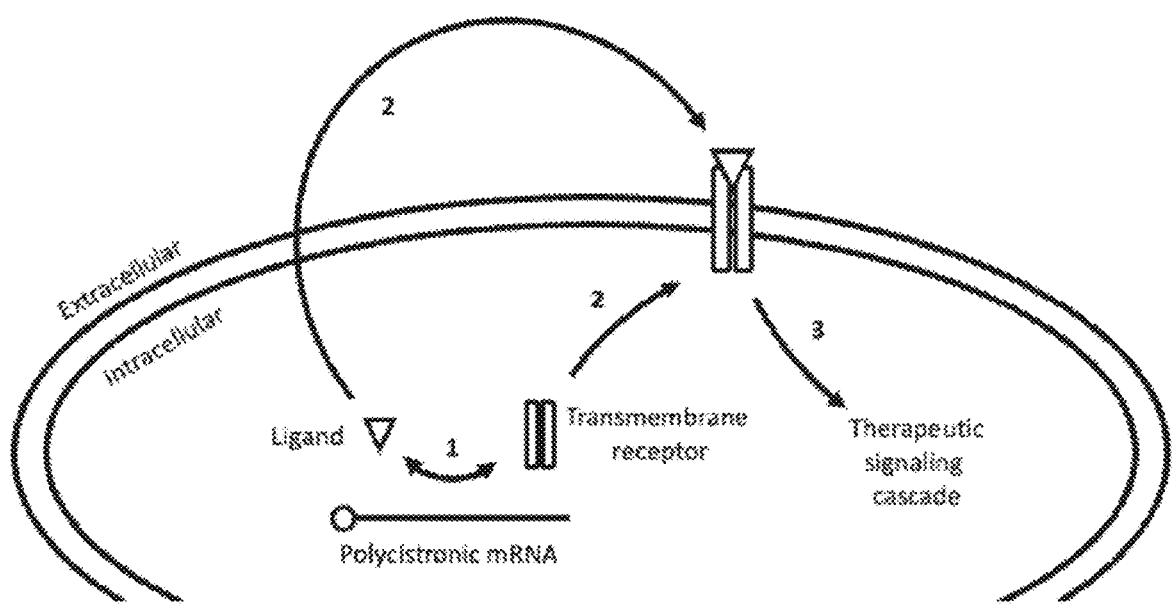

FIG. 14 is a diagram of polycistronic mRNA for synthetic auto- and paracrine signaling. This diagram depicts a cell with polycistronic mRNA introduced into the cytoplasm. The polycistronic mRNA produces both transmembrane receptors and their cognate ligand. The receptor is shuttled into the cell membrane and the ligand is secreted into the extracellular matrix. The ligand then binds receptors on the same cell it was produced by (autocrine) or on nearby cells (paracrine) to initiate the intended therapeutic signaling cascade. (1) mRNA translation. (2) protein shuttling with the ligand secreted to the extracellular space and the receptor expressed in the cell membrane. (3) secreted ligand binding the expressed receptor and initiating downstream signaling.

Figure 15:
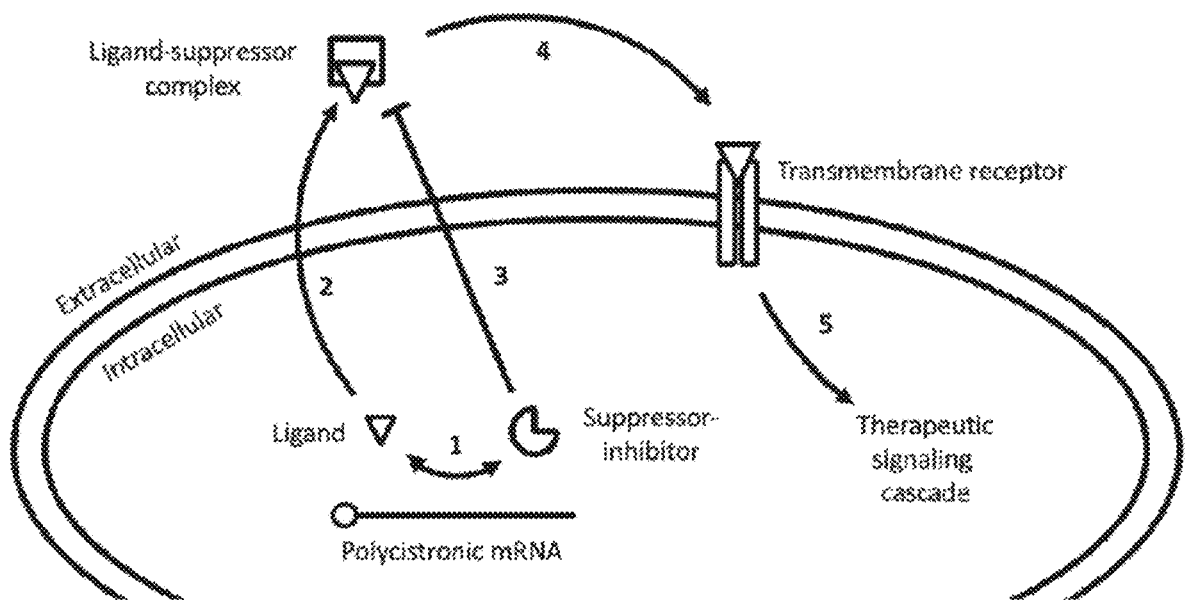

FIG. 15 is a diagram of polycistronic mRNA for synthetic potentiation of auto- and paracrine signaling. This diagram depicts a cell with polycistronic mRNA introduced into the cytoplasm that produces both a ligand and an inhibitor of a suppressor of said ligand. Both are produced and secreted into the extracellular matrix. Suppressor binding or action on the ligand is inhibited by the presence of the suppressor inhibitor. The ligand then binds its receptors on the same cell it was produced by (autocrine) or on nearby cells (paracrine) to initiate the intended therapeutic signaling cascade. (1) mRNA translation. (2) ligand secretion and suppression by a ligand-suppressor. (3) secreted suppressor inhibitor prevents ligand suppression. (4) ligand binding its cognate receptor and initiating favorable downstream signaling.

Figure 16:
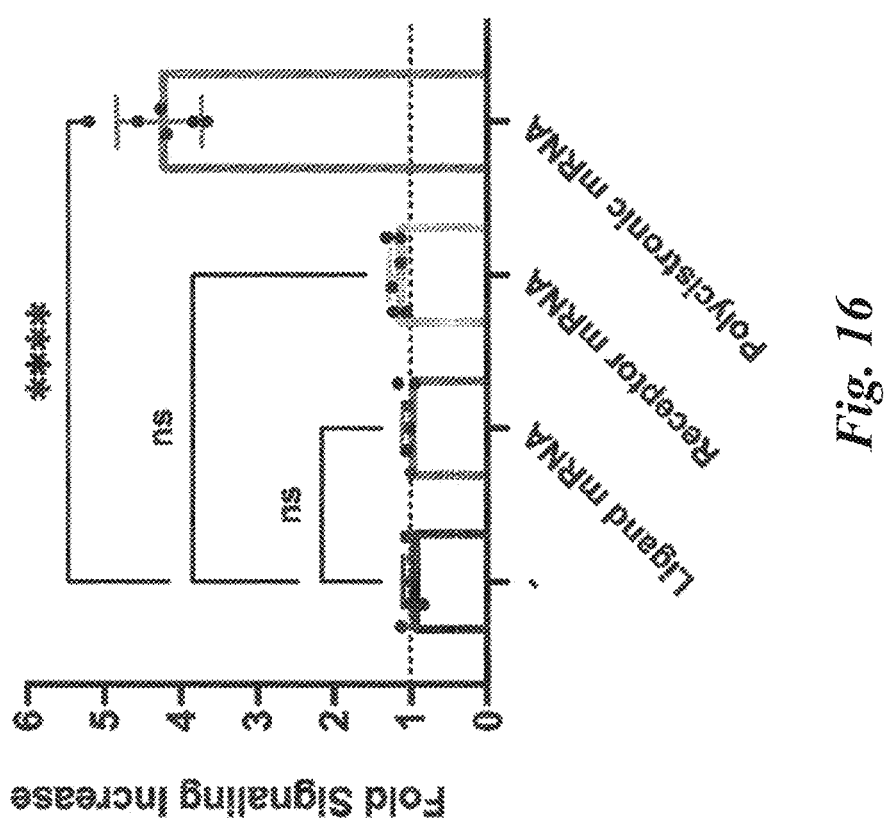

FIG. 16 demonstrates the enhanced signaling capabilities of polycistronic mRNA encoding both a receptor and its cognate ligand. Fold-increase in signaling from untreated, healthy cells demonstrates that monocistronic mRNA does not encode for a complete signaling circuit, but that the delivery of polycistronic mRNA allows for auto-induction of a targeted signaling circuit. The signal is determined by measuring RLU of gaussian luciferase produced in response to activation of the signaling circuit and secreted into culture media 24 hours after treatment.

DETAILED DESCRIPTION

Descriptions of the present invention are not intended to detail each disclosed embodiment or every implementation of the present invention. The description and examples that follow exemplify illustrative embodiments. In several places throughout the application, guidance is provided through lists of examples, which can be used in various combinations. In each instance, the recited list serves only as a representative group and should not be interpreted as an exclusive list.

The technology described herein relates to methods and compositions for generation of partial or complete cellular signaling pathways from exogenous polynucleotides. Wherein one or more signaling pathways, which involve at least one receptor and one ligand, are simultaneously initiated from a single exogenous polynucleotide.

Disclosed herein are methods and compositions for the potentiation of ligand targets to magnify the efficacy of administered corresponding ligands. The technology disclosed herein allows for overcoming previous clinical failures resulting from lack of efficacy by increasing the relative impact of a given ligand dose. Advantageously, it also allows for use of a ligand in a disease state where the target is at concentrations too low to allow for activity. Additionally, and more generally, the technology disclosed herein increases the efficacy of a ligand without necessitating an increased dose.

Nucleic Acids

Described herein are nucleic acids for use in activating a signaling pathway and/or treating a disease or disorder in a subject. In one aspect provided herein is a nucleic acid combination comprising: a first nucleic acid molecule encoding a ligand and a second nucleic acid molecule encoding a target molecule. Generally, the target is a cognate receptor of the ligand or an inhibitor of a suppressor of the ligand. In some embodiments, the first and second nucleic acid molecules are covalently linked to each other, i.e., form a polycistronic nucleic acid and both the ligand and target molecule are expressed from the same nucleic acid. Accordingly, in another aspect described herein is a nucleic acid encoding: a ligandand a target molecule.

It is noted that the ligand and the target molecule can be translated independently in a cap-dependnet (e.g., requires "cap" (i.e., a 7-methylguanylate added to the unaltered 5' end of an RNA molecule) bound to the 5'-end of the nucleic acid to initiate translation via interactions between the cap and initiation factors) or cap-independnet (e.g., via use of internal ribosome entry site (IRES)) manner. Accordingly, in some embodiments, a nucleic acid described herein comprise a cap at its 5'end. In some embodiments, a nucleic acid comprises an internal ribosome entry site.

In some embodiments, at least one of the ligand and the target molecule is translated via a cap-dependent manner and the other of the ligand and the target molecule is translated via a cap-independent manner. For example, the ligand is translated via a cap-dependent manner. In another example, the target molecule is translated via a cap-independent manner. In some embodinents, the ligand is translated via a cap-dependent manner and the target molecule is translated via a cap-independent manner.

In some embodiments, both the ligand and the target molecule are translated via a cap-dependent manner. In some other embodimets, both the ligand and the target molecule are translated via a cap-independent manner. In one embodiment, the first and/or second nucleic acid is comprised in a plasmid.

In one embodiment, the first nucleic acid molecule is comprised in a first plasmid and the second nucleic acid molecule is comprises in a second plasmid.

In one embodiment, the first nucleic acid molecule is comprised in a first plasmid and the second nucleic acid molecule is comprises in a plasmid vector.

In one embodiment, the first and second nucleic acid molecules are comprised in the same vector.

In one embodiment, the first and second nucleic acid molecules are comprised in the same plasmid.

In one embodiment, the nucleic acid further comprises an RNA replicon. As used herein, the term "RNA replicon" refers to RNA which contains all of the genetic information required for directing its own amplification or self-replication within a permissive cell. For example, an "RNA replicon" is a RNA molecule that can be replicated by RNA-dependent RNA polymerase, yielding-without DNA intermediate-one or multiple identical or essentially identical copies of the RNA replicon. A skilled person in the art can identify an RNA replicon suitable for the present invention.

In one embodiment, the first nucleic acid molecule further encodes the RNA replicon.

In one embodiment, the second nucleic acid molecule further encodes the RNA replicon.

In one embodiment, the first and second nucleic acid molecules are comprised in the same vector.

In some embodiments, a nucleic acid described herein is an mRNA. Generally, the mRNA comprises (i) a 5%-cap structure; (ii) a 5'UTR; (iii) an open reading frame (ORF) encoding the ligand and/or the target molecule; (iv) a 3'-UTR; and (v) a poly-A region. In some embodiments, at least one uridine in the ORF is modified. For example, from 70% to 100% of the uridines in the ORF are modified.

Also provided herein is a composition, cell, plasmid or vector comprising any of the nucleic acids described herein. In one embodiment, the composition further comprises a pharmaceutically acceptable carrier.

Further provided herein is a composition comprising any of the cells, plasmids, or vectors comprising any of the nucleic acids described herein. In one embodiment, the composition further comprises a pharmaceutically acceptable carrier.

Further provided herein is a cell comprising any of the plasmids or vectors comprising any of the nucleic acids described herein.

Ligand

Embodiments of the various aspects described herein include a ligand. A ligand can be a protein, a protein fragment, a fusion protein, an amino acid or a derivative thereof, a steroid, a fatty acid or a lipid. A skilled person in the art will be able to identify a ligand for use in the nucleic acids as described herein.

In one embodiment, the ligand is a cytokine. Exemplary cytokines include, but are not limited to, the group consisting of interleukin-1α (IL-1α), interleukin-1/3 (IL-1/3), interleukin-2 (IL-2), interleukin-4 (IL-4), interleukin-5 (IL-5), interleukin-6 (IL-6), interleukin-7 (IL-7), interleukin-8 (IL-8/CXCL8), interleukin-10 (IL-10), interleukin-12 (IL-12), interleukin-13 (IL-13), interleukin-15 (IL-15), interleukin-17 (IL-17), interleukin-18 (IL-18), tumor necrosis factor-α (TNF-α), interferon-α (INF-α), interferon-b (INF-b), interferon-γ (INF-γ), granulocyte-monocyte colony stimulating factor (GM-CSF), granulocyte colony stimulating factor (G-CSF), monocyte chemoattractant protein-1 (MCP-1/CCL2), macrophage inflammatory protein 1-ct (MCP-1/CCL3), macrophage inflammatory protein-1/3, RANTES (CCL5), Eotaxin (CCL11), variable endothelial growth factor (VEGF), endotheial growth factor (EGF), and fibroblast growth factor (FGF).

In one embodiment, the the ligand is an interleukin. Exemplary interleukins include but are not limited to IL-1α, IL-1J3, IL-2, IL-3, IL-4, IL-5, IL-6, IL-7, IL-8, IL-9, IL-10, IL-11, IL-12A, IL-12B, IL-13, IL-15, IL-16, IL-17A, IL-17B, IL-17C, IL-17F, IL-18, IL-19, IL-20, IL-21, IL-22, IL-23, IL-24, IL-25, IL-26, IL-27, IL-28A, IL-28B, IL-29, IL-31, IL-33, IL-34, IL-36A, IL-36B, IL-36G, IL-37, and IL-38.

In one embodiment, the ligand is a chemokine. Exemplary chemokines include but are not limited to CCL14, CCL19, CCL20, CCL21, CCL25, CCL27, CXCL12, CXCL13, CXCL-8, CCL2, CCL3, CCL4, CCL5, CCL11, and CXCL10.

In one embodiment. In one embodiment, the ligand is the ligand is interleukin-1α (IL-1α). In one embodiment, the ligand is IL-1/3. In one embodiment, the ligand is IL-2. In one embodiment, the ligand is IL-4. In one embodiment, the ligand is IL-5. In one embodiment, the ligand is IL-6. In one embodiment, the ligand is IL-7. In one embodiment, the ligand is IL-8/CXCL8. In one embodiment, the ligand is IL-10. In one embodiment, the ligand is IL-12. In one embodiment, the ligand is IL-13. In one embodiment, the ligand is IL-15. In one embodiment, the ligand is IL-17. In one embodiment, the ligand is IL-18. In one embodiment, the ligand is TNF-α). In one embodiment, the ligand is interferon-α (INF-α. In one embodiment, the ligand is INF-b. In one embodiment, the ligand is INF-γ. In one embodiment, the ligand is GM-CSF. In one embodiment, the ligand is G-CSF. In one embodiment, the ligand is MCP-1/CCL2. In one embodiment, the ligand MCP-1/CCL3. In one embodiment, the ligand is macrophage inflammatory protein-1/3. In one embodiment, the ligand is CCL5. In one embodiment, the ligand is CCL11. In one embodiment, the ligand is variable VEGF). In one embodiment, the ligand is EGF. In one embodiment, the ligand is FGF.

In one embodiment, the ligand is a hormone. Exemplary hormones include but are not limited to insulin-like growth factor (or somatomedin), adrenaline (or epinephrine), melatonin, noradrenaline (or norepinephrine), triiodothyronine, thyroxine, dopamine, prostaglandins, leukotrienes, prostacyclin, thromboxane, amylin (or islet amyloid polypeptide), anti-mullerian hormone (or mullerian-inhibiting factor/hormone), adiponectin, adrenocorticotropic hormone (or corticotropin), angiotensinogen, angiotensin, antidiuretic hormone (or vasopressin, arginine vasopressin), atrial natriuretic peptide (or atriopeptin), brain natriuretic peptide, calcitonin, cholecystokinin, corticotropin-releasing hormone, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, growth hormone-releasing hormone, hepcidin, human chorionic gonadotropin, human placental lactogen, growth hormone, inhibin, insulin, leptin, lipotropin, luteinizing hormone, melanocyte stimulating hormone, motilin, orexin, osteocalcin, oxytocin (or pitocin), pancreatic polypeptide, parathyroid hormone, pituitary adenylate cyclase-activating peptide, prolactin (or leuteotropic hormone), prolactin-releasing hormone, relaxin, renin, secretin, somatostatin (or growth hormone-inhibiting hormone or growth hormone release-inhibiting hormone or somatotropin release-inhibiting factor or somatotropin release-inhibiting hormone), thrombopoietin, thyroid-stimulating hormone (or thyrotropin), thyrotropin-releasing hormone, vasoactive intestinal peptide, guanylin, uroguanylin, testosterone, dehydroepiandrosterone, androstenedione, dihydrotestosterone, aldosterone, estradiol, estrone, estriol, cortisol, progesterone, calcitriol, and calcidiol.

In one embodiment, the ligand is insulin-like growth factor (or somatomedin). In one embodiment, the ligand is adrenaline (or epinephrine). In one embodiment, the ligand is melatonin. In one embodiment, the ligand is noradrenaline (or norepinephrine). In one embodiment, the ligand is triiodothyronine. In one embodiment, the ligand is thyroxine. In one embodiment, the ligand is dopamine. In one embodiment, the ligand is prostaglandins. In one embodiment, the ligand is leukotrienes. In one embodiment, the ligand is prostacyclin. In one embodiment, the ligand is thromboxane. In one embodiment, the ligand is amylin (or islet amyloid polypeptide). In one embodiment, the ligand is anti-müllerian hormone (or müllerian-inhibiting factor/hormone). In one embodiment, the ligand is adiponectin. In one embodiment, the ligand is adrenocorticotropic hormone (or corticotropin). In one embodiment, the ligand is angiotensinogen. In one embodiment, the ligand is angiotensin. In one embodiment, the ligand is antidiuretic hormone (or vasopressin. In one embodiment, the ligand is arginine vasopressin). In one embodiment, the ligand is atrial natriuretic peptide (or atriopeptin). In one embodiment, the ligand is brain natriuretic peptide. In one embodiment, the ligand is calcitonin. In one embodiment, the ligand is cholecystokinin. In one embodiment, the ligand is corticotropin-releasing hormone. In one embodiment, the ligand is cortistatin. In one embodiment, the ligand is enkephalin. In one embodiment, the ligand is endothelin. In one embodiment, the ligand is erythropoietin. In one embodiment, the ligand is follicle-stimulating hormone. In one embodiment, the ligand is galanin. In one embodiment, the ligand is gastric inhibitory polypeptide. In one embodiment, the ligand is gastrin. In one embodiment, the ligand is ghrelin. In one embodiment, the ligand is glucagon. In one embodiment, the ligand is glucagon-like peptide-1. In one embodiment, the ligand is gonadotropin-releasing hormone. In one embodiment, the ligand is growth hormone-releasing hormone. In one embodiment, the ligand is hepcidin. In one embodiment, the ligand is human chorionic gonadotropin. In one embodiment, the ligand is human placental lactogen. In one embodiment, the ligand is growth hormone. In one embodiment, the ligand is inhibin. In one embodiment, the ligand is insulin. In one embodiment, the ligand is leptin. In one embodiment, the ligand is lipotropin. In one embodiment, the ligand is luteinizing hormone. In one embodiment, the ligand is melanocyte stimulating hormone. In one embodiment, the ligand is motilin. In one embodiment, the ligand is orexin. In one embodiment, the ligand is osteocalcin. In one embodiment, the ligand is oxytocin (or pitocin). In one embodiment, the ligand is pancreatic polypeptide. In one embodiment, the ligand is parathyroid hormone. In one embodiment, the ligand is pituitary adenylate cyclase-activating peptide. In one embodiment, the ligand is prolactin (or leuteotropic hormone). In one embodiment, the ligand is prolactin-releasing hormone. In one embodiment, the ligand is relaxin. In one embodiment, the ligand is renin. In one embodiment, the ligand is secretin. In one embodiment, the ligand is somatostatin (or growth hormone-inhibiting hormone or growth hormone release-inhibiting hormone or somatotropin release-inhibiting factor or somatotropin release-inhibiting hormone). In one embodiment, the ligand is thrombopoietin. In one embodiment, the ligand is thyroid-stimulating hormone (or thyrotropin). In one embodiment, the ligand is thyrotropin-releasing hormone. In one embodiment, the ligand is vasoactive intestinal peptide. In one embodiment, the ligand is guanylin. In one embodiment, the ligand is uroguanylin. In one embodiment, the ligand is testosterone. In one embodiment, the ligand is dehydroepiandrosterone. In one embodiment, the ligand is androstenedione. In one embodiment, the ligand is dihydrotestosterone. In one embodiment, the ligand is aldosterone. In one embodiment, the ligand is estradiol. In one embodiment, the ligand is estrone. In one embodiment, the ligand is estriol. In one embodiment, the ligand is cortisol. In one embodiment, the ligand is progesterone. In one embodiment, the ligand is calcitriol. In one embodiment, the ligand is calcidiol.

In one embodiment, the ligand is relaxin. In one embodiment, the the ligand is relaxin-2 or variant thereof. The term "relaxin" as used herein, refers to a polypeptide belonging to the relaxin family (e.g., relaxin-2), a relaxin analog (e.g., a polypeptide that binds to a relaxin receptor), or a fragment (e.g., a bioactive fragment) or variant of any of the foregoing and/or any agent that is an agonist of an agent that binds the relaxin receptor family of proteins (RXFP1, RXFP2, RXFP3, RXFP4).

Relaxin is an approximately 6-kDa protein belonging to the insulin superfamily (Sherwood O. D., Endocr. Rev. 2004, 25(2):205-34). Like insulin, relaxin is processed from a prepro-form to the mature hormone, containing A and B peptide chains connected by two interchain disulfide bridges and one intrachain disulfide within the A chain (Chan L. J. et al., Protein Pept. Lett. 2011, 18(3):220-9). Relaxin readily decreases collagen secretion and increases collagen degradation by increasing the expression of MMPs and decreasing the expression of TIMPs (Samuel C. S. et al., Cell Mol. Life Sci. 2007, 64(12):1539-57). This hormone is involved in reproduction, where it inhibits uterine contraction and induces growth and softening of the cervix to assist child delivery (Parry L. J. et al., Adv. Exp. Med. Biol. 2007, 612:34-48). Recently, a highly purified recombinant form of H2 relaxin, or human relaxin-2, has been tested in a number of in vitro and in vivo systems to evaluate both its ability to modify connective tissue and its potential antifibrotic properties. Several studies report that relaxin-2 acts at multiple levels to inhibit fibrogenesis and collagen overexpression associated with fibrosis and is able to prevent and treat pulmonary, renal, cardiac, and hepatic fibrosis (Bennett R. G., Transl. Res. 2009, 154(1):1-6). Relaxin treatment of human fibroblasts caused a reduction in levels of collagen types I and III and fibronectin (Unemori E. N. et al., The Journal of Clinical Investigation 1996, 98(12):2739-45). In vivo, relaxin-2 decreased collagen build-up in the lung induced by bleomycin and improved the overall amount of fibrosis (Unemori E. N. et al., The Journal of Clinical Investigation 1996, 98(12):2739-45). In cultured renal fibroblasts, epithelial cells and mesangial cells, relaxin-2 decreased TGF-β-induced fibronectin levels and increased fibronectin degradation (McDonald G. A. et al., American Journal of Physiology Renal Physiology 2003, 285(1):F59-67). Relaxin-2 has been shown to have a rapid pharmacokinetic profile. Previous clinical trials investigating relaxin-2 as a treatment for scleroderma, acute heart failure, and for the induction of labor through cervical ripening, utilized continuous infusion of relaxin-2 via either intravenous adminstration or subcutaneous administration through a minipump. Efficacy of relaxin-2 requires activation of a transmembrane relaxin receptor for downstream signalling. Previous clinical trials utilized continuous infusion in an attempt to overcome pharmacokinetic limitations. The localized, sustained release of relaxin-2 achieves sustained receptor activation without necessitating continuous administration.

Unless specified to the contrary, the term "relaxin" as used herein encompasses a relaxin or an analog, a fragment (e.g., a bioactive fragment) or a variant thereof. The term "relaxin or an analog, a fragment or a variant thereof" encompasses any member of the relaxin-like peptide family which belongs to the insulin superfamily. The relaxin-like peptide family includes relaxin-like (RLN) peptides, e.g., relaxin-1 (RLN1), relaxin-2 (RLN2) and relaxin-3 (RLN3), and the insulin-like (INSL) peptides, e.g., INSL3, INSL4, INSL5 and INSL6. Representative sequences of human RLN1 are listed herein as SEQ ID NOS: 4-7; representative sequences of human RLN2 are listed herein as SEQ ID NOS: 1-3; representative sequences of human RLN3 are listed herein as SEQ ID NOS: 8-10; a representative sequence of human INSL3 is listed herein as SEQ ID NO: 11; representative sequences of human INSL4 are listed herein as SEQ ID NOS: 12-13; representative sequences of human INSL5 are listed herein as SEQ ID NOS. 14-15; and a representative sequence of human INSL6 is listed herein as SEQ ID NO: 16. In some embodiments, the term "relaxin or an analog, a fragment or a variant thereof may encompass any polypeptide having at least 70%, e.g., at least 75%, at least 80%, at least 85%, at least 90%, at least 95%, 96%, 97%, 98% or at least 99% sequence identity with any of SEQ ID NOS: 1-16, as well as any polypeptide sequence that comprises any of SEQ ID NOS: 1-16. In one embodiment of the invention, the relaxin includes RLN1, RLN2 or RLN3. In one embodiment, the relaxin is relaxin-1. In another embodiment, the relaxin is relaxin-3. In a preferred embodiment, the relaxin is relaxin-2. In another embodiment of the invention, the relaxin includes INSL3, INSL4, INSL5 or INSL6. In one embodiment, the relaxin is INSL3. In one embodiment, the relaxin is INSL4. In one embodiment, the relaxin is INSL5. In one embodiment, the relaxin is INSL6.

In some embodiments, the term relaxin encompasses any natural, synthetic, or semi-synthetic composition that is capable of interacting with a relaxin family protein receptors (RXFP1, RXFP2, RXFP3, RXPF4) that impacts the form, function, or activity of the receptor. These compounds include but are not limited to native relaxin-2, relaxin-2 variants, polypeptides, DNA or RNA polynucleotides, small molecules, as well as any of the previously listed compounds conjugated to, or associated with, the relaxin-2 protein.

The term "relaxin or an analog, a fragment or a variant thereof" may also encompass any member the relaxin-like peptide family includes relaxin-like (RLN) peptides, e.g., relaxin-1 (RLN1), relaxin-2 (RLN2) and relaxin-3 (RLN3), and the insulin-like (INSL) peptides, e.g., INSL3, INSL4, INSL5 and INSL6. Representative sequences of human RLN1 are listed herein as SEQ ID NOS: 4-7; representative sequences of human RLN2 are listed herein as SEQ ID NOS: 1-3; representative sequences of human RLN3 are listed herein as SEQ ID NOS: 8-10; representative sequence of human INSL3 is listed herein as SEQ ID NO: 11; representative sequences of human INSL4 are listed herein as SEQ ID NOS: 12-13; representative sequences of human INSL5 are listed herein as SEQ ID NOS. 14-15; and representative sequence of human INSL6 is listed herein as SEQ ID NO: 16. The term "relaxin or an analog, a fragment or a variant thereof" also in some embodiments encompasses any polypeptide having at least 70%, e.g., at least 75%, at least 80%, at least 85%, at least 90%, at least 95% or at least 99% sequence identity with any of SEQ ID NOS: 1-16, as well as any polypeptide sequence that comprises any of SEQ ID NOS: 1-16. In one embodiment of the formulation, the relaxin includes RLN1, RLN2 or RLN3. In one embodiment, the relaxin is relaxin-2. In another embodiment, the relaxin includes INSL3, INSL4, NSL5 or INSL6.

The term "relaxin or an analog, a fragment or a variant thereof" also in some embodiments may encompass any mutant member of the relaxin-like peptide family. Such mutant may be, e.g., a RLN1, RLN2, RLN3, INSL3, INSL4, INSL5 or INSL6 comprising one or more mutations, e.g., substitutions, additions or deletions of one or more amino acids (native or non-native) in the known sequence of RLN1, RLN2, RLN3, INSL3, INSL4, INSL5 or INSL6. For example, a mutant member of the relaxin-like peptide family may comprise any naturally occurring or artificially produced variants of RLN1, RLN2, RLN3, INSL3, INSL4, INSL5 or INSL6.

The term "relaxin fragment" or "a fragment of relaxin" as used herein encompasses a fragment of a relaxin, i.e., a partial sequence of any member of the relaxin-like peptide family, that retains its ability to treat stiffened joints through interaction with the relaxin family receptors. Examples include those sequences described in European Patent Office Application No. EP1641824B1 (Relaxin superfamily peptide analogues), the entire contents of which are incorporated herein by reference.

The term "relaxin analog" or an "analog of relaxin" includes any non-relaxin polypeptide sequence that possesses the biological activity of relaxin, i.e., the ability to interact with the relaxin family receptors. In one embodiment, such polypeptide sequence may comprise prolactin or an analog, a fragment or a variant thereof. In another embodiment, such sequence may comprise the truncated B-chain analogue of relaxin known as B7-33, described in ACS Appl. Mater. Interfaces 2019, 11, 49, 45511-45519.

In some embodiments, the term agent or "relaxin analog" also includes a relaxin receptor agonist, e.g., any agent, such as a small molecule, a polypeptide, a polynucleotide or a polysaccharide, that can bind to and activate a relaxin receptor, e.g., one or more of RXFP1, RXFP2, RXFP3 and RXFP4. For example, a relaxin receptor agonist may be a polypeptide comprising the receptor binding site of relaxin. A relaxin receptor agonist may also be a polypeptide comprising any other sequence capable of binding to and activating the relaxin receptor, e.g., RXFP1, RXFP2, RXFP3 and RXFP4. Other examples include those agonists described in US Patent Application No. US20130237481A1 (Modified relaxin polypeptides and their uses), US Patent Application No. US20180222960A1 (Modified relaxin polypeptides comprising a pharmacokinetic enhancer and uses thereof), US Patent Application No. U.S. Pat. No. 8,445,635B2 (Modified H2 relaxin for tumor suppression), European Patent Office Application No. EP3067365A1 (Human relaxin analogue, pharmaceutical composition of same, and pharmaceutical application of same), and US Patent Application No. US20180222960A1 (Modified relaxin polypeptides comprising a pharmacokinetic enhancer and uses thereof) the entire contents of which are incorporated herein by reference.

The term "relaxin or an analog, a fragment or a variant thereof" includes any recombinantly produced relaxin, such as, e.g., Serelaxin (RLX030) developed by Novartis. Methods for producing recombinant relaxin, e.g., relaxin-2, are described, e.g., in U.S. Pat. No. 5,464,756, the entire contents of which are incorporated herein by reference. The recombinantly produced relaxin or analog, fragment or variant thereof may comprise a relaxin sequence, e.g., RLN1, RLN2, RLN3, INSL3, INSL4, INSL5 or INSL6, and a histidine (His) tag to aid in the purification of the relaxin after being recombinantly produced.

The relaxin or analog, fragment or variant thereof may also comprise one or more chemical modifications, e.g., chemical groups covalently attached to the relaxin or an analog, a fragment or a variant thereof. Such chemical groups may include, e.g., carbohydrates or other polymers, e.g., polyethylene glycol (PEG), e.g., polypeptide, e.g., one or more lipids (Design and Synthesis of Potent, Long-Acting Lipidated Relaxin-2 Analogs, Bioconjugate Chem. 2019, 30, 1, 83-89). Other examples include fragments or variants described in US Patent Application No. US2018/0326079 (NOVEL FATTY ACIDS AND THEIR USE IN CONJUGATION TO BIOMOLECULES), U.S. Pat. No. 9,931,372B2 (SYNTHETIC APELIN FATTYACID CONJUGATES WITH IMPROVED HALF-LIFE), the entire contents of which are incorporated herein by reference.

Target Molecule

In one embodiment, the target molecule is a cognate receptor of the ligand. As used herein, the term "cognate receptor" refers to any receptors that is typically bound by the ligand of interest. Stated in another way, a "cognate receptor" refers to any receptor with which the ligand preferentially interacts with under physiological conditions, or under in vitro conditions substantially approximating physiological conditions. The term "preferentially interacts" can be synonymous with "preferentially binding" and refer to an interaction that is statistically significantly greater in degree relative to a control. In other words, a "cognate receptor" is a receptor capable of selectively binding the ligand. One skilled in the art will be able to identify a cognat receptor of a given ligand using standard protocols.

In one embodiment, the target molecule is a transmembrane receptor. In one embodiment, the target molecule is a G protein-coupled receptor, a transmembrane tyrosine kinase receptor, a transmembrane chemokine receptor, a transmembrane ligand gated ion channel, a transporter, or a membrane-embedded protein.

In one embodiment, the target molecule is a cytokine or hormone receptor.

In one embodiment, the target molecule is an interleukin receptor. Exemplary interleukin receptors include but are not limited to IL-1R1, IL-1R2, IL-1RAP, IL-1RL2, IL-2RJ3, IL-2Rα, IL-2Rγ, IL-2γ, IL-3Rα, IL-4R, IL-5Rα, IL-6RJ3, IL-6Rα, IL-7Rα, IL-9R, IL-10RJ3, IL-10Rα, IL-11Rα, IL-12J32, IL-12RJ31, IL-12RJ32, IL-13Rα1, IL-13Rα2, IL-15Rα, IL-17RA, IL-17RB, IL-17RC, IL-17RC, IL-17RD, IL-17RE, IL-18R1, IL-18RAP, IL-18Rα, IL-20RJ3, IL-20Rα, IL-20Rα1, IL-21R, IL-22Rα1, IL-23R, IL-27Rα, IL-28RA, IL-31Rα, CD4, CD9, CXCR1, and CXCR2.

In one embodiment, the target molecule is the target molecule is IL-1R1. In one embodiment, the target molecule is IL-1R2. In one embodiment, the target molecule is IL-1RAP. In one embodiment, the target molecule is IL-1RL2. In one embodiment, the target molecule is IL-2RJ3. In one embodiment, the target molecule is IL-2Rα. In one embodiment, the target molecule is IL-2Rγ. In one embodiment, the target molecule is IL-2γ. In one embodiment, the target molecule is IL-3Rα. In one embodiment, the target molecule is IL-4R. In one embodiment, the target molecule is IL-5Rα. In one embodiment, the target molecule is IL-6RJ3. In one embodiment, the target molecule is IL-6Rα. In one embodiment, the target molecule is IL-7Rα. In one embodiment, the target molecule is IL-9R. In one embodiment, the target molecule is IL-10RJ3. In one embodiment, the target molecule is IL-10Rα. In one embodiment, the target molecule is IL-11Rα. In one embodiment, the target molecule is IL-12J32. In one embodiment, the target molecule is IL-12RJ31. In one embodiment, the target molecule is IL-12RJ32. In one embodiment, the target molecule is IL-13Rα1. In one embodiment, the target molecule is IL-13Rα2. In one embodiment, the target molecule is IL-15Rα. In one embodiment, the target molecule is IL-17RA. In one embodiment, the target molecule is IL-17RB. In one embodiment, the target molecule is IL-17RC. In one embodiment, the target molecule is IL-17RC. In one embodiment, the target molecule is IL-17RD. In one embodiment, the target molecule is IL-17RE. In one embodiment, the target molecule is IL-18R1. In one embodiment, the target molecule is IL-18RAP. In one embodiment, the target molecule is IL-18Rα. In one embodiment, the target molecule is IL-20RJ3. In one embodiment, the target molecule is IL-20Rα. In one embodiment, the target molecule is IL-20Rα1. In one embodiment, the target molecule is IL-21R. In one embodiment, the target molecule is IL-22Rα1. In one embodiment, the target molecule is IL-23R. In one embodiment, the target molecule is IL-27Rα. In one embodiment, the target molecule is IL-28RA. In one embodiment, the target molecule is IL-31Rα. In one embodiment, the target molecule is CD4. In one embodiment, the target molecule is CD9. In one embodiment, the target molecule is CXCR1. In one embodiment, the target molecule is CXCR2.

In one embodiment, the target molecule is a chemokine receptor. Exemplary chemokine receptors include but are not limited to CXCR1, CXCR2, CXCR4, CXCR5, CXCR5, CXCR6, CCR1, CCR2, CCR3, CCR4, CCR5, CCR6, CCR7, CCR8, CCR9, CCR10, CCR11, XCR1 and CX3CR1.

In one embodiment, the target molecule is CXCR1. In one embodiment, the target molecule is CXCR2. In one embodiment, the target molecule is CXCR4. In one embodiment, the target molecule is CXCR5. In one embodiment, the target molecule is CXCR5. In one embodiment, the target molecule is CXCR6. In one embodiment, the target molecule is CCR1. In one embodiment, the target molecule is CCR2. In one embodiment, the target molecule is CCR3. In one embodiment, the target molecule is CCR4. In one embodiment, the target molecule is CCR5. In one embodiment, the target molecule is CCR6. In one embodiment, the target molecule is CCR7. In one embodiment, the target molecule is CCR8. In one embodiment, the target molecule is CCR9. In one embodiment, the target molecule is CCR10. In one embodiment, the target molecule is CCR11. In one embodiment, the target molecule is XCR1. In one embodiment, the target molecule is CX3CR1.

In one embodiment, the target molecule is a hormone receptor. Exemplary hormone receptors include but are not limited to calcitriol receptors, corticotropin-releasing hormone receptor 1, corticotropin releasing hormone receptor 2, estrogen receptors, follicle-stimulating hormone receptors, glucagon receptors, gonadotropin receptors, gonadotropin-releasing hormone receptors, growth hormone receptors, insulin receptor, luteinizing hormone receptor, progesterone receptors, retinoid receptors, somatostatin receptors, thyroid hormone receptors, and thyrotropin receptors.

In one embodiment, the target molecule is a calcitriol receptor. In one embodiment, the target molecule is corticotropin-releasing hormone receptor 1. In one embodiment, the target molecule is corticotropin releasing hormone receptor 2. In one embodiment, the target molecule is an estrogen receptor. In one embodiment, the target molecule is a follicle-stimulating hormone receptor. In one embodiment, the target molecule is a glucagon receptor. In one embodiment, the target molecule is a gonadotropin receptor. In one embodiment, the target molecule is a gonadotropin-releasing hormone receptor. In one embodiment, the target molecule is a growth hormone receptor. In one embodiment, the target molecule is an insulin receptor. In one embodiment, the target molecule is a luteinizing hormone receptor. In one embodiment, the target molecule is a progesterone receptor. In one embodiment, the target molecule is a retinoid receptor. In one embodiment, the target molecule is a somatostatin receptor. In one embodiment, the target molecule is a thyroid hormone receptor. In one embodiment, the target molecule is a thyrotropin receptor.

In one embodiment, the target molecule is a relaxin receptor. In one embodiment, the relaxin receptor is RXFP1.

In one embodiment, the target molecule is an inhibitor of a suppressor of the ligand. For example, the target molecule inhibits or reduces binding of the ligand to the suppressor. In one embodiment, the target molecule is an agonist of the ligand. In one embodiment, the target molecule is an antagonist of the ligand.

In one embodiment, the target molecule is an enzyme and the ligand is a substrate of the enzyme.

In one embodiment, the ligand is IL-1α, or IL-1β, or both and the target molecule is IL-1R1, or IL-1R2, or both.

In one embodiment, the ligand is IL-2 and the target molecule is IL-2Rα, or IL-2RJ3, or IL-2Rγ or all or a subset of the previous.

In one embodiment, the ligand is IL-3 and the target molecule is IL-3Rα.

In one embodiment, the ligand is IL-4 and the target molecule is IL-4R, or IL-2Rα, or IL-13Rα1 or all or a subset of the previous.

In one embodiment, the ligand is IL-5 and the target molecule is IL-5Rα.

In one embodiment, the ligand is IL-6 and the target molecule is IL-6Rα, or IL-6RJ3, or both.

In one embodiment, the ligand is IL-7 and the target molecule is IL-7Rα, or IL-2γ, or both.

In one embodiment, the ligand is IL-8 and the target molecule is CXCR1, or CXCR2, or both.

In one embodiment, the ligand is IL-9 and the target molecule is IL-9R, or IL-2Rγ, or both.

In one embodiment, the ligand is IL-10 and the target molecule is IL-10Rα, or IL-10RJ3, or both.

In one embodiment, the ligand is IL-11 and target molecule is IL-11Rα, or IL-6RJ3, or both.

In one embodiment, the ligand is IL-12A, or IL-12B, or both and the target molecule is IL-12RJ31, or IL-12RJ32, or both.

In one embodiment, the ligand is IL-13 and target molecule is IL-13Rα1, or IL-13Rα2, or IL-4R, or all, or a subset of the previous.

In one embodiment, the ligand is IL-15 and the target molecule is IL-15Rα, or IL-2RJ3, or IL-2Rγ, or all, or a subset of the previous.

In one embodiment, the ligand is IL-16 and the target molecule is CD4, or CD9, or both.

In one embodiment, the ligand is IL-17A and the target molecule is IL-17RA, or IL-17RC, or IL-17RD, or all, or a subset of the previous.

In one embodiment, the ligand is IL-17B and the target molecule is IL-17RB.

In one embodiment, the ligand is IL-17C and the target molecule is IL-17RA, or IL-17RE, or both.

In one embodiment, the ligand is IL-17F and the target molecule is IL-17RA, or IL-17RC, or both.

In one embodiment, the ligand is IL-18 and the target molecule is IL-18Rα, or IL-18RAP, or both.

In one embodiment, the ligand is IL-19 and the target molecule is IL-20Rα, or IL-20RJ3, or both.

In one embodiment, the ligand is IL-20 and the target molecule IL-20Rα, or IL-20RJ3, or IL-20Rα1, or all, or a subset of the previous.

In one embodiment, the ligand is IL-21 and the target molecule is IL-21R, or IL-2Rγ, or both.

In one embodiment, the ligand is IL-22 and the target molecule is IL-22Rα1, or IL-22Rα2, or IL-10RJ3, or all, or a subset of the previous.

In one embodiment, the ligand is IL-23 and the target molecule is IL-12RJ31, or IL-23R, or both.

In one embodiment, the ligand is IL-24 and the target molecule is IL-20Rα, or IL-20RJ3, or IL-22Rα1, or all, or a subset of the previous.

In one embodiment, the ligand IL25 and the target molecule is IL-17RA, or IL-17RB, or both.

In one embodiment, the ligand is IL-26 and the target molecule is IL-10RJ3 or IL-20Rα, or both.

In one embodiment, the ligand is IL-27 and the target molecule is IL-27Rα, or IL-6RJ3, or both.

In one embodiment, the ligand is IL-28A and the target molecule is IL-28RA, or IL-10RJ3, or both.

In one embodiment, the ligand is IL-28B and the target molecule is IL-28RA, or IL-10RJ3, or both.

In one embodiment, the ligand is IL-29 and the target molecule is IL-28RA, or IL-10RJ3, or both.

In one embodiment, the ligand is IL-31 and the target molecule is IL-31Rα.

In one embodiment, the ligand is IL-33, or IL-34, or both and the target molecule is IL-1R1, or IL-12J32, or IL-6RJ3, or both.

In one embodiment, the ligand is IL-36A, or IL-36B, or IL-36G, or all, or a subset of the previous, and the target molecule is IL-1RL2, or IL-1RAP, or both.

In one embodiment, the ligand is IL-37 and the target molecule is IL-18R1.

In one embodiment, the ligand is IL-38 and the target molecule is IL-1R1, or IL-1R2, or both.

In one embodiment, the ligand is IGF-1 and the target molecule is IGF-1R.

In one embodiment, the ligand is FGF and the target molecule is selected from the group consisting of FGFR1, FGFR2, or FGFR3.

In one embodiment, the ligand is IGF-1 and the target molecule is Pappalysin-1.

Particles

In some embodiments, the nucleic acid described herein can be comprised in a particle. As used herein, a "particle" is not limited to a particular shape and size and can include spherical, rod like, faceted, plates or other shapes, and can be monodisperse or polydisperse. The size distribution of particles can be characterized by Polydispersity index (PDI). PDI of particle size distribution is determined by methods commonly known by one of ordinary skill in the art, for example, by dynamic light scattering (DLS) measurement. With regard to DLS used for particle size determinations, the common use of second or third order cumulant analyses to fit the autocorrelation function leads to the values of PDI.

The absolute value of PDI determined from this method ranges from zero and higher, with small values indicating narrower distributions. For example, PDI ranging from 0 to about 0.3 or from 0 to about 0.4 presents relatively monodisperse particle size distributions. This criterion has been generally accepted in the art of dynamic light scattering for particle size determinations. In some embodiments the particles are monodisperse. For example, the particles have a narrow particle size distribution such as having a polydispersity index below about 0.5, such as below about 0.4, below about 0.3 or below about 0.2.

In some embodiments, the size and morphology (e.g., diameter, sphericity, and porosity) of particles may be characterized by techniques including, but not limited to, dynamic light scattering, coulter counter, microscopy, sieve analysis, dynamic image analysis, static image analysis, and laser diffraction.

In some embodiments, the particle is a microparticle. As used herein, the term "microparticle" refers to particles that are from about 1 μm to about 500 μm in size. For example, a microparticle is from about 1 μm to about 500 μm in size. In some embodiments, the microparticle is from about 1 μm to about 250 μm, from about 1 μm to about 200 μm, from about 1 μm to about 150 μm or from about 1 μm to about 100 μm in size. For example, the microparticle is from about 1 μm to about 75 μm or from about 1 μm to about 100 μm in size.

In some embodiments, the particle is a nanoparticle. As used herein, the term "nanoparticle" refers to particles that are from about 1 nm to about 950 nm in size. For example, a nanoparticle is from about 10 nm to about 500 nm in size. In some embodiments, the nanoparticle is from about 10 nm to about 250 nm, from about 25 nm to about 200 nm, from about 50 nm to about 175 nm or from about 75 nm to about 150 nm in size. For example, the nanoparticle is from about 80 nm to about 125 nm or from about 90 nm to about 120 nm in size.

In one aspect provided herein is a particle comprising: a first nucleic acid molecule encoding a ligand and a second nucleic acid molecule encoding a target molecule, and wherein the target molecule is a cognate receptor of the ligand or an inhibitor of a suppressor of the ligand. Optionally, the first and second nucleic acid molecules are covalently linked to each other. When the first and second nucleic acid molecules are covalently linked to each other, they form any of the polycistronic nucleic acids described herein.

Lipids, and Compositions and Formulations Thereof

In some embodiments, the particle is a lipid particle. Accordingly, described herein are lipid particles comprising any of the nucleic acids described herein for use in activating a signaling pathway and/or treating a disease or disorder. As used herein, the term "lipid particle" refers to a vesicle formed by one or more lipid components. Lipid particles are typically used as carriers for nucleic acid delivery in the context of pharmaceutical development. They work by fusing with a cellular membrane and repositioning its lipid structure to deliver a drug or active pharmaceutical ingredient (API). Generally, lipid particle compositions for such delivery are composed of ionizable or cationic lipids, phospholipids (especially compounds having a phosphatidylcholine group), cholesterol, and a polyethylene glycol (PEG) lipid; however, these compositions may also include other lipids. The ionizable lipid is typically employed to condense the nucleic acid cargo at low pH and to drive membrane association and fusogenicity. The phospholipid is typically employed to enhance fusogenicity. The cholesterol is typically employed to provide membrane integrity. The PEG-lipid is typically employed to provide steric stabilization. The sum composition of lipids typically dictates the surface characteristics and thus the protein (opsonization) content in biological systems thus driving biodistribution and cell uptake properties. A lipid particle can be a lipid nanoparticle (LNP).

In some embodiments, the lipid particles are solid core particles that possess at least one lipid bilayer.

In some embodiments, the lipid particle is a liposome. As used herein, the term "liposome" refers to lipid molecules assembled in a spherical configuration encapsulating an interior aqueous volume that is segregated from an aqueous exterior. Liposomes are vesicles that possess at least one lipid bilayer. They work by fusing with a cellular membrane and repositioning its lipid structure to deliver a drug or active pharmaceutical ingredient. Liposome compositions are typically composed of phospholipids, especially compounds having a phosphatidylcholine group, however these compositions may also include other lipids.

Accordingly, in another aspect provided herein is a lipid particle comprising a nucleic acid described herein and a lipid, e.g., an ionizable lipid. For example, the lipid particle comprises: a first nucleic acid molecule encoding a ligand; a second nucleic acid molecule encoding a target molecule; and an ionizable lipid, and wherein the target molecule is a cognate receptor of the ligand or an inhibitor of a suppressor of the ligand. Optionally, the first and second nucleic acid molecules are covalently linked to each other. When the first and second nucleic acid molecules are covalently linked to each other, they form any of the polycistronic nucleic acids described herein.

Liposomes may be characterized by membrane type and by size. Liposomes are also referred to as lipid vesicles in the art. In order to form a liposome the lipid molecules comprise elongated non-polar (hydrophobic) portions and polar (hydrophilic) portions. The hydrophobic and hydrophilic portions of the molecule are preferably positioned at two ends of an elongated molecular structure. When such lipids are dispersed in water they spontaneously form bilayer membranes referred to as lamellae. The lamellae are composed of two mono layer sheets of lipid molecules with their non-polar (hydrophobic) surfaces facing each other and their polar (hydrophilic) surfaces facing the aqueous medium. The membranes formed by the lipids enclose a portion of the aqueous phase in a manner similar to that of a cell membrane enclosing the contents of a cell. Thus, the bilayer of a liposome has similarities to a cell membrane without the protein components present in a cell membrane.

Liposomes include unilamellar vesicles which are comprised of a single lipid layer and generally have a diameter of 20 to 100 nanometers; large unilamellar vesicles (LUVS) are typically larger than 100 nm, which can be produced by subjecting multilamellar liposomes to ultrasound. Preferred liposomes have a diameter in the range of 20-250 nm.

In some embodiments, a lipid particle described herein comprises an ionizable lipid. As used herein, the term "ionizable lipid" refers to lipids having at least one protonatable or deprotonatable group, such that the lipid is positively charged at a pH at or below physiological pH (e.g., pH 7.4), and neutral at a second pH, preferably at or above physiological pH. Typically, ionizable lipids are lipids comprising at least one amino group that is positively charged or becomes protonated under acidic conditions, for example at pH of 6.5 or lower. It will be understood by one of ordinary skill in the art that the addition or removal of protons as a function of pH is an equilibrium process, and that the reference to a charged or a neutral lipid refers to the nature of the predominant species and does not require that all of the lipid be present in the charged or neutral form. Generally, ionizable lipids have a pK$_a$ of the protonatable group in the range of about 4 to about 7. Ionizable lipids are also referred to as cationic lipids herein. Exemplary ionizable lipids are described in the PCT and US patent publications listed in Table 1, the contents of all of which are incorporated herein by reference in their entirety.

TABLE 1

Ionizable lipids

| PCT Publication | US Publication |
|---|---|
| WO2015/095340 | US2016/0311759 |
| WO2015/199952 | US2015/0376115 |
| WO2018/011633 | US2016/0151284 |
| WO2017/049245 | US2017/0210697 |
| WO2015/061467 | US2015/0140070 |
| WO2012/040184 | US2013/0178541 |
| WO2012/000104 | US2013/0303587 |
| WO2015/074085 | US2015/0141678 |
| WO2016/081029 | US2015/0239926 |
| WO2017/004143 | US2016/0376224 |
| WO2017/075531 | US2017/0119904 |
| WO2017/117528 | |
| WO2011/022460 | US2012/0149894 |
| WO2013/148541 | US2015/0057373 |
| WO2013/116126 | |
| WO2011/153120 | US2013/0090372 |
| WO2012/044638 | US2013/0274523 |
| WO2012/054365 | US2013/0274504 |
| WO2011/090965 | US2013/0274504 |
| WO2013/016058 | |
| WO2012/162210 | |
| WO2008/042973 | US2009/0023673 |
| WO2010/129709 | US2012/0128760 |
| WO2010/144740 | US2010/0324120 |
| WO2012/099755 | US2014/0200257 |
| WO2013/049328 | US2015/0203446 |
| WO2013/086322 | US2018/0005363 |
| WO2013/086373 | US2014/0308304 |
| WO2011/071860 | US2013/0338210 |
| WO2009/132131 | |
| WO2010/048536 | |
| WO2010/088537 | US2012/0101148 |
| WO2010/054401 | US2012/0027796 |
| WO2010/054406 | |
| WO2010/054405 | |
| WO2010/054384 | US2012/0058144 |
| WO2012/016184 | US2013/0323269 |
| WO2009/086558 | US2011/0117125 |
| WO2010/042877 | US2011/0256175 |
| WO2011/000106 | US2012/0202871 |
| WO2011/000107 | US2011/0076335 |
| WO2005/120152 | US2006/0083780 |
| WO2011/141705 | US2013/0123338 |
| WO2013/126803 | US2015/0064242 |
| WO2006/07712 | US2006/0051405 |
| WO2011/038160 | US2013/0065939 |
| WO2005/121348 | US2006/0008910 |
| WO2011/066651 | US2003/0022649 |
| WO2009/127060 | US2010/0130588 |
| WO2011/141704 | US2013/0116307 |
| WO2006/069782 | US2010/0062967 |
| WO2012/031043 | US2013/0202684 |
| WO2013/006825 | US2014/0141070 |
| WO2013/033563 | US2014/0255472 |
| WO2013/089151 | US2014/0039032 |
| WO2017/099823 | US2018/0028664 |
| WO2015/095346 | US2016/0317458 |
| WO2013/086354 | US2013/0195920 |

In some embodiments, the ionizable lipid is MC3 (6Z, 9Z,28Z,31Z)-heptatriaconta-6,9,28,31-tetraen-19-yl-4-(dimethylamino) butanoate (DLin-MC3-DMA or MC3) described in in Jayaraman et al., Angew. Chem. Int. Ed Engl. (2012), 51(34): 8529-8533, content of which is incorporated herein by reference in its entirety. In some embodiments, the ionizable lipid is the lipid ATX-002 described in WO2015/074085, content of which is incorporated herein by reference in its entirety. In some embodiments, the ionizable lipid is (13Z,16Z)—N,N-dimethyl-3-nonyldocosa-13,16-dien-1-amine described in WO2012/040184, content of which is incorporated herein by reference in its entirety. In some embodiments, the ionizable lipid is Compound 6 or Compound 22 described in WO2015/199952, content of which is incorporated herein by reference in its entirety.

Without limitations, ionizable lipid can comprise 20-90% (mol) of the total lipid present in the lipid particle. For example, ionizable lipid molar content can be 20-70% (mol), 30-60% (mol) or 40-50% (mol) of the total lipid present in the lipid particle. In some embodiments, ionizable lipid comprises from about 50 mol % to about 90 mol % of the total lipid present in the lipid particle. In one embodiment, the the lipid particle comprises an ionizable lipid in an amount from about 30 mol % to about 90 mol %; 40 mol % to about 90 mol %; 50 mol % to about 90 mol %; 60 mol % to about 90 mol %; 70 mol % to about 90 mol %; 80 mol % to about 90 mol %; 20 mol % to about 80 mol %; 20 mol % to about 70 mol %; 20 mol % to about 60 mol %; 20 mol % to about 50 mol %; 20 mol % to about 40 mol %; 20 mol % to about 30 mol % of the total lipid present in the particle. In one embodiment, the the lipid particle comprises an ionizable lipid in an amount from about 20 mol %; 21 mol %; 22 mol %; 23 mol %; 24 mol %; 25 mol %; 26 mol %; 27 mol %; 28 mol %; 29 mol %; 30 mol %; 31 mol %; 32 mol %; 33 mol %; 34 mol %; 35 mol %; 36 mol %; 37 mol %; 38 mol %; 39 mol %; 40 mol %; 41 mol %; 42 mol %; 43 mol %; 44 mol %; 45 mol %; 46 mol %; 47 mol %; 48 mol %; 49 mol %; 50 mol %; 51 mol %; 52 mol %; 53 mol %; 54 mol %; 55 mol %; 56 mol %; 57 mol %; 58 mol %; 59 mol %; 60 mol %; 61 mol %; 62 mol %; 63 mol %; 64 mol %; 65 mol %; 66 mol %; 67 mol %; 68 mol %; 69 mol %; 70 mol %; 71 mol %; 72 mol %; 73 mol %; 74 mol %; 75 mol %; 76 mol %; 77 mol %; 78 mol %; 79 mol %; 80 mol %; 81 mol %; 82 mol %; 83 mol %; 84 mol %; 85 mol %; 86 mol %; 87 mol %; 88 mol %; 89 mol %; 90 mol %; or more of the total lipid present in the particle.

In some embodiments, the lipid particle comprises a non-cationic lipid. As used herein, the term "non-cationic lipid" refers to any amphipathic lipid as well as any other neutral lipid or anionic lipid. Accordingly, the non-cationic lipid can be a neutral uncharged, zwitterionic, or anionic lipid. Non-cationic lipids are typically employed to enhance fusogenicity. Exemplary non-cationic lipids include, but are not limited to, distearoyl-sn-glycero-phosphoethanolamine, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), monomethyl-phosphatidylethanolamine (such as 16-O-monomethyl PE), dimethyl-phosphatidylethanolamine (such as 16-O-dimethyl PE), 18-1-trans PE, 1-stearoyl-2-oleoyl-phosphatidyethanolamine (SOPE), hydrogenated soy phosphatidylcholine (HSPC), egg phosphatidylcholine (EPC), dioleoylphosphatidylserine (DOPS), sphingomyelin (SM), dimyristoyl phosphatidylcholine (DMPC), dimyristoyl phosphatidylglycerol (DMPG), distearoylphosphatidylglycerol (DSPG), dierucoylphosphatidylcholine (DEPC), palmitoyloleyolphosphatidylglycerol (POPG), dielaidoyl-phosphatidylethanolamine (DEPE), lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidicacid,cerebrosides, dicetylphosphate, lysophosphatidylcholine, dilinoleoylphosphatidylcholine, or mixtures thereof. It is understood that other diacylphosphatidylcholine and diacylphospiatidyletlianolamine phospholipids can also be used. The acyl groups in these lipids are preferably acyl groups derived from fatty acids having $C_{10}$-$C_{24}$ carbon chains, e.g., lauroyl, rinstoyl, palmitoyl, stearoyl, or oleoyl.

Other examples of non-cationic lipids suitable for use in the lipid particles include nonphosphorous lipids such as, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldinethyl ammoniun bromide, ceranide, sphingomyelin, and the like.

In some embodiments, the non-cationic lipid is a phospholipid. In some embodiments, the non-cationic lipid is selected from DSPC, DPPC, DMPC, DOPC, POPC, DOPE, and SM. In some preferred embodiments, the non-cationic lipid is DPSC.

Exemplary non-cationic lipids are described in PCT Publication WO2017/099823 and US patent publication US2018/0028664, the contents of both of which are incorporated herein by reference in their entirety.

The non-cationic lipid can comprise 0-30% (mol) of the total lipid present in the lipid particle. For example, the non-cationic lipid content is 5-20% (mol) or 10-15% (mol) of the total lipid present in the lipid particle. In various embodiments, the molar ratio of ionizable lipid to the neutral lipid ranges from about 2:1 to about 8:1.

In one embodiment, the the lipid particle comprises a non-cationic lipid in an amount from about 5 mol % to about 30 mol % of the total lipid present in the particle. In one embodiment, the the lipid particle comprises a non-cationic lipid in an amount from about 10 mol % to about 30 mol %; 15 mol % to about 30 mol %; 20 mol % to about 30 mol %; 25 mol % to about 30 mol %; 5 mol % to about 25 mol %; 5 mol % to about 20 mol %; 5 mol % to about 15 mol %; 5 mol % to about 10 mol % of the total lipid present in the particle. In one embodiment, the the lipid particle comprises a non-cationic lipid in an amount from about 5 mol %; 6 mol %; 7 mol %; 8 mol %; 9 mol %; 10 mol %; 11 mol %; 12 mol %; 13 mol %; 14 mol %; 15 mol %; 16 mol %; 17 mol %; 18 mol %; 19 mol %; 20 mol %; 21 mol %; 22 mol %; 23 mol %; 24 mol %; 25 mol %; 26 mol %; 27 mol %; 28 mol %; 29 mol %; 30 mol %; or more of the total lipid present in the particle.

In some embodiments, the lipid particle can further comprise a conjugated lipid molecule. As used herein, the term "conjugated lipid" refers to a lipid molecule conjugated with a non-lipid molecule, such as a PEG, polyoxazoline, polyamide, or polymer (e.g., cationic polymer), Generally, these lipids are used to inhibit aggregation of lipid particles and/or provide steric stabilization. Exemplary conjugated lipids include, but are not limited to, PEG-lipid conjugates, polyoxazoline (POZ)-lipid conjugates, polyamide-lipid conjugates (such as ATTA-lipid conjugates), cationic-polymer lipid (CPL) conjugates, and mixtures thereof. In some embodiments, the conjugated lipid molecule is a PEG-lipid conjugate, for example, a (methoxy polyethylene glycol)-conjugated lipid.

Exemplary PEG-lipid conjugates include, but are not limited to, PEG-diacylglycerol (DAG) (such as 1-(monomethoxy-polyethyleneglycol)-2,3-dimyristoylglycerol (PEG-DMG)), PEG-dialkyloxypropyl (DAA), PEG-phospholipid, PEG-ceramide (Cer), a pegylated phosphatidylethanoloamine (PEG-PE), PEG succinate diacylglycerol (PEGS-DAG) (such as 4-O-(2',3'-di(tetradecanoyloxy)propyl-1-O-(w-methoxy(polyethoxy)ethyl) butanedioate (PEG-S-DMG)), PEG dialkoxypropylcarbam, N-(carbonyl-methoxypolyethylene glycol 2000)-1,2-distearoyl-sn-glycero-3-phosphoethanolamine sodium salt, or a mixture thereof. Additional exemplary PEG-lipid conjugates are described, for example, in U.S. Pat. Nos. 5,885,613, 6,287,591, US2003/0077829, US2003/0077829, US2005/0175682, US2008/0020058, US2011/0117125, US2010/0130588, US2016/0376224, US2017/0119904, and US/099823, the contents of all of which are incorporated herein by reference in their entirety.

The PEG-DAA conjugate can be, for example, PEG-dilauryloxypropyl, PEG-dimyristyloxypropyl, PEG-dipalmityloxypropyl, or PEG-distearyloxypropyl. The PEG-lipid can be one or more of PEG-DMG, PEG-dilaurylglycerol, PEG-dipalmitoylglycerol, PEG-disterylglycerol, PEG-dilaurylglycamide, PEG-dimyristylglycamide, PEG-dipalmitoylglycamide, PEG-disterylglycamide, PEG-cholesterol (1-[8'-(Cholest-5-en-3[beta]-oxy)carboxamido-3',6'-dioxaoctanyl] carbamoyl-[omega]-methyl-poly(ethylene glycol), PEG-DMB (3,4-Ditetradecoxylbenzyl-[omega]-methyl-poly(ethylene glycol) ether), and 1,2-dimyristoyl-sn-glycero-3-phosphoethanolamine-N-[methoxy(polyethylene glycol)-2000]. In some examples, the PEG-lipid can be PEG-DMG, 1,2-dimyristoyl-sn-glycero-3-phosphoethanolamine-N-[methoxy(polyethylene glycol)-2000].

Lipids conjugated with a molecule other than a PEG can also be used in place of PEG-lipid. For example, polyoxazoline (POZ)-lipid conjugates, polyamide-lipid conjugates (such as ATTA-lipid conjugates), and cationic-polymer lipid (CPL) conjugates can be used in place of or in addition to the PEG-lipid.

Exemplary conjugated lipids, i.e., PEG-lipids, (POZ)-lipid conjugates, ATTA-lipid conjugates and cationic polymer-lipids are described in the PCT and US patent applications listed in Table 2, the contents of all of which are incorporated herein by reference in their entirety.

TABLE 2

| Conjugated lipids | |
|---|---|
| PCT Publication | US Publication |
| WO1996/010392 | U.S. Pat. No. 5,885,613 |
| WO1998/051278 | U.S. Pat. No. 6,287,591 |
| WO2002/087541 | US2003/0077829 |
| WO2005/026372 | US2005/0175682 |
| WO2008/147438 | US2008/0020058 |
| WO2009/086558 | US2011/0117125 |
| WO2012/000104 | US2013/0303587 |
| WO2017/117528 | |
| WO2017/099823 | US2018/0028664 |
| WO2015/199952 | US2015/0376115 |
| WO2017/004143 | US2016/0376224 |
| WO2015/095346 | US2016/0317458 |
| | U.S. Pat. No. 6,320,017 |
| | U.S. Pat. No. 6,586,559 |

TABLE 2-continued

Conjugated lipids

| PCT Publication | US Publication |
|---|---|
| WO2012/000104 | US2013/0303587 |
| WO2012/000104 | US2013/0303587 |
| WO2010/006282 | US2011/0123453 |

The PEG or the conjugated lipid can comprise 0-20% (mol) of the total lipid present in the lipid particle. In some embodiments, PEG or the conjugated lipid content is 0.5-10% or 2-5% (mol) of the total lipid present in the lipid particle.

In one embodiment, the the lipid particle comprises a conjugated lipid that inhibits aggregation of particles in an amount from about 0.5 mol % to about 20 mol % of the total lipid present in the particle. In one embodiment, the the lipid particle comprises a conjugated lipid that inhibits aggregation of particles in an amount from about 5 mol % to about 20 mol %; 10 mol % to about 20 mol %; 15 mol % to about 20 mol %; 0.5 mol % to about 15 mol %; 0.5 mol % to about 10 mol %; 0.5 mol % to about 5 mol % of the total lipid present in the particle. In one embodiment, the the lipid particle comprises a conjugated lipid that inhibits aggregation of particles in an amount from about 5 mol %; 6 mol %; 7 mol %; 8 mol %; 9 mol %; 10 mol %; 11 mol %; 12 mol %; 13 mol %; 14 mol %; 15 mol %; 16 mol %; 17 mol %; 18 mol %; 19 mol %; 20 mol %; or more of the total lipid present in the particle.

In some embodiments, the lipid particle can further comprise a component, such as a sterol, to provide membrane integrity. One exemplary sterol that can be used in the lipid particle is cholesterol and derivatives thereof. Non-limiting examples of cholesterol derivatives include polar analogues such as 5a-cholestanol, 5β-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5β-cholestanone, and cholesteryl decanoate; and mixtures thereof. In some embodiments, the cholesterol derivative is a polar analogue such as cholesteryl-(4'-hydroxy)-butyl ether.

Exemplary cholesterol derivatives are described in PCT publication WO2009/127060 and US patent publication US2010/0130588, contents of both of which are incorporated herein by reference in their entirety.

The component providing membrane integrity, such as a sterol, can comprise 0-50% (mol) of the total lipid present in the lipid particle. In some embodiments, such a component is 20-50% (mol) 30-40% (mol) of the total lipid content of the lipid particle.

In one embodiment, the the lipid particle comprises a sterol in an amount from about 20 mol % to about 50 mol % of the total lipid present in the particle. In one embodiment, the the lipid particle comprises a sterol in an amount from about 25 mol % to about 50 mol %; 30 mol % to about 50 mol %; 35 mol % to about 50 mol %; 40 mol % to about 50 mol %; 45 mol % to about 50 mol %; 20 mol % to about 45 mol %; 20 mol % to about 40 mol %; 20 mol % to about 35 mol %; 20 mol % to about 30 mol %; 20 mol % to about 25 mol % of the total lipid present in the particle. In one embodiment, the the lipid particle comprises a sterol in an amount from about 20 mol %; 21 mol %; 22 mol %; 23 mol %; 24 mol %; 25 mol %; 26 mol %; 27 mol %; 28 mol %; 29 mol %; 30 mol %; 31 mol %; 32 mol %; 33 mol %; 34 mol %; 35 mol %; 36 mol %; 37 mol %; 38 mol %; 39 mol %; 40 mol %; 41 mol %; 42 mol %; 43 mol %; 44 mol %; 45 mol %; 46 mol %; 47 mol %; 48 mol %; 49 mol %; 50 mol %; or more of the total lipid present in the particle.

In one embodiment, the the lipid particle comprises: an ionizable lipid; a non-cationic lipid; a conjugated lipid that inhibits aggregation of particles; and a sterol. Molar ratios of the ionizable lipid, non-cationic-lipid, sterol, and PEG/conjugated lipid can be varied as needed. For example, the lipid particle can comprise 30-70% ionizable lipid by mole or by total weight of the composition, 0-60% cholesterol by mole or by total weight of the composition, 0-30% non-cationic-lipid by mole or by total weight of the composition and 1-10% conjugated lipid by mole or by total weight of the composition. Preferably, the composition comprises 30-40% ionizable lipid by mole or by total weight of the composition, 40-50% cholesterol by mole or by total weight of the composition, and 10-20% non-cationic-lipid by mole or by total weight of the composition. In some other embodiments, the composition is 50-75% ionizable lipid by mole or by total weight of the composition, 20-40% cholesterol by mole or by total weight of the composition, and 5 to 10% non-cationic-lipid, by mole or by total weight of the composition and 1-10% conjugated lipid by mole or by total weight of the composition. The composition may contain 60-70% ionizable lipid by mole or by total weight of the composition, 25-35% cholesterol by mole or by total weight of the composition, and 5-10% non-cationic-lipid by mole or by total weight of the composition. The composition may also contain up to 90% ionizable lipid by mole or by total weight of the composition and 2 to 15% non-cationic lipid by mole or by total weight of the composition. The formulation may also be a lipid particle formulation, for example comprising 8-30% ionizable lipid by mole or by total weight of the composition, 5-30% non-cationic lipid by mole or by total weight of the composition, and 0-20% cholesterol by mole or by total weight of the composition; 4-25% ionizable lipid by mole or by total weight of the composition, 4-25% non-cationic lipid by mole or by total weight of the composition, 2 to 25% cholesterol by mole or by total weight of the composition, 10 to 35% conjugate lipid by mole or by total weight of the composition, and 5% cholesterol by mole or by total weight of the composition; or 2-30% ionizable lipid by mole or by total weight of the composition, 2-30% non-cationic lipid by mole or by total weight of the composition, 1 to 15% cholesterol by mole or by total weight of the composition, 2 to 35% conjugate lipid by mole or by total weight of the composition, and 1-20% cholesterol by mole or by total weight of the composition; or even up to 90% ionizable lipid by mole or by total weight of the composition and 2-10% non-cationic lipids by mole or by total weight of the composition, or even 100% cationic lipid by mole or by total weight of the composition. In some embodiments, the lipid particle formulation comprises ionizable lipid, phospholipid, cholesterol and a PEG-ylated lipid in a molar ratio of 50:10:38.5:1.5. In some other embodiments, the lipid particle formulation comprises ionizable lipid, cholesterol and a PEG-ylated lipid in a molar ratio of 60:38.5:1.5.

In one embodiment, the the lipid particle comprises: an ionizable lipid in an amount from about 20 mol % to about 90 mol % of the total lipid present in the particle; a non-cationic lipid in an amount from about 5 mol % to about 30 mol % of the total lipid present in the particle; a conjugated lipid that inhibits aggregation of particles in an amount from about 0.5 mol % to about 20 mol % of the total lipid present in the particle; and a sterol in an amount from about 20 mol % to about 50 mol % of the total lipid present in the particle. In some embodiments, the lipid particle comprises ionizable lipid/non-cationic-lipid/sterol/conjugated lipid at a molar ratio of 50:10:38.5:1.5.

In one embodiment, the total lipid to nucleic acid (mass or weight) ratio is from about 10:1 to about 30:1. In one embodiment, the total lipid to nucleic acid (mass or weight) ratio is from about 11:1 to about 30:1; 12:1 to about 30:1; 13:1 to about 30:1; 14:1 to about 30:1; 15:1 to about 30:1; 16:1 to about 30:1; 17:1 to about 30:1; 18:1 to about 30:1; 19:1 to about 30:1; 20:1 to about 30:1; 21:1 to about 30:1; 22:1 to about 30:1; 23:1 to about 30:1; 24:1 to about 30:1; 25:1 to about 30:1; 26:1 to about 30:1; 27:1 to about 30:1; 28:1 to about 30:1; 29:1 to about 30:1; 10:1 to about 11:1; 10:1 to about 12:1; 10:1 to about 13:1; 10:1 to about 14:1; 10:1 to about 15:1; 10:1 to about 16:1; 10:1 to about 17:1; 10:1 to about 18:1; 10:1 to about 19:1; 10:1 to about 20:1; 10:1 to about 21:1; 10:1 to about 22:1; 10:1 to about 23:1; 10:1 to about 24:1; 10:1 to about 25:1; 10:1 to about 26:1; 10:1 to about 27:1; 10:1 to about 28:1; 10:1 to about 29:1. In one embodiment, the total lipid to nucleic acid (mass or weight) ratio is about 10:1; about 11:1; about 12:1; about 13:1; about 14:1; about 15:1; about 16:1; about 17:1; about 18:1; about 19:1; about 20:1; about 21:1; about 22:1; about 23:1; about 24:1; about 25:1; about 26:1; about 27:1; about 28:1; about 29:1 or about 30:1. The amounts of lipids and nucleic acid can be adjusted to provide a desired N/P ratio, for example, N/P ratio of 3, 4, 5, 6, 7, 8, 9, 10 or higher.

In one embodiment of any aspect herein, the diameter of the lipid is 1-75 µm; or 1-50 µm; or 5-50 µm; or 25-50 µm; or 30-50 µm; or 40-50 µm; or 5-10 µm; 5-8 µm; 8-12 µm; 12-18 µm; 18-25 µm; 25-35 µm; 35-45 µm; 45-50 µm; 1 µm; 2 µm; 3 µm; 4 µm; 5 µm; 6 µm; 7 µm; 8 µm; 9 µm; 10 µm; 15 µm; 20 µm; 25 µm; 30 µm; 35 µm; 40 µm; 45 µm; 50 µm; 75 µm; 100 µm; 150 µm; or 200 µm.

In one embodiment, the lipid particle comprises a nucleic acid molecule encoding an RNA replicon. An RNA replicon can be comprised on a polycistronic nucleic acid, or a first and/or second nucleic acid.

Also provided herein is a composition or cell comprising any of the lipid particles described herein.

In one embodiment, where a feature of a formulation (such as any nucleic acid described herein, lipid component, etc) is in a specified amount expressed in a mass percentage; percent-by-weight; percent of total mass or the like; unless indicated otherwise, the percentage is based on microparticles that are not suspended in a solution. In such situations where a claimed formulation includes lipids suspended in a solution, the mass percentage still refers to the mass percentage in the lipids, and not the total solution that includes the lipid and the suspension solution.

Pharmaceutical Compositions

Various aspects herein relate to a composition comprising any of the nucleic acid or particles (e.g., lipids particles) described herein. In various embodiments, the composition is a pharmaceutical composition.

As used herein, the term "pharmaceutical composition" can include any material or substance that, when combined with an active ingredient (e.g., any of the nucleic acids or particles described herein), allows the ingredient to retain biological activity and is non-reactive with the subject's immune system. Examples include, but are not limited to, any of the standard pharmaceutical carriers such as a phosphate buffered saline solution, emulsions such as oil/water emulsion, and various types of wetting agents. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. The term "pharmaceutically acceptable carrier" excludes tissue culture media. Each carrier must be "acceptable" in the sense of being compatible with the other ingredients of the formulation, for example the carrier does not decrease the impact of the agent on the treatment. In other words, a carrier is pharmaceutically inert. The terms "physiologically tolerable carriers" and "biocompatible delivery vehicles" are used interchangeably. Non-limiting examples of pharmaceutical carriers include particle or polymer-based vehicles such as nanoparticles, microparticles, polymer microspheres, or polymer-drug conjugates.

Compositions described herein can be formulated for systemic or local administration. In some embodiments, a composition described herein is formulated for local administration. In some other embodiments, a composition described herein is formulated for systemic administration. For systemic administration, injection is preferred, including intramuscular, intravenous, intraperitoneal, or subcutaneous injection.

Compositions described herein can be formulated for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; or (3) topical application, for example, as a film, sheet, dressing, cream, ointment, liquid, gel, hydrogel, emulsion, suspension or a controlled-release patch or spray applied to the skin. Delivery using intravenous, oral or inhalation methods can be particularly advantageous. Accordingly, in some embodiments, the composition is formulated for intravenous, oral or inhalation administration.

In some embodiments, the composition is formulated for parenteral administration or inhalation administration. For example, the composition can be formulated for intravenous administration, intramuscular administration, subcutaneous administration, transdermal administration or via inhalation administration. In some embodiments, the composition is formulated for administration via inhalation as an aerosol. In some embodiments, the composition is formulated for administration via intra-articular injection. In some embodiments, the composition is formulated for administration via intramuscular injection.

In some embodiments, the pharmaceutical composition is a liquid dosage form or solid dosage form. Liquid dosage forms for oral administration include, but are not limited to, pharmaceutically acceptable emulsions, microemulsions, solutions, suspensions, syrups and elixirs. In addition, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

In some embodiments, the liquid dosage form is prepared at or near the point of care by reconstituting or resuspending a provided lyophilisate or lyophilized powder of a formulation disclosed herein using a diluent solution.

Solid dosage forms for oral administration include capsules, tablets, pills, powders, and granules. In such solid dosage forms, the agents described herein (e.g., nucleic acid or lipid described herein) are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using such excipients as lactose or milk sugar as well as high molecular weight polyethylene glycols, and the like. The solid dosage forms of tablets, dragées, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type can also be employed as fillers in soft and hard-filled gelatin capsules using such excipients as lactose or milk sugar as well as high molecular weight polyethylene glycols, and the like.

In some embodiments, the solid dosage form is a lyophilized powder.

In some dosage forms, the lyophilized powder solid dosage form is intended to be resuspended or reconstituted with diluent.

The agent, e.g., nucleic acid or particle described herein, can also be in micro-encapsulated form with one or more excipients as noted above. The solid dosage forms of tablets, dragées, capsules, pills, and granules can be prepared with coatings and shells such as enteric coatings, release controlling coatings and other coatings well known in the pharmaceutical formulating art. In such solid dosage forms, the agent can be admixed with at least one inert diluent such as sucrose, lactose and starch. Such dosage forms can also comprise, as in normal practice, additional substances other than inert diluents, e.g., tableting lubricants and other tableting aids such as magnesium stearate and microcrystalline cellulose. In the case of capsules, tablets and pills, the dosage forms can also comprise buffering agents. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Pharmaceutical compositions include formulations suitable for oral administration may be provided as discrete units, such as tablets, capsules, cachets, syrups, elixirs, prepared food items, microemulsions, solutions, suspensions, lozenges, or gel-coated ampules, each containing a predetermined amount of the active compound; as powders or granules; as solutions or suspensions in aqueous or non-aqueous liquids; or as oil-in-water or water-in-oil emulsions.

Accordingly, formulations suitable for rectal administration include gels, creams, lotions, aqueous or oily suspensions, dispersible powders or granules, emulsions, dissolvable solid materials, douches, and the like can be used. The formulations are preferably provided as unit-dose suppositories comprising the active ingredient in one or more solid carriers forming the suppository base, for example, cocoa butter. Suitable carriers for such formulations include petroleum jelly, lanolin, polyethyleneglycols, alcohols, and combinations thereof. Alternatively, colonic washes with the rapid recolonization deployment agent of the present invention can be formulated for colonic or rectal administration.

The present invention provides sustained release formulations for delivering an agent, e.g., nucleic acid or particle described herein therapeutic to a subject in need thereof. The sustained release formulations of the invention consist of a hydrogel, microparticle or some matrix encapsulation of the agent. One example of the agent is relaxin. The sustained release comprises the agent e.g., relaxin encapsulated by or chemically bound to the depot support material via a linker. The linker may, comprise a polymer, a non-cleavable linker, or a cleavable linker, either through chemical or enzymatic means. The depot may be formed in situ following mixing of the agent with the material. The depot may be formed prior to mixing of the relaxin with the material.

The sustained release formulation comprising the agent, e.g., nucleic acid or particle described herein. The polymers that may be used in the formulation may include, without limitation, polyethylene glycol (PEG), alginate, agarose, poly(ethylene glycol dimethacrylate), polylactic acid, polyglycolic acid, poly-lactide-co-glycolide, gelatin, collagen, agarose, pectin, poly(lysine), polyhydroxybutyrate, poly-epsilon-caprolactone, polyphosphazines, poly(vinyl alcohol), poly(alkylene oxide), poly(ethylene oxide), poly (allylamine), poly(acrylate), poly(4-aminomethylstyrene), pluronic polyol, polyoxamer, poly(uronic acid), poly(anhydride), poly(vinylpyrrolidone), bolaamphiphiles, glycosylnucleosides, and fluorocarbon chains.

In some embodiments of any of the aspects described herein, nucleic acid or particle described herein is administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control a compound of formula (I)'s onset of action, duration of action, plasma levels within the therapeutic window, and peak blood levels. In particular, controlled- or extended-release dosage forms or formulations can be used to ensure that the maximum effectiveness of an agent is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with any agent described herein. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185, each of which is incorporated herein by reference in their entireties. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, DUO-LITE® A568 and DUOLITE® AP143 (Rohm&Haas, Spring House, Pa. USA).

In some embodiments, any aforementioned polymers, prior to or after loading of the agent, e.g., a nucleic acid or lipid described herein, may be characterized (e.g. size, molecular weight, charge, secondary structure, and purity) by techniques including, but not limited to, gel permeation chromatography, high performance liquid chromatography, ultra-performance liquid chromatography, MALDI-TOF mass spectroscopy, viscometry, and light scattering (e.g. multi-angle, low angle laser).

In some embodiments, the rate of release of the agent, e.g., a nucleic acid or lipid described herein, may be characterized by techniques including, but not limited to, high performance liquid chromatography, ultra-performance liquid chromatography, fast protein liquid chromatography, enzyme linked immunosorbent assay, and ligand binding assay. In some embodiments, the release rate of the agent is measured as the concentration of the agent in any biologically relevant liquid solution or suspension or medium (e.g., saline, mammalian cell culture media, synthetic synovial fluid, synovial fluid, serum, synthetic serum, plasma, synthetic plasma and deionized water) that the formulation is also in. In specific embodiments, the formulation and biologically relevant liquid solution or suspension is maintained at a specific temperature. In specific embodiments, the formulation and biologically relevant liquid solution or suspension is agitated or mixed at a set or varying rate of motion. In specific embodiments, the concentration of the agent released into the biologically relevant liquid solution or suspension is measured using a direct enzyme linked immunosorbent assay. In specific embodiments, the concentration of the agent released into the biologically relevant liquid solution or suspension is measured using an indirect enzyme linked immunosorbent assay. In specific embodiments, the concentration of the agent released into the biologically relevant liquid solution or suspension is measured using a sandwich enzyme linked immunosorbent assay. In a preferred embodiment, the concentration of the agent released into the biologically relevant liquid solution or suspension is measured using the Human Relaxin-2 Quantikine ELISA Kit from Bio-techne corporation.

In some embodiments, the total loaded content of the nucleic acid in lipids (e.g. percent of nucleic acid as weight/volume, percent of nucleic acid as weight/weight) may be characterized by techniques including, but not limited to, mass balance, limited to, high performance liquid chromatography, ultra-performance liquid chromatography, fast protein liquid chromatography, enzyme linked immunosorbent assay, and ligand binding assay. In some embodiments, the formulation may be purified and dissolved to assess total loaded content of the nucleic acid.

In one embodiment of any aspect herein, the formulation is a sustained release formulation.

In one embodiment of any aspect herein, the formulation is a sustained release formulation the nucleic acid is released over an extended period of time.

For the nucleic acid to have a sustained clinical effect, it is physiologically desirable for the temporal concentration of the nucleic acid to be above the minimum effective concentration for a sustained duration.

A constant sustained dose of relaxin may be achieved by the relase of nucleic acid from a lipid with a linear rate of release (i.e., one having no bolus effect or burst-release effect).

In one embodiment of any aspect herein, the formulation is a sustained release formulation the nucleic acid is released over an extended period of least 1 day; or at least 2 days; or at least 3 days; or at least 4 days; or at least 5 days; or at least 6 days; or at least 1 week; or at least 2 weeks; or at least 3 weeks; or at least 4 weeks; or at least 5 weeks, or at least 6 weeks; or at least 8 weeks; or at least 9 weeks; at least 10 weeks; or at least 12 weeks; or at least 15 weeks; or between 1-5 days; or between 2-5 days; or between 1-2 days; or between 2-3 days; or between 3-4 days; or between 4-5 days; or between 3-10 days; or between 1-15 weeks; or between 2-10 weeks; or between 4-8 weeks; or between 8-15 weeks; or about 1 day; or about 2 days; or about 3 days; or about 4 days; or about 5 days; or about 6 days; or about 1 week; or about 2 weeks; or about 3 weeks; or about 4 weeks; or about 5 weeks; or about 6 weeks; or about 7 weeks; or about 8 weeks; or about 9 weeks; or about 10 weeks, or more.

Cells

The disclosure also provides a cell comprising a nucleic acid or particle (e.g., lipid particle) described herein described herein. As used herein, the term "cell" refers to a single cell as well as to a population of (i.e., more than one) cells. A cell can be a prokaryotic or eukaryotic cell. Exemplary cells include, but are not limited to, bacterial cells, yeast cells, plant cell, animal (including insect) or human cells. In some embodiments, the cell is a eukaryotic cell. For example, the cell is a mammalian cell. It is noted a cell can be in vivo, in vitro or ex vivo.

Vectors

In some embodiment of any of the aspects, the nucleic acid described herein can be comprises in a vector. As used herein, a "vector" refers to a compound used as a vehicle to carry foreign genetic material into another cell, where it can be replicated and/or expressed. A cloning vector containing foreign nucleic acid is termed a recombinant vector. Exemplary vectors include, but are not limited to, plasmids, phagemids, bacmids, cosmids, viral vectors, and artificial chromosomes (e.g., bacterial or yeast artificial chromosome). In some embodiments of any one of the aspects described herein, the nucleic acid described herein is a plasmid. In some other embodiments, the nucleic acid described herein is a bacmid. In yet other embodiments, the nucleic acid described herein is a cosmid. Recombinant vectors typically contain an origin of replication, a multi-cloning site, and a selectable marker. The nucleic acid sequence typically consists of an insert (recombinant nucleic acid or transgene) and a larger sequence that serves as the "backbone" of the vector. The purpose of a vector which transfers genetic information to another cell is typically to isolate, multiply, or express the insert in the target cell. Expression vectors (expression constructs) are for the expression of the exogenous gene in the target cell, and generally have a promoter sequence that drives expression of the exogenous gene/ORF. Insertion of a vector into the target cell is referred to transformation or transfection for bacterial and eukaryotic cells, although insertion of a viral vector is often called transduction. The term "vector" may also be used in general to describe items to that serve to carry foreign genetic material into another cell, such as, but not limited to, a transformed cell or a particle, e.g., nanoparticle.

Nucleic Acid Modifications

One or more chemical or nucleic acid modifications can be applied to the nucleic acids described herein. Exemplary nucleic acid modifications include, but are not limited to, nucleobase modifications, sugar modifications, inter-sugar linkage modifications, conjugates (e.g., ligands), and any combinations thereof. Nucleic acid modifications also include unnatural, or degenerate nucleobases.

In some embodiments, a nucleic acid described herein comprises a modified nucleobase. Exemplary modified nucleobases include, but are not limited to, inosine, xanthine, hypoxanthine, nubularine, isoguanosine, tubercidin, and substituted or modified analogs of adenine, guanine, cytosine and uracil, such as 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine,7-deazaadenine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases. Further purines and pyrimidines include those disclosed in U.S. Pat. No. 3,687,808, those disclosed in the Concise Encyclopedia of Polymer Science and Engineering, pages 858-859, Kroschwitz, J. I., ed. John Wiley & Sons, 1990, and those disclosed by Englisch et al., Angewandte Chemie, International Edition, 1991, 30, 613.

In some embodiments, a modified nucleobase can be selected from the group consisting of inosine, xanthine, hypoxanthine, nubularine, isoguanosine, tubercidin, 2-(halo)adenine, 2-(alkyl)adenine, 2-(propyl)adenine, 2-(amino)adenine, 2-(aminoalkyl)adenine, 2-(aminopropyl)adenine, 2-(methylthio)-$N^6$-(isopentenyl)adenine, 6-(alkyl)adenine, 6-(methyl)adenine, 7-(deaza)adenine, 8-(alkenyl)adenine, 8-(alkyl)adenine, 8-(alkynyl)adenine, 8-(amino)adenine, 8-(halo)adenine, 8-(hydroxyl)adenine, 8-(thioalkyl)adenine, 8-(thiol)adenine, $N^6$-(isopentyl)adenine, $N^6$-(methyl)adenine, $N^6$, $N^6$-(dimethyl)adenine, 2-(alkyl)guanine,2-(propyl)guanine, 6-(alkyl)guanine, 6-(methyl)guanine, 7-(alkyl)guanine, 7-(methyl)guanine, 7-(deaza)guanine, 8-(alkyl)guanine, 8-(alkenyl)guanine, 8-(alkynyl)guanine, 8-(amino)guanine, 8-(halo)guanine, 8-(hydroxyl)guanine, 8-(thioalkyl)guanine, 8-(thiol)guanine, N-(methyl)guanine, 2-(thio)cytosine, 3-(deaza)-5-(aza)cytosine, 3-(alkyl)cytosine, 3-(methyl)cytosine, 5-(alkyl)cytosine, 5-(alkynyl)cytosine, 5-(halo)cytosine, 5-(methyl)cytosine, 5-(propynyl)cytosine, 5-(propynyl)cytosine, 5-(trifluoromethyl)cytosine, 6-(azo)cytosine, $N^4$-(acetyl)cytosine, 3-(3-amino-3-carboxypropyl)uracil, 5-ethynyl-2'-deoxyuridine, 2-(thio)uracil,5-(methyl)-2-(thio)uracil, 5-(methylaminomethyl)-2-(thio)uracil, 4-(thio)uracil, 5-(methyl)-4-(thio)uracil, 5-(methylaminomethyl)-4-(thio)uracil, 5-(methyl)-2,4-(dithio)uracil, 5-(methylaminomethyl)-2,4-(dithio)uracil, 5-(2-aminopropyl)uracil, 5-(alkyl)uracil, 5-(alkynyl)uracil, 5-(allylamino)uracil, 5-(aminoallyl)uracil, 5-(aminoalkyl)uracil, 5-(guanidiniumalkyl)uracil, 5-(1,3-diazole-1-alkyl)uracil, 5-(cyanoalkyl)uracil, 5-(dialkylaminoalkyl)uracil, 5-(dimethylaminoalkyl)uracil, 5-(halo)uracil, 5-(methoxy)uracil, uracil-5-oxyacetic acid, 5-(methoxycarbonylmethyl)-2-(thio)uracil, 5-(methoxycarbonyl-methyl)uracil, 5-(propynyl)uracil, 5-(propynyl)uracil, 5-(trifluoromethyl)uracil, 6-(azo)uracil, dihydrouracil, $N^3$-(methyl)uracil, 5-uracil (i.e., pseudouracil), 2-(thio)pseudouracil,4-(thio)pseudouracil,2,4-(dithio)psuedouracil,5-(alkyl)pseudouracil, 5-(methyl)pseudouracil, 5-(alkyl)-2-(thio)pseudouracil, 5-(methyl)-2-(thio)pseudouracil, 5-(alkyl)-4-(thio)pseudouracil, 5-(methyl)-4-(thio)pseudouracil, 5-(alkyl)-2,4-(dithio)pseudouracil, 5-(methyl)-2,4-(dithio)pseudouracil, 1-substituted pseudouracil, 1-substituted 2-(thio)-pseudouracil, 1-substituted 4-(thio)pseudouracil, 1-substituted 2,4-(dithio)pseudouracil, 1-(aminocarbonylethylenyl)-pseudouracil, 1-(aminocarbonylethylenyl)-2-(thio)-pseudouracil, 1-(aminocarbonylethylenyl)-4-(thio)pseudouracil, 1-(aminocarbonylethylenyl)-2,4-(dithio)pseudouracil, 1-(aminoalkylaminocarbonylethylenyl)-pseudouracil, 1-(aminoalkylamino-carbonylethylenyl)-2-(thio)-pseudouracil, 1-(aminoalkylaminocarbonylethylenyl)-4-(thio)pseudouracil, 1-(aminoalkylaminocarbonylethylenyl)-2,4-(dithio)pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkyl-hydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidin, isoguanosine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenyl, tetracenyl, pentacenyl, difluorotolyl, 4-(fluoro)-6-(methyl)benzimidazole, 4-(methyl)benzimidazole, 6-(azo) thymine, 2-pyridinone, 5-nitroindole, 3-nitropyrrole, 6-(aza) pyrimidine, 2-(amino)purine, 2,6-(diamino)purine, 5-substituted pyrimidines, $N^2$-substituted purines, $N^6$-substituted purines, $O^6$-substituted purines, substituted 1,2,4-triazoles, and any O-alkylated or N-alkylated derivatives thereof.

In some embodiments, a nucleic acid modification can include a non-natural or modified nucleobase.

In some embodiments, a nucleic acid described herein comprises at least one sugar modified nucleotide. Exemplary sugar modified nucleotides include, but are not limited to, 2'-O-methyl (2'-OMe) nucleotides, 2'-fluoro (2'-F) nucleotides, 3'-fluoro nucleotides, 3'-OMe nucleotides, bridged nucleic acid (BNA) nucleotides (e.g., 2'-O,4'-C-methylene (locked nucleic acid, LNA) nucleotides, 2'-O,4'-C-ethylene (locked nucleic acid, ENA) nucleotides, 5'-methyl-BNA, cEt BNA, cMOE BNA, oxy amino BNA and vinyl-carbo BNA), anhydrohexitol (1,5-anhydrohexitol nucleic acid, HNA) nucleotides, cyclohexene (Cyclohexene nucleic acid, CeNA) nucleotides, 2'-methoxyethyl (2'-MOE) nucleotides, 2'-O-allyl nucleotides, 2'-C-allyl ribose nucleotides, 2'-O—N-methylacetamido (2'-O-NMA) nucleotides, a 2'-O-dimethylaminoethoxyethyl (2'-O-DMAEOE) nucleotides, 2'-O-aminopropyl (2'-O-AP) nucleotides, 2'-F arabinose (2'-ara-F) nucleotides, threose (Threose nucleic acid, TNA) nucleotides, and acyclic nucleotides (e.g., peptide nucleic acid (PNA), unlocked nucleic acids (UNA), 2,3-dihydroxylpropyl (glycol nucleic acid, GNA)), and 2'-deoxy (2'-H); a modified internucleoside linkage; a non-natural or modified nucleobase; or a combination thereof.

In some embodiments, a sugar modified nucleotides can be a 2'-OMe nucleotide, 2'-F nucleotide, 2'-MOE nucleotide, BNA (e.g., LNA or ENA) nucleotide, UNA nucleotide, GNA nucleotide, A nucleic acid modification can include replacement or modification of an inter-sugar linkage, i.e., a modified internucleoside linkage. Thus, in some embodiments, a nucleic acid described herein comprises at least one modified internucleoside linkage. Exemplary inter-sugar linkage modifications include, but are not limited to, phosphotriesters, methylphosphonates, phosphoramidate, phosphorothioates, methylenemethylimino, thiodiester, thionocarbamate, siloxane, N,N'-dimethylhydrazine (—CH2-N(CH3)-N(CH3)-), amide-3 (3'-CH$_2$—C(=O)—N(H)-5') and amide-4 (3'-CH$_2$—N(H)—C(=O)-5'), hydroxylamino, siloxane (dialkylsiloxane), carboxamide, carbonate, carboxymethyl, carbamate, carboxylate ester, thioether, ethylene oxide linker, sulfide, sulfonate, sulfonamide, sulfonate ester, thioformacetal (3'-S—CH$_2$—O-5'), formacetal (3'—O—CH$_2$—O-5'), oxime, methyleneimino, methylenecarbonylamino, methylenemethylimino (MMI, 3'-CH$_2$—N(CH$_3$)—O-5'), methylenehydrazo, methylenedimethylhydrazo, methyleneoxymethylimino, ethers (C3'—O—C5'), thioethers (C3'—S—C5'), thioacetamido (C3'—N(H)—C(=O)—CH$_2$—S—C5', C3'—O—P(O)—O—SS—C5', C3'—CH$_2$—NH—NH—C5', 3'—NHP(O)(OCH$_3$)—O-5' and 3'-NHP(O)(OCH$_3$)—O-5').

Backbone modifications such as phosphorothioates modify the charge on the phosphate backbone and can aid in the delivery and nuclease resistance of the oligonucleotide (see, e.g., Eckstein, "Phosphorothioates, essential components of therapeutic oligonucleotides," Nucl. Acid Ther., 24 (2014), pp. 374-387). Modifications of sugars, such as 2'-O-methyl (2'-OMe), 2'-F, and locked nucleic acid (LNA), can enhance both base pairing and nuclease resistance (see, e.g., Allerson et al., "Fully 2'-modified oligonucleotide duplexes with improved in vitro potency and stability compared to unmodified small interfering RNA," J Med. Chem., 48.4 (2005): 901-904). Chemically modified bases such as 2-thiouridine or N6-methyladenosine, among others, can allow for either stronger or weaker base pairing (see, e.g., Bramsen et al., "Development of therapeutic-grade small interfering RNAs by chemical engineering," Front. Genet. 2012 Aug. 20; 3: 154). Additionally, the guide nucleic acid is amenable to both 5' and 3' end conjugations with a variety of functional moieties including, but not limited to, targeting ligands, fluorescent dyes, polyethylene glycol, or proteins.

In some embodiments of any one of the aspects described herein, each modified internucleoside linkage can be selected independently from the group consisting of phosphorothioates (R, S, or racemic), phosphorodithioates, methylenemethylimino (MMI, 3'-CH$_2$—N(CH$_3$)—O-5'), phosphotriesters, alkylphosphonates (e.g., methylphosphonates), phosphoramidate, methylenemethylimino (—CH$_2$—N(CH$_3$)—O—CH$_2$—), thiodiester (—O—C(O)—S—), thionocarbamate (—O—C(O)(NH)—S—), siloxane (—O—Si(H)$_2$—O— and dialkylsiloxane), N,N'-dimethylhydrazine (—CH$_2$—N(CH$_3$)—N(CH$_3$)—), amide-3 (3'-CH$_2$—C(=O)—N(H)-5'), amide-4 (3'-CH$_2$—N(H)—C(=O)-5')), hydroxylamino, siloxane (dialkylsiloxane), carboxamide, carbonate, carboxymethyl, carbamate, carboxylate ester, thioether, ethylene oxide linker, sulfide, sulfonate, sulfonamide, sulfonate ester, thioformacetal (3'-S—CH$_2$—O-5'), formacetal (3'—O—CH$_2$—O-5'), oxime, methyleneimino, methykenecarbonylamino, methylenehydrazo, methylenedimethylhydrazo, methyleneoxymethylimino, ethers (C3'—O—C5'), thioethers (C3'—S—C5'), thioacetamido (C3'—N(H)—C(=O)—CH$_2$—S—C5', C3'—O—P(O)—O—SS—C5'), C3'—CH$_2$—NH—NH—CS', 3'-NHP(O)(OCH$_3$)—O-5', 3'—NHP(O)(OCH$_3$)—O-5'), 2'→5' internucleoside linkages, 2'→3' internucleoside linkages, 3'→3' internucleoside linkages, and 5'→5' internucleoside linkages.

In some embodiments, a nucleic acid described herein comprises at least one uridine nucleotide that is modified. For example, 75-100% of uridine nucleotides in the nucleic acid are modified.

In some embodiments, a nucleic acid described herein comprises at least one nucleoside modification is selected from the group consisting of pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

Treatment of Diseases or Disorders

The nucleic acids described herein or the particles and compositions comprising same are useful in activating signaling pathways, e.g., in a cell. The term "signaling pathway" as used herein refers to a series of interactions between cellular and optionally extra-cellular components that conveys a change in one component to one or more other components, which in turn may convey a change to additional components, which is optionally propagated to other signaling pathway components. As used herein, a particular "signaling pathway" may be named according to the cell surface receptor that triggers the cascade of intracellular signaling or according to any of the components involved in the intracellular signaling. For example, binding of EGF to EGFR initiates signaling pathway activation that can include MAPK and/or PI3K. Thus, the terms "EGFR signaling pathway", "MAPK signaling pathway" and "PI3K signaling" pathway each can be used to encompass the signaling pathway that is initiated by binding of EGF to EGFR.

Accordingly, in another aspect provided herein is a method for activating a signaling patheay in a cell. The method comrpsies administering to the cell a nucleic acid described herein or a particle or composition comprising same. It is noted that the cell in which the signaling pathway is activated can be in vitro, in vivo or ex vivo. When the cell is in vivo, the method comprises admiistering a nucleic acid described herein or a particle or composition comprising same to the subject.

Without wishing to be bound by a theory, activating a partial or complete signaling pathway biological effect (e.g., therapeutic effect) of the signaling pathway can be amplified and can become cell-type or disease-state independent. In other words, activating the signaling pathway results in a therapeutic effect. Exemplary therapeutic effects due to activating a signaling pathway include, but are not limited to, antifibrotic, vasodilatory, hemodynamic, angiogenic, apoptotic, antiviral, increases cell proliferation, antifibrogenic, cytotoxic, proliferative, regenerative, immunomodulatory, regulates cell cycle or results in epigenetic alterations. Accordingly, nucleic acids described herein or the particles and compositions comprising same are also useful for treating a disease or disorder in a subject. Accoridngly, in another aspect provided a method for treating a disease or disorder in a subject. The method comprises administering an effective amount of a nucleic acid described herein or a particle or composition comprising same to a subject in need thereof.

Examplry dieseses and disorders include, but are not limited to osteoarthritis, autism, diabetes mellitus, a central nervous system disorder, a developmental disorder, a neuromuscular disorder, diabetic neuropathy, ischemia-reperfusion injuries, chronic heart failure, a chronic wasting disease, cancer cachexia, arthrofibrosis, a cardiovascular disease, an interstitial pulmonary disease, systemic sclerosis, a vascular disease, and hypertrophic, keloid scars, Duchenne Muscular Dystrophy, Becker Muscular Dystrophy, stroke, traumatic brain injury, peripheral nerve injury, Spinal Muscular Atrophy (Type I, II, III, or IV), Cerebral Palsy, Arthrogryposis Multiplex Congenita, fibrosis of the humeroradial joint, fibrosis of the humeroulnar joint, fibrosis of the glenohumeral joint, fibrosis of the tibiofemoral joint, fibrosis of the acetabulofemoral joint, fibrosis of the talocrural joint, fibrosis of the temporomandibular joint, fibrosis of the metacarpophalangeal joint, fibrosis of the metatarsophalangeal joint, fibrosis of the peri-articular musculature, cellulite, or interstitial lung disease. In some embodiments, the disease or disorder is selected from the group consisting of osteoarthritis; autism; diabetes mellitus; a central nervous system disorder; a developmental disorder; a neuromuscular disorder; diabetic neuropathy; ischemia-reperfusion injuries; chronic heart failure; a chronic wasting disease; and cancer cachexia. In some embodiments, the disease or disorder is selected from the group consisting of arthrofibrosis, a cardiovascular disease, an interstitial pulmonary disease, systemic sclerosis, a vascular disease, and hypertrophic or keloid scars.

In one embodiment, the ligand is relaxin-2, the target molecule is RXFP1, and the disease or disorder to be treated is selected from the group consisting of arthrofibrosis, a cardiovascular disease, an interstitial pulmonary disease, systemic sclerosis, a vascular disease, and hypertrophic or keloid scars.

In one embodiment, the ligand is IGF-1, the translated target is Pappalysin-1, Pappalysin-2, or IGF-1R, and the disease or disorder to be treated is selected from the group consisting of osteoarthritis; autism; diabetes mellitus; a central nervous system disorder; a developmental disorder; a neuromuscular disorder; diabetic neuropathy; ischemia-reperfusion injuries; chronic heart failure; a chronic wasting disease; and cancer cachexia.

In one embodiment, the subject has or is diagnosed with osteoarthritis, autism, diabetes mellitus, a central nervous system disorder, a developmental disorder, a neuromuscular disorder, diabetic neuropathy, ischemia-reperfusion injuries, chronic heart failure, a chronic wasting disease, cancer cachexia, arthrofibrosis, a cardiovascular disease, an interstitial pulmonary disease, systemic sclerosis, a vascular disease, and hypertrophic, keloid scars, Duchenne Muscular Dystrophy, Becker Muscular Dystrophy, stroke, traumatic brain injury, peripheral nerve injury, Spinal Muscular Atrophy (Type I, II, III, or IV), Cerebral Palsy, Arthrogryposis Multiplex Congenita, fibrosis of the humeroradial joint, fibrosis of the humeroulnar joint, fibrosis of the glenohumeral joint, fibrosis of the tibiofemoral joint, fibrosis of the acetabulofemoral joint, fibrosis of the talocrural joint, fibrosis of the temporomandibular joint, fibrosis of the metacarpophalangeal joint, fibrosis of the metatarsophalangeal joint, fibrosis of the peri-articular musculature, cellulite, or interstitial lung disease.

In one embodiment, administering is via inhalation as an aerosol. In one embodiment, administering is via intraarticular injection. In one embodiment, administering is via intramuscular injection. In one embodiment, administering is via intradermal injection. In one embodiment, administering is via subcutaneous injection. In one embodiment, administering is via intracapsular injection. In one embodiment, administering is via pericapsular injection. In one embodiment, administering is via musculotendinous injection. In one embodiment, administering is via intraligamentous injection. In one embodiment, administering is via periligamentous injection. In one embodiment, administering is via intratendinous injection. In one embodiment, administering is via peritendinous injection. In one embodiment, administering is via intraosteotendinous injection. In one embodiment, administering is via periosteotendinous injection.

In one embodiment, the disease is Duchene's muscular dystrophy and said administering is via intramuscular injection. In one embodiment, the disease is Duchene's muscular dystrophy and said administering is via intraarticular injection. In one embodiment, the disease is Becker's muscular dystrophy and said administering is via intramuscular injection. In one embodiment, the disease is Becker's muscular dystrophy and said administering is via intraarticular injection. In one embodiment, the disease is Spinal Muscular Dystrophy and said administering is via intramuscular injection. In one embodiment, the disease is Spinal Muscular Dystrophy and said administering is via intraarticular injection. In one embodiment, the disease is Arthrogryposis Multiplex Congenita and said administering is via intramuscular injection. In one embodiment, the disease is Arthrogryposis Multiplex Congenita and said administering is via intraarticular injection. In one embodiment, the disease is Cerebral Palsy and said administering is via intramuscular injection. In one embodiment, the disease is Cerebral Palsy and said administering is via intraarticular injection. In one embodiment, the disease is stroke and said administering is via intramuscular injection. In one embodiment, the disease is stroke and said administering is via intraarticular injection. In one embodiment, the disease is traumatic brain injury and said administering is via intramuscular injection. In one embodiment, the disease is traumatic brain injury and said administering is via intraarticular injection. In one embodiment, the disease is peripheral nerve injury and said administering is via intramuscular injection. In one embodiment, the disease is peripheral nerve injury and said administering is via intraarticular injection.

In some embodiments, a nucleic acid as described herein or a particle or composition comprising same is administered to a subject. In some embodiments, a nucleic acid as described herein or a particle or composition comprising same is used to treat an organ or location on the body of a subject, a disease or indication in a subject and or using an administration route as described in Table 3 and/or Table 4.

TABLE 3

| Administration routes and targets | Sites (non-joints) | Lung, kidney, liver, heart, skin, eye; tendons, osteotendinous junctions, tendon-bone interfaces, entheses, or muscle-tendon insertions, mentioning a slew of tendons throughout the body |
|---|---|---|
| | Sites (joints) | Jaw, spine, shoulder, elbow, wrist, hand, finger, hip, knee, ankle, foot, toe; or any other synovial or non-synovial joint |
| | Routes of administration | JOINT INJECTIONS (JI): Intraarticular, periarticular, intracapsular, pericapsular NON-JOINT DENSE CONNECTIVE TISSUE INJECTIONS (NJDCTI): intraligamentous, periligamentous, intratendinous, peritendinous, intraosteotendinous, or periosteotendinous; intramusculotendinous, perimusculotendinous, perimuscularly, OTHER, NON-ORTHOPEDIC: intravenously, intramuscularly, subcutaneously, intradermally, intranasally, orally, transcutaneously (ionto/electrophoresis), mucosally, gel, cream, ointment, lotion, drop, suppository, spray, liquid, powder, pulmonary inhalation, ocular. |
| Indications | When to administer treatment | During or just after a medical procedure; for patients with stiffened joint or at risk for stiffened joint (treatment or prophylactic) |

TABLE 4

| General causes of fibrosis | Idiopathic, injury (trauma, medical procedure e.g. surgery), immobility for whatever reason, inflammation, or disease/medical condition |
|---|---|
| Diseases/conditions: joints (admin via joint injection) | adhesive capsulitis (injury, idiopathic, post-surgical, post-implant) |
| Diseases/conditions: lung (admin via inhalation) | idiopathic pulmonary fibrosis, cystic fibrosis, hypertension |
| Diseases/conditions: liver | hepatitis B or C, long-term alcohol abuse, non-alcoholic steatohepatitis, non-alcoholic fatty liver disease, Cholestasis, autoimmune hepatitis cirrhosis |

TABLE 4-continued

| | |
|---|---|
| Diseases/conditions: kidney | chronic kidney disease, end-stage renal disease, renal interstitial fibrosis |
| Diseases/conditions: heart | heart failure, myocardial infarction, aortic stenosis, hypertrophic cardiomyopathy |
| Diseases/conditions: intestine | Crohn's disease, inflammatory bowel disease, enteropathies |
| Diseases/conditions: skin (admin via intradermal injection, or transdermal) | scleroderma, keloids, hypertrophic scars, cellulite |
| Diseases/conditions: urogenital/gynecological | Peyronie's disease, uterine fibroids, urethral strictures |
| Diseases/conditions: ocular | Congenital Fibrosis of the Extraocular Muscles, subretinal fibrosis, epiretinal fibrosis, corneal fibrosis |
| Diseases/conditions: connective tissue, fascia | Dupuytren's disease, capsular contracture of breast, Plantar fibromatosis, |
| Diseases/conditions: neuromuscular (admin via joint or peri-joint injection) | Duchenne, Becker, congenital, and other muscular dystrophies, SMA, Charcot-Marie-Tooth, arthrogryposis, ALS, club foot, post-polio, CP. |

In some embodiments, a method is provided in which the method involves identifying a subject diagnosed with one or more diseases selected from the group of diseases listed in Table 3 or Table 4 and administering a nucleic acid described herein or a particle or composition comprising same to the subject. In some embodiments, a method is provided in which the method involves identifying a subject diagnosed with one or more diseases selected from the group of diseases consisting of Duchenne Muscular Dystrophy, Becker Muscular Dystrophy, Spinal Muscular Atrophy-Type I, Spinal Muscular Atrophy-Type II, Spinal Muscular Atrophy-Type III, Spinal Muscular Atrophy-Type IV, Cerebral Palsy, Stroke, Traumatic Brain Injury, peripheral nerve injury, and Arthrogryposis Multiplex Congenita, fibrosis of the humeroradial joint, fibrosis of the humeroulnar joint, fibrosis of the glenohumeral joint, fibrosis of the tibiofemoral joint, fibrosis of the acetabulofemoral joint, fibrosis of the talocrural joint, fibrosis of the temporomandibular joint, fibrosis of the metacarpophalangeal joint, fibrosis of the metatarsophalangeal joint, fibrosis of the peri-articular musculature and cellulite and administering to said patient a nucleic acid described herein or a particle or composition comprising same.

Methods for Treating a Stiffened Joint

Some aspects of the present invention provide methods for treating or preventing a stiffened joint. As used herein, the terms "treating", "treat" or "treatment" refer to a beneficial or desired result including, but not limited to, alleviation or amelioration of one or more symptoms associated with a stiffened joint (e.g., pain on movement of the joint, loss of motion of the joint or loss of the range of motion of the joint); diminishing the restriction of movement resulting from a stiffened joint; stabilization (i.e., not worsening) of the joint stiffness; amelioration or palliation of the restriction of movement resulting from a stiffened joint (e.g., pain on movement of the joint, loss of motion of the joint or loss of the range of motion of the joint) whether detectable or undetectable.

In some embodiments, methods of the present invention result in a treatment of the stiffened joint, such that pain on movement of the joint is reduced, e.g., by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or more, and is preferably down to a level accepted within the range of normal for an individual who is not affected by a stiffened joint.

In some embodiments, methods of the present invention result in restoration of the movement, or a range of the movement, of a joint affected by joint stiffness. For example, treatment of the stiffened joint according to the methods of the invention may result in restoration of the movement, or a range of movement, of a joint affected by joint stiffness, to levels that are at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or 100% of the levels accepted within the range of normal for an individual not affected by a stiffened joint.

In some embodiments, prevention or treatment of a stiffened joint in a subject provided by the methods of the present invention is accomplished without significant adverse events, without significant damage to collagenous structures or tissues in the subject, e.g., collagenous structures or tissues of the joint, such as articular cartilage of the joint. For example, methods of the present invention provide prevention and treatment of stiffened joint that do not disrupt architecture of the joint. Damage to collagenous structures in the body, e.g., collagenous structures of a joint, may be assessed by methods known in the art, e.g., by measuring levels of various markers in the synovial fluid, such as Cartilage Oligomeric Matrix Protein (COMP), aggrecans, collagen II, proteoglycans, MMPs and inflammatory mediators and cytokines. Imaging techniques such as MRI can also be used to visualize the joint and the cartilage architecture.

One aspect provided herein is a method, said method comprising identifying a subject diagnosed with one or more diseases selected from the group of diseases listed in Table 3 or Table 4 and administering a nucleic acid described herein or a particle (e.g., lipid particle) or composition comprising same to the subject.

Another aspect provided herein is a method, said method comprising identifying a subject diagnosed with Duchenne Muscular Dystrophy and administering to said patient a nucleic acid described herein or a particle (e.g., lipid particle) or composition comprising same.

Another aspect provided herein is a method, said method comprising identifying a subject diagnosed with Becker Muscular Dystrophy and administering to said patient a nucleic acid described herein or a particle (e.g., lipid particle) or composition comprising same.

Another aspect provided herein is a method, said method comprising identifying a subject diagnosed with Spinal Muscular Atrophy, Type I, and administering to said patient a nucleic acid described herein or a particle (e.g., lipid particle) or composition comprising same.

Another aspect provided herein is a method, said method comprising identifying a subject diagnosed with Spinal Muscular Atrophy, Type II, and administering to said patient a nucleic acid described herein or a particle (e.g., lipid particle) or composition comprising same.

Another aspect provided herein is a method, said method comprising identifying a subject diagnosed with Spinal Muscular Atrophy, Type III, and administering to said patient a nucleic acid described herein or a particle (e.g., lipid particle) or composition comprising same.

Another aspect provided herein is a method, said method comprising identifying a subject diagnosed with Spinal Muscular Atrophy, Type IV, and administering to said patient a nucleic acid described herein or a particle (e.g., lipid particle) or composition comprising same.

Another aspect provided herein is a method, said method comprising identifying a subject diagnosed with Cerebral Palsy and administering to said patient a nucleic acid described herein or a particle (e.g., lipid particle) or composition comprising same.

Another aspect provided herein is a method, said method comprising identifying a subject diagnosed with Arthrogryposis Multiplex Congenita and administering to said patient a nucleic acid described herein or a particle (e.g., lipid particle) or composition comprising same.

Another aspect provided herein is a method, said method comprising identifying a subject with fibrosis of the humeroradial joint and administering to said patient a nucleic acid described herein or a particle (e.g., lipid particle) or composition comprising same.

Another aspect provided herein is a method, said method comprising identifying a subject with fibrosis of the humeroulnar joint and administering to said patient a nucleic acid described herein or a particle (e.g., lipid particle) or composition comprising same.

Another aspect provided herein is a method, said method comprising identifying a subject with fibrosis of the glenohumeral joint and administering to said patient a nucleic acid described herein or a particle (e.g., lipid particle) or composition comprising same.

Another aspect provided herein is a method, said method comprising identifying a subject with fibrosis of the tibiofemoral joint and administering to said patient a nucleic acid described herein or a particle (e.g., lipid particle) or composition comprising same.

Another aspect provided herein is a method, said method comprising identifying a subject with fibrosis of the acetabulofemoral joint and administering to said patient a nucleic acid described herein or a particle (e.g., lipid particle) or composition comprising same.

Another aspect provided herein is a method, said method comprising identifying a subject with fibrosis of the talocrural joint and administering to said patient a nucleic acid described herein or a particle (e.g., lipid particle) or composition comprising same.

Another aspect provided herein is a method, said method comprising identifying a subject with fibrosis of the temporomandibular joint and administering to said patient a nucleic acid described herein or a particle (e.g., lipid particle) or composition comprising same.

Another aspect provided herein is a method, said method comprising identifying a subject with fibrosis of the metacarpophalangeal joint and administering to said patient a nucleic acid described herein or a particle (e.g., lipid particle) or composition comprising same.

Another aspect provided herein is a method, said method comprising identifying a subject with fibrosis of the metatarsophalangeal joint and administering to said patient a nucleic acid described herein or a particle (e.g., lipid particle) or composition comprising same.

Another aspect provided herein is a method, said method comprising identifying a subject with fibrosis of the periarticular musculature and administering to said patient a nucleic acid described herein or a particle (e.g., lipid particle) or composition comprising same.

Another aspect provided herein is a method, said method comprising identifying a subject with cellulite and administering to said patient a nucleic acid described herein or a particle (e.g., lipid particle) or composition comprising same.

Another aspect provided herein is a method, said method comprising identifying a subject with interstitial lung disease and administering to said patient a nucleic acid described herein or a particle (e.g., lipid particle) or composition comprising same.

Another aspect provided herein is a method, said method comprising administering, to any of the preceding subjects, a nucleic acid described herein or a particle (e.g., lipid particle) or composition comprising same, via inhalation as an aerosol.

Another aspect provided herein is a method, said method comprising administering, to any of the preceding subjects, a nucleic acid described herein or a particle (e.g., lipid particle) or composition comprising same, via intra-articular injection.

Another aspect provided herein is a method, said method comprising administering, to any of the preceding subjects, a nucleic acid described herein or a particle (e.g., lipid particle) or composition comprising same, via intramuscular injection.

Another aspect provided herein is a method, said method comprising administering, to any of the preceding subjects, a nucleic acid described herein or a particle (e.g., lipid particle) or composition comprising same, via intradermal injection.

Another aspect provided herein is a method, said method comprising administering, to any of the preceding subjects, a nucleic acid described herein or a particle (e.g., lipid particle) or composition comprising same, via subcutaneous injection.

Another aspect provided herein is a method, said method comprising administering, to any of the preceding subjects, a nucleic acid described herein or a particle (e.g., lipid particle) or composition comprising same, via intracapsular injection.

Another aspect provided herein is a method, said method comprising administering, to any of the preceding subjects, a nucleic acid described herein or a particle (e.g., lipid particle) or composition comprising same, via pericapsular injection.

Another aspect provided herein is a method, said method comprising administering, to any of the preceding subjects, a nucleic acid described herein or a particle (e.g., lipid particle) or composition comprising same, via intraligamentous injection.

Another aspect provided herein is a method, said method comprising administering, to any of the preceding subjects, a c nucleic acid described herein or a particle (e.g., lipid particle) or composition comprising same, via periligamentous injection.

Another aspect provided herein is a method, said method comprising administering, to any of the preceding subjects, a nucleic acid described herein or a particle (e.g., lipid particle) or composition comprising same, via intratendinous injection.

Another aspect provided herein is a method, said method comprising administering, to any of the preceding subjects, a nucleic acid described herein or a particle (e.g., lipid particle) or composition comprising same, via peritendinous injection.

Another aspect provided herein is a method, said method comprising administering, to any of the preceding subjects, a nucleic acid described herein or a particle (e.g., lipid particle) or composition comprising same, via intramusculotendinous injection.

Another aspect provided herein is a method, said method comprising administering, to any of the preceding subjects, a nucleic acid described herein or a particle (e.g., lipid particle) or composition comprising same, via perimusculotendinous injection.

Another aspect provided herein is a method, said method comprising administering, to any of the preceding subjects, a nucleic acid described herein or a particle (e.g., lipid particle) or composition comprising same, via intraosteotendinous injection.

Another aspect provided herein is a method, said method comprising administering, to any of the preceding subjects, a nucleic acid described herein or a particle (e.g., lipid particle) or composition comprising same, via periosteotendinous injection.

Another aspect provided herein is a method, said method comprising administering, to a subject diagnosed with Duchene's muscular dystrophy, a nucleic acid described herein or a particle (e.g., lipid particle) or composition comprising same, via intramuscular injection.

Another aspect provided herein is a method, said method comprising administering, to a subject diagnosed with Duchene's muscular dystrophy, a nucleic acid described herein or a particle (e.g., lipid particle) or composition comprising same, via intraarticular injection.

Another aspect provided herein is a method, said method comprising administering, to a subject diagnosed with Becker's muscular dystrophy, a nucleic acid described herein or a particle (e.g., lipid particle) or composition comprising same, via intramuscular injection.

Another aspect provided herein is a method, said method comprising administering, to a subject diagnosed with Becker's muscular dystrophy, a nucleic acid described herein or a particle (e.g., lipid particle) or composition comprising same, via intraarticular injection Another aspect provided herein is a method, said method comprising administering, to a subject diagnosed with Spinal Muscular Dystrophy, a nucleic acid described herein or a particle (e.g., lipid particle) or composition comprising same, via intramuscular injection.

Another aspect provided herein is a method, said method comprising administering, to a subject diagnosed with Spinal Muscular Dystrophy, a nucleic acid described herein or a particle (e.g., lipid particle) or composition comprising same, via intraarticular injection.

Another aspect provided herein is a method, said method comprising administering, to a subject diagnosed with Arthrogryposis Multiplex Congenita, a nucleic acid described herein or a particle (e.g., lipid particle) or composition comprising same, via intramuscular injection.

Another aspect provided herein is a method, said method comprising administering, to a subject diagnosed with Arthrogryposis Multiplex Congenita, a nucleic acid described herein or a particle (e.g., lipid particle) or composition comprising same, via intraarticular injection.

Another aspect provided herein is a method, said method comprising administering, to a subject diagnosed with Cerebral Palsy, a nucleic acid described herein or a particle (e.g., lipid particle) or composition comprising same, via intramuscular injection.

Another aspect provided herein is a method, said method comprising administering, to a subject diagnosed with Stroke, nucleic acid described herein or a particle (e.g., lipid particle) or composition comprising same, via intramuscular injection.

Another aspect provided herein is a method, said method comprising administering, to a subject diagnosed with Stroke, a nucleic acid described herein or a particle (e.g., lipid particle) or composition comprising same, via intraarticular injection.

Another aspect provided herein is a method, said method comprising administering, to a subject diagnosed with Traumatic Brain Injury, a nucleic acid described herein or a particle (e.g., lipid particle) or composition comprising same, via intramuscular injection.

Another aspect provided herein is a method, said method comprising administering, to a subject diagnosed with Traumatic Brain Injurt, a nucleic acid described herein or a particle (e.g., lipid particle) or composition comprising same, via intraarticular injection.

Another aspect provided herein is a method, said method comprising administering, to a subject diagnosed with Peripheral Nerve Injury, a nucleic acid described herein or a particle (e.g., lipid particle) or composition comprising same, via intramuscular injection.

Another aspect provided herein is a method, said method comprising administering, to a subject diagnosed with Peripheral Nerve Injury, a nucleic acid described herein or a particle (e.g., lipid particle) or composition comprising same, via intraarticular injection.

Another aspect provided herein is a method, said method comprising administering, to a subject diagnosed with Cerebral Palsy, a nucleic acid described herein or a particle (e.g., lipid particle) or composition comprising same, via intraarticular injection.

Another aspect provided herein is a method, said method comprising administering a particle (e.g., a lipid particle) comprising a nucleic acid described herein with sizes between 1 um-10 µm via inhalation as an aerosol.

Another aspect provided herein is a method, said method comprising administering a particle (e.g., a lipid particle) comprising a nucleic acid described herein with sizes between 20 um-100 µm via intramuscular injection.

Another aspect provided herein is a method, said method comprising administering a particle (e.g., a lipid particle) comprising a nucleic acid described herein with sizes between 5 um-50 µum via intraarticular injection.

Another aspect provided herein is a method, said method comprising administering, to a subject diagnosed with interstitial lung disease a nucleic acid described herein or a particle or composition comprising same via inhalation as an aerosol.

Another aspect provided herein is a method, said method comprising administering, to a subject diagnosed with interstitial lung disease a nucleic acid described herein or a particle or composition comprising same via inhalation as an aerosol.

Another aspect provided herein is a method, said method comprising administering, to a subject diagnosed with interstitial lung disease a particle (e.g., a lipid particle) comprising a nucleic acid described herein, wherein the diameter of the particle is 1-10 µm, via inhalation as an aerosol.

Another aspect provided herein is a method, said method comprising administering, to a subject diagnosed with Duchene's Muscular Dystrophy a particle (e.g., a lipid particle) comprising a nucleic acid described herein, wherein the diameter of the particle is 10-30 µm, via intraarticular injection.

Another aspect provided herein is a method, said method comprising administering, to a subject diagnosed with Duchene's Muscular Dystrophy any of the preceding embodiments, wherein the diameter of the microparticle is 25-50 µm, via intraarticular injection.

Another aspect provided herein is a method, said method comprising administering, to a subject diagnosed with Duchene's Muscular a particle (e.g., a lipid particle) comprising a nucleic acid described herein, wherein the diameter of the particle is 10-30 µm, via intramuscular injection.

Another aspect provided herein is a method, said method comprising administering, to a subject diagnosed with Duchene's Muscular Dystrophy a particle (e.g., a lipid particle) comprising a nucleic acid described herein, wherein the diameter of the particle is 25-50 µm, via intramuscular injection.

Another aspect provided herein is a method, said method comprising administering, to a subject diagnosed with Spinal Muscular Atrophy a particle (e.g., a lipid particle) comprising a nucleic acid described herein, wherein the diameter of the particle is 10-30 µm, via intraarticular injection.

Another aspect provided herein is a method, said method comprising administering, to a subject diagnosed with Spinal Muscular Atrophy a particle (e.g., a lipid particle) comprising a nucleic acid described herein, wherein the diameter of the particle is 25-50 µm, via intraarticular injection.

Another aspect provided herein is a method, said method comprising administering, to a subject diagnosed with Spinal Muscular Atrophy a particle (e.g., a lipid particle) comprising a nucleic acid described herein, wherein the diameter of the particle is 10-30 µm, via intramuscular injection.

Another aspect provided herein is a method, said method comprising administering, to a subject diagnosed with Spinal Muscular Atrophy a particle (e.g., a lipid particle) comprising a nucleic acid described herein, wherein the diameter of the particle is 25-50 µm, via intramuscular injection.

Another aspect provided herein is a method, said method comprising administering, to a subject diagnosed with joint arthrofibrosis a particle (e.g., a lipid particle) comprising a nucleic acid described herein, wherein the diameter of the particle is 10-30 µm, via intraarticular injection.

Another aspect provided herein is a method, said method comprising administering, to a subject diagnosed with joint arthrofibrosis a particle (e.g., a lipid particle) comprising a nucleic acid described herein, wherein the diameter of the particle is 25-50 µm, via intraarticular injection.

In one embodiment, the nucleic acid is administered to a subject at a dose between 1-2000 µg/kg body weight; or between 10-100 µg/kg body weight; or between 100-200 µg/kg body weight; or between 200-500 µg/kg body weight; or between 500-1000 µg/kg body weight; or 25-75 µg/kg body weight; or 30-70 µg/kg body weight; or 40-60 µg/kg body weight; or between 1-10 µg/kg body weight; or between 1-5 µg/kg body weight; or between 4-8 µg/kg body weight; or about 2 µg/kg body weight; or about 5 µg/kg body weight; or about 10 µg/kg body weight; or about 20 µg/kg body weight; or about 25 µg/kg body weight; or about 30 µg/kg body weight; or about 35 µg/kg body weight; or about 40 µg/kg body weight; or about 45 µg/kg body weight; or about 50 µg/kg body weight; or about 55 µg/kg body weight; or about 60 µg/kg body weight; or about 65 µg/kg body weight; or about 70 µg/kg body weight; or about 75 µg/kg body weight; or about 100 µg/kg body weight; or about 200 µg/kg body weight; or about 500 µg/kg body weight.

Administration

In some embodiments, methods of the invention comprise administering an agent e.g., a nucleic acid described herein or a particle comprising same, to a subject using a depot. The terms "administer", "administering" or "administration" include any method of delivery of agent e.g., a nucleic acid described herein or a particle comprising same into the subject's system or to a particular region in or on the subject. For example, agent loaded depot may be administered intravenously, intramuscularly, subcutaneously, intradermally, intranasally, orally, transcutaneously, mucosally, intraarticularly, periarticularly, intracapsularly, pericapsularly, intratendinously, peritendinously, intraligamentously, periligamentously, by pulmonary inhalation or by ocular specific routes of administration. Administering the agent loaded depot can be performed by a number of people working in concert and can include, for example, prescribing a therapyf to be administered to a subject and/or providing instructions, directly or through another, to take the nucleic acid either by self-delivery, e.g., as by oral delivery, subcutaneous delivery, intravenous delivery through a central line, etc., or for delivery by atrained professional, e.g., intraarticular delivery, intravenous delivery, intramuscular delivery, intratumoral delivery, etc.

In a preferred embodiment, the agent loaded depot is administered locally, e.g., directly to or into a joint of a subject using a depot. Local administration of the agent loaded depot by an intraarticular injection or by topical application to the joint, or in the tissue surrounding the joint is advantageous because it allows delivery of a smaller dose of the agent to the subject and avoids the side-effects associated with systemic delivery, such as back pain and joint pain.

In one embodiment, the agent loaded depot is administered to the subject by an intraarticular injection. In one embodiment, the agent is administered to the subject by an intraarticular, periarticular, intracapsular, pericapsular, intraligamentous, periligamentous, intratendinous, peritendinous, intraosteotendinous, or periosteotendinous injection (collectively "joint injections"), or combination thereof. In one embodiment, the agent loaded depot is administered to the subject via a single joint injection. In one embodiment, the agent loaded depot is administered to the subject via multiple joint injections. The multiple joint injections of the agent loaded depot may be administered to a subject at regularly spaced time intervals, e.g., every day, every 2 days, every 3 days, every 4 days, every 5 days, every 6 days, every 7 days, every 8 days, every 9 days, every 10 days, every 11 days, every 12 days every 13 days or every 14 days. A course of treatment consisting of multiple joint injections of agent loaded depot may be repeated.

In one embodiment, the agent is administered to or near tendons, osteotendinous junctions, tendon-bone interfaces, entheses, or muscle-tendon insertions. Such tissues may be selected from the following tendinous tissues, among others: shoulder (e.g., *teres* minor tendons (rotator cuff) infraspinatus tendons supraspinatus tendons subscapularis tendons), elbow/forearm (e.g., deltoid tendons biceps tendons triceps tendons brachioradialis tendons extensor carpi radialis *brevis* tendons extensor carpi radialis longus tendons supinator tendons), wrist (e.g., flexor carpi radialis tendons flexor carpi ulnaris tendons extensor capri radialis tendons extensor carpi radialis *brevis* tendons), hip/groin (e.g., iliopsoas tendons obturator intermus tendons adductor longus, *brevis*, and magnus tendons gluteus maximus and gluteus medius tendons iliotibial band), knee (e.g., quadriceps tendons patellar tendons hamstring tendons sartorius tendons), ankle gastrocnemius tendons achilles tendons soleus tendons tibialis anterior tendons peroneus longus tendons), fingers (e.g., flexor digitorum longus tendons interosseus tendons flexor digitorum *profundus* tendons abductor digiti minimi tendons), thumb (e.g., opponens pollicis tendons flexor pollicis tendons extensor and abductor pollicis tendons), toes (e.g., flexor hallucis longus tendons flexor digitorum *brevis* tendons lumbrical tendons abductor hallucis tendons flexor digitorum longus tendons abductor digiti minimi tendons plantar fasciitis), and back (e.g., multifidus tendons quadratus lumborum tendons longissmus thoracis tendons iliocostalis tendons spinalis thoracis tendons psoas major tendons).

The joint injection of the agent loaded depot may be accomplished by using a syringe with a needle suited for a joint injection. A needle suitable for anjoint injection may be selected from the group consisting of a 30G needle, a 29G needle, a 28G needle, a 27G needle, a 26sG needle, a 26G needle, a 25.5G needle, a 25sG needle, a 25G needle, a 24.5G needle, a 24G needle, a 23.5G needle, a 23sG needle, a 23G needle, a 22.5G needle, a 22sG needle, a 22G needle, a 21.5G needle, a 21G needle, a 20.5G needle, a 20G needle, a 19.5G needle, a 19G needle, a 18.5G needle and an 18G needle. In a specific embodiment, the agent loaded depot is administered via a 21G needle.

In another preferred embodiment, the agent loaded depot may be administered to a subject topically, e.g., transcutaneously. For example, the agent loaded depot may be administered as a gel, a cream, an ointment, a lotion, a drop, a suppository, a spray, a liquid or a powder composition that is applied topically to a joint, e.g., a finger joint.

In some embodiments, the agent loaded depot may be administered to a subject during a medical procedure, e.g., a surgery, to treat or prevent a stiffened joint. Because stiffened joint may result from a surgery, administering relaxin during surgery may prevent formation of a stiffened joint in a subject. In one embodiment, the agent loaded depot may be administered through a cannula or an incision.

In another embodiment, the agent loaded depot may be administered during an outpatient arthroscopic, fluoroscopic or ultrasound guided procedure.

In a preferred embodiment, the agent loaded depot is administered to the subject locally in as a sustained release formulation. Administering the nucleic acid as a sustained release formulation is advantageous because it avoids repeated injections and can deliver a therapeutic dose of the relaxin in a consistent and reliable manner, and over a desired period of time. Exemplary sustained release formulations that may be used to delivery polypeptides, are described in Vaishya et al., *Expert. Opin. Drug Deliv.* 2015, 12(3):415-40, the entire contents of which are incorporated herein by reference.

Certain embodiments of the invention provide a solution to secondary arthrofibrosis developed in neuromotor degenerative diseases by the local intra-articular delivery ofa nucleic acid described herein, for example in a sustained release formulation. In some embodiments, the nucleic acid may reduce fibrosis in an in-vivo neuromotor degenerative arthrofibrosis large animal model by inhibiting TGF-β1 signaling via the NO-sGC-cGMP pathway, thereby decreasing joint stiffness and increasing range of motion.

In some embodiments, the formulation is provided as a lyophilized powder for resuspension or reconstitution with diluent at or near the point of care.

Clinically, the treating physician may inject a formulation as disclosed herein, such as nucleic acid or lipid formulation, in the afflicted contracted joints and periarticular tissues of patients with progressive neuromotor degenerative conditions. These injections will take place in an office setting using anatomical landmarks or under ultrasound guidance. The injections may be followed by a standard course of physical therapy. For more difficult joint injections (i.e., hip, spine), fluoroscopic guided injections can also be performed by an orthopedic surgeon or an interventional radiologist. In some embodiments, advantages may be: Elimination of surgery in a high-risk; Reduction of lifetime health care costs; Local injection of the formulation in the synovial joint space via standard office injection techniques; Minimization of dose as a result of local and not systemic delivery; reduction of off-target side effects and increased safety due to local delivery.

In addition to the tissues around joint, the formulation can treat fibrosis in additional target organs that express the target molecule, e.g., relaxin receptor, through different routes of administration.

For lung fibrosis such as insterstitial lung disease, idiopathic pulmonary fibrosis, cystic fibrosis, hypertension, the formulation can be administered by pulmonary inhalation or intranasally as a sustained release formulation and may be provided a single injections or doses or a series of injections or doses.

For liver fibrosis such as hepatitis B or C, long-term alcohol abuse, non-alcoholic steatohepatitis, non-alcoholic fatty liver disease, Cholestasis, autoimmune hepatitis cirrhosis; kidney fibrosis such as chronic kidney disease, end-stage renal disease, renal interstitial fibrosis; and heart disease such as heart failure, myocardial infarction, aortic stenosis, hypertrophic cardiomyopathy, the formulation can be administered intravenously, intramuscularly or intravenously (such as by catheter) as a sustained release formulation and may be provided a single injections or doses or a series of injections or doses.

For intestinal diseases such as Crohn's disease, inflammatory bowel disease, enteropathies, and other intestinal fibrosis, the formulations can be administered intranasally, orally, mucosally, as a sustained release formulation and may be provided a single injections or doses or a series of injections or doses.

For skin conditions such as scleroderma, keloids, hypertrophic scars, cellulite, the formulations can be administered intramuscularly, subcutaneously, intradermally, or transcutaneously as a sustained release formulation and may be provided a single injections or doses or a series of injections or doses.

For urogenital and gynecological conditions such as Peyronie's disease and uterine fibroids, the formulations can be administered transcutaneously or transmucosally as a sustained release formulation and may be provided a single injections or doses or a series of injections or doses.

For ocular diseases such as Congenital Fibrosis of the Extraocular Muscles, subretinal fibrosis, epiretinal fibrosis, corneal fibrosis, the formulation can be administered topically, by local ocular administration (ie, subconjunctival, subretinal, intravitreal, retrobulbar, intracameral), or systemically (ie orally, intravenously, nasally) as a sustained release formulation and may be provided a single injections or doses or a series of injections or doses. Additional diseases and conditions suitable for treatment include Dupuytren's Disease (the formation of a collagen cord in the palm that contracts and limits range of motion of fingers) Peyronie's Disease (excess of inelastic collagen causes penis curvature; distorts erection), Canine and Human Lipomas encapsulated deposits of benign fatty tumors), Uterine Fibroids (benign tumors with significant co-morbidities), Plantar Fibromatosis (pain and disability caused by the thickening of the feet's deep connective tissue), Capsular Contracture, Breast (post-surgical complication that can deform the breast and cause pain), Hypertrophic Scars & Keloids (scars that form on the skin at site of injury), Dercum's Disease (obesity and overly sensitive painful adipose tissue) Knee Arthrofibrosis (adhesions that form post-implant that may affect range of motion), Urethral Strictures Narrowing (Narrowing of the urethra that affects urine flow).

The lipids and agents described herein can be administered to a subject having or diagnosed as having a disease or disorder associated with fibrosis. In some embodiments, the methods described herein comprise administering an effective amount of a lipid or agent to a subject in order to alleviate at least one symptom of the disease or disorder. As used herein, "alleviating at least one symptom of the disease or disorder associated with fibrosis" is ameliorating any condition or symptom associated with the fibrotic disease or disorder. As compared with an equivalent untreated control, such reduction is by at least 5%, 10%, 20%, 40%, 50%, 60%, 80%, 90%, 95%, 99% or more as measured by any standard technique. A variety of means for administering the agents described herein to subjects are known to those of skill in the art. In one embodiment of any of the aspects, the agent is administered systemically or locally (e.g., to the brain, or other affected organ, e.g., the colon).

In one embodiment of any of the aspects, the agent is administered intravenously. In one embodiment of any of the aspects, the agent is administered continuously, in intervals, or sporadically.

The term "effective amount" as used herein refers to the amount of a lipids and agents as described herein can be administered to a subject having or diagnosed as having a disease or disorder associated with fibrosis needed to alleviate at least one or more symptom of the disease or disorder. The term "therapeutically effective amount" therefore refers to an amount of an agent that is sufficient to provide a particular anti-disease or disorder effect when administered to atypical subject. An effective amount as used herein, in various contexts, would also include an amount of a lipids and agents sufficient to delay the development of a symptom of the disease or disorder, alter the course of a symptom of the disease or disorder (e.g., inflammation, stiffening of a joint, pain, loss of mobility, difficulty breathing), or reverse a symptom of the disease or disorder (e.g., inflammation, stiffening of a joint, pain, loss of mobility, difficulty breathing). Thus, it is not generally practicable to specify an exact "effective amount". However, for any given case, an appropriate "effective amount" can be determined by one of ordinary skill in the art using only routine experimentation.

In one embodiment of any of the aspects, the lipids and agents is administered continuously (e.g., at constant levels over a period of time). Continuous administration of an agent can be achieved, e.g., by epidermal patches, continuous release formulations, or on-body injectors.

Effective amounts, toxicity, and therapeutic efficacy can be evaluated by standard pharmaceutical procedures in cell cultures or experimental animals. The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the agent, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., measuring neurological function, or blood work, among others. The dosage can be determined by a physician and adjusted, as necessary, to suit observed effects of the treatment.

Dosage

"Unit dosage form" as the term is used herein refers to a dosage for suitable one administration. By way of example a unit dosage form can be an amount of therapeutic disposed in a delivery device, e.g., a syringe or intravenous drip bag. In one embodiment of any of the aspects, a unit dosage form is administered in a single administration. In another, embodiment more than one unit dosage form can be administered simultaneously.

The dosage of the agent as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to administer further cells, discontinue treatment, resume treatment, or make other alterations to the treatment regimen. The dosage should not be so large as to cause adverse side effects, such as cytokine release syndrome. Generally, the dosage will vary with the age, condition, and sex of the patient and can be determined by one of skill in the art. The dosage can also be adjusted by the individual physician in the event of any complication.

The effective dose can be estimated initially from cell culture assays. A dose can be formulated in animals. Generally, the compositions are administered so that a compound of the invention herein is used or given at a dose from 1 µg/kg to 1000 mg/kg; 1 µg/kg to 500 mg/kg; 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. Further contemplated is a dose (either as a bolus or continuous infusion) of about 0.1 mg/kg to about 10 mg/kg, about 0.3 mg/kg to about 5 mg/kg, or 0.5 mg/kg to about 3 mg/kg. It is to be further understood that the ranges intermediate to those given above are also within the scope of this invention, for example, in the range 1 mg/kg to 10 mg/kg, for example use or dose ranges such as 2 mg/kg to 8 mg/kg, 3 mg/kg to 7 mg/kg, 4 mg/kg to 6 mg/kg, and the like.

Combinational Therapy

In one embodiment of any of the aspects, the nucleic acids or lipids described herein is used as a monotherapy. In another embodiment of any of the aspects, the nucleic acids or lipids described herein can be used in combination with other known agents and therapies (i.e., co-therapies) for a disease, condition, or disorder, such as a disease, condition, or disorder associated with fibrosis. Administered "in combination," as used herein, means that two (or more) different treatments are delivered to the subject during the course of the subject's affliction with the disorder, e.g., the two or more treatments are delivered after the subject has been diagnosed with the disorder (a fibrotic disease or disorder) and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. The agents described herein and the at least one additional therapy can be administered simultaneously, in the same or in separate compositions, or sequentially. For sequential administration, the agent described herein can be administered first, and the additional agent can be administered second, or the order of administration can be reversed. The agent and/or other therapeutic agents, procedures or modalities can be administered during periods of active disorder, or during a period of remission or less active disease. The microparticle or agent of this disclosure can be administered before another treatment, concurrently with the treatment, post-treatment, or during remission of the disorder.

When administered in combination, the nucleic acids or lipids and the additional agent (e.g., second or third agent), or all, can be administered in an amount or dose that is higher, lower or the same as the amount or dosage of each agent used individually, e.g., as a monotherapy. In certain embodiments, the administered amount or dosage of the agent, the additional agent (e.g., second or third agent), or all, is lower (e.g., at least 20%, at least 30%, at least 40%, or at least 50%) than the amount or dosage of each agent used individually. In other embodiments, the amount or dosage of agent, the additional agent (e.g., second or third agent), or all, that results in a desired effect (e.g., treatment of a fibrotic disease or disorder) is lower (e.g., at least 20%, at least 30%, at least 40%, or at least 50% lower) than the amount or dosage of each agent individually required to achieve the same therapeutic effect.

In some embodiments, the cotherapy is a drug, such as aspirin, acetaminophen, non-steroidal anti-inflammatory drugs, steroids, nerve blockers, and analgesic drugs common in the art.

In some embodiments, the cotherapy is a drug for muscular dystrophies, including but not limited to deflazacourt, eteplirsen, casimersen, golodirsen, ataluren, givinostat, viltolarsen, pamrevlumab, SRP-9001, SRP-5051, DS-5141B, SCAAV9.U7.ACCA, PF-06939926, SGT-001, or AT702.

In some embodiments, the cotherapy is a drug for spinal muscular atrophy, including but not limited to Spinraza, Zolgensma, Evrysdi, SRK-015, CK-2127107, LMI070, AVXS-101, BIIB110, or p38aMAPK inhibitors.

In some embodiments, the cotherapy is a drug for cerebral palsy, stroke, traumatic brain injury, or peripheral nerve injury, including but not limited to anticholinergics such as Benztropine mesylate, Carbidopa-levodopa (Sinemet), Glycopyrrolate (Robinul), Procyclidine hydrochloride (Kemadrin), and Trihexyphenidyl hydrochloride; anticonvulsants such as Gabapentin (Neurontin), Lamotrigine (Lamictal), Oxcarbazepine (Trileptal), Topiramate (Topamax), and Zonisamide (Zonegran); or antispastics i.e. muscle relaxants such as Baclofen, Botulinum toxin, Diazepam (Valium(R)), Dantrolene, Flexeril (Cyclobenzadrine), Dantrium (Dantrolene), or Tizanidine.

In some embodiments, the cotherapy is physical therapy.

In some embodiments, the cotherapy is a surgical intervention, including but not limited to surgical release, capsular release, or surgical repair.

In some embodiments, the cotherapy is an energy-based technique, including but not limited to radiofrequency energy application e.g. radiofrequency ablation, thermal energy application or removal e.g. cryoablation, sonic energy application e.g. ultrasound-based therapeutic techniques, electrical energy application e.g. transcutaneous electrical nerve stimulation (TENs), or other electromagnetic energy application or removal methods such as light exposure.

In some embodiments, the cotherapy is an exoskeleton designed to assist ambulation or other motion in patients with ambulatory or other motion-based dysfunction.

Parenteral Dosage Forms

Parenteral dosage forms of an agents (e.g., nucleic acids or lipids) described herein can be administered to a subject by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

The phrases "parenteral administration" and "administered parenterally" as used herein means modes of administration other than enteral and topical administration, usually by injection, and includes, without limitation, intravenous, intramuscular, perimuscular, intraarterial, intrathecal, intraventricular, intracapsular, pericapsular, intraorbital, intracardiac, intradermal, peridermal, intraperitoneal, transtracheal, subcutaneous, subcuticular, intraarticular, periarticular, sub capsular, subarachnoid, intraspinal, intracerebro spinal, and intrasternal injection, infusion and other injection or infusion techniques, without limitation. Without limitations, oral administration can be in the form of solutions, suspensions, tablets, pills, capsules, sustained-release formulations, oral rinses, powders and the like. Suitable vehicle solutions that can be used to provide parenteral dosage forms of the invention are well known to those skilled in the art. As used herein, the phrase "vehicle solutions" include, without limitation: sterile water; water for injection USP; saline solution; sodium carboxymethylcellulose; glucose solution; aqueous vehicles such as but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Efficacy

The efficacy of an agents described herein, e.g., for the treatment of a disease or disorder, for example, associated with fibrosis, can be determined by the skilled practitioner. However, a treatment is considered "effective treatment," as the term is used herein, if one or more of the signs or symptoms of the disease or disorder are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate. Efficacy can also be measured by a failure of an individual to worsen as assessed by hospitalization, or need for medical interventions (i.e., progression of the disease or disorder, as measured by symptoms of the disease or disorder). Methods of measuring these indicators are known to those of skill in the art and/or are described herein.

Efficacy can be assessed in animal models of a condition described herein, for example, a mouse model or an appropriate animal model of a fibrotic disease or disorder, as the case may be. When using an experimental animal model, efficacy of treatment is evidenced when a statistically significant change in a marker is observed.

In some embodiments, efficacy of treatment includes the minimization of foreign-body-response or immune reaction after administration. For example, the administration of a vehicle control formulation (e.g., a a lipid containing no nucleic acid) may elicit macrophage and immune activation as well as inflammation, whereas the administration of a formulation described by the present disclosure may ellict a lower immune response or entirely abrogate the elicited immune response at any point throughout the treatment and assessment after administration.

In some embodiments, foreign body response resulting from administration of a formulation described by the present disclosure may be reduced or abrogated compared to foreign body response resulting from administration of a lipid containing a steroid as the therapeutic agent.

The inventions illustratively described herein may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present inventions have been specifically disclosed by preferred embodiments and optional features, modification and variation of the concepts herein disclosed may be resorted to by those skilled in the art, and that such modifications and variations are considered to be within the scope of the inventions as defined by the appended embodiments and elsewhere in the invention.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

Some embodiments of the technology described herein can be defined according to any of the following numbered paragraphs:

1. A method, wherein the simultaneous production of one or more ligand(s) and one or more target(s) from exogenously delivered nucleotides results in activation of a signaling pathway with a therapeutic effect.
2. A method of paragraph 1, wherein the produced ligand is secreted to the extracellular space and the produced target is a transmembrane receptor or set of transmembrane receptors.
3. A method of any preceding paragraph, wherein the produced ligand and produced target are expressed in the cell cytoplasm.
4. A method of any preceding paragraph, wherein the produced target is a receptor or set of receptors and/or an inhibitor of a ligand suppressor.
5. A method of any preceding paragraph, wherein the target is an enzyme and the ligand is the target's substrate.
6. A method of any preceding paragraph, wherein the ligand is a peptide hormone; wherein the ligand is a chemokine; wherein the ligand is a hormone; wherein the ligand is a protein; wherein the ligand is a protein fragment; wherein the ligand is a fusion protein;
7. A method of any preceding paragraph, wherein the target is a G protein coupled receptor; wherein the target is a transmembrane tyrosine kinase receptor; wherein the target is a transmembrane chemokine receptor; wherein the receptor is a transmembrane ligand gated ion channel; wherein the target is a transporter; wherein the target is a membrane-embedded protein.
8. A method of any preceding paragraph, wherein binding of the ligand to the target initiates a signaling cascade which utilizes endogenous cellular mechanisms and/or components.
9. A method of any preceding paragraph, wherein binding of the ligand to the target initiates a signaling cascade which utilizes exogenously delivered components to complete a previously incomplete cellular mechanism.

10. A method of any preceding paragraph, wherein the exogenously delivered nucleotides additionally encode for an RNA replicon.

11. A method, wherein the ligand is IL-1α, or IL-1β, or both and the target is IL-1R1, or IL-1R2, or both; wherein the ligand is IL-2 and the target is IL-2Rα, or IL-2Rβ, or IL-2Rγ or all or a subset of the previous; wherein the ligand is IL-3 and the target is IL-3Rα; wherein the ligand is IL-4 and the target is IL-4R, or IL-2Rα, or IL-13Rα1 or all or a subset of the previous; wherein the ligand is IL-5 and the target is IL-5Rα; wherein the ligand is IL-6 and the target is IL-6Rα, or IL-6Rβ, or both; wherein the ligand is IL-7 and the target is IL-7Rα, or IL-2γ, or both; wherein the ligand is IL-8 and the target is CXCR1, or CXCR2, or both; wherein the ligand is IL-9 and the target is IL-9R, or IL-2Rγ, or both; wherein the ligand is IL-10 and the target is IL-10Rα, or IL-10Rβ, or both; wherein the ligand is IL-11 and target is IL-11Rα, or IL-6Rβ, or both; wherein the ligand is IL-12A, or IL-12B, or both and the target is IL-12Rβ1, or IL-12Rβ2, or both; wherein the ligand is IL-13 and target is IL-13Rα1, or IL-13Rα2, or IL-4R, or all, or a subset of the previous; wherein the ligand is IL-15 and the target is IL-15Rα, or IL-2Rβ, or IL-2Rγ, or all, or a subset of the previous; wherein the ligand is IL-16 and the target is CD4, or CD9, or both; wherein the ligand is IL-17A and the target is IL-17RA, or IL-17RC, or IL-17RD, or all, or a subset of the previous; wherein the ligand is IL-17B and the target is IL-17RB; wherein the ligand is IL-17C and the target is IL-17RA, or IL-17RE, or both; wherein the ligand is IL-17F and the target is IL-17RA, or IL-17RC, or both; wherein the ligand is IL-18 and the target is IL-18Rα, or IL-18RAP, or both; wherein the ligand is IL-19 and the target is IL-20Rα, or IL-20Rβ, or both; wherein the target is IL-20 and the target IL-20Rα, or IL-20Rβ, or IL-20Rα1, or all, or a subset of the previous; wherein the ligand is IL-21 and the target is IL-21R, or IL-2Rγ, or both; wherein the ligand is IL-22 and the target is IL-22Rα1, or IL-22Rα2, or IL-10Rβ, or all, or a subset of the previous; wherein the ligand is IL-23 and the target is IL-12Rβ1, or IL-23R, or both; wherein the ligand is IL-24 and the target is IL-20Rα, or IL-20Rβ, or IL-22Rα1, or all, or a subset of the previous; wherein the ligand 25 and the target is IL-17RA, or IL-17RB, or both; wherein the ligand is IL-26 and the target is IL-10Rβ or IL-20Rα, or both; wherein the ligand is IL-27 and the target is IL-27Rα, or IL-6Rβ, or both; wherein the ligand is IL-28A and the target is IL-28RA, or IL-10Rβ, or both; wherein the ligand is IL-28B and the IL-28RA, or IL-10Rβ, or both; wherein the ligand is IL-29 and the target is IL-28RA, or IL-10Rβ, or both; wherein the ligand is IL-31 and the target is IL-31Rα; wherein the ligand is IL-33, or IL-34, or both and the target is IL-1R1, or IL-12J32, or IL-6Rβ, or both; wherein the ligand is IL-36A, or IL-36B, or IL-36G, or all, or a subset of the previous, and the target is IL-1RL2, or IL-1RAP, or both; wherein the ligand is IL-37 and the target is IL-18R1; wherein the ligand is IL-38 and the target is IL-1R1, or IL-1R2, or both;

12. A method, wherein delivery of ligand and target by exogenous nucleotide occurs in a cell type independent manner.

13. A method, wherein delivery of ligand and target by exogenous nucleotide occurs in a cell type dependent manner.

14. A method whereby the production of target from exogenously delivered nucleotides increases target expression, concentration, or surface density, with the purpose of magnifying the therapeutic effect of the ligand.

15. A method, wherein the simultaneous production of relaxin-2 and RXFP1 from exogenous nucleotides results in activation of the relaxin-2, RXFP1 signaling cascade.

16. A method of any preceding paragraph, wherein the relaxin-2 is secreted into the extracellular space and RXFP1 is expressed as a transmembrane protein.

17. A method of any preceding paragraph, wherein the exogenous nucleotides are delivered to a patient diagnosed with arthrofibrosis; to a patient diagnosed with a cardiovascular disease; to a patient diagnosed with an interstitial pulmonary disease; to a patient diagnoses with systemic sclerosis; to a patient diagnosed with a vascular disease; to a patient diagnosed with hypertrophic or keloid scars;

18. A method, wherein the simultaneous production of IGF-1 and Pappalysin-1 or Pappalysin-2 from exogenous nucleotides results in activation of the IGF-1-IGF-1R signaling cascade.

19. A method, wherein the simultaneous production of IGF-1 and IGF-1R from exogenous nucleotides results in activation of the IGF-1-IGF-1R signaling cascade.

20. A method of any preceding paragraph, wherein the IGF-1 and Pappalysin-1 or pappalysin-2 is secreted into the extracellular space.

21. A method of any preceding paragraph, wherein the IGF-1 is secreted into the extracellular space and IGF-1R is expressed as a transmembrane protein.

22. A method of any preceding paragraph, wherein the exogenous nucleotides are delivered to a patient diagnosed with osteoarthritis; to a patient diagnosed with autism; to a patient diagnosed with diabetes mellitus; to a patient diagnosed with a central nervous system disorder; to a patient diagnoses with a developmental disorder; to a patient diagnosed with a neuromuscular disorder; to a patient diagnosed with diabetic neuropathy; to a patient diagnosed with ischemia-reperfusion injuries; to a patient diagnosed with chronic heart failure; to a patient diagnosed with a chronic wasting disease; to a patient diagnosed with cancer cachexia;

23. A method of any preceding paragraph, wherein the nucleotides are delivered intracellularly by a carrier; wherein the carrier is a lipid nanoparticle; wherein the carrier is a peptide conjugated to the nucleotides; wherein the carrier is a cationic polymer; wherein the carrier is of bacterial origin; wherein the carrier is of viral origin; wherein the carrier is of phage origin.

24. A method of any preceding paragraph, wherein the therapeutic effect is antifibrotic; wherein the therapeutic effect is vasodilatory; wherein the therapeutic effect is hemodynamic; wherein the therapeutic effect is angiogenic; wherein the therapeutic effect is apoptotic; wherein the therapeutic effect is antiviral; wherein the therapeutic effect increases cell proliferation; wherein the therapeutic effect is antifibrogenic; wherein the therapeutic effect is cytotoxic; wherein the therapeutic effect is proliferative; wherein the therapeutic effect is regenerative; wherein the therapeutic effect regulates cell cycle; wherein the therapeutic results in epigenetic alterations; wherein the therapeutic is immunomodulatory;

25. A method of any preceding paragraph, wherein translation of encoded components of the exogenous nucleotide occurs simultaneously.
26. A method of any preceding paragraph, wherein translation of encoded components of the exogenous nucleotide occurs in a temporally differentiated manner.
27. A method of any preceding paragraph, wherein the encoded components are amplified in situ by an encoded RNA replicon.
28. A method of any preceding paragraph, wherein the RNA amplicon acts in cis on the encoded ligand(s) and target(s)
29. A method of any preceding paragraph, wherein the RNA amplicon acts in trans on the encoded ligand(s) and target(s)
30. A formulation, wherein the ligand and target(s) are encoded on a single nucleotide polymer.
31. A formulation, wherein the ligand and target(s) are encoded on multiple nucleotide polymers.

Aspects to the technology described herein can also be defined according to any of the following numbered embodiments:

1. A nucleic acid combination comprising:
   (i) a first nucleic acid molecule encoding a ligand; and
   (ii) a second nucleic acid molecule encoding a target molecule, wherein the target is a cognate receptor of the ligand or an inhibitor of a suppressor of the ligand, and wherein one of the ligand and the target molecule is translated via a cap-dependent manner.
2. The nucleic acid combination of paragraph 1, wherein the first and second nucleic acid are covalently linked to form a nucleic acid encoding both the ligand and the target molecule, and optionally, one of the ligand and the target molecule is translated via a cap-dependent manner and the other of the ligand and the target molecule is translated via a cap-independent manner.
3. The nucleic acid combination of any preceding paragraph, wherein the ligand is translated via a cap-dependent manner or the target molecule is translated via a cap-independent manner.
4. The nucleic acid combination of any preceding paragraph, wherein the ligand is a protein, a protein fragment, a fusion protein, an amino acid or a derivative thereof, a steroid, a fatty acid or a lipid.
5. The nucleic acid combination of any preceding paragraph, wherein the ligand is a cytokine or a hormone.
6. The nucleic acid combination of any preceding paragraph, wherein the ligand is an interleukin or chemokine.
7. The nucleic acid combination of any preceding paragraph, wherein the ligand is an interleukin selected from the group consisting of IL-1α, IL-1J3, IL-2, IL-3, IL-4, IL-5, IL-6, IL-7, IL-8, IL-9, IL-10, IL-11, IL-12A, IL-12B, IL-13, IL-15, IL-16, IL-17A, IL-17B, IL-17C, IL-17F, IL-18, IL-19, IL-20, IL-21, IL-22, IL-23, IL-24, IL-25, IL-26, IL-27, IL-28A, IL-28B, IL-29, IL-31, IL-33, IL-34, IL-36A, IL-36B, IL-36G, IL-37, and IL-38.
8. The nucleic acid combination of any preceding paragraph, wherein the ligand is a chemokine selected from the group consisting of CCL14, CCL19, CCL20, CCL21, CCL25, CCL27, CXCL12, CXCL13, CXCL-8, CCL2, CCL3, CCL4, CCL5, CCL11, and CXCL10
9. The nucleic acid of any preceding paragraph, wherein the ligand is a hormone.
10. The nucleic acid combination of any preceding paragraph, wherein the ligand is a hormone selected from the group consisting of insulin-like growth factor (or somatomnedin), adrenaline (or epinephrine), melatonin, noradrenaline (or norepinephrine), triiodothyronine, thyroxine, dopamine, prostaglandins, leukotrienes, prostacyclin, thromboxane, amylin (or islet amyloid polypeptide), anti-müllerian hormone (or müllerian-inhibiting factor/hormone), adiponectin, adrenocorticotropic hormone (or corticotropin), angiotensinogen, angiotensin, antidiuretic hormone (or vasopressin, arginine vasopressin), atrial natriuretic peptide (or atriopeptin), brain natriuretic peptide, calcitonin, cholecystokinin, corticotropin-releasing hormone, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, growth hormone-releasing hormone, hepcidin, human chorionic gonadotropin, human placental lactogen, growth hormone, inhibin, insulin, leptin, lipotropin, luteinizing hormone, melanocyte stimulating hormone, motilin, orexin, osteocalcin, oxytocin (or pitocin), pancreatic polypeptide, parathyroid hormone, pituitary adenylate cyclase-activating peptide, prolactin (or leuteotropic hormone), prolactin-releasing hormone, relaxin, renin, secretin, somatostatin (or growth hormone-inhibiting hormone or growth hormone release-inhibiting hormone or somatotropin release-inhibiting factor or somatotropin release-inhibiting hormone), thrombopoietin, thyroid-stimulating hormone (or thyrotropin), thyrotropin-releasing hormone, vasoactive intestinal peptide, guanylin, uroguanylin, testosterone, dehydroepiandrosterone, androstenedione, dihydrotestosterone, aldosterone, estradiol, estrone, estriol, cortisol, progesterone, calcitriol, and calcidiol.
11. The nucleic acid combination of any preceding paragraph, wherein the ligand is relaxin.
12. The nucleic acid combination of any preceding paragraph, wherein the ligand is relaxin-2 or variant thereof.
13. The nucleic acid combination of any preceding paragraph, wherein the target molecule is a cognate receptor of the ligand.
14. The nucleic acid combination of any preceding paragraph, wherein the target molecule is a transmembrane receptor.
15. The nucleic acid combination of any preceding paragraph, wherein the target molecule is a G protein-coupled receptor, a transmembrane tyrosine kinase receptor, a transmembrane chemokine receptor, a transmembrane ligand gated ion channel, a transporter, or a membrane-embedded protein.
16. The nucleic acid of any preceding paragraph, wherein the target molecule is a cytokine or hormone receptor.
17. The nucleic acid of any preceding paragraph, wherein the target molecule is an interleukin or chemokine receptor.
18. The nucleic acid combination of any preceding paragraph, wherein the target molecule is an interleukin receptor selected from the group consisting of IL-1R1, IL-1R2, IL-1RAP, IL-1RL2, IL-2RJ3, IL-2Rα, IL-2Rγ, IL-2γ, IL-3Rα, IL-4R, IL-5Rα, IL-6RJ3, IL-6Rα, IL-7Rα, IL-9R, IL-10RJ3, IL-10Rα, IL-11Rα, IL-12J32, IL-12RJ31, IL-12RJ32, IL-13Rα1, IL-13Rα2, IL-15Rα, IL-17RA, IL-17RB, IL-17RC, IL-17RC, IL-17RD, IL-17RE, IL-18R1, IL-18RAP, IL-18Rα, IL-20RJ3, IL-20Rα, IL-20Rα1, IL-21R, IL-22Rα1, IL-23R, IL-27Rα, IL-28RA, IL-31Rα, CD4, CD9, CXCR1, and CXCR2.

19. The nucleic acid combination of any preceding paragraph, wherein the target molecule is a chemokine receptor selected from the group consisting of CXCR1, CXCR2, CXCR4, CXCR5, CXCR5, CXCR6, CCR1, CCR2, CCR3, CCR4, CCR5, CCR6, CCR7, CCR8, CCR9, CCR10, CCR11, XCR1 and CX3CR1.

20. The nucleic acid combination of any preceding paragraph, wherein the target molecule is a hormone receptor.

21. The nucleic acid combination of any preceding paragraph, wherein the target molecule is a hormone receptor selected from the group consisting of calcitriol receptors, corticotropin-releasing hormone receptor 1, corticotropin releasing hormone receptor 2, estrogen receptors, follicle-stimulating hormone receptors, glucagon receptors, gonadotropin receptors, gonadotropin-releasing hormone receptors, growth hormone receptors, insulin receptor, luteinizing hormone, progesterone receptors, retinoid receptors, somatostatin receptors, thyroid hormone receptors, and thyrotropin receptors.

22. The nucleic acid combination of any preceding paragraph, wherein the target molecule is a relaxin receptor.

23. The nucleic acid combination of any preceding paragraph, wherein the target molecule is an inhibitor of a suppressor of the ligand.

24. The nucleic acid combination of any preceding paragraph, wherein the target molecule inhibits or reduces binding of the ligand to the suppressor.

25. The nucleic acid combination of any preceding paragraph, wherein the target molecule is an enzyme and the ligand is a substrate of the enzyme.

26. The nucleic acid combination of any preceding paragraph, wherein the ligand is IL-1α, or IL-1β, or both and the target molecule is IL-1R1, or IL-1R2, or both; wherein the ligand is IL-2 and the target molecule is IL-2Rα, or IL-2Rβ3, or IL-2Rγ or all or a subset of the previous; wherein the ligand is IL-3 and the target molecule is IL-3Rα; wherein the ligand is IL-4 and the target molecule is IL-4R, or IL-2Rα, or IL-13Rα1 or all or a subset of the previous; wherein the ligand is IL-5 and the target molecule is IL-5Rα; wherein the ligand is IL-6 and the target molecule is IL-6Rα, or IL-6Rβ3, or both; wherein the ligand is IL-7 and the target molecule is IL-7Rα, or IL-2γ, or both; wherein the ligand is IL-8 and the target molecule is CXCR1, or CXCR2, or both; wherein the ligand is IL-9 and the target molecule is IL-9R, or IL-2Rγ, or both; wherein the ligand is IL-10 and the target molecule is IL-10Rα, or IL-10Rβ3, or both; wherein the ligand is IL-11 and target molecule is IL-11Rα, or IL-6Rβ3, or both; wherein the ligand is IL-12A, or IL-12B, or both and the target molecule is IL-12Rβ31, or IL-12Rβ32, or both; wherein the ligand is IL-13 and target molecule is IL-13Rα1, or IL-13Rα2, or IL-4R, or all, or a subset of the previous; wherein the ligand is IL-15 and the target molecule is IL-15Rα, or IL-2Rβ3, or IL-2Rγ, or all, or a subset of the previous; wherein the ligand is IL-16 and the target molecule is CD4, or CD9, or both; wherein the ligand is IL-17A and the target molecule is IL-17RA, or IL-17RC, or IL-17RD, or all, or a subset of the previous; wherein the ligand is IL-17B and the target molecule is IL-17RB; wherein the ligand is IL-17C and the target molecule is IL-17RA, or IL-17RE, or both; wherein the ligand is IL-17F and the target molecule is IL-17RA, or IL-17RC, or both; wherein the ligand is IL-18 and the target molecule is IL-18Rα, or IL-18RAP, or both; wherein the ligand is IL-19 and the target molecule is IL-20Rα, or IL-20Rβ3, or both; wherein the ligand is IL-20 and the target molecule IL-20Rα, or IL-20Rβ3, or IL-20Rα1, or all, or a subset of the previous; wherein the ligand is IL-21 and the target molecule is IL-21R, or IL-2Rγ, or both; wherein the ligand is IL-22 and the target molecule is IL-22Rα1, or IL-22Rα2, or IL-10Rβ3, or all, or a subset of the previous; wherein the ligand is IL-23 and the target molecule is IL-12Rβ31, or IL-23R, or both; wherein the ligand is IL-24 and the target molecule is IL-20Rα, or IL-20Rβ3, or IL-22Rα1, or all, or a subset of the previous; wherein the ligand IL25 and the target molecule is IL-17RA, or IL-17RB, or both; wherein the ligand is IL-26 and the target molecule is IL-10Rβ3 or IL-20Rα, or both; wherein the ligand is IL-27 and the target molecule is IL-27Rα, or IL-6Rβ3, or both; wherein the ligand is IL-28A and the target molecule is IL-28RA, or IL-10Rβ3, or both; wherein the ligand is IL-28B and the target molecule is IL-28RA, or IL-10Rβ3, or both; wherein the ligand is IL-29 and the target molecule is IL-28RA, or IL-10Rβ3, or both; wherein the ligand is IL-31 and the target molecule is IL-31Rα; wherein the ligand is IL-33, or IL-34, or both and the target molecule is IL-1R1, or IL-12J32, or IL-6Rβ3, or both; wherein the ligand is IL-36A, or IL-36B, or IL-36G, or all, or a subset of the previous, and the target molecule is IL-1RL2, or IL-1RAP, or both; wherein the ligand is IL-37 and the target molecule is IL-18R1; wherein the ligand is IL-38 and the target molecule is IL-1R1, or IL-1R2, or both.

27. The nucleic acid combination of any preceding paragraph, wherein the ligand is IGF-1 and the target molecule is IGF-1R; or wherein the ligand is FGF and the target molecule is selected from the group consisting of FGFR1, FGFR2, or FGFR3.

28. The nucleic acid combination of any preceding paragraph, wherein the ligand is IGF-1 and the target molecule is Pappalysin-1.

29. The nucleic acid combination of any preceding paragraph, further encoding an RNA replicon.

30. The nucleic acid combination of any preceding paragraph, wherein the nucleic acid is a polycistronic RNA (e.g., polycistronic mRNA).

31. A composition comprising a nucleic acid of any preceding paragraph.

32. A cell comprising a nucleic acid of any preceding paragraph.

33. A vector comprising a nucleic acid of any preceding paragraph.

34. A composition comprising a vector of any preceding paragraph.

35. A cell comprising a vector of any preceding paragraph.

36. A plasmid comprising a nucleic acid of any preceding paragraph.

37. A composition comprising a plasmid of any preceding paragraph.

38. A cell comprising a plasmid of any preceding paragraph.

39. Use of a nucleic acid of any preceding paragraph, a composition of any preceding paragraph, a vector of any preceding paragraph, or a plasmid of any preceding paragraph for activating a signaling pathway.

40. Use of a nucleic acid of any preceding paragraph, a composition of any preceding paragraph, a vector of any preceding paragraph, or a plasmid of any preceding paragraph for treating a disease or disorder in a subject.
41. A lipid particle comprising:
    (i) a first nucleic acid molecule encoding a ligand;
    (ii) a second nucleic acid molecule encoding a target molecule; and
    (iii) an ionizable lipid, and
    wherein the target molecule is a cognate receptor of the ligand or an inhibitor of a suppressor of the ligand.
42. The lipid particle of any preceding paragraph, wherein the first and second nucleic acid molecules are covalently linked to each other.
43. The lipid particle of any preceding paragraph, wherein the first and second nucleic acid molecules are covalently linked to each other and together form a polycistronic nucleic acid of any preceding paragraph.
44. The lipid particle of any preceding paragraph, wherein the lipid particle is a nanoparticle.
45. The lipid particle of any preceding paragraph, wherein the lipid particle further comprises a non-cationic lipid.
46. The lipid particle of any preceding paragraph, wherein the lipid particle further comprises a conjugated lipid that inhibits aggregation of particles.
47. The lipid particle of any preceding paragraph, wherein the lipid particle further comprises a sterol.
48. The lipid particle of any preceding paragraph, wherein the lipid particle comprises:
    (i) an ionizable lipid;
    (ii) a non-cationic lipid;
    (iii) a conjugated lipid that inhibits aggregation of particles; and
    (iv) a sterol.
49. The lipid particle of any preceding paragraph, wherein the lipid particle comprises:
    a. an ionizable lipid in an amount from about 20 mol % to about 90 mol % of the total lipid present in the particle;
    b. a non-cationic lipid in an amount from about 5 mol % to about 30 mol % of the total lipid present in the particle;
    c. a conjugated lipid that inhibits aggregation of particles in an amount from about 0.5 mol % to about 20 mol % of the total lipid present in the particle; and
    d. a sterol in an amount from about 20 mol % to about 50 mol % of the total lipid present in the particle.
50. The lipid particle of any preceding paragraph, wherein total lipid to nucleic acid (mass or weight) ratio is from about 10:1 to about 30:1.
51. The lipid particle of any preceding paragraph, wherein one of the ligand and the target molecule is translated via a cap-dependent manner and the other of the ligand and the target molecule is translated via a cap-independent manner
52. The lipid particle of any preceding paragraph, wherein the ligand is translated via a cap-dependent manner.
53. The lipid particle of any preceding paragraph, wherein the target molecule is translated via a cap-independent manner.
54. The lipid particle of any preceding paragraph, wherein the ligand is a protein, a protein fragment, a fusion protein, an amino acid or a derivative thereof, a steroid, a fatty acid or a lipid.
55. The lipid particle of any preceding paragraph, wherein the ligand is a cytokine or a hormone.
56. The lipid particle of any preceding paragraph, wherein the ligand is an interleukin or chemokine.
57. The lipid particle of any preceding paragraph, wherein the ligand is an interleukin selected from the group consisting of IL-1α, IL-1J3, IL-2, IL-3, IL-4, IL-5, IL-6, IL-7, IL-8, IL-9, IL-10, IL-11, IL-12A, IL-12B, IL-13, IL-15, IL-16, IL-17A, IL-17B, IL-17C, IL-17F, IL-18, IL-19, IL-20, IL-21, IL-22, IL-23, IL-24, IL-25, IL-26, IL-27, IL-28A, IL-28B, IL-29, IL-31, IL-33, IL-34, IL-36A, IL-36B, IL-36G, IL-37, and IL-38.
58. The lipid particle of any preceding paragraph, wherein the ligand is a chemokine selected from the group consisting of CCL14, CCL19, CCL20, CCL21, CCL25, CCL27, CXCL12, CXCL13, CXCL-8, CCL2, CCL3, CCL4, CCL5, CCL11, and CXCL10.
59. The lipid particle of any preceding paragraph, wherein the ligand is a hormone.
60. The lipid particle of any preceding paragraph, wherein the ligand is a hormone selected from the group consisting of insulin-like growth factor (or somatomedin), adrenaline (or epinephrine), melatonin, noradrenaline (or norepinephrine), triiodothyronine, thyroxine, dopamine, prostaglandins, leukotrienes, prostacyclin, thromboxane, amylin (or islet amyloid polypeptide), anti-müllerian hormone (or müllerian-inhibiting factor/hormone), adiponectin, adrenocorticotropic hormone (or corticotropin), angiotensinogen, angiotensin, antidiuretic hormone (or vasopressin, arginine vasopressin), atrial natriuretic peptide (or atriopeptin), brain natriuretic peptide, calcitonin, cholecystokinin, corticotropin-releasing hormone, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, growth hormone-releasing hormone, hepcidin, human chorionic gonadotropin, human placental lactogen, growth hormone, inhibin, insulin, leptin, lipotropin, luteinizing hormone, mnelanocyte stimulating hormone, motilin, orexin, osteocalcin, oxytocin (or pitocin), pancreatic polypeptide, parathyroid hormone, pituitary adenylate cyclase-activating peptide, prolactin (or leuteotropic hormone), prolactin-releasing hormone, relaxin, renin, secretin, somatostatin (or growth hormone-inhibiting hormone or growth hormone release-inhibiting hormone or somatotropin release-inhibiting factor or somatotropin release-inhibiting hormone), thrombopoietin, thyroid-stimulating hormone (or thyrotropin), thyrotropin-releasing hormone, vasoactive intestinal peptide, guanylin, uroguanylin, testosterone, dehydroepiandrosterone, androstenedione, dihydrotestosterone, aldosterone, estradiol, estrone, estriol, cortisol, progesterone, calcitriol, and calcidiol.
61. The lipid particle of any preceding paragraph, wherein the ligand is relaxin.
62. The lipid particle of any preceding paragraph, wherein the ligand is relaxin 2 or variant thereof.
63. The lipid particle of any preceding paragraph, wherein the target molecule is a cognate receptor of the ligand.
64. The lipid particle of any preceding paragraph, wherein the target molecule is a transmembrane receptor.
65. The lipid particle of any preceding paragraph, wherein the target molecule is a G protein-coupled receptor, a transmembrane tyrosine kinase receptor, a transmembrane chemokine receptor, a transmembrane ligand gated ion channel, a transporter, or a membrane-embedded protein.

66. The lipid particle of any preceding paragraph, wherein the target molecule is a cytokine or hormone receptor.

67. The lipid particle of any preceding paragraph, wherein the target molecule is an interleukin or chemokine receptor.

68. The lipid particle of any preceding paragraph, wherein the target molecule is an interleukin receptor selected from the group consisting of IL-1R1, IL-1R2, IL-1RAP, IL-1RL2, IL-2RJ3, IL-2Rα, IL-2Rγ, IL-2γ, IL-3Rα, IL-4R, IL-5Rα, IL-6RJ3, IL-6Rα, IL-7Rα, IL-9R, IL-10RJ3, IL-10Rα, IL-11Rα, IL-12J32, IL-12RJ31, IL-12RJ32, IL-13Rα1, IL-13Rα2, IL-15Rα, IL-17RA, IL-17RB, IL-17RC, IL-17RC, IL-17RD, IL-17RE, IL-18R1, IL-18RAP, IL-18Rα, IL-20RJ3, IL-20Rα, IL-20Rα1, IL-21R, IL-22Rα1, IL-23R, IL-27Rα, IL-28RA, IL-31Rα, CD4, CD9, CXCR1, and CXCR2.

69. The lipid particle of any preceding paragraph, wherein the target molecule is a chemokine receptor selected from the group consisting of CXCR1, CXCR2, CXCR4, CXCR5, CXCR5, CXCR6, CCR1, CCR2, CCR3, CCR4, CCR5, CCR6, CCR7, CCR8, CCR9, CCR10, CCR11, XCR1 and CX3CR1.

70. The lipid particle of any preceding paragraph, wherein the target molecule is a hormone receptor.

71. The lipid particle of any preceding paragraph, wherein the target molecule is a hormone receptor selected from the group consisting of calcitriol receptors, corticotropin-releasing hormone receptor 1, corticotropin releasing hormone receptor 2, estrogen receptors, follicle-stimulating hormone receptors, glucagon receptors, gonadotropin receptors, gonadotropin-releasing hormone receptors, growth hormone receptors, insulin receptor, luteinizing hormone, progesterone receptors, retinoid receptors, somatostatin receptors, thyroid hormone receptors, and thyrotropin receptors.

72. The lipid particle of any preceding paragraph, wherein the target molecule is a relaxin receptor.

73. The lipid particle of any preceding paragraph, wherein, wherein the target molecule is an inhibitor of a suppressor of the ligand.

74. The lipid particle of any preceding paragraph, wherein the target molecule inhibits or reduces binding of the ligand to the suppressor.

75. The lipid particle of any preceding paragraph, wherein the target molecule is an enzyme and the ligand is a substrate of the enzyme.

76. The lipid particle of any preceding paragraph, wherein the ligand is IL-1α, or IL-1J3, or both and the target molecule is IL-1R1, or IL-1R2, or both; wherein the ligand is IL-2 and the target molecule is IL-2Rα, or IL-2RJ3, or IL-2R$_y$, or all or a subset of the previous; wherein the ligand is IL-3 and the target molecule is IL-3Rα; wherein the ligand is IL-4 and the target molecule is IL-4R, or IL-2Rα, or IL-13Rα1 or all or a subset of the previous; wherein the ligand is IL-5 and the target molecule is IL-5Rα; wherein the ligand is IL-6 and the target molecule is IL-6Rα, or IL-6RJ3, or both; wherein the ligand is IL-7 and the target molecule is IL-7Rα, or IL-2γ, or both; wherein the ligand is IL-8 and the target molecule is CXCR1, or CXCR2, or both; wherein the ligand is IL-9 and the target molecule is IL-9R, or IL-2Rγ, or both; wherein the ligand is IL-10 and the target molecule is IL-10Rα, or IL-10RJ3, or both; wherein the ligand is IL-11 and target molecule is IL-11Rα, or IL-6RJ3, or both; wherein the ligand is IL-12A, or IL-12B, or both and the target molecule is IL-12RJ31, or IL-12RJ32, or both; wherein the ligand is IL-13 and target molecule is IL-13Rα1, or IL-13Rα2, or IL-4R, or all, or a subset of the previous; wherein the ligand is IL-15 and the target molecule is IL-15Rα, or IL-2RJ3, or IL-2Rγ, or all, or a subset of the previous; wherein the ligand is IL-16 and the target molecule is CD4, or CD9, or both; wherein the ligand is IL-17A and the target molecule is IL-17RA, or IL-17RC, or IL-17RD, or all, or a subset of the previous; wherein the ligand is IL-17B and the target molecule is IL-17RB; wherein the ligand is IL-17C and the target molecule is IL-17RA, or IL-17RE, or both; wherein the ligand is IL-17F and the target molecule is IL-17RA, or IL-17RC, or both; wherein the ligand is IL-18 and the target molecule is IL-18Rα, or IL-18RAP, or both; wherein the ligand is IL-19 and the target molecule is IL-20Rα, or IL-20RJ3, or both; wherein the ligand is IL-20 and the target molecule IL-20Rα, or IL-20RJ3, or IL-20Rα1, or all, or a subset of the previous; wherein the ligand is IL-21 and the target molecule is IL-21R, or IL-2Rγ, or both; wherein the ligand is IL-22 and the target molecule is IL-22Rα1, or IL-22Rα2, or IL-10RJ3, or all, or a subset of the previous; wherein the ligand is IL-23 and the target molecule is IL-12RJ31, or IL-23R, or both; wherein the ligand is IL-24 and the target molecule is IL-20Rα, or IL-20RJ3, or IL-22Rα1, or all, or a subset of the previous; wherein the ligand IL25 and the target molecule is IL-17RA, or IL-17RB, or both; wherein the ligand is IL-26 and the target molecule is IL-10RJ3 or IL-20Rα, or both; wherein the ligand is IL-27 and the target molecule is IL-27Rα, or IL-6RJ3, or both; wherein the ligand is IL-28A and the target molecule is IL-28RA, or IL-10RJ3, or both; wherein the ligand is IL-28B and the target molecule is IL-28RA, or IL-10RJ3, or both; wherein the ligand is IL-29 and the target molecule is IL-28RA, or IL-10RJ3, or both; wherein the ligand is IL-31 and the target molecule is IL-31Rα; wherein the ligand is IL-33, or IL-34, or both and the target molecule is IL-1R1, or IL-12J32, or IL-6RJ3, or both; wherein the ligand is IL-36A, or IL-36B, or IL-36G, or all, or a subset of the previous, and the target molecule is IL-1RL2, or IL-1RAP, or both; wherein the ligand is IL-37 and the target molecule is IL-18R1; wherein the ligand is IL-38 and the target molecule is IL-1R1, or IL-1R2, or both.

77. The lipid particle of any preceding paragraph, wherein the ligand is IGF-1 and the target molecule is IGF-1R; or whrein the ligand is FGF and the target molecule is selected from the group consisting of FGFR1, FGFR2, or FGFR3.

78. The lipid particle of any preceding paragraph, wherein the ligand is IGF-1 and the target molecule is Pappalysin-1.

79. The lipid particle of any preceding paragraph, wherein the lipid particle comprises a nucleic acid molecule encoding an RNA replicon.

80. The lipid particle of any preceding paragraph, wherein the first nucleic acid molecule further encodes the RNA replicon.

81. The lipid particle of any preceding paragraph, wherein the second nucleic acid molecule further encodes the RNA replicon.

82. The lipid particle of any preceding paragraph, wherein the first and/or second nucleic acid is comprised in a vector.

83. The lipid particle of any preceding paragraph, wherein the first nucleic acid molecule is comprised in a first vector and the second nucleic acid molecule is comprises in a second vector,
84. The lipid particle of any preceding paragraph, wherein the first and second nucleic acid molecules are comprised in the same vector.
85. The lipid particle of any preceding paragraph, wherein the first and/or second nucleic acid is comprised in a plasmid.
86. The lipid particle of any preceding paragraph, wherein the first nucleic acid molecule is comprised in a first plasmid and the second nucleic acid molecule is comprises in a plasmid vector,
87. The lipid particle of any preceding paragraph, wherein the first and second nucleic acid molecules are comprised in the same plasmid.
88. A composition or cell comprising a lipid particle of any preceding paragraph.
89. Use of a lipid particle of any preceding paragraph for activating a signaling pathway.
90. Use of a lipid particle any preceding paragraph for treating a disease or disorder in a subject.
91. A composition comprising a first nucleic acid molecule encoding a ligand and a second nucleic acid molecule encoding a target molecule, wherein the target molecule is a cognate receptor of the ligand or an inhibitor of a suppressor of the ligand.
92. The composition of any preceding paragraph, wherein the first and second nucleic acid molecules are covalently linked to each other.
93. The composition of any preceding paragraph, wherein the first and second nucleic acid molecules are covalently linked to each other and form a polycistronic nucleic acid of any preceding paragraph.
94. The composition of any preceding paragraph, wherein one of the ligand and the target molecule is translated via a cap-dependent manner and the other of the ligand and the target molecule is translated via a cap-independent manner.
95. The composition of any preceding paragraph, wherein the ligand is translated via a cap-dependent manner.
96. The composition of any preceding paragraph, wherein the target molecule is translated via a cap-independent manner.
97. The composition of any preceding paragraph, wherein the ligand is a protein, a protein fragment, a fusion protein, an amino acid or a derivative thereof, a steroid, a fatty acid or a lipid.
98. The composition of any preceding paragraph, wherein the ligand is a cytokine or a hormone.
99. The composition of any preceding paragraph, wherein the ligand is an interleukin or chemokine.
100. The composition of any preceding paragraph, wherein the ligand is an interleukin selected from the group consisting of IL-1α, IL-1J3, IL-2, IL-3, IL-4, IL-5, IL-6, IL-7, IL-8, IL-9, IL-10, IL-11, IL-12A, IL-12B, IL-13, IL-15, IL-16, IL-17A, IL-17B, IL-17C, IL-17F, IL-18, IL-19, IL-20, IL-21, IL-22, IL-23, IL-24, IL-25, IL-26, IL-27, IL-28A, IL-28B, IL-29, IL-31, IL-33, IL-34, IL-36A, IL-36B, IL-36G, IL-37, and IL-38.
101. The composition of any preceding paragraph, wherein the ligand is a chemokine selected from the group consisting of CCLA4, CCL19, CCL20, CCL21, CCL25, CCL27, CXCL12, CXCL13, CXCL-8, CCL2, CCL3, CCL4, CCL5, CCL, and CXCL10.
102. The composition of any preceding paragraph, wherein the ligand is a hormone.
103. The composition of any preceding paragraph, wherein the ligand is a hormone selected from the group consisting of insulin-like growth factor (or somatomedin), adrenaline (or epinephrine), melatonin, noradrenaline (or norepinephrine), triiodothyronine, thyroxine, dopamine, prostaglandins, leukotrienes, prostacyclin, thromboxane, amylin (or islet amyloid polypeptide), anti-müllerian hormone (or müllerian-inhibiting factor/hormone), adiponectin, adrenocorticotropic hormone (or corticotropin), angiotensinogen, angiotensin, antidiuretic hormone (or vasopressin, arginine vasopressin), atrial natriuretic peptide (or atriopeptin), brain natriuretic peptide, calcitonin, cholecystokinin, corticotropin-releasing hormone, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, growth horn none-releasing hormone, hepcidin, human chorionic gonadotropin, human placental lactogen, growth hormone, inhibin, insulin, leptin, lipotropin, luteinizing hormone, melanocyte stimulating hormone, motilin, orexin, osteocalcin, oxytocin (or pitocin), pancreatic polypeptide, parathyroid hormone, pituitary adenylate cyclase-activating peptide, prolactin (or leuteotropic horn none), prolactin-releasing hormone, relaxin, renin, secretin, somatostatin (or growth hormone-inhibiting hormone or growth hormone release-inhibiting hormone or somatotropin release-inhibiting factor or somatotropin release-inhibiting ionone), thrombopoietin, thyroid-stimulating hormone (or thyrotropin), thyrotropin-releasing hormone, vasoactive intestinal peptide, guanylin, uroguanylin, testosterone, dehydroepiandrosterone, androstenedione, dihydrotestosterone, aldosterone, estradiol, estrone, estriol, cortisol, progesterone, calcitriol, and calcidiol.
104. The composition of any preceding paragraph, wherein the ligand is relaxin.
105. The composition of any preceding paragraph, wherein the ligand is realxin-2 or variant thereof.
106. The composition of any preceding paragraph, wherein the target molecule is a cognate receptor of the ligand.
107. The composition of any preceding paragraph, wherein the target molecule is a transmembrane receptor.
108. The composition of any preceding paragraph, wherein the target molecule is a G protein-coupled receptor, a transmembrane tyrosine kinase receptor, a transmembrane chemokine receptor, a transmembrane ligand gated ion channel, a transporter, or a membrane-embedded protein.
109. The composition of any preceding paragraph, wherein the target molecule is a cytokine or hormone receptor.
110. The composition of any preceding paragraph, wherein the target molecule is an interleukin or chemokine receptor.
111. The composition of any preceding paragraph, wherein the target molecule is an interleukin receptor selected from the group consisting of IL-1R1, IL-1R2, IL-1RAP, IL-1RL2, IL-2RJ3, IL-2Rα, IL-2Rγ, IL-2γ, IL-3Rα, IL-4R, IL-5Rα, IL-6RJ3, IL-6Rα, IL-7Rα, IL-9R, IL-10RJ3, IL-10Rα, IL-11Rα, IL-12J32, IL-12RJ31, IL-12RJ32, IL-13Rα1, IL-13Rα2, IL-15Rα, IL-17RA, IL-17RB, IL-17RC, IL-17RC, IL-17RD, IL-17RE, IL-18R1, IL-18RAP, IL-18Rα, IL-20RJ3, IL-20Rα, IL-20Rα1, IL-21R, IL-22Rα1, IL-23R, IL-27Rα, IL-28RA, IL-31Rα, CD4, CD9, CXCR1, and CXCR2.

112. The composition of any preceding paragraph, wherein the target molecule is a chemokine receptor selected from the group consisting of CXCR1, CXCR2, CXCR4, CXCR5, CXCR5, CXCR6, CCR1, CCR2, CCR3, CCR4, CCR5, CCR6, CCR7, CCR8, CCR9, CCR10, CCR11, XCR1 and CX3CR1.

113. The composition of any preceding paragraph, wherein the target molecule is a hormone receptor.

114. The composition of any preceding paragraph, wherein the target molecule is a hormone receptor selected from the group consisting of calcitriol receptors, corticotropin-releasing hormone receptor 1, corticotropin releasing hormone receptor 2, estrogen receptors, follicle-stimulating hormone receptors, glucagon receptors, gonadotropin receptors, gonadotropin-releasing hormone receptors, growth hormone receptors, insulin receptor, luteinizing hormone, progesterone receptors, retinoid receptors, somatostatin receptors, thyroid hormone receptors, and thyrotropin receptors.

115. The composition of any preceding paragraph, wherein the target molecule is a relaxin receptor.

116. The composition of any preceding paragraph, wherein, wherein the target molecule is an inhibitor of a suppressor of the ligand.

117. The composition of any preceding paragraph, wherein the target molecule inhibits or reduces binding of the ligand to the suppressor.

118. The composition of any preceding paragraph, wherein the target molecule is an enzyme and the ligand is a substrate of the enzyme.

119. The composition of any preceding paragraph, wherein the ligand is IL-1α, or IL-1β, or both and the target molecule is IL-1R1, or IL-1R2, or both; wherein the ligand is IL-2 and the target molecule is IL-2Rα, or IL-2RJ3, or IL-2R$_y$, or all or a subset of the previous; wherein the ligand is IL-3 and the target molecule is IL-3Rα; wherein the ligand is IL-4 and the target molecule is IL-4R, or IL-2Rα, or IL-13Rα1 or all or a subset of the previous; wherein the ligand is IL-5 and the target molecule is IL-5Rα; wherein the ligand is IL-6 and the target molecule is IL-6Rα, or IL-6RJ3, or both; wherein the ligand is IL-7 and the target molecule is IL-7Rα, or IL-2γ, or both; wherein the ligand is IL-8 and the target molecule is CXCR1, or CXCR2, or both; wherein the ligand is IL-9 and the target molecule is IL-9R, or IL-2Rγ, or both; wherein the ligand is IL-10 and the target molecule is IL-10Rα, or IL-10RJ3, or both; wherein the ligand is IL-11 and target molecule is IL-11Rα, or IL-6RJ3, or both; wherein the ligand is IL-12A, or IL-12B, or both and the target molecule is IL-12RJ31, or IL-12RJ32, or both; wherein the ligand is IL-13 and target molecule is IL-13Rα1, or IL-13Rα2, or IL-4R, or all, or a subset of the previous; wherein the ligand is IL-15 and the target molecule is IL-15Rα, or IL-2RJ3, or IL-2Rγ, or all, or a subset of the previous; wherein the ligand is IL-16 and the target molecule is CD4, or CD9, or both; wherein the ligand is IL-17A and the target molecule is IL-17RA, or IL-17RC, or IL-17RD, or all, or a subset of the previous; wherein the ligand is IL-17B and the target molecule is IL-17RB; wherein the ligand is IL-17C and the target molecule is IL-17RA, or IL-17RE, or both; wherein the ligand is IL-17F and the target molecule is IL-17RA, or IL-17RC, or both; wherein the ligand is IL-18 and the target molecule is IL-18Rα, or IL-18RAP, or both; wherein the ligand is IL-19 and the target molecule is IL-20Rα, or IL-20RJ3, or both; wherein the ligand is IL-20 and the target molecule IL-20Rα, or IL-20RJ3, or IL-20Rα1, or all, or a subset of the previous; wherein the ligand is IL-21 and the target molecule is IL-21R, or IL-2Rγ, or both; wherein the ligand is IL-22 and the target molecule is IL-22Rα1, or IL-22Rα2, or IL-10RJ3, or all, or a subset of the previous; wherein the ligand is IL-23 and the target molecule is IL-12RJ31, or IL-23R, or both; wherein the ligand is IL-24 and the target molecule is IL-20Rα, or IL-20RJ3, or IL-22Rα1, or all, or a subset ofthe previous; wherein the ligand IL25 and the target molecule is IL-17RA, or IL-17RB, or both; wherein the ligand is IL-26 and the target molecule is IL-10RJ3 or IL-20Rα, or both; wherein the ligand is IL-27 and the target molecule is IL-27Rα, or IL-6RJ3, or both; wherein the ligand is IL-28A and the target molecule is IL-28RA, or IL-10RJ3, or both; wherein the ligand is IL-28B and the target molecule is IL-28RA, or IL-10RJ3, or both; wherein the ligand is IL-29 and the target molecule is IL-28RA, or IL-10RJ3, or both; wherein the ligand is IL-31 and the target molecule is IL-31Rα; wherein the ligand is IL-33, or IL-34, or both and the target molecule is IL-1R1, or IL-12J32, or IL-6RJ3, or both; wherein the ligand is IL-36A, or IL-36B, or IL-36G, or all, or a subset of the previous, and the target molecule is IL-1RL2, or IL-1RAP, or both; wherein the ligand is IL-37 and the target molecule is IL-18R1; wherein the ligand is IL-38 and the target molecule is IL-1R1, or IL-1R2, or both.

120. The composition of any preceding paragraph, wherein the ligand is IGF-1 and the target molecule is IGF-1R; or wherein the ligand is FGF and the target molecule is selected from the group consisting of FGFR1, FGFR2, or FGFR3.

121. The composition of any preceding paragraph, wherein the ligand is IGF-1 and the target molecule is Pappalysin-1.

122. The composition of any preceding paragraph, wherein the lipid particle comprises a nucleic acid molecule encoding an RNA replicon.

123. The composition of any preceding paragraph, wherein the first nucleic acid molecule further encodes the RNA replicon.

124. The composition of any preceding paragraph, wherein the second nucleic acid molecule further encodes the RNA replicon.

125. The composition of any preceding paragraph, wherein the first and/or second nucleic acid is comprised in a vector.

126. The composition of any preceding paragraph, wherein the first nucleic acid molecule is comprised in a first vector and the second nucleic acid molecule is comprises in a second vector, 127. The lipid particle of any preceding paragraph, wherein the first and second nucleic acid molecules are comprised in the same vector.

128. The composition of any preceding paragraph, wherein the first and/or second nucleic acid is comprised in a plasmid.

129. The composition of any preceding paragraph, wherein the first nucleic acid molecule is comprised in a first plasmid and the second nucleic acid molecule is comprises in a plasmid vector,
130. The composition of any preceding paragraph, wherein the first and second nucleic acid molecules are comprised in the same plasmid.
131. The composition of any preceding paragraph, wherein the composition further comprises a pharmaceutically acceptable carrier or excipient.
132. The composition of any preceding paragraph, wherein the composition is formulated for formulated for systemic administration.
133. The composition of any preceding paragraph, wherein the composition is formulated for parenteral administration or inhalation administration.
134. The composition of any preceding paragraph, wherein the composition is formulated for intravenous administration, intramuscular administration, subcutaneous administration, transdermal administration or via inhalation administration.
135. The composition of any preceding paragraph, wherein the composition is formulated for administration via inhalation as an aerosol, administration via intra-articular injection or administration via intramuscular injection.
136. Use of a composition of any preceding paragraph for activating a signaling pathway.
137. Use of a composition of any preceding paragraph for treating a disease or disorder in a subject.
138. Use of any preceding paragraph, wherein the ligand is relaxin-2, the target molecule is RXFP1, and wherein the disease or disorder is selected from the group consisting of arthrofibrosis, a cardiovascular disease, an interstitial pulmonary disease, systemic sclerosis, a vascular disease, and hypertrophic or keloid scars.
139. Use of any preceding paragraph, wherein the ligand is IGF-1, the translated target is Pappalysin-1, Pappalysin-2, or IGF-1R, and wherein the disease or disorder is selected from the group consisting of osteoarthritis; autism; diabetes mellitus; a central nervous system disorder; a developmental disorder; a neuromuscular disorder; diabetic neuropathy; ischemia-reperfusion injuries; chronic heart failure; a chronic wasting disease; and cancer cachexia.
140. Use of any preceding paragraph, wherein the disease is selected from the group consisting of Duchenne Muscular Dystrophy, Becker Muscular Dystrophy, stroke, traumatic brain injury, peripheral nerve injury, Spinal Muscular Atrophy (Type I, II, III, or IV), Cerebral Palsy, Arthrogryposis Multiplex Congenita, fibrosis of the humeroradial joint, fibrosis of the humeroulnar joint, fibrosis of the glenohumeral joint, fibrosis of the tibiofemoral joint, fibrosis of the acetabulofemoral joint, fibrosis of the talocrural joint, fibrosis of the temporomandibular joint, fibrosis of the metacarpophalangeal joint, fibrosis of the metatarsophalangeal joint, fibrosis of the peri-articular musculature, cellulite, and interstitial lung disease.
141. Use of any preceding paragraph, wherein activating the signaling pathway results in a therapeutic effect.
142. Use of any preceding paragraph, wherein the therapeutic effect is antifibrotic, vasodilatory, hemodynamic, angiogenic, apoptotic, antiviral, increases cell proliferation, antifibrogenic, cytotoxic, proliferative, regenerative, immunomodulatory, regulates cell cycle or results in epigenetic alterations.
143. A method for activating a signaling pathway, the method comprising: administering to subject a nucleic acid combination of any preceding paragraph, a lipid particle of any preceding paragraph, or a composition of any preceding paragraph.
144. The method of any preceding paragraph, wherein activating the signaling pathway results in a therapeutic effect.
145. The method of any preceding paragraph, wherein the therapeutic effect is antifibrotic, vasodilatory, hemodynamic, angiogenic, apoptotic, antiviral, increases cell proliferation, antifibrogenic, cytotoxic, proliferative, regenerative, immunomodulatory, regulates cell cycle or results in epigenetic alterations.
146. A method for treating a disease or disorder, the method comprising administering to a subject in need thereof a nucleic acid combination of any preceding paragraph, a lipid particle of any preceding paragraph, or a composition of any preceding paragraph.
147. The method of any preceding paragraph, wherein the ligand is relaxin-2, the target molecule is RXFP1, and wherein the disease or disorder is selected from the group consisting of arthrofibrosis, a cardiovascular disease, an interstitial pulmonary disease, systemic sclerosis, a vascular disease, and hypertrophic or keloid scars.
148. The method of any preceding paragraph, wherein the ligand is IGF-1, the translated target is Pappalysin-1, Pappalysin-2, or IGF-1R, and wherein the disease or disorder is selected from the group consisting of osteoarthritis; autism; diabetes mellitus; a central nervous system disorder; a developmental disorder; a neuromuscular disorder; diabetic neuropathy; ischemia-reperfusion injuries; chronic heart failure; a chronic wasting disease; and cancer cachexia.
149. The method of any preceding paragraph, wherein the disease is selected from the group consisting of Duchenne Muscular Dystrophy, Becker Muscular Dystrophy, stroke, traumatic brain injury, peripheral nerve injury, Spinal Muscular Atrophy (Type I, II, III, or IV), Cerebral Palsy, Arthrogryposis Multiplex Congenita, fibrosis of the humeroradial joint, fibrosis of the humeroulnar joint, fibrosis of the glenohumeral joint, fibrosis of the tibiofemoral joint, fibrosis of the acetabulofemoral joint, fibrosis of the talocrural joint, fibrosis of the temporomandibular joint, fibrosis of the metacarpophalangeal joint, fibrosis of the metatarsophalangeal joint, fibrosis of the peri-articular musculature, cellulite, and interstitial lung disease.
150. The method of any preceding paragraph, wherein the subject has or is diagnosed with osteoarthritis, autism, diabetes mellitus, a central nervous system disorder, a developmental disorder, a neuromuscular disorder, diabetic neuropathy, ischemia-reperfusion injuries, chronic heart failure, a chronic wasting disease, or cancer cachexia.
151. The method of any preceding paragraph, wherein said administering is via inhalation as an aerosol, via intra-articular injection, via intramuscular injection, via intradermal injection, via subcutaneous injection, via intracapsular injection, via pericapsular injection, via musculotendinous injection, via intraligamentous injection, via periligamentous injection, via intratendinous injection, via peritendinous injection, via intraosteotendinous injection, via periosteotendinous injection.
152. The method of any preceding paragraph, wherein the disease is Duchene's muscular dystrophy and said administering is via intramuscular injection; the disease is Duchene's muscular dystrophy and said administering is via intraarticular injection; the disease is Becker's muscular dystrophy and said administering is via intramuscular injection; the disease is Becker's muscular dystrophy and said administering is via intraarticular injection; the disease is Spinal Muscular Dystrophy and said administering is via intramuscular injection; the disease is Spinal Muscular Dystrophy and said administering is via intraarticular injection; the disease is Arthrogryposis Multiplex Congenita and said administering is via intramuscular injection; the disease is Arthrogryposis Multiplex Congenita and said administering is via intraarticular injection; the disease is Cerebral Palsy and said administering is via intramuscular injection; the disease is Cerebral Palsy and said administering is via intraarticular injection; the disease is stroke and said administering is via intramuscular injection; the disease is stroke and said administering is via intraarticular injection; the disease is traumatic brain injury and said administering is via intramuscular injection; the disease is traumatic brain injury and said administering is via intraarticular injection; the disease is peripheral nerve injury and said administering is via intramuscular injection; the disease is peripheral nerve injury and said administering is via intraarticular injection.

Definitions

For convenience, the meaning of some terms and phrases used in the invention, examples, and appended claims, are provided. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

The term "target" or "biological target" as used herein refers to a biological substance, compound, or molecule, which after activation or inhibition, has a specific and intended downstream therapeutic effect. The term "target" encompasses cell surface receptors such as G protein-coupled receptors, tyrosine kinase transmembrane receptors, hormone receptors, chemokine receptors, and ligand gated ion channels. The term "target" or "biological target" may also encompass enzymes, voltage gated ion channels, structural proteins, nucleic acids, transporters, signaling proteins, or another ligand. The term "target" may refer to a single entity or a set of entities comprising multiple components of a shared signaling pathway.

The term "ligand" as used herein refers to a molecule or arrangement of molecules or biomacromolecule with an intended therapeutic effect through interaction with a biological target. The term "ligand" does not restrict the molecule or arrangement of molecules to only those which specifically bind or localize to a receptor, enzyme, nucleic acid, or other biological target. The term "ligand" encompasses a molecule or an arrangement of molecules which may transiently or permanently interact or bind with a biological target.

The term "ligand suppressor" or "suppressor of ligand" as used herein refers to a biological substance, compound, molecule or arrangement of molecules, or biomacromolecule, which prevents, attenuates, inhibits, blocks, or otherwise alters the interaction of the ligand and target. This effect may manifest as competitive binding to the ligand active site on the target, allosteric inhibition by ligand suppressor binding the ligand, allosteric inhibition by the ligand suppressor binding the target at a location other than the active site, ligand suppressor binding and altering the target conformation, or any other mechanism through which the binding of ligand and target is altered.

As used herein, an "effective amount," is intended to include the amount of any of the polycistronic nucleic acids, lipid particles, or compositions thereof that, when administered to a subject via a depot having a stiffened joint, is sufficient to affect treatment of a disease or disorder. The "effective amount" may vary depending on the sequence of the polycistronic nucleic acids, lipid particles, or compositions thereof; how the polycistronic nucleic acids, lipid particles, or compositions thereof are administered; the severity of the disease or disorder and the history, age, weight, family history, genetic makeup, the types of preceding or concomitant treatments, if any, and other individual characteristics of the subject to be treated. Ameliorating the disease or disorder includes slowing the course of the progression of the disease or disorder or reducing the severity of the disease or disorder.

As used herein, a "subject" is an animal, such as a mammal, including a primate (e.g., a human), a non-human primate, (e.g., a monkey and a chimpanzee), a non-primate (e.g., a cow, a pig, a camel, a llama, a horse, a goat, a rabbit, a sheep, a hamster, a guinea pig, a cat, a dog, a rat, a mouse, a horse, and a whale), or a bird (e.g., a duck or a goose). In an embodiment, the subject is a human, such as a human being assessed for a stiffened joint, a human at risk for developing a stiffened joint, a human having a stiffened joint, and/or a human being treated for a disease or disorder.

Preferably, the subject is a mammal. The mammal can be a human, non-human primate, mouse, rat, dog, cat, horse, or cow, but is not limited to these examples. Mammals other than humans can be advantageously used as subjects that represent animal models of disease e.g., a disease or disorder associated with fibrosis. A subject can be male or female.

A subject can be one who has been previously diagnosed with or identified as suffering from or having a disease or disorder in need of treatment or one or more complications related to such a disease or disorder, and optionally, have already undergone treatment for the disease or disorder or the one or more complications related to the disease or disorder. Alternatively, a subject can also be one who has not been previously diagnosed as having such disease or disorder or related complications. For example, a subject can be one who exhibits one or more risk factors for the disease or disorder or one or more complications related to the disease or disorder or a subject who does not exhibit risk factors.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" includes both methods practiced on the human body and also the foregoing activities.

As used herein, the term "parenteral administration," refers to administration through injection or infusion. Parenteral administration includes, but is not limited to, subcutaneous administration, intravenous administration, or intramuscular administration.

As used herein, the term "subcutaneous administration" refers to administration just below the skin. "Intravenous administration" means administration into a vein.

As used herein, the terms "treat," "treatment," "treating," or "amelioration" refer to therapeutic treatments, wherein the object is to reverse, alleviate, ameliorate, inhibit, slow down or stop the progression or severity of a disease or disorder, e.g., a fibrotic disease and disorder. The term "treating" includes reducing or alleviating at least one adverse effect or symptom of a disease and disorder (e.g., inflammation, stiffening of a joint, contracture of a joint, contracture of a joint not caused by muscle contracture, contracture of a joint associated with muscle contracture, pain, loss of mobility, difficulty breathing, muscle stiffness, muscle dysfunction, skin dimpling, keloid scarring, burn-associated scarring). Treatment is generally "effective" if one or more symptoms or clinical markers are reduced. Alternatively, treatment is "effective" if the progression of a disease or disorder is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, "prevention" or "preventing," when used in reference to a disease or disorder, refers to a reduction in the likelihood that a subject, e.g., a human subject, will develop a symptom associated with such disease or disorder, or a reduction in the frequency and/or duration of a symptom associated with a disease or disorder. The likelihood of developing a given disease or disorder is reduced, for example, when a subject having one or more risk factors for the disease or disorder either fails to develop or develops with less severity relative to a population having the same risk factors and not receiving treatment as described herein. The failure to develop a disease or disorder, or the reduction in the development of a symptom associated with disease or disorder (e.g., by at least about 10%), or the exhibition of delayed symptoms (e.g., delayed by days, weeks, months or years) is considered effective prevention.

As used herein, the term "administering," refers to the placement of a therapeutic (e.g., polycistronic nucleic acid, lipid particle described herein) or composition as disclosed herein into a subject by a method or route which results in at least partial delivery of the agent to the subject. Compositions, e.g., pharmaceutical composition comprising agents as disclosed herein can be administered by any appropriate route which results in an effective treatment in the subject.

In some embodiments, polycistronic nucleic acids and compositions described herein comprise an antifibrotic agent, e.g., relaxin or functional variant thereof. As used herein, "Relaxin 2" refers to the gene encodes a member of the relaxin subfamily and insulin superfamily of peptide hormones. Sequences for relaxin 2, also known as H2; RLXH2; H2-RLX; bA12D24.1.1; and bA12D24.1.2, are known for a number of species, e.g., human relaxin 2 (NCBI Gene ID: 6019) polypeptide (e.g., NCBI Ref Seq NP_001316120.1) and mRNA (e.g., NCBI Ref Seq NM_001329191.2). Relaxin 2 can refer to human Relaxin 2, including naturally occurring variants, molecules, and alleles thereof. Relaxin 2 refers to the mammalian Relaxin 2 of, e.g., mouse, rat, rabbit, dog, cat, cow, horse, pig, and the like.

The term "decrease", "reduced", "reduction", or "inhibit" are all used herein to mean a decrease by a statistically significant amount. In some embodiments, "decrease", "reduced", "reduction", or "inhibit" typically means a decrease by at least 10% as compared to an appropriate control (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to an appropriate control.

The terms "increase", "enhance", or "activate" are all used herein to mean an increase by a reproducible statistically significant amount. In some embodiments, the terms "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, a 20 fold increase, a 30 fold increase, a 40 fold increase, a 50 fold increase, a 6 fold increase, a 75 fold increase, a 100 fold increase, etc. or any increase between 2-fold and 10-fold or greater as compared to an appropriate control. In the context of a marker, an "increase" is a reproducible statistically significant increase in such level.

As used herein, a "reference level" refers to a normal, otherwise unaffected cell population or tissue (e.g., a biological sample obtained from a healthy subject, or a biological sample obtained from the subject at a prior time point, e.g., a biological sample obtained from a patient prior to being diagnosed with a fibrotic disease or disorder, or a biological sample that has not been contacted with an agent disclosed herein).

As used herein, an "appropriate control" refers to an untreated, otherwise identical cell or population (e.g., a patient who was not administered a polycistronic nucleic acid, lipid particle, or composition thereof described herein, or was administered by only a subset of polycistronic nucleic acids, lipid particles, or compositions thereof described herein, as compared to a non-control cell).

The term "statistically significant" or "significantly" refers to statistical significance and generally means a two standard deviation (2SD) or greater difference.

As used herein the term "comprising" or "comprises" is used in reference to compositions, methods, and respective component(s) thereof, that are essential to the method or composition, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "about" as used herein means in quantitative terms plus or minus 10%. For example, "About 3%" would encompass 2.7-3.3% and "About 10%" would encompass 9-11%. Moreover, where "about" is used herein in conjunction with a quantitative term it is understood that in addition to the value plus or minus 10%, the exact value of the quantitative term is also contemplated and described— for example, the term "about 3%" expressly contemplates, describes and includes exactly 3%.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the inventions claimed. Thus, it should be understood that although the present inventions have been specifically disclosed by preferred embodiments and optional features, modification and variation of the inventions embodied therein herein disclosed may be resorted to by those skilled in the art, and that such modifications and variations are considered to be within the scope of various aspects and embodiments of inventions contemplated herein.

Certain aspects and embodiments of the invention and inventions have been described broadly and generically herein. Each of the narrower species and subgeneric groupings falling within the generic invention also form part of some aspects and embodiments of inventions contemplated herein. This includes the generic description of inventions with a proviso or negative limitation removing any subject matter from the genus, regardless of whether or not the excised material is specifically recited herein.

In addition, where features or aspects of the invention are described in terms of Markush groups, those skilled in the art will recognize that some aspects and embodiments of inventions contemplated herein are also thereby described in terms of any individual member or subgroup of members of the Markush group.

While preferred embodiments of the present invention have been shown and described herein, it will be obvious to those skilled in the art that such embodiments are provided by way of example only. Numerous variations, changes, and substitutions will now occur to those skilled in the art without departing from the inventions. It should be understood that various alternatives to the embodiments of the inventions described herein may be employed in practicing the inventions. It is intended that the following embodiments define the scope of the inventions and that methods and structures within the scope of these embodiments and their equivalents be covered thereby.

Unless defined otherwise, all technical and scientific terms used herein have the same meaning as commonly understood by one of ordinary skill in the art to which these inventions belong. Although any methods and materials similar or equivalent to those described herein can be used in the practice or testing of the inventions, it will be understood that modifications and variations are encompassed within the spirit and scope of the instant invention. The preferred methods and materials are now described.

All publications, patents, and patent applications mentioned in this specification are herein incorporated by reference to the same extent as if each individual publication, patent, or patent application was specifically and individually indicated to be incorporated by reference. In the case of conflict, the specification, including definitions, will control.

EXAMPLES

The present invention will be further described in the following examples, which do not limit the scope of the present invention.

Example 1

An Exogenous Signaling Circuit for Restoration of Antifibrotic Effect in Systemic Sclerosis Patients.

There is evidence that in scleroderma patients, an altered isoform of RXFP1 is expressed, which is hypothesized to have led to the failure of relaxin as a treatment for scleroderma in previous clinical trials (Corallo C., et al., *N. Cin Exp Rheumatol*. 2019 Jul.-Aug.; 37 Suppl 119(4):69-75). To overcome these barriers, RXFP1 is simultaneously expressed with relaxin in fibrotic cells to restore the antifibrotic activity of relaxin. mRNA is synthesized such that relaxin is translated via traditional cap-dependent translation and RXFP1 translation is initiated in a cap-independent manner. Intracellular delivery of this construct results in the simultaneous extracellular secretion of relaxin and transmembrane expression of RXFP1. By expression of the mature isoform of RXFP1, tissue lacking in the relaxin receptor can be stimulated with relaxin to initiate antifibrotic signaling. The secreted extracellular relaxin binds to RXFP1 expressed in the transmembrane and initiates the canonical relaxin antifibrotic signaling cascade. For example, a systemic sclerosis patient with moderate to severe scleroderma receives microneedle patches loaded with functionalized mRNA encoding for both relaxin and RXFP1. Functionalized mRNA is dosed at 10 µg/in$^2$; total dose per treatment location not to exceed 250 µg/kg of functionalized mRNA. The patient is monitored for improvement in skin? fibroses. Tissue mobility and elasticity as well as Rodnan skin score is assessed overtime to determine severity of scleroderma after treatment.

Example 2

An Exogenous Signaling Circuit for Potentiation of Relaxin Antifibrotic Effect in Treatment of Musculoskeletal Fibrosis.

Lipid nanoparticles (LNPs) loaded with a 3:1 mixture of mRNA that encodes relaxin and RXFP1, respectively. Both mRNA strands bear identical 5' and 3' untranslated regions, with different open reading frames. A suspension of LNPs are administered to a patient diagnosed with shoulder adhesive capsulitis. Relaxin/RXFP1 loaded LNPs are administered in the form of about a 1 ml intraarticular injection using a 25G needle, such that the final dose of loaded LNPs is 2 mg/kg. As the articular cells translate the two mRNA strands, relaxin is secreted into the synovial fluid and RXFP1 is membrane expressed. The secreted extracellular relaxin binds to the transmembrane expressed RXFP1 and initiates the canonical relaxin antifibrotic signaling cascade. Following injection, the patient is monitored for changes in joint range of motion, (e.g. internal rotation, external rotation, pronation, supination, flexion, extension, abduction, and adduction) patient-reported pain, mobility, patient-reported autonomy, and patient-reported quality of life.

Example 3

An Exogenous Signaling Circuit for Potentiation of Antifibrotic Effect in Acute Heart Failure Patients.

Previous clinical exploration of relaxin for the treatment of acute heart failure (AHF) failed to demonstrate efficacy in primary endpoints in a multicenter phase III clinical trial (Metra et al., *N Engl J Med* 2019; 381:716-726). To potentiate the angiogenic and hemodynamic effects of relaxin, acute heart failure patients are administered cardiomyocyte-targeting lipid nanoparticles loaded with mRNA that encodes for relaxin and RXFP1 on a single strand. mRNA is synthesized such that relaxin is translated via traditional cap-dependent translation and RXFP1 translation is initiated in a cap-independent manner. Intracellular delivery of this construct results in the simultaneous extracellular secretion of relaxin and transmembrane expression of RXFP1. Patients administered to the hospital for myocardial infarction are given IV injection of loaded lipid nanoparticles once every 12 hours for 72 hours, at a dose of 4 mg/kg/day. Patients are continually monitored for respiratory rate, blood pressure, heart rate, and infarct reoccurrence. All-cause mortality is assessed 180 days after treatment to determine treatment efficacy at prevention of future infarcts.

Example 4

An Exogenous Signaling Circuit for Potentiation of Antifibrotic Effect in Hepatic Fibrosis Patients.

mRNA-loaded lipid nanoparticles, 90-110 nm in diameter, are administered via intravenous injection to a patient with hepatic fibrosis (nonalcoholic steatohepatitis; NASH) due to non-alcoholic fatty liver disease. The natural tendency of nanoparticles to localize to the liver will allow for targeted delivery of mRNA encoding relaxin and RXFP1 to the diseased tissue. Patients are primarily monitored for changes in histological NASH activity score, as well as changes in insulin sensitivity and serum alanine aminotransferase levels.

Example 5

An Exogenous Signaling Circuit for Restoration of Antifibrotic Effect in Progressive Pulmonary Fibrosis Patients.

There is evidence that suggests a lack of sufficient RXFP1 expression in the pulmonary tissue of patients with pulmonary fibrosis (Tan J, et al. *Am J Respir Crit Care Med.* 2016 Dec. 1; 194(11):1392-1402)(Bahudhanapati H, et al. *J Biol Chem.* 2019 Mar. 29; 294(13):5008-5022). The nebulized administration of lipid nanoparticles loaded with mRNA that encodes for relaxin and RXFP1 on a single strand results in the simultaneous extracellular secretion of relaxin and transmembrane expression of RXFP1. mRNA is synthesized such that relaxin is translated via traditional cap-dependent translation and RXFP1 translation is initiated in a cap-independent manner. mRNA-loaded lipid nanoparticles are administered three times daily for 7 days via vibrating mesh nebulizer as a 5 min nebulization session with a total pre-nebulization dose of 25 mg/kg/session. Following administration, the patient is monitored for decreases in pathological hallmarks of fibrosis via CT scan, as well as for increased forced vital capacity, and decrease in respiratory distress symptoms.

Example 6

An Exogenous Signaling Circuit to Potentiate IGF-1's Effect for the Treatment of Patients with Osteoarthritic Joints.

A hallmark of osteoarthritis is the overexpression of insulin like growth factor (IGF) binding proteins in the synovial fluid (Martel-Pelletier J, et al. *Inflamm. Res.* 1998 Mar. 47(3):90-100). This expression results in the sequestration of IGF-1 away from its cognate receptor, IGF-1R, and suppression of the proliferative signaling necessary for chondrocyte health. To restore the IGF-1/IGF-1R signaling pathway to a healthy, non-osteoarthritic state, creation of an exogenous signaling circuit using mRNA that encodes for IGF-1 and Papplysin-2 on a single strand is administered to the patient via intraarticular administration. mRNA is synthesized such that IGF-1 is translated via traditional cap-dependent translation and Pappalysin-1 translation is initiated in a cap-independent manner. Intracellular delivery of this construct results in the simultaneous extracellular secretion of IGF-1 and Pappalysin-1 into the synovial space. Pappalysin-1 acts to inhibit the binding of IGF binding proteins to IGF-1, and thus potentiates the proliferative signaling of IGF-1 through binding of IGF-1R. IGF-1/Pappalysin-1-loaded LNPs are administered in the form of about a 1 ml intraarticular injection using a 25G needle, such that the final dose of loaded LNPs is 2 mg/kg. Osteoarthritis patients are monitored for joint range of motion, pain, and total chondrocyte coverage as assessed via commuted tomography and magnetic resonance imaging.

Example 7

The Potentiation of a Ligand by Co-Expression of its Cognate Receptor Target.

The present invention provides compositions of matter and methods for treating diseases including stiffened fibrotic joint capsules, muscle fibrosis (e.g. contractures due to Duchene's muscular dystrophy, spinal muscular atrophy, cerebral palsy, traumatic brain injury, immobilization), lung fibrosis (e.g. idiopathic pulmonary fibrosis, cystic fibrosis, hypertension), liver fibrosis (e.g. hepatitis B or C, long-term alcohol abuse, nonalcoholic steatohepatitis, non-alcoholic fatty liver disease, Cholestasis, autoimmune hepatitis cirrhosis), kidney fibrosis (e.g. chronic kidney disease, end-stage renal disease, renal interstitial fibrosis), heart disease (i.e. heart failure, myocardial infarction, aortic stenosis, hypertrophic cardiomyopathy), intestinal disease (e.g. Crohn's disease, inflammatory bowel disease, enteropathies, and other intestinal fibrosis), skin conditions (e.g. scleroderma, keloids, hypertrophic scars, cellulite), urogenital and gynecological conditions (e.g. Peyronie's disease, uterine fibroids) and ocular diseases (e.g. Congenital Fibrosis of the Extraocular Muscles, subretinal fibrosis, epiretinal fibrosis, corneal fibrosis) in a subject by administering a nucleotide capable of simultaneous production and expression of a signaling pathway ligand and its target. The agent will be the native ligand of the receptor (e.g. relaxin for RXFP1, IGF1 for IGFR1, IL10 for IL10RA). The polynucleotide(s) encoding both ligand and/or target may be administered intravenously, intramuscularly, subcutaneously, intradermally, intranasally, orally, transcutaneously, mucosally, intraarticularly, periarticularly, intracapsularly, pericapsularly, intratendinously, peritendinously, intraligamentously, periligamentously, by pulmonary inhalation or by ocular specific routes of administration. Alternatively, the polynucleotide(s) encoding both ligand and/or target may be administered

Example 8

A Self-Amplifying, Exogenous Signaling Circuit to Potentiate IGF-1's Effect for the Treatment of Patients with Osteoarthritic Joints.

A hallmark of osteoarthritis is the overexpression of insulin like growth factor (IGF) binding proteins in the synovial fluid (Martel-Pelletier J, et al. *Inflamm. Res.* 1998 Mar. 47(3):90-100). This expression results in the sequestration of IGF-1 away from its cognate receptor, IGF-1R, and suppression of the proliferative signaling necessary for chondrocyte health. To restore the IGF-1/IGF-1R signaling pathway to a healthy, non-osteoarthritic state, creation of an exogenous signaling circuit using mRNA that encodes for IGF-1 and Papplysin-1 or -2 on a single strand is administered to the patient via intraarticular administration. mRNA is synthesized such that IGF-1 is translated via traditional cap-dependent translation and Pappalysin-1/-2 translation is initiated in a cap-independent manner. Additionally, this mRNA strand encodes for a subset of non-structural proteins of a viral replicase, which upon translation, amplify the open reading frame of interest, here either IGF-1, IGF-1R, or Pappalysin-1/-2, by further production of mRNA in situ. Intracellular delivery of this construct results in the simultaneous extracellular secretion of IGF-1 and Pappalysin-1/-2 into the synovial space (FIG. 16). The self-amplifying nature of this mRNA encoding the ligand/receptor/potentiator combination results in sustained, multi-day to multi-week expression. Pappalysin-1/-2 acts to inhibit the binding of IGF binding proteins to IGF-1, and thus potentiates the proliferative signaling of IGF-1 through binding of IGF-1R. IGF-1/Pappalysin-1/-2-loaded LNPs are administered in the form of about a 1 ml intraarticular injection using a 25G needle, such that the final dose of loaded LNPs is 2 mg/kg. Osteoarthritis patients are monitored for joint range of motion, pain, and total chondrocyte coverage as assessed via commuted tomography and magnetic resonance imaging.

Example 9

A Disease-State Independent Biotherapeutic Circuit for the Treatment of Musculoskeletal Conditions Abstract Most therapeutics achieve bioactivity by co-opting all or part of a naturally occurring pathway. In the absence of external drugs, these pathways have endogenous ligands which regulate signal transduction. Endogenous ligands are an attractive therapeutic modality due to their specificity, target affinity, and non-immunogenic nature. Most importantly, the combinatorial space of the different signaling pathways in mammalian cells encompass nearly all possible therapeutic effects. However, while endogenous ligands can be potent in vitro and show great promise pre-clinically, many fail in human trials. In this chapter, we explore the disease-state dependent pitfalls of endogenous ligands through the lens of three unique musculoskeletal diseases: Arthrofibrosis, rheumatoid arthritis, and osteoarthritis. These diseases, which affect the synovial space and musculoskeletal system more broadly, are traditionally overlooked in modern biotherapeutic development. We design and characterize an mRNA-based, disease-state independent biotherapeutic circuit capable of harnessing endogenous ligands as potent treatments for each disease. We accomplish this by simultaneously treating with the ligand and restoring the dysregulated component of the its natural signaling pathway. This work extends far beyond musculoskeletal disease and is a both a call to action to better understand ligand-receptor relationships in human diseases as well as a demonstration of a platform technology capable of simultaneous pathway restoration and activation, independent of disease-state or tissue type.

Introduction

As the collective understanding of disease biology deepens and the number of potential treatment modalities expands, it is essential to pull back and understand the shared feature of all therapies. Whether it is a small-molecule, a protein, or a gene therapy, the underlying mechanism of action is perturbation of a biological signaling network in order to bias the outcome towards a new state. Modem drug development takes a disease phenotype and then design a targeted treatment to either suppress symptomatic presentation or treat disease etiology directly. Substantial preclinical and clinical investments are made into designing novel molecules and mechanisms to alter biological pathways. Yet, endogenously occurring ligands can often regulate biological processes with far higher fidelity than designed therapeutics because they fully harness natural signaling cascades, rather than co-opting them.

Regardless of whether a therapy is artificially designed for or borrowed from natural pathways, a critical aspect of successful translational drug development is the characterization of target density in the tissue or cell type of interest. Next-generation omics studies have started to show the hypervariability of the tissue and cell-type specific proteome and transcriptome(174). This becomes particularly pertinent when harnessing endogenous ligands as therapeutics. A ligand could be uniquely suited to treated multiple aspects of a given disease, but without the ligand's receptor or target present in the tissue of interest, the treatment will fail. This is further complicated by disease-state dependent dysregulation of natural signaling pathways which manifests as suppression of a cell surface receptor, decreased ligand bioavailability, alteration to post-translational processing, or suppression via epigenetic remodeling, among many potential alterations.

In this Example, we disclose a platform for harnessing endogenously occurring ligands in a disease-state and tissue-type independent manner. We detail an mRNA therapeutics platform capable of simultaneously producing ligand and restoring the minimum essential components of a natural signaling pathway in the tissue of interest. We call these systems transient biotherapeutic circuits. They allow for auto-induction of a biological signaling cascade independent of the disease-state or tissue-type. mRNA is uniquely suited for generation of these biotherapeutic circuits because it avoids risks of genomic integration and is temporally limited, which allows tissue homeostasis to return once the biotherapeutic circuit successfully treats the disease. To further demonstrate the versatility of this platform, we apply it to a class of diseases with a significant lack of modern biotherapeutic options: musculoskeletal disease.

The absence of biotherapeutics that target musculoskeletal (MSK) diseases leave patients with only conventional treatment options such as pain management, physical therapy, and surgery, which are non-curative and often highly invasive. This disparity becomes even more stark when considering the rate at which patients seek treatment for these diseases, with over 70 million medical visits each year for musculoskeletal concerns (8, 11). Many MSK diseases significantly impact patient quality of life, yet do not receive the same research focus or clinical development as other diseases with the same population size (175, 176). To showcase how even complex MSK diseases may be readily treated by harnessing the power of endogenous ligands, we develop biotherapeutic circuits for three unique synovial diseases with high incidence in the population: arthrofibrosis, rheumatoid arthritis (RA), and osteoarthritis (OA). Each disease has a distinct and chronic phenotype that severely impacts patient quality of life. Luckily, endogenous ligands exist that are suited to not just treat disease symptoms and arrest progression, but potentially cure the underlying dysregulation.

Arthrofibrosis is a common musculoskeletal disease impacting more than 4% of the population (8). At the molecular level, it manifests as fibrosis stemming from the dysregulation of myofibroblast activity (5, 11). Myofibroblast dysregulation leads to excessive extracellular matrix (ECM) protein deposition in the joint space due to aberrant transforming growth factor-$\beta$1 (TGF-$\beta$1) signaling (69, 73). This results in the tightening of the synovial capsule, reducing range of motion and causing long-term pain (4). There are no pathology-targeted therapies available for patients with arthrofibrosis. Pain and symptom management via physical therapy, non-steroidal anti-inflammatory drugs (NSAIDs), oral or intraarticular injections of corticosteroids, and sodium hyaluronate injections are the treatment options currently available to patients (11). Without curative therapies, millions of patients every year seek out invasive surgery to escape from their pain (8). An idealized treatment for arthrofibrosis would be a two-part mechanism of action with parallelized anti-fibrotic tissue remodeling and anti-fibrogenic suppression of myofibroblast activity.

Also driven by dysregulation, but of inflammatory as opposed to fibrotic pathways, RA is an auto-immune disease affecting 5 in 1,000 people worldwide (14, 177). In RA, auto-bodies and auto-reactive immune cells infiltrate and degrade synovial tissue. If left untreated, RA can result in irreversible joint damage and chronic pain (12). The frontline treatment for RA, adalimumab, decreases the bioavailable concentration of tumor necrosis factor $\alpha$ (TNF$\alpha$). TNF$\alpha$ is an inflammatory cytokine which drives the symptomatic presentation of RA but does not address the underlying dysregulation of immune activation associated with the disease (13, 15, 178, 179). An optimal treatment for RA would not only decrease inflammation but bias immune cell populations towards a healthy and non-inflammatory phenotype by inducing tolerance.

The third indication we will explore in this chapter is OA. OA is the most common musculoskeletal disease in the world, afflicting more that 220 million patients (180). It is a progressive disease that manifests as the degeneration joints and cartilage. Clinically, it is staged based on a patient's cartilage thickness and surface characteristics (21). Cartilage is a dense collagen and proteoglycan network that lines the surface of bones in the joint, which, in conjunction with the synovial fluid, allows for smooth, pain-free joint articulation and load bearing during ambulation or use. As OA progresses, synovial fluid loses lubricity (181, 182) and the glycosaminoglycan (GAG) content of the cartilage proteoglycan network precipitously decreases (20). This leads to a loss of interstitial fluid load support and contributes to further deterioration. Similar to arthrofibrosis, clinically approved treatment options for OA are limited to pain and symptom management, with the exception of invasive surgical procedures such as total knee arthroplasty (TKA). TKA is the most commonly performed orthopedic surgery in the United States, highlighting the fact that there are no highly-effective, non-surgical treatments for OA (183). An optimal treatment for OA would tackle the two primary drivers of degeneration: loss of GAG density and chondrocyte senescence and apoptosis (181, 184). This requires a therapy capable of stimulating GAG deposition from surviving chondrocytes while simultaneous driving chondrogenesis and reversing the senescent phenotype.

In sum, patients suffering from arthrofibrosis, OA, or RA represent ~26% of the adult population (8, 12, 14, 180, 185). Despite this, a majority have no access to treatments capable of anything more than symptom management. Endogenous ligands initiate powerful phenotypic changes by harnessing natural signaling pathways and are poised as potent, low toxicity biotherapeutics. However, their efficacy is predicated upon target density in the tissue of interest. Here, we propose the use of a transient biotherapeutic circuit to treat each disease with a potent, endogenously occurring ligands in a disease-state and tissue-type independent manner. In this work we convey the power of this platform technology while simultaneously applying cutting edge biotherapeutics to patient populations desperately in need of modernized treatments.

Disease State Dependent Regulation of Endogenous Signaling Pathways

Three endogenously occurring ligands, relaxin-2 (RLX), interleukin-10 (IL-10), and insulin like growth factor-1 (IGF-1), standout as potential therapeutics for the treatment of arthrofibrosis, RA, and OA, respectively. Each ligand tackles both the symptomatic presentation and underlying etiology of the disease. RLX is a pleiotropic peptide hormone with hemodynamic, anti-fibrotic, and anti-fibrogenic activity. It signals through its cognate GPCR, relaxin family peptide receptor 1 (RXFP1) (75, 79). IL-10 is an immunosuppressive cytokine secreted by multiple classes of immune cells. IL-10 binding to a tetrameric complex of two IL-10 receptor a (IL-10R$\alpha$) subunits and two IL-10 receptor p (IL-10R$\beta$) sub-units results in anti-inflammatory effects (186-188). IGF-1 is one of the major anabolic growth factors associated with musculoskeletal development and signals through its tyrosine kinase receptor, IGF-1 receptor (IGF-1R). In the joint space, IGF-1 stimulates GAG deposition and activates chondrocyte proliferation pathway (189, 190).

On paper, these ligands promise to be catch-all solutions to a myriad of diseases, particularly the three in questions here. In fact, the preclinical profiles of RLX, IL-10, and IGF-1 are so encouraging that they have all been pursued clinically for diseases related to fibrosis, immune activation, and tissue degeneration, respectively. RLX was pursued as an anti-fibrotic in a late-stage clinical trial for the treatment of cutaneous systemic sclerosis (80, 82). However, it ultimately failed to achieve any significant improvement over the standard of care. IL-10 was explored as a treatment for RA, but the primary endpoint of anti-inflammatory activity was not met (191). Finally, IGF-1 has been taken through multiple clinical trials for musculoskeletal conditions. In a trial for spinal muscular atrophy (SMA), treated patients saw no recovery of muscle strength, and there was high incidence of adverse events (192). Additionally, during a phase III trial for Rett's Syndrome, IGF-1 showed only marginal benefit in a sub-set of primary endpoints associated with perceived patient impact (193).

With several high-profile clinical failures, post-mortem analysis on RLX trials begin to point towards why these ligands may be faltering in the clinic (79-81). There is an emerging body of evidence that suggests disease-state specific receptor regulation was a primary driver of RLX's clinical failure in scleroderma (146). In fact, further evidence of fibrotic dysregulation of RXFP1 expression was independently observed in pre-clinical work on tissue derived from idiopathic pulmonary fibrosis patients (IPF) (147). This indicates that the fibrotic disease state suppresses the activity of RLX-RXFP1 signaling, a pathway directly associated with anti-fibrotic activity. Connecting the dots between failed trials and preclinical work suggest that while RLX may be a potent anti-fibrotic, an inherent aspect of fibrosis is suppressing expression of its receptor, without which RLX cannot be efficacious.

To determine if the phenomenon of RXFP1 suppression extends to arthrofibrosis, we characterize receptor expression in fibrotic, human fibroblast-like synoviocytes (hFLS). FIG. 1A displays the impact of growth factor treatments on RXFP1 gene expression as assessed by RT-qPCR. TGF-β1 suppresses RXFP1 expression by >75% at a concentration of 100 pg/ml (4.12 pM). The suppressive effects of fibrosis on RXFP1 expression continue in a dose dependent manner before plateauing (FIG. 1A). The only other growth factor which demonstrates RXFP1 suppression is the fibrosis-associated homodimer, platelet derived growth factor-BB (PDGF-BB). However, TGF-β1 induced suppression of RXFP1 is 400-fold more potent with respect to $EC_{50}$. (FIG. 1A). VEGFα, a growth factor closely associated with RLX signaling during wound repair (148) and fibroblast growth factor (FGF) do not suppress RXFP1 signaling (FIG. 1A). Longitudinal gene expression recovery after fibrosis induction reveals that RXFP1 expression recovers back to baseline within 72 hours (FIG. 1B). Continual exposure to a fibrotic stimulus results in >95% suppression of RXFP1 expression.

Unfortunately, the same robust body of work that details RLX-RXFP1 expression in various fibrotic diseases does not have a corollary for IL-10-IL-10R in auto-immune disease. However, preliminary evidence does point towards potential alterations to the IL-10 signaling axis in RA. Decreased expression of the ligand has been observed in various auto-immune diseases (194), and a study looking at single nucleotide polymorphisms (SNPs) identified altered IL-10Rα isoforms in RA patients (195). RA is an extremely complex disease, making it difficult for in vitro models to robustly mimic the auto-immune cellular phenotype (196). Acknowledging this limitation, we use a mixed-lymphocyte reaction (MLR) to simulate antigen-presenting cell (APC) activation of T cells by auto-antigens. By using MLR, we abstract both the subtype of APC and the specific auto-antigen that activate T cells during RA, with a more general donor-donor induced activation.

Immune stimulation significantly suppresses IL-10Rα gene expression in the lymphocyte sub-population of PBMCs from unique human donors (n=3) (FIG. 1A). Down regulation occurs with both an equal ratio of donor cells as well as each permutation of 1:10 donor to donor ratios. Lymphocyte IL-10Rβ expression decreases in a similar manner to IL-10Rα. The monocyte sub-population did not experience any significant activation-induced alterations to IL-10Rα or IL-10Rβ expression (FIG. 1A). IFNγ expression is significantly higher in all conditions for both the monocyte and lymphocyte sub-populations (FIG. 1A). This, combined with TNFα over-expression in the MLR serum, as well as CD69 and 4-1BB upregulation, demonstrates that MLR acts as a robust, albeit simplified, model for APC induced T cell activation. In a purified population of lymphocytes, specifically CD3+ T cells, activation results in significant down regulation of IL-10Rα expression with no impact on IL-10R3. This effect is longitudinally maintained with and without activation co-stimulation (FIG. 1B) This result was further confirmed by analysis of CD3+ T cells isolated from multiple human donors at day 4 post-activation (n=4) (FIG. 2C). Expression of activation markers CD69 and 4-1BB confirms immune cell stimulation (FIG. 2D). Protein-level suppression of IL-10Rα, observed via flow cytometry, provides further evidence for immune-activation induced down regulation of IL-10Rα (FIGS. 2D and 2E).

Synovial fluid samples derived from human donors provide a window into the barriers blocking IGF-1 efficacy in OA. Literature suggests decreased IGF-1 efficacy is not due to receptor suppression. In fact, there is an over-abundance of IGF-1R binding sites on diseased chondrocytes when compared to bioavailable IGF-1 (197). Instead, sequestration of IGF-1 by IGF-1 binding proteins (IGFBP), specifically IGFBP-3, is indicated as a driving factor in OA progression (198, 199). Upregulation of IGFBP-3 in the synovial fluid of OA patients binds IGF-1 and prevents it from interacting with IGF-1R. This contributes to disease progression by preventing GAG deposition and driving chondrocyte apoptosis (184, 190). In synovial fluid samples harvested from normal and diseased human donors, we confirmed significantly increased IGFBP-3 concentrations in the osteoarthritic condition (FIG. 2F). Normal synovial fluid samples were harvested from cadaveric donors with a non-inflammatory cause of death. RA and OA samples were harvested during surgical procedures on live patients. Here we present three distinct musculoskeletal conditions each with disease-state dysregulation preventing activation of a well-suited protein therapeutic's signaling pathway. The conditions considered here encompass multiple different receptor classes and mechanisms of action, providing an exemplary set of diseases to demonstrate the power of ligand potentiation.

Synovial fluid harvested from OA and RA patients during surgical procedures under an approved IRB. Synovial fluid from healthy donors was harvested from cadaveric donors within 24 hours of death.

A Disease-State Independent mRNA Biotherapeutic Circuit

The three musculoskeletal diseases discussed, arthrofibrosis, rheumatoid arthritis, and osteoarthritis, each present with both a unique phenotype and underlying disease etiology. There are endogenously occurring ligands with mechanisms of action distinctly suited to treat each disease, yet clinical efforts to harness their properties have repeatedly failed (80, 82, 191-193). We hypothesize that each pathway is missing a critical link in the signaling cascade. To address disease-state dependent dysregulation, we propose an mRNA-based biotherapeutic circuit capable of simultaneously restoring the healthy signaling cascade and activating the pathway via production and secretion of the endogenous ligand (FIG. 2A-C). The cargo versatility of mRNA is uniquely suited for restoration of biological signaling pathways because it allows for intracellular, transmembrane, or extracellular expression. The transient nature of expression and inherent de-risking of genomic integration point towards a strong safety profile. Expression of multiple proteins can be accomplished via delivery of a monocistronic mRNA cocktail or a single polycistronic construct. Here, we harness internal ribosome entry sites (IRES), which allow for cap-independent translation, to simultaneously express multiple components of a signaling cascade from a single polycistronic construct.

Each biotherapeutic circuit was rationally designed to restore the ligand's natural signaling cascade independent of dysregulation. RLX-RXFP1 signaling results in anti-fibrotic and anti-fibrogenic effects by activating the PI3K cascade, increasing nitric oxide synthase (NOS) concentrations, inhibiting the SMAD phosphorylation pathway, and upregulating expression of matrix metalloproteinases (MMPs) (137). Its hemodynamic effects are primary mediated via the increased cAMP concentrations due to adenyl cyclase stimulation by the $g\alpha_s$ intracellular sub-unit (FIG. 2A, left). In the fibrotic disease state, RXFP1 expression is suppressed (FIG. 2A, middle). An mRNA biotherapeutic circuit simultaneously expressing RLX and RXFP1 (mRNA expressed proteins are forward denoted with an m-prefix. e.g., mRLX and mRXFP1), restores receptor density in fibrotic tissue and produces ligands capable of potent anti-fibrotic and anti-fibrogenic signaling (FIG. 2A, right).

The natural anti-inflammatory signaling cascade of IL-10 and IL-10R is driven through JAK/STAT signaling (FIG. 2B, left). The effects of IL-10 signaling result from nuclear translocation and transcriptional activity of phosphorylated STAT3 (187, 188, 200). Immune activation decreases IL-10Rα sub-unit expression, in turn preventing IL-10 mediated immunosuppression (FIG. 2B, middle). We propose an mRNA biotherapeutic circuit expressing both mIL-10 and mIL-10Rα. This circuit will restore a sub-unit expression in diseased auto-immune cells while simultaneously expressing mIL-10 to drive anti-inflammatory and immunosuppressive signaling in RA patients' synovial immune cells (FIG. 2B, right).

With respect to chondrocytes, interaction of IGF-1 with IGF-1R results in parallel chondrogenesis and deposition of glycosaminoglycans (190, 201). (FIG. 2C, left). IGF-1's potent effects on connective tissue suggests it would be a promising treatment for multiple MSK diseases. However, particularly in OA, the balance of bioavailable IGF-1 is shifted by the sequestration of IGF-1 by IGFBP-3 (180, 198, 199). This prevents IGF-1-IGF-1R interaction and furthers OA progression (FIG. 2C, middle). As opposed to the mRNA circuit for the treatment of arthrofibrosis and RA, where the dysregulation was caused by suppression of the receptor, in OA the barrier to endogenous ligand efficacy is overexpression of a binding protein. To address this challenge, we propose a mRNA biotherapeutic circuit capable of simultaneously expressing IGF-1 as well as a protease to cleave IGFBP-3, thus releasing IGF-1 (FIG. 2C, right). A small family of metalloproteinases, pappalysin A1 (PAPPA1) and pappalysin A2 (PAPPA2), have specific proteolytic activity on IGF binding proteins (202). Pappalysins regulate systemic IGF-1 bioavailability and their expression is tightly regulated during early development (203-206). Therapeutic administration of PAPPA2 in female patients with idiopathic short stature (ISS) resulted in increased serum IGF-1 bioavailability (207). Here, we propose the first known instance of PAPPA2 as a treatment for OA.

Validation of Expression and Bioactivity Characterization

Plasmid templates for monocistronic and polycistronic expression of each biotherapeutic circuit include identical 5' and 3' UTRs. mIL-10 and mIGF-1 are encoded as the endogenous ligand. However, RLX is naturally produced as a prepropeptide. During post-translational processing, the C-chain is cleaved by prohormone convertase-1 (PC1), which is expressed in a cell type dependent manner (165). To maximize cell-type independence and bypass variability in PC1 expression as a determining factor in circuit efficacy, we validate expression of single-chain relaxin variants with varying length flexible linkers expression in both a test cell line as well as the disease relevant tissue, hFLS, reveals that the mRLX-F9 variant is the optimal single chain variant with a natural leader peptide (FIG. 3A). mIL-10 robustly expresses in all tested cell lines (FIG. 3B). Similarly, mIGF-1 and mPAPPA-2 successfully express from the designed mRNA constructs (FIG. 3C).

To determine the bioactivity of mRLX-F9, mIL-10, and mIGF-1, we generated ligand specific luciferase reporter cells lines. mRLX bioactivity was measured using a reporter cell expressing RXFP1 constitutively and luciferase driven by a cAMP sensitive promoter. In the presence of bioactive RLX, adenyl cyclase activation increases intracellular cAMP concentrations and drives luciferase expression. Conditioned media containing mRLX-F7, mRLX-F9, and mRLX-F11 were compared to recombinant RLX (rRLX, also referred to as serelaxin, the trade name for the GMP rRLX used during AHF clinical trials). All flexibly linked variants demonstrate ~2-fold reduced bioactivity compared to the native variants. However, they all maintain picomolar $EC_{50}$ (FIG. 4A). mIL-10 bioactivity was assessed in a STAT3 reporter cell line. To account for the absence of IL-10Rα expression in HEK293T, the cells were transfected with a plasmid encoding IL-10Rα prior to treatment with conditioned media. rIL-10 and mIL-10 demonstrate no difference in bioactivity at all tested concentrations (FIG. 4B). PAPPA2 from conditioned media efficiently cleaves IGFBP-3, as measured by an ELISA for intact IGFBP-3, with and without bound IGF-1 (FIG. 4C). Furthermore, IGFBP-3 sequesters IGF-1 and decreases its bioavailability but is released upon PAPPA2 treatment (FIG. 4D). mIGF-1 bioactivity is equivalent to rIGF-1 at all dosed concentrations using an activator protein-1 (AP-1) responsive system in insulin depleted media. To increase sensitivity, IGF-1R was overexpressed via plasmid transfection prior to treatment with conditioned mIGF-1 media (FIG. 4E). In conclusion, all secreted ligands and protease demonstrate robust bioactivity with their endogenous targets.

RXFP1 and IL-10Rα require far more complex translational and post-translational processes than their respective ligands due to overall size and the directional nature as transmembrane proteins. Validating successful membrane embedding is essential for biotherapeutic circuit function. To observe receptor trafficking, we synthesized a FLAG-tagged RXFP1 variant with a C-terminal miRFP670nano fluorescent protein fusion tag (208). To maintain miRFP670nano activity, a 30 amino acid flexible linker was placed between the receptor and fluorescent protein. Confocal microscopy of non-permeabilized NIH3T3 cells, with and without miRFP670nano tag, confirms an extracellular ectodomain as well as successful membrane embedding through FLAG-tag/miRFP670nano co-localization (FIG. 5A). Flow cytometry further verifies mRXFP1 expression after mRNA treatment (FIG. 5B). RXFP1 expression is not detected from the polycistronic construct. mIL-10Rα robustly expresses after treatment with both the monocistronic and polycistronic construct (FIG. 5C). As anticipated, expression from the polycistronic construct is significantly reduced compared to monocistronic mIL-10Rα.

Biotherapeutic Circuit Autoactivation

The proposed biotherapeutic circuit platform is based on the premise that an exogenous mRNA-expressed ligand and its receptor can auto-induce a natural signaling cascade. This requires secretion of a bioactive ligand (FIG. 3A-4E) and then subsequent interaction with a properly oriented receptor (FIG. 5A-5C). To the authors' knowledge, this is the first published instance of auto-activation of a signaling cascade from an mRNA-based system. To fully validate the auto-activation capabilities of the biotherapeutic circuit platform, we selected the RLX-RXFP1 signaling cascade based on the following rational: 1) the reporter cell line of interest, HEK293T-CRE-GLuc, does not naturally express RXFP1 and as a result is non-reactive to rRLX without the presence of an exogenous RXFP1 gene; 2) RXFP1 is the most complex receptor of those explored in this work, and proof-of-function with this receptor is a conservative measure for other transmembrane receptors; and 3) the RLX-RXFP1 pathway has multiple, distinct signaling cascades which will allow for verification that the biotherapeutic circuit results in complete activation of a receptor's natural signaling pathway (137).

The anti-fibrotic biotherapeutic circuit is capable of auto-activation to produce cAMP at levels equivalent to forskolin, a small molecule agonist of adenyl cyclase (FIG. 6A). In the presence of serelaxin, mRLX-F9, or mRXFP1 alone, the circuit is incomplete, and no signaling results. However, when mRXFP1 is combined with either serelaxin or mRLX-F9, significant cAMP production occurs. The polycistronic system encoding mRLX-F9 via cap-dependent translation and mRXFP1 via cap-independent translation auto-activates cAMP production without any other treatment, demonstrating that a single mRNA construct can complete a missing biological signaling cascade. After supplementation with additional serelaxin, cAMP levels slightly increase beyond that of the polycistronic construct alone, but do not reach the same fold-activation observed with the mRXFP1 monocistronic system (FIG. 6A). Serelaxin dose-escalation studies demonstrate that activation of mRXFP1 expressed from the monocistronic construct was tunable based on RLX concentration. By contrast, the polycistronic construct saturates at a low dose of serelaxin. This suggests that mRXFP1 expression from the polycistronic construct was both lower in cell surface density compared to monocistronic mRXFP1, as well as below the effective $EC_{50}$ of the mRLX produced by the same construct. Thus, the addition of exogenous serelaxin, does significantly alter cAMP production.

Initial confirmation of signaling auto-induction was performed in a luciferase expressing cell line. To rule out the possibility that only a small population of high-performing cells would bias the results, we designed, and isolated via cell sorting, a HEK293T-CRE-mCherry reporter line. In the presence of only serelaxin, mRLX-F9, or mRXFP1, the signaling cascade is incomplete, and only basal mCherry expression is observed (FIGS. 6B and 6C). Significant induction of mCherry occurs upon completion of the RLX-RXFP1 signaling cascade with mRLX-F9 and mRXFP1, either via mono- or polycistronic construct (FIGS. 6B and 6C). Interestingly, a slightly smaller population of cells expressing a complete signaling cascade is observed with the polycistronic construct. This suggests decreased efficiency of transmembrane trafficking due to non-canonical translational initiation after the IRES or loss of RNA integrity with the larger construct (FIGS. 6B and 6C). Regardless, induction of mCherry expression in an equivalent population to forskolin treatment demonstrates that biotherapeutic circuits are capable of auto-induction across a large percentage of a treated cell population.

Both the luciferase and mCherry induction systems utilize cAMP as the intracellular modulator of transcriptional activity. While systems to detect cAMP are exceptionally sensitive, the cAMP stimulatory branch of the RLX-RXFP1 signaling cascade is primarily responsible for the hemodynamic effects of RLX. To both validate that mRXFP1 signals in a manner similar to the natural pathway as well as verify the anti-fibrotic and anti-fibrogenic capabilities of the mRLX biotherapeutic circuit, we developed a SMAD-sensitive reporter cell line. Upon TGF-31 stimulation, SMAD phosphorylation induces luciferase expression in a dose dependent manner. In exploring the capabilities of the anti-fibrotic circuit, we wanted to mimic a patient with both fibrosis established prior to treatment as well as continued fibrotic signaling during treatment. To this end, the reporter system was first induced with TGF-31 alone, and then the anti-fibrogenic biotherapeutic circuit was transfected into the reporter cells alongside continued TGF-31 stimulation (FIG. 6D). When mRXFP1 and mRLX or serelaxin treatment are applied in combination, SMAD activity is significantly inhibited. Both the polycistronic and monocistronic circuits exhibit anti-fibrotic effects. In the absence of fibrotic stimuli, no SMAD signaling occurs (FIG. 6D). Simultaneous application of the biotherapeutic circuit and induction of fibrosis validates the anti-fibrotic efficacy in a model meant to mimic the fibrosis resultant from orthopedic surgery, where the treatment could be applied at the time of injury. The combined results of the CRE-GLuc, CRE-mCherry, and SMAD-GLuc characterization demonstrate that the biotherapeutic circuit platform elicits robust signal activation on par with small molecule agonist, functions broadly throughout a cell population, and activates all signaling pathways associated with the endogenous biological cascade.

The bioactivity of the mIL-10 circuit was characterized with the same STAT3-Gluc cell line used for determination of mIL-10 bioactivity. Treatment with either the mono- or polycistronic formulation of the anti-inflammatory mRNA circuit potently induces STAT3 activity (FIG. 7A). Polycistronic mIL-10-IRES-mIL-10Rα was as potent a STAT3 activator as mIL-10Rα when combined with mIL-10 or rIL-10. From expression characterization experiments, it is known that mIL-10Rα expresses at significantly higher cell-surface densities than mIL-10-IRES-mIL-10Rα (FIG. 5C). This suggests that the receptor density induced by the polycistronic circuit, in concert with the mIL-10 produced from cap-dependent translation of the same construct, is sufficient to saturate the JAK/STAT signaling pathways present in the model cell line.

The proposed biotherapeutic circuit for osteoarthritis does not involve restoration of receptor expression. Instead, it is the dual-secretion of a ligand and a modulator of the ligand's disease-state bioavailability. As opposed to previously demonstrated circuits, only the ligand is required for signaling. IGF-1 alone induces robust activation in the modeled non-diseased condition (FIG. 7B). In the presence of IGFBP-3, to mimic OA, IGF-1 activity significantly decreases. Treatment with PAPPA2 allows for robust IGF-1 signaling in the modeled healthy and disease-state (FIG. 7B).

Disease-State Independent Rescue of Function in Clinically Relevant Tissues

The goal of the anti-fibrotic therapeutic circuit is successful introduction of the RLX-RXFP1 circuit into fibrotic synovial tissue to allow for endogenous relaxin signaling independent of the disease state. Given the size and complexity of RXFP1, we first verify that delivery of mRXFP1 results in receptor over-expression in human synovial tissue (FIG. 8A). The monocistronic construct significantly over-expresses mRXFP1, while mRXFP1 expression from the polycistronic construct was not detectable (FIG. 8A). To mimic the clinical disease, hFLS were induced to a fibrotic state with TGF-31 prior to treatment with the anti-fibrotic circuit. Treatment with mRLX, mRXFP1, or rRLX alone does not significantly impact intracellular cAMP concentrations (FIG. 8B). However, mRXFP1 combined with either rRLX or mRLX increases cAMP by greater than >15-fold independent of disease-state. Successful RLX-RXFP1 in human-derived tissue provides strong preclinical evidence for downstream anti-fibrotic efficacy.

In patient derived lymphocytes, specifically CD3+ T cells, immune activation results in sub-unit specific downregulation of IL-10Rα. To determine if the anti-inflammatory biotherapeutic circuit could function in clinically relevant cell types, we treated activated patient-derived T cells with the mIL-10 circuit (FIG. 9A-9C). Unactivated T cells present with low IL-10Rβ expression and basal expression of IL-10Rα (FIG. 9A). Upon activation, significant suppression of IL-10Rα expression occurs in a subset of the T cell population. Preliminary immunophenotyping reveals that IL-10Rα surface density is maintained in the CD4+, CD8− and CD4−, CD8+ populations, but decreases in the CD4−, CD8− population (FIG. 9B). Treatment with mIL-10 alone induces significant loss of cell-surface IL-10Rα expression, which is not observed for IL-10Rβ, suggesting a sub-unit specific ligand-mediated receptor internalization mechanism of action and a potential contributing factor to the inefficacy of previous IL-10 therapies (FIG. 9C). mIL-10Rα treatment increases IL-10Rα expression across all analyzed CD3+ subtypes, and importantly rescues expression in the CD4−, CD8− population which presented with decreased expression. Treatment with the polycistronic construct results in receptor rescue as well as resistance to the ligand-mediated receptor internalization of mIL-10 alone (FIG. 9B). This demonstrates the potential for sustained anti-inflammatory signaling that bypasses natural negative feedback regulation. Sustained cell-surface receptor expression can be achieved in a modeled disease-state as well as during IL-10-IL-10R interaction.

Figure 10B:
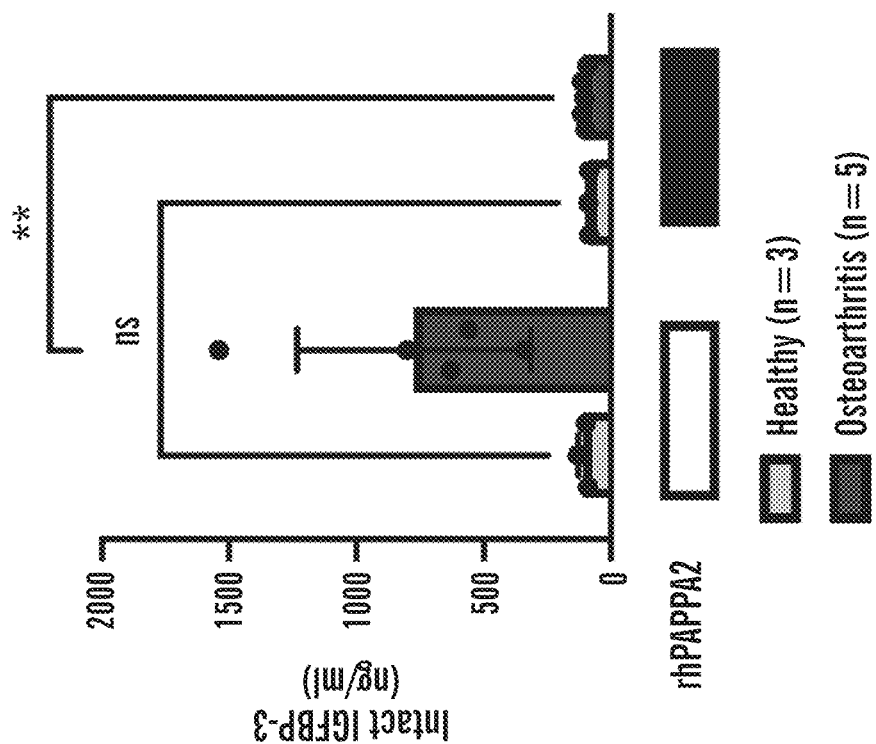

IGFBP-3 is significantly overexpression in human synovial fluid harvested from osteoarthritic patients compared to both healthy patients and patients with rheumatoid arthritis (FIG. 1F). Treatment of healthy or diseased human synovial fluid with conditioned media containing PAPPA2 results in a significant decrease in intact IGFBP-3 (FIG. 10A). However, concentrations of bioavailable IGF-1 did not significantly increase in PAPPA2-treated human synovial fluid from healthy or OA patients, demonstrating the need for simultaneous ligand production (FIG. 10B). Validating the bioactivity of PAPPA2 on IGFBP-3 in patient-derived synovial fluid is powerful for downstream translation. However, because synovial fluid is acellular, it cannot demonstrate the impacts of the IGF-1-PAPPA2 biotherapeutic circuit on GAG deposition or altering cartilage mechanical properties, which are the truly relevant outcomes for the patient.

Chondrocytes naturally grow in a complex 3D cartilaginous scaffold under semi-hypoxic and avascularized conditions. This makes 2D culture of chondrocytes relatively ineffective and has led to the development of reproducible 3D culture models (209). These models rely heavily on supra-physiologic concentration of insulin to maintain cellular health. This supplementation allows for serum-free growth, which is essential for reproducibly studying OA given the impact of variable growth factors concentrations in serum on chondrocyte phenotype. However, to explore the impacts of altered IGF-1 bioavailability on chondrocyte health and ECM composition, insulin-free growth conditions are required due to the cross-reactivity of insulin with IGF-1R (210). Long-term culture of agarose embedded bovine chondrocytes in insulin-free conditions demonstrates that supplementation with IGF-1 increases GAG deposition compared to untreated controls (FIG. 10C). The modeled disease-state of IGFBP-3 over-expression and IGF-1 sequestration results in a construct with GAG content equivalent to the untreated control. Treatment with PAPPA2 increases GAG content beyond that of the IGF-1 treated control independent of disease state or IGF-1 concentration (FIG. 10C). The modeled disease-state, over-expression of IGFBP-3, treated with the biotherapeutic circuit results in the most significant upregulation of GAG content. Mechanical testing of the same 3D culture constructs further confirms the impact of PAPPA2 signaling on cartilage ECM composition. The equilibrium moduli of untreated constructs were equivalent to that of un-seeded agarose, which suggests that insulin-free cultures without IGF-1 supplementation were effectively dormant with respect to ECM deposition (FIG. 10D). Construct stiffness significantly increases in the IGF-1 treated condition or any PAPPA2 treatment. The largest increase in stiffness is observed in the completed IGF-1-PAPPA2 biotherapeutic circuit condition in the modeled disease state (FIG. 10D). In conclusion, a biotherapeutic circuit capable of simultaneously expressing a potent growth hormone, IGF-1, and a disease-specific modulator of its bioavailability, PAPPA2, significantly increases 3D culture GAG content and mechanical properties.

Figures 11C, 11D:
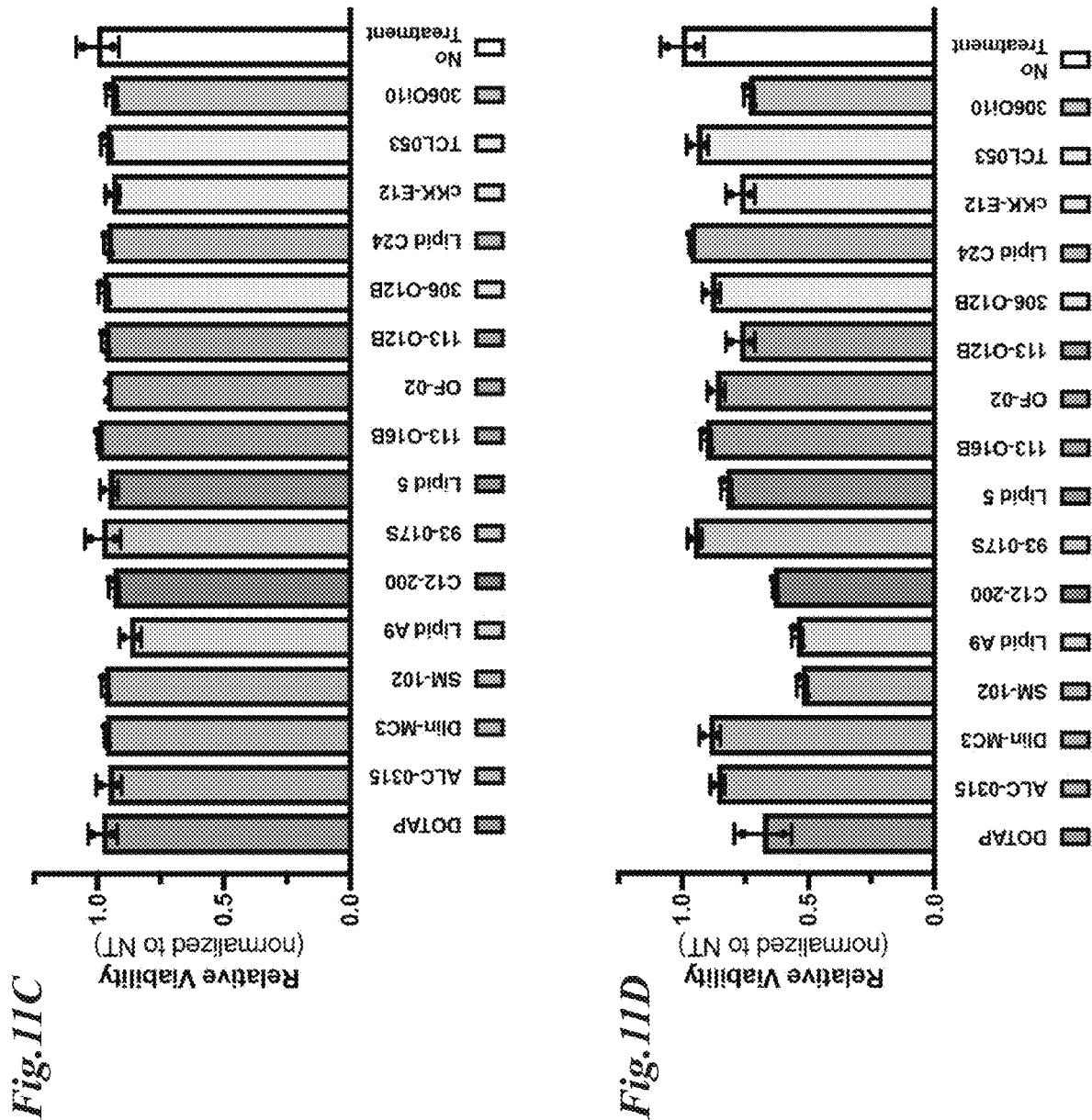

In Vivo Delivery of the Biotherapeutic Circuit, its Biodistribution, and Future Directions As with any gene therapy, efficacy is predicated upon efficient delivery of the nucleic acid cargo to the cell-type of interest. All three proposed biotherapeutic circuits are intended for intra-articular delivery of mRNA via lipid nanoparticle (LNP) and each act upon specific cell types that are dysregulated in their respective disease-state: arthrofibrosis originates in synovial tissue, rheumatoid arthritis in immune cells, and osteoarthritis in chondrocytes. Recent work provides a blueprint for efficient in vivo transfection of immune cells using an optimized ionizable lipid and antibody conjugation method (211, 212). To enable transfection of the RLX-RXFP1 and IGF-1-PAPPA2 treatments into synovial tissue, we screen a library of ionizable lipids and commonly utilized helper lipids against human synoviocyte-like fibroblasts. hFLS are a high-value tissue type for the remaining treatments. In vivo hFLS transfection will allow for restoration of RXFP1 expression in fibrotic synovial tissue and secretion of IGF-1 and PAPPA2 in osteoarthritic joints. Direct transfection of chondrocytes requires LNP optimization that accounts for cartilage diffusion. Secreted IGF-1 can diffuse more readily into cartilage than LNPs and PAPPA2 can act upon IGF-1-IGFBP-3 complexes in the synovial fluid. Library screening reveals that regardless of ionizable lipid, 1,2-distearoyl-sn-glycero-3-phosphocholine (DSPC) does not deliver sufficient reporter mRNA (FIG. 11A). Of the screened ionizable lipids, ALC-0315 and SM-102 most efficiently transfect hFLS when formulated with 1,2-dioleoyl-sn-glycero-3-phosphoethanolamine (DOPE) (FIG. 11B). DOPE is slightly more cytotoxic than DPSC, likely due to the primary, charged amine in DOPE (FIGS. 11C and 11D). ALC-0315 in combination with DOPE was identified as the optimal lipid formulation capable of efficient transfection while maintaining low cytotoxicity. This screen is a foundational advancement for MSK biotherapeutics because synovial tissue is a strong candidate for any intraarticular mRNA therapy.

To characterize the intraarticular mRNA expression kinetics of transmembrane receptors and secretory proteins, we designed a set of far-red shifted in vivo reporter mRNAs based on Antares2 (213). To mimic transmembrane protein expression, Antares2 was fused to the transmembrane domain of PDGFR-β. Similarly, an Antares2 variant preceded by a secretory leader peptide was generated to study secreted ligand or protease kinetics. Membrane-tethered Antares2 is selectively embedded and retained in the cell membrane. Secretory Antares2 is over-expressed into media supernatant. Ongoing in vivo biodistribution studies will allow for the characterization of intra-articular mRNA expression kinetics of both transmembrane and secretory proteins. This will pave the way for an optimized intraarticular dosing regimen of the anti-osteoarthritis biotherapeutic circuit in a transgenic, chondrodysplasia murine model of OA.

Discussion & Conclusions

In this chapter we propose and characterize an mRNA-based platform technology capable of disease-state and cell-type independent potentiation of endogenous ligands. While these proteins benefit from immune tolerance and potent biological effects, they have continually failed in clinical trials. We hypothesize that these translational issues directly result from signaling pathway dysregulation, and, with rational therapeutic design, endogenous ligands could be leveraged as powerful therapeutics. We apply this platform technology to musculoskeletal disease, which, despite impacting millions of patients, remain as an under-research area of biotherapeutics. Using three distinct musculoskeletal conditions, arthrofibrosis, rheumatoid arthritis, and osteoarthritis, we identify an endogenous ligand uniquely suited for each disease and identify the signaling pathway dysregulation that has prevented successful clinical translation.

This work proposes a novel treatment platform while simultaneously deepening the foundational understanding behind multiple MSK. In fibrotic synovial tissue, RXFP1 expression is significantly decreased (FIG. 1A). This receptor suppression has been hypothesized in previous literature; however this is the first reported evidence of synovial dysregulation. In OA, over-expression of IGFBP-3 results in the sequestration of IGF-1 (FIG. 1F). Binding protein expression is known to occur in OA, but this work is the first to propose a direct treatment harnessing the IGF-1-IGFBP-3 interaction. In RA, immune activation drives suppression of the IL-10 receptor complex. We hypothesize that the alpha subunit is selectively down-regulated in lymphocytes and thus, restoration of IL-10Rα will restore IL-10 signaling efficacy. The anti-inflammatory biotherapeutic circuit produces mIL-10 as well as mIL-10Rα. Our characterization reveals that immune activation induced suppression of IL-10R is unique to lymphocyte populations of stimulated PBMCs (FIG. 1A). IL-10Rα and IL-10Rβ are down-regulated in a similar manner. However, upon isolation of CD3+ T cells, only IL-10Rα suppression is observed. Our results demonstrate that the biotherapeutic circuit restores IL-10Rα expression in immune activated CD3+ T cells. However, T cell and PBMC data taken together suggests that IL-10Rβ dysregulation may also occur in other lymphocyte subtypes. Given that disease progression is closely linked to dysregulated B cell acting as professional APCs, this result raises further questions about the natural mechanisms for immunosuppression in RA (214). In fact, previous work has shown that B cells in RA patients undergo significant repertoire change compared to non-rheumatic B cells (178, 215). This implies that dysregulation of the IL-10 axis extends beyond just T cells, to B cells. Further research should include detailed immunophenotyping of complex lymphocyte populations with respect to IL-10Rα and IL-10Rβ expression before and after immune stimulation. More broadly, this work is an example of how understanding a given disease state is essential for downstream success of a rationally designed therapeutics.

After establishing the regulatory state of each disease and identifying the necessary components to be replaced or modulated in each signaling pathway, we moved to fully validate this platform, starting with ligand bioactivity. Determining each mRNA-produced ligand's potency is essential for the translational success of this technology. A promising result for efficacy, the $EC_{50}$ of all RLX variants indicate that flexibly linked RLX is only slightly less bioactive than the recombinant control and maintains picomolar affinity (FIG. 4A). Unfortunately, $EC_{50}$ could not be determined for mIL-10 or mIGF-1. This was primarily due to limitations imposed by the maximum concentration of each ligand in its conditioned media and, for IGF-1, low sensitivity of the signaling cell line, which is detailed at length further below. After transfection with a given mRNA, the concentration of ligand in the media was determined via ELISA, and then used to treat a reporter cell line. This means that the maximum measurable concentration for $EC_{50}$ was capped by ligand production. However, at each possible concentration, the response from the signaling cell line was equivalent to the recombinant protein (FIGS. 5B and 5E). Ligand bioactivity was further confirmed in downstream circuit activation assays. Combining both results suggests that the limitation encountered with respect to $EC_{50}$ determination is merely a reporter system limitation, and will not be a barrier to clinical efficacy.

Of all the signaling systems, determining IGF-1 bioactivity proved the most difficult, and it highlights the complexity of studying endogenous ligands which are foundational to cell proliferation and growth. IGF-1 and/or insulin are present in almost all cell culture media because they are essential for cell health. This proved complex to design around. Chondrocyte constructs are traditionally grown in minimal media which is supplemented with a cocktail of insulin, human transferrin, and selenous acid. The final insulin concentration is supraphysiologic, but also essential for maintaining chondrocyte health in vitro. Due to the cross reactivity of insulin with the IGF-1R and the IGF-1 signaling cascade, we reconstituted a minimal media will all required components besides insulin. The rational being that supplementation with IGF-1 would restore this signaling axis and allow for cellular proliferation and GAG deposition. In IGF-1 and PAPPA2 treated conditions, both GAG deposition and matrix stiffness increased (FIGS. 10C and 10D). However, in the untreated or IGFBP-3 conditions the cells are receiving little to no growth factor stimulation. As a result, the tissue properties of these plugs were closer to that of pure agarose gels, without any seeded cells (FIG. 10D). This same minimal media was utilized to determine IGF-1 and PAPPA2 bioactivity with the HEK293T signaling cell line. A MAPK/ERK responsive promoter cell line was not stimulated by IGF-1 signaling and drove us to use an AP-1 promoter. However, the low specificity of AP-1 prevented the reporter system from achieving the same fold-induction the RLX and IL-10 sensitive cell lines.

The limitations of the IGF-1 activity reporter system are offset by the robust response observed in primary cells. In human synovial fluid samples from diseased patients, PAPPA2 demonstrates potent protease activity against IGFBP-3 (FIG. 10A). However, with respect to free IGF-1 in OA synovial fluid, there is no observable increase in bioavailability after PAPPA2 treatment (FIG. 10B). This provides patient-derived support for the power of a biotherapeutic circuit capable of simultaneous IGF-1 and PAPPA2 expression. Yet data from the long-term 3D culture of bovine chondrocytes suggests that the IGF-1-PAPPA2 circuit may signal through additional pathways beyond IGF-1-IGF-1R. In the absence of IGF-1, PAPPA2 treatment stimulates GAG deposition that is significantly greater than that of IGF-1 alone and equivalent to IGF-1+ PAPPA2 (FIG. 10C). It is only in the condition meant to mimic the biotherapeutic circuit treat disease state, that GAG surpasses the PAPPA2 group. This suggests that the cleavage of IGFBP-3 generates a complex that is capable of stimulating GAG deposition independent of IGF-1. There is some evidence to support this hypothesis, but it requires further study (216).

A potential limitation of this platform for the treatment of auto-immune or inflammatory disease is foundational to mRNA. Introduction of mRNA into primary cells can drive strong immune response. If the cells recognize the exogenous mRNA as foreign, they attempt to clear the foreign RNA via immune activation and inflammation (64). Cells recognize RNA via pattern recognition receptors (PRRs), such as toll tike receptors (TLR) in the endosome and cytoplasmic ssRNA and dsRNA sensors (217). RNA recognition by TLRs drives IFNγ production as well as the early interferon response. The early interferon response will decrease RNA efficacy and increased IFNγ will result in tissue inflammation. This is a unique barrier for applying the biotherapeutic circuit to inflammatory disease because it has the potential to exacerbate immune activation as opposed to acting as an immunosuppressive. Luckily, foundational discoveries in the field of RNA therapeutics at the University of Pennsylvania paved the way for low-immunogenicity mRNA therapies (65). The incorporation of modified nucleotides, specifically N1-methylpseudouridine, into IVT generated mRNA significantly decreases TLR recognition. This, in combination with careful purification to remove dsRNA contaminants, can prevent exogenous mRNA from causing unwanted inflammatory effects.

A second limitation of this system for treatment of musculoskeletal disease has to do with the expression kinetics of mRNA therapeutics. The rate of new ligand expression peaked 8-12 hours after transfection regardless of cell type or nature of the ligand (FIG. 3A-3E). Musculoskeletal disease often involves slow growing, relatively non-responsive tissue-types and cell-types. The promise of harnessing endogenous ligands is that the powerful signaling cascade they activate can stimulate long term change in these complex tissues. However, the pharmacodynamics of mRNA may necessitate repeated intraarticular injections. The benefit of LNPs, is that a small needle can accomplish these injections, but it still necessitates high patient compliance to ensure a successful therapy. One possible strategy to overcome the short expression profiles of traditional mRNA is to harness the extended duration expression of self-amplifying RNA. This concept will be discussed at length in the following chapter.

In conclusion, this work provides the first embodiment of a biotherapeutic circuit capable of potentiating endogenous ligands as biotherapeutics. The disease explored here are meant to both highlight the need for additional pre-clinical drug development efforts for MSK diseases and to demonstrate the versatility of the platform to potentiate any endogenous ligand, given the proper characterization and deep understanding of disease mechanism of action. However, the central idea behind this technology, which is the completion of a natural signaling pathway does not need to be limited to endogenous ligands. Any protein therapeutic that interacts with a natural signaling pathway can be potentiated via biotherapeutic circuit. By design, the generation of biotherapeutic circuits requires a deep understanding of the expression of a target signaling pathway. As a result, this technology accounts for disease-state dysregulation which in turn will decrease late-stage clinical failures and increase the number of patients who have access to targeted therapies.

Materials and Methods

IVT Templates

Linearized plasmid was used as the template for all IVT reactions unless otherwise specified. Linearization was performed using either 10 units HindIII-HF of AflII per g template in CutSmart Buffer (New England Biolabs) at 37° C. for 4 hours followed by either immediate purification or storage at −20° C. QIAquick PCR purification kit (Qiagen) was used to purify all linearized templates and eluted into RNAse/DNase free $H_2O$. Concentration was determined by $A_{260}$ using a NanoDrop2000 (Thermo Fisher Scientific). After purification, RNAsecure (Thermo Fisher Scientific) was added to the template to 1× concentration, and the resulting mixture was incubated at 55° C. for 10 minutes. Linearized, RNAsecure treated template was either used immediately for IVT or stored at −20° C. for up to 4 weeks.

IVT

Prior to IVT, all surfaces, pipettes, tube racks, and other equipment were cleaned with 70% EtOH followed by RNAseZap reagent (Thermo Fisher Scientific). All IVT reactions were performed using MEGAscript T7 Transcription kit (Thermo Fisher Scientific) with 1 µg template, co-transcriptional capping using CleanCap AU (TriLink BioTechnologies) (final conc. 4 mM) and a 3 hour incubation. All other steps were performed as detailed in the manufacturer's protocol. Following IVT, reactions were treated with Turbo DNase (Invitrogen) for 10 minutes at 37° C. Templates that do not contain an internal poly-adenylation sequence were poly-adenylated using a Poly(A) Tailing Kit Thermo Fisher Scientific) according to the manufacturer's protocol. mRNA was purified using either MEGAclear Transcription Clean-Up (Thermo Fisher Scientific) or RNeasy Mini kits (Qiagen) depending on the reaction scale and column loading capacity. mRNA was eluted into THE RNA storage solution (Invitrogen). Concentration was determined by $A_{260}$ using a NanoDrop2000 (Thermo Fisher Scientific).

Lentivirus Transfection and Transduction

Lenti-X cells (Takara Bio) were plated at 250,000 cells/cm² in DMEM+10% FBS+1 mM sodium pyruvate+1% PS and allowed to adhere overnight at 37° C. and 5% $CO_2$. 3rd generation lentiviral vectors were utilized for lentiviral packaging and formulated at a 1:1:1 mixture at lmg/ml. A plasmid encoding the genetic insert of interest was mixed in equal mass to mixture of packaging plasmid. Transfection was performed using TransIT-Lenti reagent (MirusBio) according to manufacturer's protocols. After 72 hours of growth, cell culture supernatant was harvested and centrifuged at 300 g for 5 minutes. Supernatant was filtered using a 0.45 m PVDF syringe filter. Viral stocks were immediately flash frozen and stored at 80° C. Transduction was performed using the Broad Institute protocol titled "Optimized of Lentiviral Spinfection" and tittered for each lentiviral stock and cell line.

HEK293T Flow Cytometry

HEK293T cells were grown in DMEM+10% FBS+1 mM sodium pyruvate+1% PS at 37° C. and 5% $CO_2$. For assaying cytoplasmic fluorescent reporters: cells were gently washed once with 1×PBS and then incubated with trypsin for 2 minutes at 37° C. Trypsinized cells were diluted 1:4 in FACS buffer (1× PBS+3% BSA, 0.22 m filtered) and washed twice via centrifugation at 300 g for 5 minutes at 4° C. in a V-bottom 96 well plate. Cells were resuspended in 200 d FACS buffer prior to analysis. For assaying cell-surface proteins: cells were gently washed once with 1×PBS and then incubated with 1×PBS+2.5 mM EDTA for 5 minutes. Cells were thoroughly resuspended via pipetting, and single cell suspension was confirmed via brightfield microscopy. If LIVE/DEAD analysis was performed, cells were washed twice in 1×PBS and then incubated with a 1:1000 dilution of the eFluor® series Fixable Viability Dye (eBiosciences). Cells were washed twice in FACS buffer and then resuspended with fluorophore conjugated antibody in 1 test/1×10$^6$ cells. Cells were washed twice in FACS buffer and then resuspended in 200 µl FACS buffer prior to analysis. HEK293T cells stably expressing mCherry under a cAMP responsive element (HEK293T-CRE-mCherry) were sorted to enhance the cAMP-stimulation responsive population. HEK293T-CRE-mCherry were stimulated with 10 µM Forskolin for 24 hours prior to preparation for sorting. All preparation was done under sterile conditions. Cells were gated for the highest 10% of mCherry expression. Flow analysis was performed on a LSR II (BD Biosciences), an NtX Attune (Thermo Fisher Scientific) or an Aurora (Cytek Bio). Sorting was performed on an SH800 Cell Sorter (Sony).

Secreted Luminescent Reporter Assay

Coelenterazine (Gold Bio) was dissolved at 5 mg/ml in acidified methanol (MeOH+10 mM HCl) aliquoted and stored at –80° C. Gaussia luciferase working solution (1× PBS+0.5 mM MgCl$_2$+1 mM CaCl$_2$+20 µm Coelenterazine) was allowed to rest in the dark at RT for 30 minutes. 60 µl of media from treated luminescent reporter lines was carefully transferred into black, flat bottomed 96 well plates and allowed to come to room temperature, while covered and in the dark. MTS reagent (Promega) was diluted 1:3 in prewarmed complete media, and 60 µl was carefully added back onto the live cells. Total cell viability for normalization of luminescent readout was measured by absorbance of the MTS assay at 490 nm. In a well-by-well format, 60 µl of Gaussia luciferase working solution was injected, mixed for 3 seconds by orbital shaking, and then total luminesce was measured using a 500 ms exposure time. Assays were performed using an iD3 plate reader with injector module (Molecular Devices).

SMAD Inhibition Assay

HEK293T cells stably expressing Gaussia luciferase under a SMAD responsive promoter (HEK293T-SMAD-Gluc) were grown in DMEM+10% FBS+1 mM sodium pyruvate+1% PS+0.5 µg/ml Puromycin. HEK293T-SMAD-Gluc cells were plated at 50,000 cells/cm$^2$ in TC coated, flat bottom, 96 well plates and allowed to adhere overnight without selection. Prior to plating, all wells were coated with 10 g/ml bovine fibronectin for 1 hour at RT and washed once with warmed 1× PBS. TGF-31 stimulated conditions were treated with 5 ng/ml TGF-31 for 24 hours. Prior to mRNA treatment, media was exchanged for Opti-MEM I (Gibco). mRNA transfection was performed using MessengerMax (Thermo Fisher Scientific) according to manufacturer's protocol. mRNA was dosed at 100 ng/well. Recombinant relaxin-2 control was added at 50 ng/ml. After 24 hours of mRNA treatment, SMAD activity was measured via luminescent reporter assay and normalized to total cell viability.

cAMP Stimulation Assay

HEK293T cells stably expressing Gaussia luciferase or mCherry under a cAMP responsive promoter (HEK293T-CRE-Gluc or HEK293T-CRE-mCherry) were grown in DMEM+10% FBS+1 mM sodium pyruvate+1% PS+0.5 g/ml Puromycin. HEK293T-CRE-Gluc or HEK293T-CRE-mCherry cells were plated at 80,000 cells/cm$^2$ in TC coated, flat bottom, 96 well plates and allowed to adhere overnight without selection. Prior to plating, all wells were coated with 10 g/ml bovine fibronectin for 1 hour at RT and washed once with warmed 1× PBS. Prior to mRNA treatment, media was exchanged for complete media without selection agent. mRNA transfection was performed using MessengerMax (Thermo Fisher Scientific) according to manufacturer's protocol. mRNA was dosed at 100 ng/well. Forskolin control was added at 50 µM and recombinant relaxin-2 control was added at 50 ng/ml. Whole population auto-induction of cAMP production was measured using HEK293T-CRE-Gluc cells via luminescent reporter assay and normalized to total cell viability. The percent of the population capable of cAMP production from auto-induction was measured using HEK293T-CRE-mCherry via flow cytometry.

Immune Suppression Assay

HEK293T cells stably expressing Gaussia luciferase under a STAT3 responsive promoter (HEK293T-STAT3-Gluc) were grown in DMEM+10% FBS+1 mM sodium pyruvate+1% PS+0.5 µg/ml Puromycin. HEK293T-STAT3-Gluc cells were plated at 80,000 cells/cm$^2$ in TC coated, flat bottom, 96 well plates and allowed to adhere overnight without selection. Prior to plating, all wells were coated with 10 g/ml bovine fibronectin for 1 hour at RT and washed once with warmed 1× PBS. Prior to mRNA treatment, media was exchanged for Opti-MEM I (Gibco). mRNA transfection was performed using MessengerMax (Thermo Fisher Scientific) according to manufacturer's protocol. mRNA was dosed at 100 ng/well. Recombinant IL-10 control was added at 100 ng/ml. After 24 hours of mRNA treatment, STAT3 activity was measured via luminescent reporter assay and normalized to total cell viability.

Growth Factor Activation Assay

HEK293T cells stably expressing Gaussia luciferase under an AP-1 responsive promoter (HEK293T-AP1-Gluc) were grown in DMEM+10% FBS+1 mM sodium pyruvate+1% PS+0.5 g/ml Puromycin. HEK293T-AP1-Gluc cells were plated at 60,000 cells/cm$^2$ in TC coated, flat bottom, 96 well plates and allowed to adhere overnight without selection. Prior to plating, all wells were coated with 10 µg/ml bovine fibronectin for 1 hour at RT and washed once with warmed 1× PBS. Prior to treatment, media was exchanged for insulin depleted media (see 3D Chondrocyte Culture). Except for corresponding receptor deficient control, all wells were transfected using Lipofectamine3000 with a plasmid constitutively expressing IGF-1R. Disease state was simulated by the addition of 250 ng/ml recombinant IGFBP-3 (SinoBiological). Recombinant IGF-1 was added at 100 ng/ml (PeproTech). PAPPA2 conditioned media produced by an identical template to mRNA IVT was added at 1 ng/ml. After 24 hours of treatment, AP-1 activity was measured via luminescent reporter assay and normalized to total cell viability. For IGF-1 signaling, total cell viability was assessed via CyQuant assay (Promega) to avoid growth-factor induced alterations to mitochondrial respiratory rate, which can impact MTS readout. Luminesce was normalized to total DNA content.

Production of PAPPA2 Conditioned Media

Recombinant PAPPA2 was produced as previously described (Andrew, M. J Endo Soc. 2018). In brief, HEK293T cells were plated at 250,000 cells/cm$^2$ in DMEM+10% FBS+1 mM sodium pyruvate+1% PS and allowed to adhere overnight. The mRNA IVT template plasmid for PAPPA2 was transfected into cells using Lipofectamine3000 (Invitrogen). Media was exchanged for Opti-MEM I (Gibco) after 6 hours and expression was allowed to continue for 72 hours before purification. Conditioned media was washed and concentrated using 1× PBS and a 100,000 MWCO filter three times. Final concentration was determined by ELISA.

PAPPA2 ELISA

A custom sandwich ELISA was developed for determination of PAPPA2 concentration. Monoclonal capture antibody (R&D Systems—MAB1688) was coated at 1 µg/ml, overnight at 4° C. onto untreated, flat-bottomed, 96-well plates. Plates were washed four times with wash buffer (1× PBS+0.05% Tween-20) and blocked with 200 µl reagent buffer (1× PBS+1% BSA, 0.22 m filtered) for 1 hour at RT. Sample and standard (R&D Systems—1668-ZN) were diluted in reagent buffer and incubated for 2 hours at RT. The working range of the standard curve was 6,000-90 ng/ml. Plates were washed four times with wash buffer. Polyclonal detection antibody (R&D Systems—AF1668) was diluted to a working concentration of 0.2 g/ml in reagent buffer and incubated for 1.5 hours at RT. Plates were washed four times with wash buffer. Donkey anti-goat HRP conjugate (Jackson Immuno Research—705-035-003) was diluted to a working concentration of 20 µg/ml (1:40,000 dilution) and incubated for 30 minutes. Plates were washed four times with wash buffer. 100 µl of 1:1 dilution of Pierce TMB substrate (Thermo Fisher Scientific) was added to the plate and incubated 20 mins prior to the addition of 100 µl of 2N $H_2SO_4$. Absorbance at 452 nm was read within 10 minutes of stop solution addition.

Intact IGFBP-3 ELISA

Intact IGFBP-3 ELISA kit (Anash Labs) was used, following manufacturer's protocol, to quantify intact IGFBP-3 in human synovial fluid samples from diseased and healthy patients, as well as for in vitro characterization of PAPPA2 activity. Human synovial fluid samples from patients with osteoarthritis and rheumatoid arthritis were generously donated by Dr. Brian Snyder, BIDMC. Human synovial fluid samples from healthy, cadaveric donors were purchased from Articular Engineering. Healthy donors were classified as those whose cause of death was not inflammatory, degenerative, or musculoskeletal in nature. These synovial samples acted as controls against OA and RA samples. Characterization of PAPPA2 activity against endogenous IGFBP-3 in human synovial samples was assessed after 2 hours incubation at 37° C. in OptiMEM I (Gibco)+0.1% UltraPure BSA (Invitrogen) with 500 ng/ml PAPPA2. In vitro characterization of PAPPA2 activity against recombinant IGFBP-3 was assessed after 2 hours incubation at 37° C. in OptiMEM I (Gibco)+0.1% UltraPure BSA (Invitrogen). Recombinant protein concentrations were as follows: 400 ng/mL IGFBP-3, 875 ng/mL PAPPA2, and 100 ng/mL IGF-1.

Linoleic Acid BSA Complexation

Linoleic acid was conjugated to fatty acid-free BSA Fatty acid-free BSA as previously described (218). In brief, fatty acid-free BSA (Sigma—126575) was dissolved at 6.7% w/v in glucose free DMEM. It was heated in a water bath to 40-45° C. prior to the addition of 400 mM Linoleic acid dissolved in DMSO. Addition of Linoleic acid was performed dropwise to a final concentration of 4 mM. Store at −80° C. and thaw immediately before use.

3D Chondrocyte Culture

Bovine chondrocytes were aseptically harvested from the knee joint of freshly butchered cows, dissociated, and seeded in agarose constructs at 90M cells/ml. 2 mm cylindrical constructs were harvested via biopsy punch and allowed to rest for 2 days in ITS media (High Glucose DMEM+1 mM sodium pyruvate+50 ug/mL L-proline (Sigma—P5607)+1× ITS+ Universal Culture Supplement (Corning—CB-40352)+100 nM dexamethasone (Sigma—D2915)+1% PS, immediately before use, add ascorbic acid to 50 g/ml). To observe subtle differences in IGF-1 signaling, 3D chondrocyte cultures were then transitioned to insulin depleted media (High Glucose DMEM+1 mM sodium pyruvate+50 ug/mL L-proline (Sigma—P5607)+1× ITS+ Universal Culture Supplement (Corning—CB-40352)+100 nM dexamethasone (Sigma—D2915)+6.25 µg/mL human holotransferrin (Sigma—T8158)+0.915 mg/mL bovine serum albumin+1% PS, immediately before use, add ascorbic acid to 50 µg/ml and 5.35 µg/mL linoleic acid-BSA complex (see Linoleic acid BSA Complexation). 3D chondrocyte constructs where then transferred into Insulin depleted media. Each 3D chondrocyte construct was added to a well of a 96 well plate containing 200 µl of insulin depleted media or ITS media. Culture media with or without treatment was changed every 72 hours. Treatment concentrations were as follows: IGF-1 (200 ng/ml), IGFBP-3 (250 ng/ml), and PAPPA2 (1.5 g/ml). The corresponding volume of 1×PBS was added to each condition without PAPPA2 to adjust for ionic strength. 3D chondrocyte constructs were grown for 45 days prior to mechanical measurement and glycosaminoglycan glycan determination.

3D Chondrocyte Culture Mechanical Testing

Prior to mechanical testing, each chondrocyte construct was washed twice in 1×PBS, incubating for 3 minutes with gentle agitation during each wash. The height and diameter of each chondrocyte construct was determined via caliper. Immersed in a bath of 1×PBS, each construct was subjected to 10% strain followed by 10-minute relaxation to determine the equilibrium modulus. To minimize noise, initial load was determined by averaging the first five data points and equilibrium load was determined by averaging the final 20 seconds of data points.

Glycosaminoglycan Glycan Content

GAG content of the 3D chondrocyte culture was determined via DMMB assay. Chondrocyte constructs were digested overnight with 0.5 mg/ml Proteinase K (MP Biomedicals—193504) in Proteinase K buffer (50 mM Tris, 1 mM EDTA, 1 mM iodoacetamide, 10 µg/mL pepstatin A, pH 8.0). Chondrocyte constructs were transferred to V-bottom 96 deep-well plates, and 400 d of digestion buffer was added to each sample. Samples were incubated overnight at 55° C. After digestion, any remaining agarose in the sample was pulverized with a clean glass stir rod to ensure homogenization and release of GAG. Samples were centrifuged at 1,000 g for 5 minutes, and the clarified supernatant was either immediately assayed for GAG content or stored at −20° C. GAG content was determined via DMMB assay, as previously described (Farndale, 1986). In brief, 30 µl of neat or diluted, clarified sample were combined with 200 µl of DMMB reagent and immediately mixed via orbital shaking absorbance was read at 540 and 595 nm. $\Delta A$ ($A_{540}$-$A_{590}$) of each sample was interpolated from a standard curve of chondroitin-6-sulfate (50 µg/mL to 2.5 µg/ml) to determine GAG content. GAG content was normalized to total DNA content per well as determined by CyQuant reagent (Promega).

PBMC Culture and Mixed Lymphocyte Reaction

PBMCs were isolated from apheresis collars, generously donated by Boston Children's Hospital. Isolation was carried out according to manufacturer's protocol using SepMate™-50 columns containing Lymphoprep (StemCell Technologies). Isolated PBMCs were either immediately used or stored in 90% Human AB serum+10% DMSO in a liquid nitrogen cryotank. PBMCs were rested overnight in X-VIVO 15 (Lonza)+5% human AB serum+1% PS. Any monocytes that may have adhere to the TC flask were gently dissociated using a sterile spatula. Donors were mixed at a 1:1 and 1:9 ratio, with 4M cells per well in 6-well plates.

MLR conditions were cultured in X-VIVO 15 (Lonza)+1% human serum AB+1% PS for 7 days. At 2 days post-exposure, 2 mL of additional media was added to each well. At 4 days post-exposure, plate supernatant was centrifuged at 300 g for 5 minutes. 2 mL of the conditioned media was mixed with 2 mL of fresh media and replaced into their respective wells with adhered monocytes. At day 7, supernatant was centrifuged, as previously described, and media was collected for cytokine analysis via ELISA. Lymphocyte and monocyte populations were separately washed twice with ice-cold 1× PBS and lysed for mRNA extraction using RNeasy mini kits (Qiagen).

CD3+ T cell Culture

CD3+ T cells were selectively enriched from PBMCs, which were isolated from apheresis collars, generously donated by Boston Children's Hospital. Simultaneous isolation and enrichment was carried out using SepMate™-50 columns containing Lymphoprep and RosetteSep™ Human T Cell Enrichment Cocktail (StemCell Technologies). Isolation and enrichment procedures were carried out according to manufacturer's protocol. Isolated T cells were either immediately used or stored in 90% Human AB serum+10% DMSO in a liquid nitrogen cryotank. After thawing, T cells were rested overnight in T cell media (OpTmizer T-cell expansion basal medium (Gibco)+OpTmizer™ T-cell expansion supplement (Gibco)+5% human AB serum+1 mM L-glutamine+10 mM NAC+10 mM HEPES+1% PS, immediately before use add 50 IU IL-2/mL). T cells were activated using Dynabeads (Invitrogen) at a 1:1 bead:cell ratio, according to manufacturer's protocols. Dynabeads were removed from cells via magnetic purification prior to mRNA extraction of analysis via flow cytometry.

cDNA Synthesis and qPCR

All mRNA extraction was performed using RNeasy mini purification columns (Qiagen) according to manufacturer's protocols. mRNA concentration was quantified by $A_{260}$ using a Nanodrop2000 (Thermo Fisher Scientific) cDNA was generated using High-Capacity cDNA Reverse Transcription Kit (Applied Biosystems), according to manufacturer's protocols. qPCR for specific genes was carried out using TaqMan probes in TaqMan advanced master mix (Thermo Fisher Scientific). UBC—VIC was multiplexed as the endogenous control for all immune cell qPCR (CD3+ T Cells, lymphocytes, & monocytes) GAPDH-VIC was multiplexed as the endogenous control for all other qPCR.

```
LISTING OF SEQUENCES
>gi|16497221|gb|AA126416.1| Relaxin 2 [Homo sapiens]
                                                         SEQ ID NO: 1
MPRLFFFHLLGVCLLLNQFSRAVADSWMEEVIKLCGRELVRAQIAICGMSTWSKRSLSQEDAP

QTPRPVAEIVPSFINKDTETINMMSEFVANLPQELKLTLSEMQPALPQLQQHVPVLKDSSLLFEE

FKKLIRNRQSEAADSSPSELKYLGLDTHSRKKRQLYSALANKCCHVGCTKRSLARFC

>gi|116496899|gb|AAI26420.1| Relaxin 2 [Homo sapiens]
                                                         SEQ ID NO: 2
MPRLFFFHLLGVCLLLNQFSRAVADSWMEEVIKLCGRELVRAQIAICGMSTWSKRSLSQEDAP

QTPRPVAEIVPSFINKDIETINMMSEFVANLPQELKLILSEMQPALPQLQQHVPVLKDSSLLFEE

FKKLIRNRQSEAADSSPSELKYLGLDTHSRKKRQLYSALANKCCHVGCTKRSLARFC

>gi|313884020|gb|ADR83496.1| relaxin 2, partial [synthetic construct]
                                                         SEQ ID NO: 3
MPRLFFFHLLGVCLLLNQFSRAVADSWMEEVIKLCGRELVRAQIAICGMSTWSKRSLSQEDAP

QTPRPVAEIVPSFINKDIETINMMSEFVANLPQELKLILSEMQPALPQLQQHVPVLKDSSLLFEE

FKKLIRNRQSEAADSSPSELKYLGLDTHSRKKRQLYSALANKCCHVGCTKRSLARFC

>gi|13543609|gb|AAH05956.1| Relaxin 1 [Homo sapiens]
                                                         SEQ ID NO: 4
MPRLFLFHLLEFCLLLNQFSRAVAAKWKDDVIKLCGRELVRAQIAICGMSTWSKRSLSQED

APQTPRPVAEIVPSFINKDIETIIIMLEFIANLPPELKAALSERQPSLPELQQYVPALKDSNLSFEE

FKKLIRNRQSEAADSNPSELKYLGLDTHSQKKRRPYVALFEKCCLIGCTKRSLAKYC

>gi|119579171|gb|EAW58767.1| relaxin 1, isoform CRA_a [Homo sapiens]
                                                         SEQ ID NO: 5
MPRLFLFHLLEFCLLLNQFSRAVAAKWKDDVIKLCGRELVRAQIAICGMSTWSKRSLSQEDAP

QTPRPV A EIVPSFINKDIETIIIMLEFIANLPPELKAALSERQPSLPELQQYVPALKDSNLSFEEF

KKLIRNRQSEAADSNPSELKYLGLDTHSQKKRRPYVALFEKCCLIGCTKRSLAKYC

>gi|119579172|gb|EAW58768.1| relaxin 1, isoform CRA b [Homo sapiens]
                                                         SEQ ID NO: 6
MPRLFLFHLLEFCLLLNQFSRAVAAKWKDDVIKLCGRELVRAQIAICGMSTWSKRSLSQEDAPQTPRP

VAGISSSLLRRRLFEDHDGPSFLV

>gi|119579173|gb|EAW58769.1| relaxin 1, isoform CRA c [Homo sapiens]
                                                         SEQ ID NO: 7
MLEFIANLPPELKAALSERQPSLPELQQYVPALKDSNLSFEEFKKLIRNRQSEAADSNPSELKY

LGLDTHSQKKRRPYVALFEKCCLIGCTKRSLAKYC
```

-continued

>gi119604794gbEAW84388.1 relaxin 3 [Homo sapiens]
SEQ ID NO: 8
MARYMLLLLLAVWVLTGELWPGAEARAAPYGVRLCGREFIRAVIFTCGGSRWRRSDIL

AHEAMGDTFPDADADEDSLAGELDEAMGSSEWLALTKSPQAFYRGRPSWQGTPGVLR

GSRDVLAGLSSSCCKWGCSKSEISSLC

>gi187954661gbAAI40936.1 Relaxin 3 [Homo sapiens]
SEQ ID NO: 9
MARYMLLLLLAVWVLTGELWPGAEARAAPYGVRLCGREFIRAVIFTCGGSRWRRSDIL

AHEAMGDTFPDADADEDSLAGELDEAMGSSEWLALTKSPQAFYRGRPSWQGTPVVLR

GSRDVLAGLSSSCCKWGCSKSEISSLC

>gi17484096HgbAAL40345.1AF447451 1 relaxin 3 [Homo sapiens]
SEQ ID NO: 10
MARYMLLLLLAVWVLTGELWPGAEARAAPYGVRLCGREFIRAVIFTCGGSRWRRSDILAHE

AMGDTFPDADADEDSLAGELDEAMGSSEWLALTKSPQAFYRGRPSWQGTPGVLRGSRDVL

AGLSSSCCKWGCSKSEISSLC

>gi317373369spJ)51460.2INSL3 HUMAN RecName: Full = Insulin like 3;
SEQ ID NO: 11
MDPRLPAWALVLLGPALVFALGPAPTPEMREKLCGHHEVRALVRVCGGPRWSTEARRPAT

GGDRELLQWLERRHLLHGLVADSNLTLGPGLQPLPQTSHHHRHHRAAATNPARYCCLSGCT

QQDLLTLCPY

>gi119579176gbEAW58772.1 insulin-like 4 (placenta) [Homo sapiens]
SEQ ID NO: 12
MASLFRSYLPAIWLLLSQLLRESLAAELRGCGPRFGKHLLSYCPMPEKTFTTTPGGWLLES

GRPKEMVSTSNNKDGQALGTTSEFIPNLSPELKKPLSEGQPSLKKIILSRKKRSGRHRFDPF

CCEVICDDGTSVKLCT

>gi20070773HgbAAH26254.1 Insulin-like 4 (placenta) [Homo sapiens]
SEQ ID NO: 13
MASLFRSYLPAIWLLLSQLLRESLAAELRGCGPRFGKHLLSYCPMPEKTFTTTPGGWLLES

GRPKEMVSTSNNKDGQALGTTSEFIPNLSPELKKPLSEGQPSLKKIILSRKKRSGRHRFDPF

CCEVICDDGTSVKLCT

>gi37183171AQ89389.1 INSL5 [Homo sapiens]
SEQ ID NO: 14
MKGSIFTLFLFSVLFAISEVRSKESVRLCGLEYIRTVIYICASSRWRRHLEGIPQAQQAETGNSF

QLPHKREFSEENPAQNLPKVDASGEDRLWGGQMPTEELWKSKKHSVMSRQDLQTLCCTDG

CSMTDLSALC

>giH4768935gbAAD29686.1AF133816 1 insulin-like peptide INSL5 [Homo sapiens]
SEQ ID NO: 15
MKGSIFTLFLFSVLFAISEVRSKESVRLCGLEYIRTVIYICASSRWRRHLEGIPQAQQAETG

NSFQLPHKREFSEENPAQNLPKVDASGEDRLWGGQMPTEELWKSKKHSVMSRQDLQTL

CCTDGCSMTDLSALC

>gik5059419gbAAD39003.1AF156094 1 insulin-like protein 6 [Homo sapiens]
SEQ ID NO: 16
MPRLLRLSLLWLGLLLVRFSRELSDISSARKLCGRYLVKEIEKLCGHANWSQFRFEEETP

FSRLIAQASEKVEAYSPYQFESPQTASPARGRGTNPVSTSWEEAVNSWEMQSLPEYKDKKGYSP

LGKTREFSSSHNINVYIHENAFFQKKRRNKIKTLSNLFWGHHPQRKRRGYSEKCCLTGCTKEELS

IACLPYIDFKRLKEKRSSLVTKIY

What is claimed is:

1. A nucleic acid combination comprising:
   (i) a first nucleic acid molecule encoding a ligand; and
   (ii) a second nucleic acid molecule encoding a target molecule, wherein the target is a cognate receptor of the ligand or an inhibitor of a suppressor of the ligand,
   wherein one of the ligand and the target molecule is translated via a cap-dependent manner and the other of the ligand and the target molecule is translated via a cap-independent manner,
   wherein the first and second nucleic acid are covalently linked to form a nucleic acid encoding both the ligand and the target molecule,
   wherein the ligand is a protein, a protein fragment, a fusion protein, and wherein the target molecule is a protein or a polypeptide.

2. The nucleic acid combination of claim 1, wherein the ligand is translated via a cap-dependent manner or the target molecule is translated via a cap-independent manner.

3. The nucleic acid combination of claim 1, wherein the ligand is selected from the group consisting of a cytokine, an interleukin, a chemokine, and a hormone.

4. The nucleic acid combination of claim 1, wherein the target molecule is a cognate receptor of the ligand.

5. The nucleic acid combination of claim 4, wherein the target molecule is a transmembrane receptor, a cytokine receptor, a hormone receptor, an interleukin receptor, or a chemokine receptor.

6. The nucleic acid combination of claim 1, wherein the target molecule is an inhibitor of a suppressor of the ligand.

7. The nucleic acid combination of claim 1, wherein the target molecule inhibits or reduces binding of the ligand to the suppressor.

8. The nucleic acid combination of claim 1, wherein the target molecule is an enzyme and the ligand is a substrate of the enzyme.

9. The nucleic acid combination of claim 1, further encoding an RNA replicon.

10. The nucleic acid combination of claim 1, wherein the nucleic acid is a polycistronic RNA.

11. A composition comprising a nucleic acid combination of claim 1.

12. A lipid particle comprising: a nucleic acid combination of claim 1 and an ionizable lipid.

13. The lipid particle of claim 12, wherein the lipid particle is a nanoparticle.

14. The lipid particle of claim 12, wherein the lipid particle further comprises a non-cationic lipid, a conjugated lipid that inhibits aggregation of particles, or a sterol.

15. The lipid particle of claim 12, wherein the lipid particle comprises:
   (i) an ionizable lipid;
   (ii) a non-cationic lipid;
   (iii) a conjugated lipid that inhibits aggregation of particles; and
   (iv) a sterol.

16. The lipid particle of claim 12, wherein the lipid particle comprises:
   a. an ionizable lipid in an amount from about 20 mol % to about 90 mol % of the total lipid present in the particle;
   b. a non-cationic lipid in an amount from about 5 mol % to about 30 mol % of the total lipid present in the particle;
   c. a conjugated lipid that inhibits aggregation of particles in an amount from about 0.5 mol % to about 20 mol % of the total lipid present in the particle; and
   d. a sterol in an amount from about 20 mol % to about 50 mol % of the total lipid present in the particle.

* * * * *

SEQUENCE LISTING

```
Sequence total quantity: 16
SEQ ID NO: 1                moltype = AA  length = 185
FEATURE                     Location/Qualifiers
source                      1..185
                            mol_type = protein
                            organism = Homo sapiens
SEQUENCE: 1
MPRLFFFHLL GVCLLLNQFS RAVADSWMEE VIKLCGRELV RAQIAICGMS TWSKRSLSQE   60
DAPQTPRPVA EIVPSFINKD TETINMMSEF VANLPQELKL TLSEMQPALP QLQQHVPVLK  120
DSSLLFEEFK KLIRNRQSEA ADSSPSELKY LGLDTHSRKK RQLYSALANK CCHVGCTKRS  180
LARFC                                                              185

SEQ ID NO: 2                moltype = AA  length = 185
FEATURE                     Location/Qualifiers
source                      1..185
                            mol_type = protein
                            organism = Homo sapiens
SEQUENCE: 2
MPRLFFFHLL GVCLLLNQFS RAVADSWMEE VIKLCGRELV RAQIAICGMS TWSKRSLSQE   60
DAPQTPRPVA EIVPSFINKD IETINMMSEF VANLPQELKL ILSEMQPALP QLQQHVPVLK  120
DSSLLFEEFK KLIRNRQSEA ADSSPSELKY LGLDTHSRKK RQLYSALANK CCHVGCTKRS  180
LARFC                                                              185

SEQ ID NO: 3                moltype = AA  length = 185
FEATURE                     Location/Qualifiers
source                      1..185
                            mol_type = protein
                            organism = synthetic construct
SEQUENCE: 3
MPRLFFFHLL GVCLLLNQFS RAVADSWMEE VIKLCGRELV RAQIAICGMS TWSKRSLSQE   60
DAPQTPRPVA EIVPSFINKD IETINMMSEF VANLPQELKL ILSEMQPALP QLQQHVPVLK  120
DSSLLFEEFK KLIRNRQSEA ADSSPSELKY LGLDTHSRKK RQLYSALANK CCHVGCTKRS  180
LARFC                                                              185

SEQ ID NO: 4                moltype = AA  length = 185
FEATURE                     Location/Qualifiers
source                      1..185
                            mol_type = protein
                            organism = Homo sapiens
SEQUENCE: 4
MPRLFLFHLL EFCLLLNQFS RAVAAKWKDD VIKLCGRELV RAQIAICGMS TWSKRSLSQE   60
DAPQTPRPVA EIVPSFINKD IETIIIMLEF IANLPPELKA ALSERQPSLP ELQQYVPALK  120
DSNLSFEEFK KLIRNRQSEA ADSNPSELKY LGLDTHSQKK RRPYVALFEK CCLIGCTKRS  180
LAKYC                                                              185

SEQ ID NO: 5                moltype = AA  length = 185
FEATURE                     Location/Qualifiers
source                      1..185
                            mol_type = protein
                            organism = Homo sapiens
SEQUENCE: 5
MPRLFLFHLL EFCLLLNQFS RAVAAKWKDD VIKLCGRELV RAQIAICGMS TWSKRSLSQE   60
DAPQTPRPVA EIVPSFINKD IETIIIMLEF IANLPPELKA ALSERQPSLP ELQQYVPALK  120
DSNLSFEEFK KLIRNRQSEA ADSNPSELKY LGLDTHSQKK RRPYVALFEK CCLIGCTKRS  180
LAKYC                                                              185

SEQ ID NO: 6                moltype = AA  length = 92
FEATURE                     Location/Qualifiers
source                      1..92
                            mol_type = protein
                            organism = Homo sapiens
SEQUENCE: 6
MPRLFLFHLL EFCLLLNQFS RAVAAKWKDD VIKLCGRELV RAQIAICGMS TWSKRSLSQE   60
DAPQTPRPVA GISSSLLRRR LFEDHDGPSF LV                                 92

SEQ ID NO: 7                moltype = AA  length = 99
FEATURE                     Location/Qualifiers
source                      1..99
                            mol_type = protein
                            organism = Homo sapiens
SEQUENCE: 7
MLEFIANLPP ELKAALSERQ PSLPELQQYV PALKDSNLSF EEFKKLIRNR QSEAADSNPS   60
ELKYLGLDTH SQKKRRPYVA LFEKCCLIGC TKRSLAKYC                          99

SEQ ID NO: 8                moltype = AA  length = 142
FEATURE                     Location/Qualifiers
source                      1..142
                            mol_type = protein
```

```
                          organism = Homo sapiens
SEQUENCE: 8
MARYMLLLLL AVWVLTGELW PGAEARAAPY GVRLCGREFI RAVIFTCGGS RWRRSDILAH    60
EAMGDTFPDA DADEDSLAGE LDEAMGSSEW LALTKSPQAF YRGRPSWQGT PGVLRGSRDV   120
LAGLSSSCCK WGCSKSEISS LC                                           142

SEQ ID NO: 9            moltype = AA   length = 142
FEATURE                 Location/Qualifiers
source                  1..142
                        mol_type = protein
                        organism = Homo sapiens
SEQUENCE: 9
MARYMLLLLL AVWVLTGELW PGAEARAAPY GVRLCGREFI RAVIFTCGGS RWRRSDILAH    60
EAMGDTFPDA DADEDSLAGE LDEAMGSSEW LALTKSPQAF YRGRPSWQGT PVVLRGSRDV   120
LAGLSSSCCK WGCSKSEISS LC                                           142

SEQ ID NO: 10           moltype = AA   length = 142
FEATURE                 Location/Qualifiers
source                  1..142
                        mol_type = protein
                        organism = Homo sapiens
SEQUENCE: 10
MARYMLLLLL AVWVLTGELW PGAEARAAPY GVRLCGREFI RAVIFTCGGS RWRRSDILAH    60
EAMGDTFPDA DADEDSLAGE LDEAMGSSEW LALTKSPQAF YRGRPSWQGT PGVLRGSRDV   120
LAGLSSSCCK WGCSKSEISS LC                                           142

SEQ ID NO: 11           moltype = AA   length = 131
FEATURE                 Location/Qualifiers
source                  1..131
                        mol_type = protein
                        organism = Homo sapiens
SEQUENCE: 11
MDPRLPAWAL VLLGPALVFA LGPAPTPEMR EKLCGHHEVR ALVRVCGGPR WSTEARRPAT    60
GGDRELLQWL ERRHLLHGLV ADSNLTLGPG LQPLPQTSHH HRHHRAAATN PARYCCLSGC   120
TQQDLLTLCP Y                                                       131

SEQ ID NO: 12           moltype = AA   length = 139
FEATURE                 Location/Qualifiers
source                  1..139
                        mol_type = protein
                        organism = Homo sapiens
SEQUENCE: 12
MASLFRSYLP AIWLLLSQLL RESLAAELRG CGPRFGKHLL SYCPMPEKTF TTTPGGWLLE    60
SGRPKEMVST SNNKDGQALG TTSEFIPNLS PELKKPLSEG QPSLKKIILS RKKRSGRHRF   120
DPFCCEVICD DGTSVKLCT                                               139

SEQ ID NO: 13           moltype = AA   length = 139
FEATURE                 Location/Qualifiers
source                  1..139
                        mol_type = protein
                        organism = Homo sapiens
SEQUENCE: 13
MASLFRSYLP AIWLLLSQLL RESLAAELRG CGPRFGKHLL SYCPMPEKTF TTTPGGWLLE    60
SGRPKEMVST SNNKDGQALG TTSEFIPNLS PELKKPLSEG QPSLKKIILS RKKRSGRHRF   120
DPFCCEVICD DGTSVKLCT                                               139

SEQ ID NO: 14           moltype = AA   length = 135
FEATURE                 Location/Qualifiers
source                  1..135
                        mol_type = protein
                        organism = Homo sapiens
SEQUENCE: 14
MKGSIFTLFL FSVLFAISEV RSKESVRLCG LEYIRTVIYI CASSRWRRHL EGIPQAQQAE    60
TGNSFQLPHK REFSEENPAQ NLPKVDASGE DRLWGGQMPT EELWKSKKHS VMSRQDLQTL   120
CCTDGCSMTD LSALC                                                   135

SEQ ID NO: 15           moltype = AA   length = 135
FEATURE                 Location/Qualifiers
source                  1..135
                        mol_type = protein
                        organism = Homo sapiens
SEQUENCE: 15
MKGSIFTLFL FSVLFAISEV RSKESVRLCG LEYIRTVIYI CASSRWRRHL EGIPQAQQAE    60
TGNSFQLPHK REFSEENPAQ NLPKVDASGE DRLWGGQMPT EELWKSKKHS VMSRQDLQTL   120
CCTDGCSMTD LSALC                                                   135

SEQ ID NO: 16           moltype = AA   length = 213
FEATURE                 Location/Qualifiers
source                  1..213
```

```
                    mol_type = protein
                    organism = Homo sapiens
SEQUENCE: 16
MPRLLRLSLL  WLGLLLVRFS  RELSDISSAR  KLCGRYLVKE  IEKLCGHANW  SQFRFEEETP   60
FSRLIAQASE  KVEAYSPYQF  ESPQTASPAR  GRGTNPVSTS  WEEAVNSWEM  QSLPEYKDKK  120
GYSPLGKTRE  FSSSHNINVY  IHENAFFQKK  RRNKIKTLSN  LFWGHHPQRK  RRGYSEKCCL  180
TGCTKEELSI  ACLPYIDFKR  LKEKRSSLVT  KIY                                 213
```